US010196693B2

(12) United States Patent
Peterson et al.

(10) Patent No.: US 10,196,693 B2
(45) Date of Patent: Feb. 5, 2019

(54) METHOD FOR PREDICTING RESPONSE TO BREAST CANCER THERAPEUTIC AGENTS AND METHOD OF TREATMENT OF BREAST CANCER

(71) Applicant: MEDIVATION PROSTATE THERAPEUTICS, LLC, San Francisco, CA (US)

(72) Inventors: Amy Christian Peterson, San Francisco, CA (US); Hirdesh Uppal, San Ramon, CA (US)

(73) Assignee: MEDIVATION PROSTATE THERAPEUTICS LLC, San Francisco, CA (US)

( * ) Notice: Subject to any disclaimer, the term of this patent is extended or adjusted under 35 U.S.C. 154(b) by 0 days.

(21) Appl. No.: 14/962,864

(22) Filed: Dec. 8, 2015

(65) Prior Publication Data

US 2016/0168646 A1 Jun. 16, 2016

Related U.S. Application Data

(60) Provisional application No. 62/091,195, filed on Dec. 12, 2014, provisional application No. 62/142,504, filed on Apr. 3, 2015, provisional application No. 62/167,110, filed on May 27, 2015.

(51) Int. Cl.
*A61K 31/415* (2006.01)
*C12Q 1/6886* (2018.01)
*A61K 31/337* (2006.01)
*A61K 31/4166* (2006.01)
*A61K 45/06* (2006.01)

(52) U.S. Cl.
CPC .......... *C12Q 1/6886* (2013.01); *A61K 31/337* (2013.01); *A61K 31/4166* (2013.01); *A61K 45/06* (2013.01); *C12Q 2600/106* (2013.01); *C12Q 2600/112* (2013.01); *C12Q 2600/158* (2013.01)

(58) Field of Classification Search
CPC .................................................. C07D 233/76
USPC ........................................................ 514/389
See application file for complete search history.

(56) References Cited

U.S. PATENT DOCUMENTS

| | | | |
|---|---|---|---|
| 8,110,594 B2 | 2/2012 | Jung et al. | |
| 8,183,274 B2 | 5/2012 | Sawyers et al. | |
| 8,648,105 B2 | 2/2014 | Jung et al. | |
| 9,126,941 B2 | 9/2015 | Sawyers et al. | |
| 9,517,229 B2 | 12/2016 | Protter et al. | |
| 2007/0004753 A1 | 1/2007 | Sawyers et al. | |
| 2008/0139634 A2 | 6/2008 | Jung et al. | |
| 2009/0111864 A1 | 4/2009 | Jung et al. | |
| 2009/0154681 A1 | 6/2009 | Kung et al. | |
| 2009/0299640 A1 | 12/2009 | Ellis et al. | |
| 2010/0172975 A1 | 7/2010 | Sawyers et al. | |
| 2010/0210665 A1 | 8/2010 | Sawyers et al. | |
| 2011/0003839 A1 | 1/2011 | Jung et al. | |
| 2011/0130296 A1 | 6/2011 | Benz et al. | |
| 2011/0145176 A1 | 6/2011 | Perou et al. | |
| 2011/0152348 A1 | 6/2011 | Worm et al. | |
| 2012/0214864 A1 | 8/2012 | Richer et al. | |
| 2013/0004482 A1 | 1/2013 | Perou et al. | |
| 2013/0345161 A1 | 12/2013 | Perou et al. | |
| 2014/0107180 A1* | 4/2014 | Macleod | C12N 15/1138 514/44 A |
| 2014/0154681 A1 | 6/2014 | Wallden | |
| 2016/0078167 A1* | 3/2016 | Rosner | G06F 19/20 424/133.1 |
| 2017/0087132 A1 | 3/2017 | Protter et al. | |

FOREIGN PATENT DOCUMENTS

| | | |
|---|---|---|
| WO | 2006124118 A1 | 11/2006 |
| WO | 2010099238 A1 | 9/2010 |
| WO | 2010118354 A1 | 10/2010 |
| WO | 2011044327 A1 | 4/2011 |
| WO | WO-2012/125858 A1 | 9/2012 |
| WO | 2013066440 A1 | 5/2013 |
| WO | 2014031164 A1 | 2/2014 |

OTHER PUBLICATIONS

International Search Report and Written Opinion from the EPO in PCT/US2015/064500 dated Apr. 25, 2016, 16 pages.
Traina T A et al: "Stage Stage 1 results from MDV3100-11: A 2-stage study of enzalutamide (ENZA), an androgen receptor (AR) inhibitor, inadvanced AR+ triple-negative breast cancer (TNBC)", SABCS 2014 San Antonio Breast Cancer Symposium, P5-19-09, p. 1130, retrieved from the Internet: URL:https://www.sabcs.org/Portals/SABCS2016/Documents/2014SABCSCall4Abstracts.pdf.
Mrklic et al., "Expression of androgen receptors in triple negative breast carcinomas", ACTA Histochemica, vol. 115, No. 4, May 1, 2013, pp. 344-348.
Fioretti et al, "Revising the role of the androgen receptor in breast cancer", Journal of Molecular Endocrinology, vol. 52, No. 3, May 27, 2014, pp. R257-R265.
Sundem, "Study Shows Anti-Androgen Receptor Therapy for Triple-Negative Breast Cancer May Benefit More than Just High-Androgen Receptor Tumors—Colorado Cancer Blogs", Jun. 23, 2014 (Jun. 23, 2014), Retrieved from the Internet: URL:http://www.coloradocancerblogs.org/study-shows-anti-androgen-receptor-therapy-triple-negative-breast-cancer-may-benefit-just-high-androgen-receptor-tumors/[retrieved on Mar. 24, 2016].
Thicke et al, "Loss of androgen receptor expression predicts early recurrence in triple-negative and basal-like breast cancer", Modern Pathology, vol. 27, No. 3, Mar. 2014, pp. 352-360.
Bertucci et al., "How basal are triple-negative breast cancers?", International Journal of Cancer, vol. 123, No. 1, Jul. 1, 2008, pp. 236-240.

(Continued)

*Primary Examiner* — Raymond Henley, III
(74) *Attorney, Agent, or Firm* — Drinker Biddle & Reath LLP

(57) ABSTRACT

Methods for treating triple negative breast cancer with an androgen receptor inhibitor are provided, as well as methods for screening for the likelihood of the effectiveness of such treatment.

61 Claims, 29 Drawing Sheets
Specification includes a Sequence Listing.

(56) References Cited

OTHER PUBLICATIONS

Parker et al, "Supervised risk predictor of breast cancer based on intrinsic subtypes", Journal of Clinical Oncology, vol. 27, No. 8, Mar. 10, 2009, pp. 1160-1167.
Cheang et al, "Basal-Like Breast Cancer Defined by Five Biomarkers Has Superior Prognostic Value than Triple-Negative Phenotype", Clinical Cancer Research, vol. 14, No. 5.
Cochrane et al, "Role of the androgen receptor in breast cancer and preclinical analysis of enzalutamide", Breast Cancer Research, GB, vol. 16, No. 1, Jan. 22, 2014.
Choo et al, "Biomarkers for Basal-like Breast Cancer", Cancers 2010, vol. 2, No. 2, 2010, pp. 1040-1065.
Ogawa et al., "Androgen receptor expression in breast cancer: relationship with clinicopathological factors and biomarkers", Int J. Olin, Oncol., vol. 13, pp. 431-435 (2008).
Notice of Allowance in U.S. Appl. No. 14/236,036 dated Mar. 24, 2016.
Office Action in U.S. Appl. No. 14/236,036 dated May 20, 2015.
International Search Report and Written Opinion dated Apr. 1, 2013 in PCT/US2012/048471.
International Preliminary Report on Patentability in PCT/US2012/048471, dated Feb. 4, 2014.
Supplemental Search Report and Search Opinion for EP 12 84 6720, dated Feb. 9, 2015.
De Amicis et al. "Androgen Receptor Overexpression Induces Tamoxifen Resistance in Human Breast Cancer Cells" Breast Cancer Res. Treat. 2010, 121(1), 1-11.
"Tamoxifen" Dec. 2004 [online]: Wikipedia [retrieved on May 5, 2015]. Retrieved from <http://en.wikipedia.org/wiki/Tamoxifen>.
Cochrane et al., "Role of the androgen receptor in breast cancer and preclinical analysis of enzalutamide," Breast Cancer Research, vol. 16, No. 1, Jan. 22, 2014.
Doane et al., "An estrogen receptor-negative breast cancer subset characterized by a hormonally regulated transcriptional program and response to androgen," Oncogene, vol. 25, No. 28, Feb. 20, 2006, pp. 3994-4008.
Graham et al., "Reciprocal regulation of ZEB1 and AR in triple negative breast cancer cells", Breast Cancer Research and Treatment, vol. 123, No. 1, Nov. 18, 2009, pp. 139-147.
Ni et al., "Targeting Androgen Receptor in Estrogen Receptor-Negative Breast Cancer," Cancer Cell, vol. 20, No. 1, May 27, 2011, pp. 119-131.
Robinson et al., "Androgen receptor driven transcription in molecular apocrine breast cancer is mediated by FoxA1," The EMBO Journal, vol. 31, No. 6, Jun. 24, 2011, pp. 3019-3027.
Santana-Davila et al., "Treatment options for patients with triple-negative breast cancer," Journal of Hematology & Oncology, vol. 3, No. 1, Oct. 27, 2010, pp. 1-11.
Parker et al., A novel biomarker to predict sensitivity to enzalutamide (ENZA) in TNBC, Journal of Clinical Oncology 33, No. 15_suppl (May 2015) 1083-1038.
Traina, et al., Results from a phase 2 study of enzalutamide (ENZA), an androgen receptor (AR) inhibitor, in advanced AR+triple-negative breast cancer (TNBC).
Lehmann et al., "Identification of human triple-negative breast cancer subtypes and preclinical modesl for selection of targeted therapies," Journal of Clinical Investigation, vol. 121, No. 7, Jul. 1, 2011, pp. 2750-2767.
Zhao et al., "A Phase Ii Clinical Trial of Flutamide in the Treatment of Advanced Breast Cancer", Medical Oncology Department, Shanghai Cancer Hospital Shanghai, China, Tumori, 74: 53-56, 1988.
Perrault, et al. "Phase Ii study of flutamide in patients with metastatic breast cancer. A National Cancer Institute of Canada ClinicalTrials Group Study", Investigational New Drugs 6: 207-210 (1988) Co Kluwer Academic Publishers Printed in the Netherlands.
Barton et al, "Multiple Molecular Subtypes of Triple-Negative Breast Cancer Critically Rely on Androgen Receptor and Respond to Enzalutamide in Vivo", Mol Cancer Ther; 14(3) Mar. 2015, 769-778, Published OnlineFirst Feb_ 23, 2015.

3ochrane et al, Abstract P2-14-02: Preclinical Evaluation of Enzalutamide in Breast Cancer Models, Cancer Res 2012; 7 (24Suppl):Abstract nrP2-14-02, Doi: 10_1158/0008-5472_SABCS12-P2-14-02, Published Dec. 2012.
Audis et al., "Triple-Negative Breast Cancer: an Unmet Medical Need", the Oncologist 2011;16 (suppl 1): 1-11 www. TheOncologist.com, 11 pgs.
Gucalp, et al., "Triple-Negative Breast Cancer Role of the Androgen Receptor", the Cancer Journal vol. 16, No. 1, Jan./Feb. 2010.
Park et al., "Expression of androgen receptors in primary breast cancer", Annals of Oncology vol. 21, No. 3 Mar. 2010, 488-492.
Venkitaraman, Ramachandran, "Triple-negative/basal-like breast cancer: clinical, pathologic and molecular features", Expert Review of Anticancer Therapy, 10:2, 199-207, (2010).
Dgawa, et al., "Androgen receptor expression in breast cancer: relationship with clinicopathological factors and biomarkers", Int J Clin Oncol (2008) 13:431-435.
Tan, "Therapeutic Strategies for Triple-Negative Breast Cancer", the Cancer Journal, vol. 14, No. 6, 343-351, Nov./Dec. 2008.
Islahleh, Zeina M.D., "Androgen receptor as a target for the treatment of hormone receptor-negative breast cancer: an unchartered territory", Future Oncol_ (2008) 4(1), 15-21.
Loibi, et al., "Androgen-Receptor Expression in Triple Negative Breast Cancer Results from the Neoadjuvant Gepartrio Trial", Annals of Oncology 20 (Suppl. 2): 1145, 2009.
Cimino-Mathews, et al., "Androgen Receptor Expression Is Usually Maintained in Initial Surgically-Resected Breast cancer Metastases, but Often Lost in Terminal Metastases Found at Autopsy", United States and Canadian Academy of Pathology, Annual Meeting, USCAP 2011, 91, pp. 33A, San Antonio, TX, Abstract #127, (Feb. 2011).
Cimino-Mathews, et al., "Androgen receptor expression is usually maintained in initial surgically resected breast cancer metastases but is often lost in end-stage metastases found at autopsy", Human Pathology (2012) 43, 1003-1011.
Minami et al., "Management Options in Triple-Negative Breast Cancer", Breast Cancer Basic and Clinical Research (2011) 5:175-179.
Chen, et al., "Expression of androgen receptor in breast carcinoma and its relationship with estrogen receptor, progesterone receptor and HER2 status", Chin J. Pathol, Nov. 2010, vol. 39, No. 11, 743-746.
Richer, et al., "P2.22 MDV3100, an Androgen Receptor Signaling Inhibitor, Abrogates Breast Cancer Proliferation and Tumor Growth in Preclinical Models", Annals of Oncology, vol. 23, Supp. 1, Mar. 2012, p. i31.
Elias, et al., "MDV3100-08: A phase I open-label, dose-escalation study evaluating the safety, tolerability, and pharmacokinetics of MDV3100 in women with incurable breast cancer", Journal of Clinical Oncology, 30, 15_suppl. 2012. DOI 10.1200/jce.2012.30.15.
D'Amato, et al., "Abstract 4756: Elucidating the role of AR in breast cancer", Cancer Research, Suppl 1 (Apr. 2013).
Barton, et al., "Abstract A047: Targeting androgen receptor decreases proliferation of triple-negative breast cancer", Molecular Cancer Research, 11(10 Suppl.) (Oct. 2013).
Barton et al., "Abstract OR38-2: Targeting Androgen Receptor Decreases Proliferation and Invasion in Preclinical Models of Triple Negative Breast Cancer", Therapies for Cancer, Endocrine Society's 96th Annual Meeting and Expo, Jun. 21-24, 2014, Chicago.
Barton, et al., "Androgen Receptor Biology in Triple Negative Breast Cancer: a Case for Classification as AR+ or Duadruple Negative Disease", HORM CANC (2015) 6:206-213.
Barton, et al., "Abstract P3-04-02: Multiple subtypes of triple negative breast cancer are dependent on androgen receptor", Cancer Research, 75 (Suppl. 9), p. 3-04-02, May 1, 2015.
Gordon, et al., Abstract P6-03-07: Targeting multiple pathways in breast cancer: Androgen receptor, HER2, and mTOR, Cancer Research, 75 (9 Suppl. 1) (May 1, 2015).
Gordon, et al., "Abstract SAT-312: The Anti-Androgen Enzalutamide Synergizes with Trastuzumab and Everolimus to Inhibit Breast Cancer Growth Via Distinct Mechanisms", Biomarkers and Hormone-

(56) References Cited

OTHER PUBLICATIONS

Dependent Cancers, Endocrine Society's 97th Annual Meeting and Expo, Mar. 5-8, 2015, San Diego, 2 pgs.
Barton, et al., "Anti-androgen therapy in triple-negative breast cancer", Ther Adv Med Oncol, 2016, vol. 8(4) 305-308.
Notice of Allowance, and Notice of Allowability including Reasons for Allowance dated Aug. 16, 2017 in U.S. Appl. No. 16/373,914.
Original and Allowed claims from U.S. Appl. No. 15/373,914 filed Dec. 9, 2016.
Robert Tibshirani et al., "Diagnosis of multiple cancer types by shrunken centroids of gene expression ," PNAS USA 99(10): 6567-6572 (2002).
Amendment Accompanying Request for Continued Examination filed Jun. 24, 2016 in U.S. Appl. No. 14/236,036 now U.S. Pat. No. 9,517,229.
Notice of Allowance and Notice of Allowability Including Reasons for Allowance dated Aug. 19, 2016 in U.S. Appl. No. 14/236,036 now U.S. Pat. No. 9,517,229.
Richer, et al., "The Role of Androgen Receptors in Postmenopausal Breast Cancer," one page abstract, presented at the Department of Defense Era of Hope conference, Aug. 2-5, 2011, available on-line Jul. 26, 2011.
Preliminary Amendment filed Jan. 29, 2014 in U.S. Appl. No. 14/236,036 now U.S. Pat. No. 9,517,229.
Response to Office Action filed Nov. 20, 2015 in U.S. Appl. No. 14/236,036 now U.S. Pat. No. 9,517,229.
Perou et al., " Molecular portraits of human breast tumours", Nature, vol. 406, pp. 747-752 (2000).
Sorlie et al. "Gene expression patterns of breast carcinomas distinguish tumor subclasses with clinical implications", PNAS, vol. 98, No. 19, pp. 10869-10874 (2001).
Bertucci et al., "How basal are triple-negative breast cancers?" Int. J. Cancer, vol. 123, pp. 236-240 (2008).
Ogawa et al., "Androgen receptor expression in breast cancer: relationship with clinicopathological factors and biomarkers", Int J. Clin, Oncol., vol. 13, pp. 431-435 (2008).
Wang et al," Increased expression of osteopontin in patients with triple-negative breast cancer", Eur. J. Clin. Invest., vol. 38, pp. 438-446 (2008).
Parker et al., "Supervised Risk Predictor of Breast Cancer Based on Intrinsic Subtypes", J Clin Oncol., vol. 27, No. 8, pp. 1160-1167 (2009).
Choo et al., "Biomarkers for Basal-like Breast Cancer", Cancers, vol. 2, pp. 1040-1065 (2010).
Collins et al., "Androgen receptor expression in breast cancer in relation to molecular phenotype: results from the Nurses' Health Study" Mod Pathol, vol. 24, No. 7, pp. 924-931 (2011).
Garay et al., "Androgen receptor as a targeted therapy for breast cancer", Am. J. Cancer Res., vol. 2, No. 4, pp. 434-445 (2012).
Kelly et al, "Agreement in Risk Prediction Between the 21-Gene Recurrence Score Assay (Oncotype DX) and the PAM50 Breast Cancer Intrinsic Classifier™ in Early-Stage Estrogen Receptor-Positive Breast Cancer", The Oncologist, vol. 17, pp. 492-498 (2012).
Gucalp et al., "Phase II Trial of Bicalutamide in Patients with Androgen Receptor-Positive, Estrogen Receptor-Negative Metastatic Breast Cancer", Cancer Res, vol. 19, No. 19, pp. 5505-5512 (2013).
Nielsen et al., " Immunohistochemical and clinical characterization of the basal-like subtype of invasive breast carcinoma", Clinical Cancer Research, vol. 10, pp. 5367-5374 (2014).
Prat et al., "Predicting response and survival in chemotherapy-treated triple-negative breast cancer" British Journal of Cancer, vol. 111, pp. 1532-1541 (2014).
Traina et al., "A Phase 1 Open-Label Study Evaluating the Safety, Tolerability, and Pharmacokinetics of Enzalutamide Alone or Combined With an Aromatase Inhibitor in Women With Advanced Breast Cancer" Ann Oncol., vol. 25(suppl 1): i4. doi: 10.1093/annonc/mdu064.1 (2014).

IMPAKT 2014 News: "Enzalutamide With or Without an Aromatase Inhibitor for Advanced Breast Cancer", 2014 Breast Cancer Conference (May 8-10, 2014, Brussels, Belgium): https://www.esmo.org/Conferences/Past-Conferences/IMPAKT-2014-Breast-Cancer/News/Enzalutamide-With-or-Without-an-Aromatase-Inhibitor-for-Advanced-Breast-Cancer.
Chacon, Reinaldo, D., et al., "Triple-negative breast cancer," Chacón and Costanzo Breast Cancer Research, 2010, 12 (Suppl 2): S3, pgs. 1-9.
The Cancer Genome Atlas Network, "Comprehensive molecular portraits of human breast tumours", Nature 490: 61-70, 2012.
Bullard, James, H., et al., "Evaluation of statistical methods for normalization and differential expression in mRNA-Seq experiments", Bmc Bioinformatics, 2010, vol. 11: 94, pgs. 1-13.
Wang, Kai, et al., "MapSplice: Accurate mapping of Rna-seq reads for splice junction discovery", Nucleic Acids Research, 2010, vol. 38(18): pgs. 1-14, Aug. 28, 2010,.
Carey, Lisa, a., et al., "Tbcrc 001: Randomized Phase Ii Study of Cetuximab in Combination with Carboplatin in Stage Iv Triple-Negative Breast Cancer", Journal of Clinical Oncology, 30(21): 2615-2623, Jul. 20, 2012.
von Minckwitz, Gunter, et al., "Bevacizumab plus chemotherapy versus chemotherapy alone as second-line treatment for patients with HER2-negative locally recurrent or metastatic breast cancer after first-line treatment with bevacizumab plus chemotherapy (Tania): an open-label, randomised phase 3 trial", Lancet Oncology 15: 1269-78, 2014.
Carey, L.A., et al., "Tbcrc 001: Egfr inhibition with cetuximab added to carboplatin in metastatic triple-negative (basal-like) breast cancer", Journal of Clinical Oncology, 26(15 Supp.) 1009-1009, Feb. 3, 2018.
Gerratana, L., et al., "Pattern of metastasis and outcome in patients with breast cancer", Clin. Exp. Metastasis 32: 125-133, 2015.
Hanzelmann, S., et al., "Gsva: gene set variation analysis for microarray and Rna-Seq data," Bmc Bioinformatics, 2013, vol. 14: 7, pgs. 1-15.
Hatsiz, Christos, et al., "Effects of Tissue Handling on Rna Integrity and Microarray Measurements From Resected Breast Cancers", J. Nat'l Cancer Inst. 103: 1871-1883 , 2011.
Hoadley, Katherine, A., et al., "Multiplatform Analysis of 12 Cancer Types Reveals Molecular Classification within and across Tissues of Origin", Cell158: 929-944, 2014.
Kassam, Farrah, et al., "Survival Outcomes for Patients with Metastatic Triple-Negative Breast Cancer: Implications for Clinical Practice and Trial Design", Clinical Breast Cancer, Feb. 2009, 9(1): 29-33.
Kast, Karin, et al., "Impact of breast cancer subtypes and patterns of metastasis on outcome", Breast Cancer Res. Treat., 150: 621-629, 2015.
Loibl, et al., "Androgen receptor expression in primary breast cancer and its predictive and prognostic value in patients treated with neoadjuvant chemotherapy," Breast Cancer Res. Treat., 2011, 130: 477-487.
Miller, K., et al., "Abstract P3-07-25: Improved clinical outcomes on enzalutamide observed in patients with PREDICT AR+ triple-negative breast cancer: prognosis or prediction?", Cancer Research, 76(4 Supp.): Abstract nr P3-07-25.
Twelves, C., et al "Effective Management of Quality of Life in Metastatic Breast Cancer", Clinical Advances in Hematology & Oncology, 12(2 Supp. 4) Feb. 2014, pp. 1-16.
Prat, A., et al., "A PAM50-Based Chemoendocrine Score for Hormone Receptor-Positive Breast Cancer with an Intermediate Risk of Relapse", Clin. Cancer Res.23(12):3035-44, Nov. 30, 2016.
Schneider, B. P., et al., "Triple-Negative Breast Cancer: Risk Factors to Potential Targets", Clin. Cancer Res., 2008, vol. 14, No. 24, Dec. 15, 2008, pp. 8010-8018.
Nielsen, T. O., et al., "A Comparison of PAM50 Intrinsic Subtyping with Immunohistochemistry and Clinical Prognostic Factors in Tamoxifen-Treated Estrogen Receptor-Positive Breast Cancer", Clinical Cancer Research, vol. 16, No. 21, Nov. 1, 2010, pp. 5222-5232.
O'Shaughnessy, J., et al., "Iniparib plus Chemotherapy in Metastatic Triple-Negative Breast Cancer", The New England Journal of Medicine, vol. 364, No. 3, Jan. 20, 2011, pp. 205-214.

(56) References Cited

OTHER PUBLICATIONS

Prat, A., et al., "Molecular Characterization of Basal-Like and Non-Basal-Like Triple-Negative Breast Cancer", The Oncologist, vol. 18, 2013, pp. 123-133.
Rodriguez, A. A., et al., "A randomized, parallel-arm, phase II trial to assess the efficacy of preoperative ixabepilone with or without cetuximab in patients with triple-negative breast cancer (TNBC)", Journal of Clinical Oncology, vol. 32, No. 15, May 2014, 1133-1133.
Storey, J. D., et al., "Statistical significance for genomewide studies", PNAS, vol. 100, No. 16, Aug. 5, 2003, pp. 9440-9445.
Thomas, E. S., et al., "Ixabepilone Plus Capecitabine for Metastatic Breast Cancer Progressing After Anthracycline and Taxane Treatment", Journal of Clinical Oncology, vol. 25, No. 33, Nov. 20, 2007, pp. 5210-5217.
Traina, T. A., et al., "Enzalutamide for the Treatment of Androgen Receptor-Expressing Triple-Negative Breast Cancer", Journal of Clinical Oncology, vol. 36, 2018, pp. 1-9.
Farmer, Pierre, et al., "Identification of molecular apocrine breast tumours by microarray analysis," Oncogene24: 4660-4671, 2005.
U.S. Office Action that issued in U.S. Appl. No. 15/373,914, dated Feb. 16, 2018.
Zhang, et al., "Novel therapeutic strategies for patients with triple-negative breast cancer," OncoTargets and Therapy, 2016, vol. 9, pp. 6519-6528.
Wu, et al., "Androgen Receptor-mTOR Crosstalk in Regulated by Testosterone Availablilty: Implication for Prostate Cancer Cell Survival," Anticancer Res., 2010, vol. 30, No. 10, pp. 3895-3901.
Thakkar, et al., "Vitamin D androgen receptor-targeted therapy for triple-negative breast cancer," Breast Cancer Res. Treat, vol. 157, 2016, pp. 77-90.
Tentler, et al., "Patient-derived tumour xenografts as models for oncology drug development," Nat. Rev. Clin. Oncol., 2012, vol. 9, No. 6, pp. 338-350.
Takayama, et al., "TET2 repression by androgen hormone regulated global hydroxymethylation status and prostate cancer progression," Nature Comm., 2015, vol. 6, No. 8219, pp. 1-16.
Lehmann, et al., "Identification of human triple-negative breast cancer subtypes and preclinical models for selection of targeted therapies," Journal of Clinical Investigation, vol. 121, No. 7, pp. 2750-2767.
Sun, et al., "The role of microRNA-221 and -222 in Androgen-independent Prostate Cancer Cell Lines," Cancer Res., 2009, vol. 69, No. 8, pp. 3356-3363.
Saha et al., "Concepts and targets in triple-negative breast cancer: recent results and clinical implications," Therapeutic Advances in Medical Oncology, 2016, vol. 8, No. 5., pp. 351-359.
Ricciardi, et al., "Androgen Receptor (AR), E-Cadherin, and Ki-67 as Emerging Targets and Novel Prognostic Markers in Triple-Negative Breast Cancer (TNBC) Patients," PLOS One, vol. 10, No. 6, pp. 1-11.
Rampurwala, et al., "Role of the Androgen Receptor in Triple-Negative Breast Cancer," Clinical Advances in Hematology and Oncology, 2016, vol. 14, Issue 3, pp. 186-193.
Phipps, et al., "Body size and risk of luminal, HER2-overexpressing, and triple-negative breast cancer in postmenopausal women," Cancer Epidemiol. Biomarkers Prev., 2008, vol. 17, No. 8, pp. 2078-2086.
Palma, et al., "Triple negatice breast cancer: looking for the missing link between biology and treatments," Oncotarget, 2016, vol. 6, No. 29, pp. 26560-26574.
Niemeier, et al., "Androgen receptor in breast cancer: expression in estrogen receptor-positive tumors and in estrogen receptor-negative tumors with apocrine differentiation," Modern Pathology, 2010, vol. 23, pp. 205-212.
Narayanan, et al., "Androgen Receptor: a Complex Therapeutic Target for Breast Cancer," Cancers, 2016, vol. 8, pp. 1-17.
Mizokami, et al., "Prostate cancer stromal cells and LNCaP cells coordinately activate the androgen receptor through synthesis of testosterone and dihydrotestosterone from dehydroepiandrosterone," Endocrine-Related Cancer, vol. 16, 2009, pp. 1139-1155.
Masiello, et al., "Bicalutamide Functions as an Androgen Receptor Antagonist by Assembly of a Transcriptionally Inactive Receptor," Journal of Biology, 2002, vol. 277, No. 29, pp. 26321-26326.
Mancini, et al., "Standard Care and Promising New Agents for Triple Negative Metastatic Breast Cancer," Cancers, 2014, vol. 6, pp. 2187-2201.
Levine, et al., "A phase II evaluation of goserelin and bicalutamide in patients with ovarian cancer in second or higher complete clinical disease remission," Cancer, 2007, vol. 110, No. 11, pp. 2448-2256, Abstract Only.
Jiang, et al., "Androgen receptor expression predicts different clinical outcomes for breast cancer patients stratified by hormone receptor status," Oncotarget, 2016, vol. 7, No. 27, pp. 41285-41293.
Choi, et al., "Triple-negative, basal-like, and quintuple-negative breast cancers: better prediction model for survival," BMC Cancer, 2010, vol. 10, pp. 1-15.
Carey, et al., "Triple-negative breast cancer: disease entity or title of convenience?," Nat. Rev. Clin. Oncol., 2010, vol. 7, No. 12, pp. 683-92, Abstract only.
Asano, et al., "Expression and Clinical Significance of Androgen Receptor in Triple-Negative Breast Cancer," Cancers, 2017, vol. 9, No. 4, pp. 1-10.
"Different subtypes of triple-negative breast cancer respond to different therapies," Science News, Jun. 27, 2011, 2 pages.
Anders, et al., "Understanding and Treating Triple-Negative Breast Cancer," Oncology, 2008, vol. 22, No. 11, pp. 1233-43.
Anders, et al., "Biology, Metastatic Patterns, and Treatment of Patients with Triple-Negative Breast Cancer," Clin. Breast Cancer, 2009, vol. 9 (Suppl 2), pp. S73-S81.
Adam, et al., "Heparin-Binding Epidermal Growth Factor-Like Growth Factor Stimulates Androgen-Independent Prostate Tumor Growth and Antagonizes Androgen Receptor Function," Endocrinology, 2002, vol. 143, No. 12, pp. 4599-4608.
Abstracts, Royal College of Radiologists Breast Group Annual Scientific Meeting, Brighton, UK, Nov. 1-2, 2010, Breast Cancer Research, 2010, vol. 12, Suppl. 3, pp. S1-S16.
Abramson, et al., "Subtyping of triple-negative breast cancer: implications for therapy," Cancer, Jan. 1, 2015, vol. 121, No. 1, pp. 8-16.
Amiri-Kordestani, L., et al., "Association of clinical benefit rate (CBR) with survival: A pooled-analysis of metastatic breast cancer (MBC) trials submitted to the U.S. Food and Drug Administration (FDA)", Journal of Clinical Oncology, 34(15_Suppl.): pp. e18091-e18091, 2016.
Vera-Badillo, F. E., et al, "Androgen receptor expression and outcomes in early breast cancer: A systematic review and meta-analysis", Journal of National Cancer Inst., 106(1): djt319, pp. 1-11, 2014.
Krop, I., et al, "Abstract GS4-07: Results from a randomized placebo-controlled phase 2 trial evaluating exemestane ± enzalutamide in patients with hormone receptor—positive breast cancer", Presented at the 2017 San Antonio Breast Cancer Symposium, Dec. 5-9, 2017, San Antonio, TX, pp. 1-5.
Ramos, C., et al, "Androgen receptor (AR) activation in breast cancer (BC) liver metastases", Journal of Clinical Oncology, 35(15 Supp.): 11619, 2017, pp. 1-3.
Kumar, V., et al, "Androgen receptor immunohistochemistry as a companion diagnostic approach to predict clinical response to enzalutamide in triple-negative breast cancer", JCO Precision Oncology, vol. 1, pp. 1-19, 2017.
Hammond, M.E., et al, "American Society of Clinical Oncology/College of American Pathologists guideline recommendations for immunohistochemical testing of estrogen and progesterone receptors in breast cancer", Journal of Clinical Oncology, 28(15): 2784-2795, 2010.
Traina, T. A., et al, "Overall survival (OS) in patients (PTS) with diagnostic positive (DX+) breast cancer: Subgroup analysis from a phase 2 study of enzalutamide (ENZA), an androgen receptor (AR) inhibitor, in AR+ triple-negative breast cancer (TNBC) treated with 0-1 prior lines of therapy", Journal of Clinical Oncology, vol. 35(15 Supp.): 1089, pp. 1-3, 2017.

(56) References Cited

OTHER PUBLICATIONS

European Office Action dated Apr. 4, 2018 that issued in EP Patent Application No. 15 831 013.6-1111.
Twelves, C., M.D., "Clinical Roundtable Monograph: Effective Management of Quality of Life in Metastatic Breast Cancer", Clinical, Advances in Hematology & Oncology, Feb. 2014, vol. 12, Issue 2, Suppl. 4, pp. 1-14; Quiz pp. 15-16.
Iaskoff, "Triple Negative Breast Cancer: Role of Specific Chemotherapy Agents," Cancer J., 2010, vol. 16, No. 1, pp. 53-61.
Ieni, et al., "Prognostic value of androgen receptor expression in triple negative breast carcinomas: personal experience and comments on a review about "Triple-negative breast cancer: treatment challenges and solutions" by Collignon et al.," Breast Cancer-Targets and Therapy, 2016, vol. 8, pp. 157-159.
Gonzalez-Angulo, et al., "Metformin: A Therapeutic Opportunity in Breast Cancer," 2010, Clinical Cancer Research, vol. 16, No. 6, pp. 1695-1700.
Foulkes, et al., "Triple-Negative Breast Cancer," The New England Journal of Medicine, 2010, vol. 363, pp. 1938-1948.
Farla, et al., "Antiandrogens prevent stable DNA-binding of the androgen receptor," Journal of Cell Science, 2005, vol. 118, pp. 4187-4198.
de Ruijter, et al., "Characteristics of triple-negative breast cancer," J. Cancer Res. Clin. Oncol., 2011, vol. 137, pp. 183-192.
De Leon, et al., "Targeting the regulation of androgen receptor signaling by the heat shock protein 90 cochaperone FKBP52 in prostate cancer cells," Proc. Nat'l, Academy of Science, USA, 2011, vol. 108, No. 29, pp. 11878-83.
Davis, et al., "Triple-negative breast cancer: bridging the gap from cancer genomics to predictive biomarkers," Therapeutic Advances in Medical Oncology, 2014, vol. 6, No. 3, pp. 88-100.
Cummings, et al., "Serum Estradiol Level and Risk of Breast Cancer During Treatment with Raloxifene," JAMA, 2002, vol. 287, No. 2, pp. 216-220.
Collignon, et al., "Triple-negative breast cancer: treatment challenges and solutions," Breast Cancer Targets and Therapy, 2016, vol. 8, pp. 93-107.

\* cited by examiner

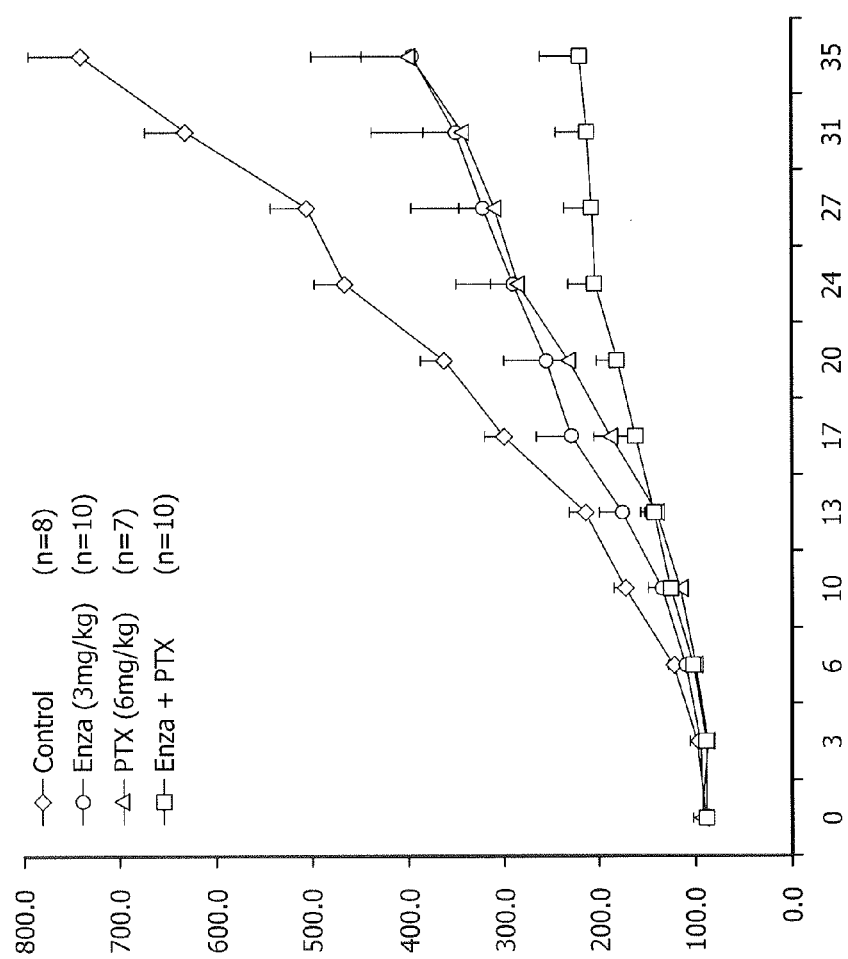

METHOD FOR PREDICTING RESPONSE TO BREAST CANCER THERAPEUTIC AGENTS AND METHOD OF TREATMENT OF BREAST CANCER

CROSS-REFERENCE TO RELATED APPLICATIONS

This application claims the benefit of the following U.S. Provisional applications, the entire disclosures of which are incorporated herein by reference: No. 62/091,195, filed Dec. 12, 2014; No. 62/142,504, filed Apr. 3, 2015; and No. 62/167,110, filed May 27, 2015.

SEQUENCE LISTING

The instant application contains a Sequence Listing which has been submitted in ASCII format via EFS-Web and is hereby incorporated by reference in its entirety. Said ASCII copy, created on Dec. 4, 2015, is named 212181_0001_00_WO_SeqListing_ST25 and is 262,467 bytes in size.

FIELD OF THE INVENTION

The field relates to breast cancer therapy.

BACKGROUND OF THE INVENTION

Breast cancer is considered a genetically heterogeneous and biologically diverse disease. The long-recognized clinical and phenotypic differences have been shown to correlate with differences in gene expression. Previous studies of breast tumors have identified five distinct subtypes of breast carcinomas that are associated with different clinical outcomes: luminal A (estrogen receptor (ER)+); luminal B (ER+); HER2 overexpressing; normal breast-like; and basal-like. See, Perou et al. Nature, 406(6797):747-52 (2000); Sorlie et al. PNAS, 98(19):10869-74 (2001).

Analysis of breast cancer biopsy and surgical specimens typically includes an assessment of nuclear and cell surface receptors (ER, PgR, and HER2), gene amplification of HER2 (if HER2 analysis by immunohistochemistry (IHC) is not definitive), and other prognostic tests such as microvessel invasion and proliferation markers. Endocrine therapies that target ER signaling pathways for ER+ disease and HER2-targeted therapies for HER2+ disease play a critical role in the treatment of most patients with breast cancer. However, little progress has been made in identifying effective targeted therapies for patients whose disease lacks these receptors, i.e., the so-called "triple negative" breast cancers or "TNBC", and nonselective cytotoxic chemotherapy remains the primary therapeutic option.

The androgen receptor (AR) is the most commonly expressed nuclear hormone receptor in breast cancer, though its functional role in initiating or driving malignancy is not yet well understood. In a study of 3093 breast cancers, AR expression (10% or more nuclear staining by IHC) was observed in 77% of invasive breast tumors and across all molecular phenotypes (Collins et al., Mod Pathol 2011; 24(7):924-931). However, androgen receptor levels are not routinely assessed, since they have not been shown to predict responses to currently used therapies.

The use of AR inhibitors has been proposed as part of a therapeutic regimen for the treatment of breast cancer. See, e.g., Garay and Park, Am. J. Cancer Res. 2012; 2(4):434-445. Interest has been generated recently in the treatment of TNBC. Lack of expression of all three of estrogen receptor, progesterone receptor and HER2 predicts non-response to available endocrine (tamoxifen, aromatase inhibitors) and anti-HER2 (trastuzumab) targeted therapies. From 10 to 35% of such TNBC tumors express androgen receptor (Ogawa et al., Int J. Clin, Oncol. 2008; 13:431435). AR-targeted therapies may prove to be a valuable treatment for a large proportion of breast cancers, including triple negative cancers.

Despite the interest in androgen receptor signaling inhibition as a modality for the treatment of breast cancer, and in the treatment of TNBC in particular, there remains a need for predicting whether the individual patient will be responsive in advance of therapy. A test to predict the likelihood of whether or not a particular patient will respond to a therapy that inhibits androgen receptor signaling, and TNBC patients in particular, would be a valuable tool in planning patient treatment.

SUMMARY OF THE INVENTION

In one embodiment, provided is a method of screening a treatment for triple negative breast cancer comprising the use of an androgen receptor inhibitor, the method comprising assaying a biological sample obtained from a subject to determine whether the biological sample obtained from the subject is classified as basal-like subtype or another subtype. If the biological sample is classified as other than a basal-like subtype, the breast cancer treatment comprising an androgen receptor inhibitor is more likely to be effective than if the sample were classified as basal-like subtype.

Also provided is a method of screening for the likelihood of the effectiveness of a treatment for triple negative breast cancer comprising an androgen receptor inhibitor, in a subject in need of such treatment. The method comprises:
  assaying a biological sample obtained from the subject to determine whether the biological sample is classified as a basal-like subtype or another subtype; and
  wherein if the biological sample is classified as other than a basal-like subtype, the breast cancer treatment comprising an androgen receptor inhibitor is more likely to be effective than if the sample were classified as basal-like subtype.

Also provided is a method of classifying a biological sample from a subject as an indicator of the likelihood of the effectiveness of a treatment of the patient for triple negative breast cancer, said treatment comprising an androgen receptor inhibitor, the method comprising:
  assaying a biological sample obtained from the subject to determine whether the biological sample is classified as a basal-like subtype or another subtype; and
  wherein the biological sample classified as other than basal-like subtype indicates that the breast cancer treatment comprising an androgen receptor inhibitor is more likely to be effective than if the sample were classified as basal-like subtype.

In certain embodiments of the screening and classifying methods (collectively "the aforementioned methods"), assaying the biological sample to determine whether the biological sample is classified as a basal-like subtype or another subtype is performed by detecting the expression of the set of intrinsic genes listed in Table 1.

In certain embodiments of the aforementioned methods, the Basal Centroid classifier score of the sample is determined from the expression of the set of intrinsic genes listed in Table 1.

In one embodiment of the aforementioned methods, if the Basal Centroid classifier score is less than or equal to 0.9, the breast cancer treatment comprising an androgen receptor inhibitor is determined to be likely more effective in treating the subject than if the Basal Centroid classifier score is greater than 0.9. In another embodiment, if the Basal Centroid classifier score is less than or equal to 0.6, the breast cancer treatment comprising an androgen receptor inhibitor is determined to be likely more effective in treating the subject than if the Basal Centroid classifier score is greater than 0.6. In another embodiment, if the Basal Centroid classifier score is in the range from 0.2 to 0.8, the breast cancer treatment comprising an androgen receptor inhibitor is likely to be effective in treating the subject. In another embodiment, if the Basal Centroid classifier score is in the range from 0.4 to 0.7, the breast cancer treatment comprising an androgen receptor inhibitor is likely to be effective in treating the subject.

In certain embodiments of the aforementioned methods, the Basal Centroid classifier score and the Luminal A Centroid classifier score of the sample are determined from the expression of the set of intrinsic genes listed in Table 1. The methods further comprises calculating a Weighted Basal and Luminal A classifier score from the Basal Centroid classifier score and the Luminal A Centroid classifier score according to the following equation:

Weighted Basal and Luminal A classifier score=
−0.25(Basal Centroid classifier score)+0.27(Luminal A Centroid classifier score)

wherein if the Weighted Basal and Luminal A classifier score is greater than −0.3, the breast cancer treatment comprising an androgen receptor inhibitor is more likely to be effective in the subject than if the Weighted Basal and Luminal A classifier score is less than or equal to −0.3. In another embodiment, if the Weighted Basal and Luminal A classifier score is greater than −0.2, the breast cancer treatment comprising an androgen receptor inhibitor is more likely to be effective in the subject than if the Weighted Basal and Luminal A classifier score is less than or equal to −0.2. In another embodiment, if the Weighted Basal and Luminal A classifier score is greater than −0.25, the breast cancer treatment comprising an androgen receptor inhibitor is more likely to be effective in the subject than if the Weighted Basal and Luminal A classifier score is less than or equal to −0.25.

In some embodiments, the equation for determining the Weighted Basal and Luminal A classifier score takes the form:

Weighted Basal and Luminal A classifier score=
−0.2468275(Basal Centroid classifier score)+
0.2667110(Luminal A Centroid classifier score)

In certain embodiments of the aforementioned methods, the breast cancer is characterized by the presence of androgen receptor-positive tumor cells.

In certain embodiments of the aforementioned methods, the biological sample is selected from the group consisting of a cell, tissue and bodily fluid. In certain embodiments, the body fluid is selected from the group consisting of blood, lymph, urine, saliva, fluid from ductal lavage and nipple aspirate. In some embodiments, the tissue is obtained from a biopsy.

In any of the aforementioned methods, an assay to determine the androgen receptor status of the cells of the sample, i.e. AR-positive vs. AR-negative, may be carried out.

Also provided is a method of treating triple negative breast cancer in a subject, said subject having a breast cancer comprising breast cancer cells that have been classified as other than basal-like subtype, said method comprising administering a breast cancer treatment to the subject comprising an androgen receptor inhibitor, thereby treating the triple negative breast cancer in the subject.

In one embodiment of the treatment method, the breast cancer cells of the subject are characterized by a Basal Centroid classifier score of less than or equal to 0.9, determined from the expression by said cells of the set of intrinsic genes listed in Table 1. In another embodiment of the treatment method, the breast cancer cells of the subject are characterized by a Basal Centroid classifier score of less than or equal to 0.6. In another embodiment of the treatment method, the breast cancer cells of the subject are characterized by a Basal Centroid classifier score in the range from 0.2 to 0.8. In another embodiment of the treatment method, the breast cancer cells of the subject are characterized by a Basal Centroid classifier score in the range from 0.4 to 0.7.

In another embodiment of the treatment method, the breast cancer cells of the subject are characterized by Weighted Basal and Luminal A classifier score greater than −0.3. In another embodiment of the treatment method, the breast cancer cells of the subject are characterized by a Weighted Basal and Luminal A classifier score greater than −0.2. In another embodiment of the treatment method, the breast cancer cells of the subject are characterized by a Weighted Basal and Luminal A classifier score greater than −0.25.

Also provided is a triple negative breast cancer treatment comprising an androgen receptor inhibitor for use in the treatment of a triple negative breast cancer in a subject in need thereof, wherein said method of treatment comprises: (a) assaying a biological sample from the subject to determine whether the biological sample is classified as basal-like subtype or another subtype; and (b) administering said triple negative breast cancer treatment to the subject if the biological sample is classified as other than basal-like subtype.

Also provided is a therapeutic agent for triple negative breast cancer therapy or treatment for use in a subject in need thereof, wherein said agent is an androgen receptor inhibitor, comprising: (a) assaying a biological sample from the subject to determine whether the biological sample is classified as basal-like subtype or another subtype; and (b) administering said agent to the subject if the biological sample is classified as other than basal-like subtype.

Also provided is an androgen receptor inhibitor for use in the treatment of a triple negative breast cancer in a subject wherein a biological sample from the subject has been assayed to determine whether sample is classified as basal-like subtype or another subtype.

Also provided is a method of treating triple negative breast cancer in a subject in need of such treatment comprising: (a) assaying the biological sample to determine whether the biological sample is classified as a basal-like subtype or another subtype; and (b) if the biological sample is classified as other than a basal-like subtype, administering a breast cancer treatment to the subject comprising an androgen receptor inhibitor, thereby treating the breast cancer in the subject.

In certain embodiments of the aforementioned methods of treatment, treatments and androgen receptor inhibitors for use in treatment, assaying the biological sample to determine whether the biological sample is classified as a basal-like subtype or another subtype is performed by detecting the expression of the intrinsic genes listed in Table 1.

In certain embodiments of the aforementioned methods of treatment, treatments and androgen receptor inhibitors for use in treatment, assaying the biological sample comprises determining the Basal Centroid classifier score of the sample from the expression of the set of intrinsic genes listed in Table 1, wherein the breast cancer treatment is administered if the Basal Centroid classifier score is less than or equal to 0.9. In one embodiment, the breast cancer treatment is administered if the Basal Centroid classifier score is less than or equal to 0.6. In one embodiment, the breast cancer treatment is administered if the Basal Centroid classifier score is in the range from 0.2 to 0.8. In another embodiment, the breast cancer treatment is administered if the Basal Centroid classifier score is in the range from 0.4 to 0.7.

In certain embodiments of the aforementioned methods of treatment, treatments and androgen receptor inhibitors for use in treatment, assaying the biological sample comprises determining the Basal Centroid classifier score and the Luminal A Centroid classifier score of the sample from the expression of the set of intrinsic genes listed in Table 1, and calculating a Weighted Basal and Luminal A classifier score, wherein the breast cancer treatment is administered to the subject if the Weighted Basal and Luminal A classifier score greater than −0.3. In one embodiment, the breast cancer treatment is administered if the Weighted Basal and Luminal A classifier score is greater than −0.2. In another embodiment, the breast cancer treatment is administered if the Weighted Basal and Luminal A classifier score is greater than −0.25.

In certain embodiments of the aforementioned methods of treatment, treatments and androgen receptor inhibitors for use in treatment, the breast cancer of the subject is further characterized by the presence of androgen receptor-positive tumor cells.

In embodiments of the aforementioned methods of treatment, treatments and androgen receptor inhibitors for use in treatment, the androgen receptor inhibitor is selected from the group consisting of enzalutamide, bicalutamide, flutamide, nilutamide, ARN509, ketoconazole, abiraterone acetate, VN/124-1 (TOK-001), orteronel (TAK-700), finasteride, galeterone, cyproterone acetate, andarine and combinations thereof. The list of androgen receptor inhibitor is exemplary and not meant to be limiting.

In certain embodiments, the androgen receptor inhibitor is enzalutamide. In once such embodiment, enzalutamide is orally administered once daily at a dose of 160 mg. In some embodiments, enzalutamide is administered as a single capsule comprising 160 mg enzalutamide. In other embodiments, enzalutamide is administered as four capsules, each capsule comprising 40 mg enzalutamide.

In embodiments of the aforementioned methods of treatment, treatments and androgen receptor inhibitors for use in treatment, the breast cancer treatment comprising an androgen receptor inhibitor further comprises one or more other anti-cancer agents that is not an androgen receptor inhibitor. Such other anti-cancer agents that are not androgen receptor inhibitors may be selected from the group consisting of cyclophosphamide, fluorouracil, 5-fluorouracil, methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserelin, goserelin, megestrol acetate, risedronate, pamidronate, ibandronate, alendronate, denosumab, zoledronate, trastuzumab, tykerb or bevacizumab, and combinations thereof. The list of other anti-cancer agents is exemplary and not meant to be limiting.

In one embodiment, the non-AR inhibitor anticancer agent is paclitaxel. In another embodiment, the AR inhibitor is enzalutamide and the non-AR inhibitor anticancer agent is paclitaxel.

In certain embodiments, the treatment method comprises a step of testing the subject to determine whether the subject has a breast cancer comprising breast cancer cells that are other than basal-like subtype.

In certain embodiments, the treatment method comprises a step of testing the subject to determine the Basal Centroid classifier score of breast cancer cells of the subject.

In certain embodiments, the treatment method comprises a step of testing the subject to determine the Weighted Basal and Luminal A classifier score of breast cancer cells of the subject.

In some embodiments of the aforementioned methods of treatment, treatments and androgen receptor inhibitors for use in treatment, the subject has received zero or one rounds of prior treatment with an anti-cancer agent, other than an androgen receptor inhibitor, for treatment of triple negative breast cancer.

In embodiments of the aforementioned screening methods, classifying methods, treatment methods, treatments, and androgen receptor inhibitors for use in treatment, the biological sample may be selected from the group consisting of a cell, tissue and bodily fluid In certain embodiments, the body fluid is selected from the group consisting of blood, lymph, urine, saliva, fluid from ductal lavage and nipple aspirate. In some embodiments, the tissue is obtained from a biopsy.

In any of the aforementioned screening methods, classifying methods, treatment methods, treatments, and androgen receptor inhibitors for use in treatment, an assay to determine the androgen receptor status of the cells of the sample, i.e. AR-positive vs. AR-negative, may be carried out.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DEFINITIONS

The articles "a" and "an" are used herein to refer to one or to more than one (i.e. to at least one) of the grammatical object of the article. By way of example, "an element" means one element or more than one elements.

"About" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

"Androgen receptor inhibitor" means a compound or molecule that directly or indirectly inhibits the androgen receptor (AR) signaling pathway. In one embodiment, direct inhibitors of the AR receptor include enzalutamide, bicalutamide (Casodex), flutamide, nilutamide, ARN509 and the like. In another embodiment, indirect inhibitors of AR include Cyp 17 inhibitors such as ketoconazole, abiraterone acetate, VN/124-1 (TOK-001), orteronel (TAK-700) and the like. In another embodiment, AR inhibitors include finasteride, galeterone, cyproterone acetate, and andarine, and the like.

By "detecting expression" is intended determining the quantity or presence of an RNA transcript or its expression product of an intrinsic gene.

By "inhibit" or other forms of inhibit means to hinder or restrain a particular characteristic. It is understood that this is typically in relation to some standard or expected value, in other words it is relative, but that it is not always necessary for the standard or relative value.

As used throughout, by a "subject" is meant an individual, typically a mammal or fowl. Mammals can include, for example, domesticated animals (e.g., cat or dog), livestock (e.g., cattle, horses, pigs, sheep, goats, etc.), laboratory animals (e.g., mouse, rabbit, rat, guinea pig, etc.) and primates. Preferably, the mammal is a human being.

"Triple negative breast cancer" or "TNBC" refers to any breast cancer that does not express the genes for estrogen receptor (ER), progesterone receptor (PR) and Her2/neu. The term includes primary epithelial TNBCs, as well as TNBC that involved with other tumors. The cancer can include a triple negative carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. TNBC can also include any stage of triple negative breast cancer, and can include breast neoplasms having histologic and ultrastructual heterogeneity (e.g., mixed cell types).

"A TNBC treatment comprising androgen receptor inhibitor" is a TNBC treatment that includes administration of an androgen receptor inhibitor. The treatment may include other anti-cancer or chemotherapeutic agents.

A subject "in need of" treatment for TNBC is a subject having TNBC or presenting with one or more symptoms of TNBC, or a subject having an increased risk of developing TNBC relative to the population at large. Preferably, a subject "in need" of treatment for TNBC is a subject who is afflicted with TNBC.

As used herein, "therapeutically effective amount" or "therapeutically effective dose" refers to an agent, compound, material, or composition containing a compound that is at least sufficient to produce a therapeutic effect. An effective amount is the quantity of a therapeutic agent necessary for preventing, curing, ameliorating, arresting or partially arresting a symptom of a disease or disorder.

"Treating" or "treatment" does not mean a complete cure. It means that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease.

Weighted Basal and Luminal A classifier score=
−0.2468275(Basal Centroid classifier score)+
0.2667110(Luminal A Centroid classifier score).

Figure 14A:
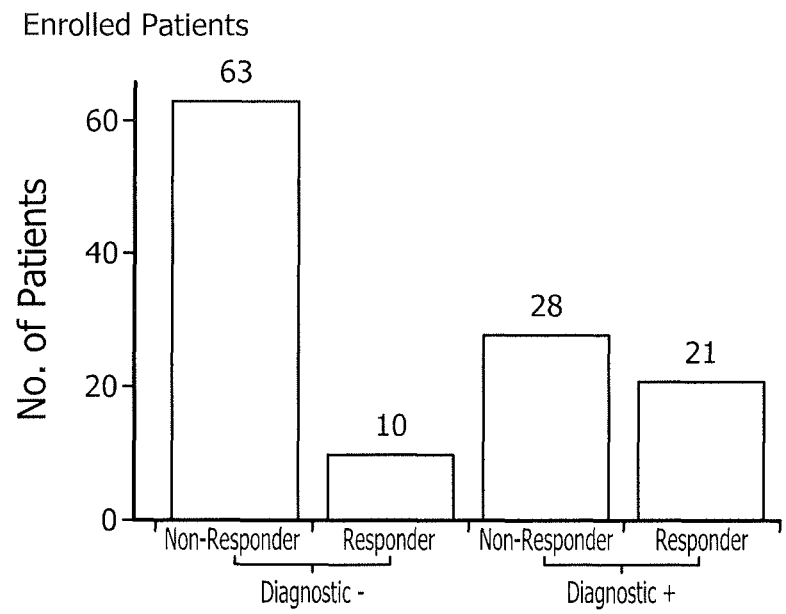
FIGS. 14A-14D comprise the results of patient responses in the clinical trial of the drug enzalutamide for the treatment of TNBC. Gene expression analysis was carried out on patient breast tumor samples using PAM50 intrinsic gene set of Table 1. The Spearman rank correlation to the Basal-like gene expression centroid was evaluated for each sample and assigned as the "Basal Centroid classifier score". The Spearman rank correlation to the Luminal A gene expression centroid was evaluated for each sample and assigned as the "Luminal A classifier score". A Weighted Basal and Luminal A classifier score of the patient samples was determined from the following formula.
Figure 14B:
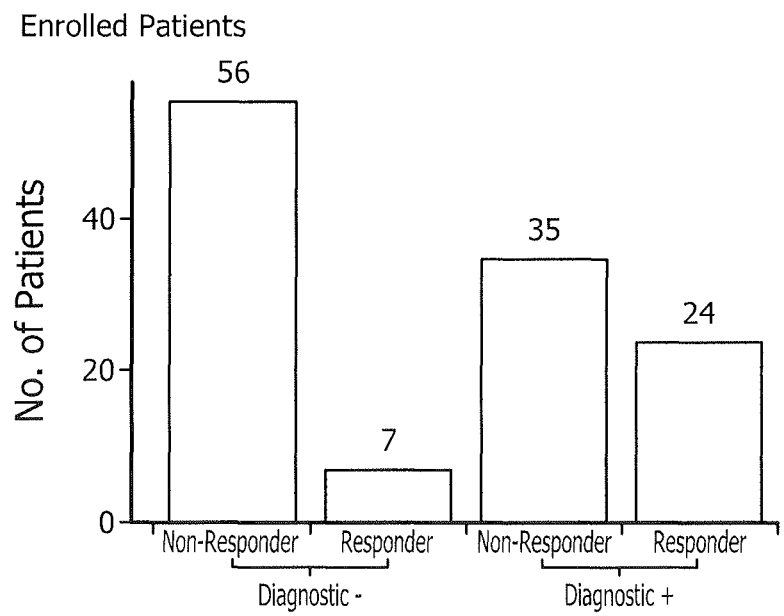
Figure 14C:
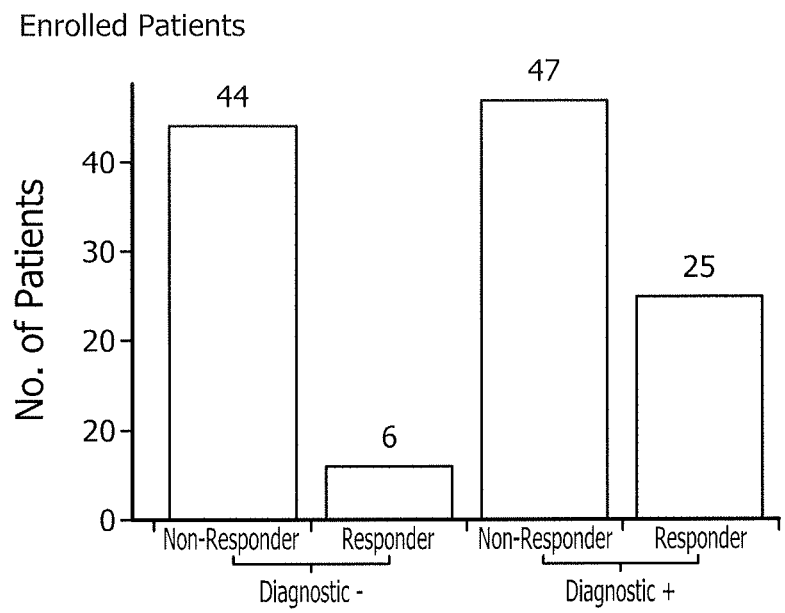
Figure 14D:
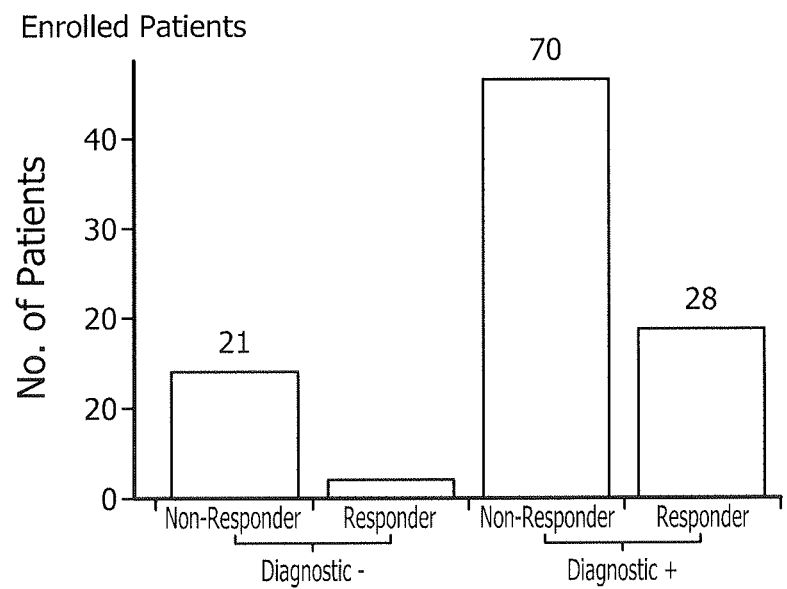

The enzalutamide response/non-response data was analyzed using Weighted Basal and Luminal A classifier score cut-offs of >−0.2 (FIG. 14A), >−0.25 (FIG. 14B), >−0.3 (FIG. 14C) and >−0.35 (FIG. 14D). The data is set forth in FIG. 14A-14D. In each figure, "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.

Figure 15:
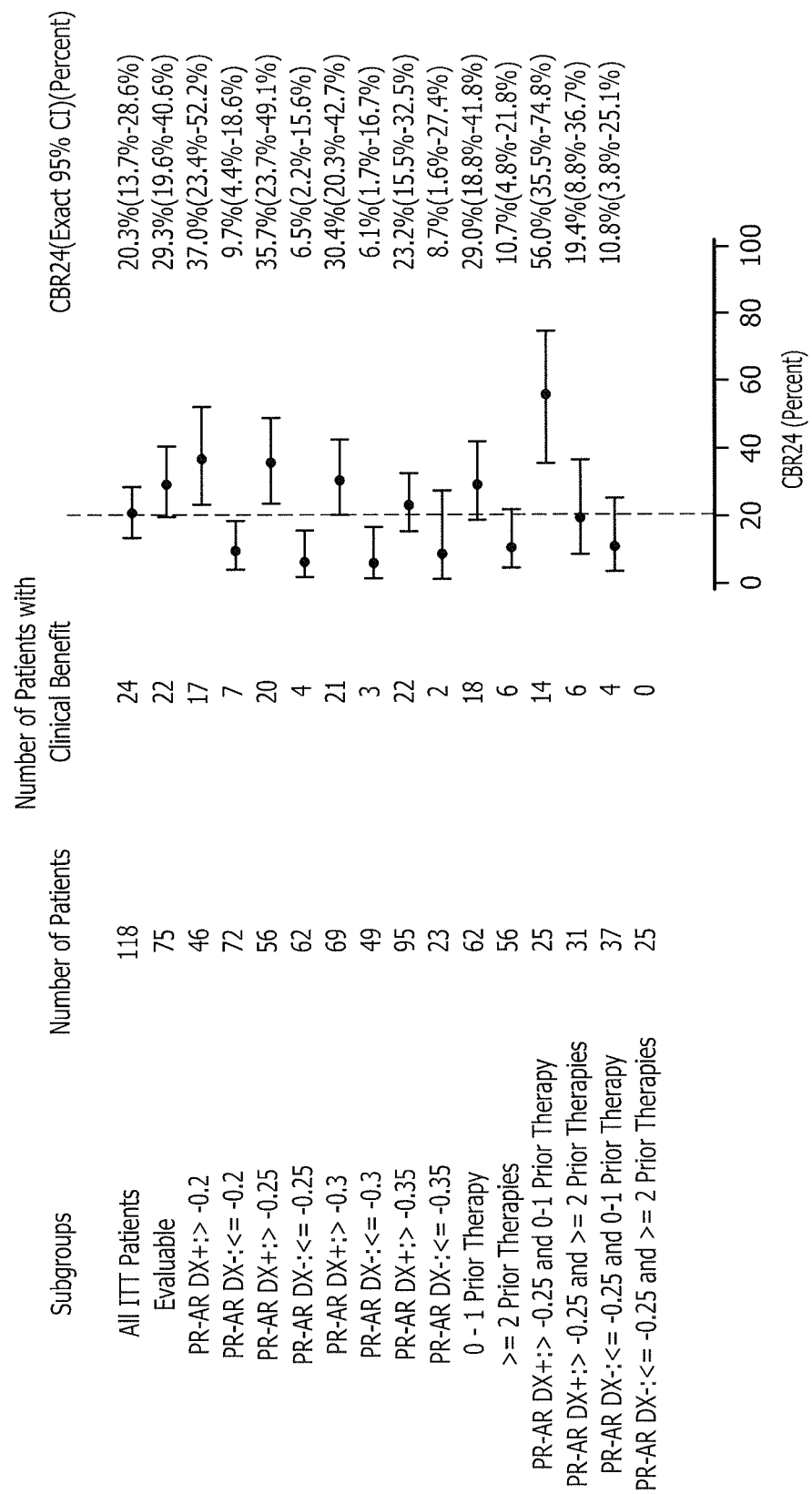

FIG. 15 comprises a representation of the response to enzalutamide of various patient subgroups treated with enzalutamide in the clinical trial. Response is shown in terms of Clinical Benefit Rate at ≥24 weeks (CBR24). The subgroups include Intent-To-Treat (ITT) patients; Evaluable Patients; patients whose breast tumor tissue was classified as a non-Basal like subtype by the PAM50 subtype classifier (PAM50 non-basal); patients whose tumors were classified as Basal-like subtype (PAM50 basal); and patients whose breast tumor tissue samples were analyzed to by applying the indicated cut-offs of >−0.2, >−0.25, >−0.3, and >−0.35 to the Weighted Basal and Luminal A classifier score. "PR-AR DX −" signifies patients whose samples did not meet the indicated threshold cut-off. "PR-AR DX +" signifies patients whose samples did meet the indicated threshold cut-off. Also shown are response data (applying a Weighted Basal and Luminal A classifier score cut-off of >−0.25) for samples from patients in the study receiving enzalutamide therapy after having received from zero to one prior therapies for treatment of TNBC with a drug other than an androgen receptor inhibitor ("and 0-1 prior therapy") or after having received two or more prior therapies for treatment of TNBC with a drug other than an androgen receptor inhibitor ("and >=2 prior therapies").

Figure 16:
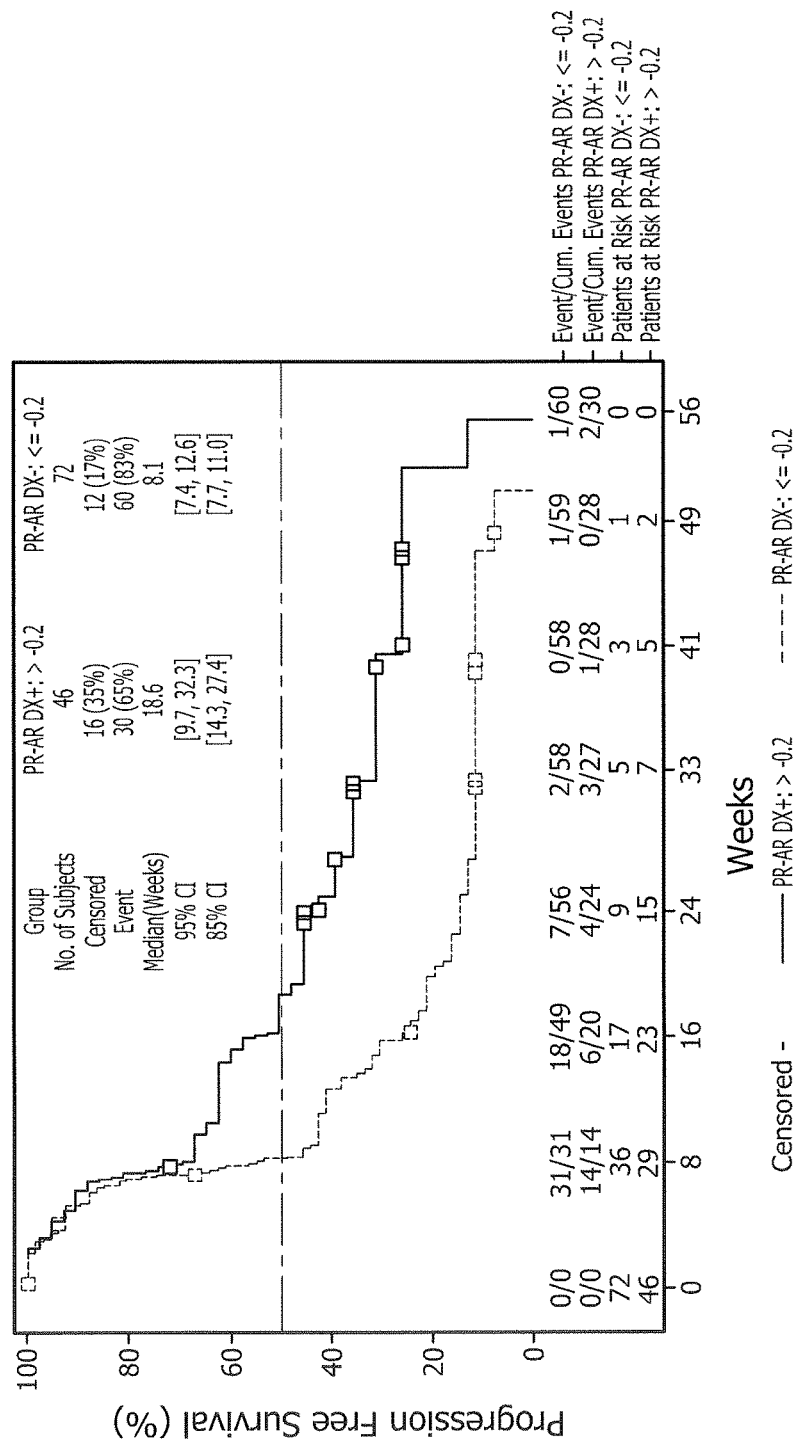

FIG. 16 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than −0.2 ("PR-AR DX+: >−0.2", top curve) versus a classifier score of less than or equal to −0.2 ("PR-AR DX−: <=−0.2", bottom curve).

Figure 17:
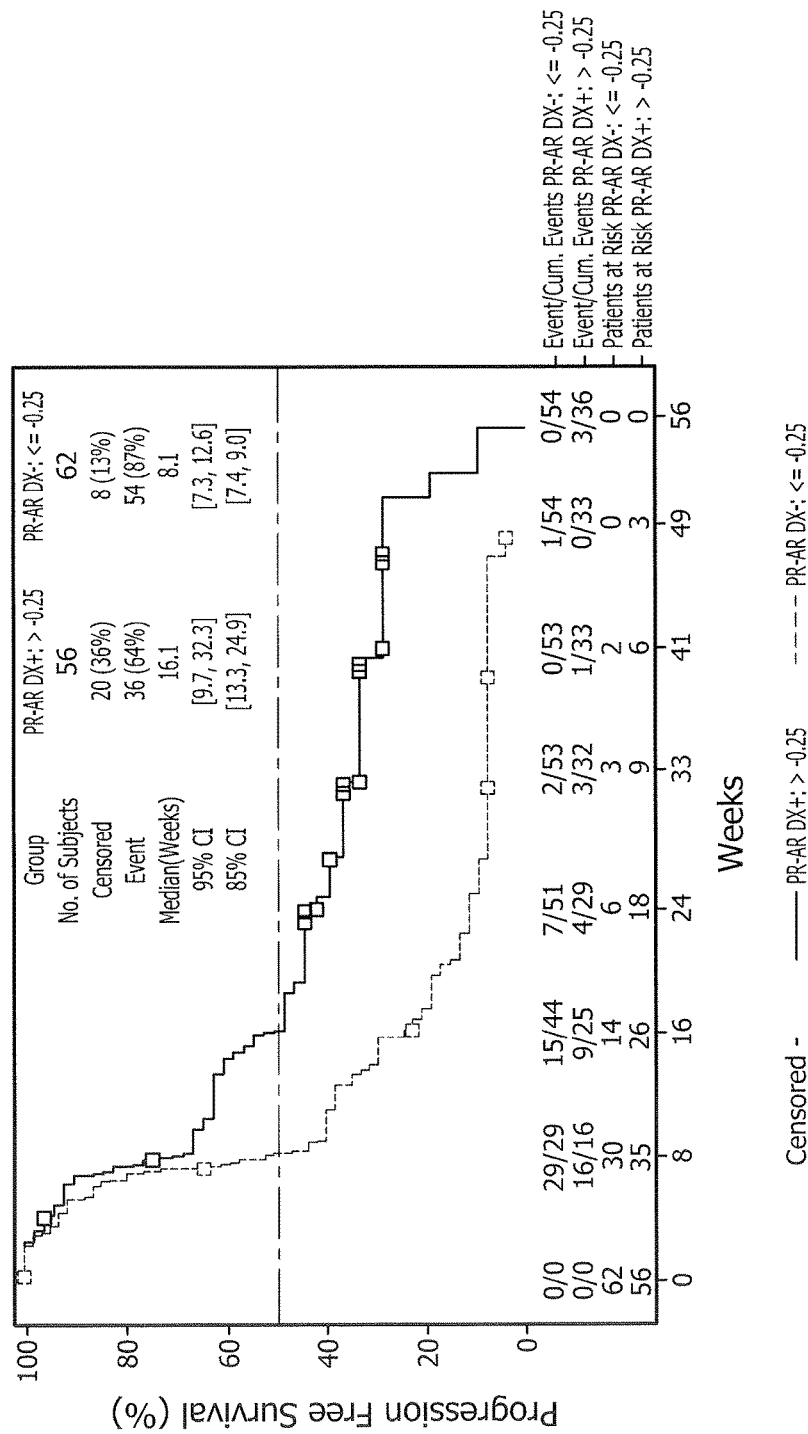

FIG. 17 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than −0.25 ("PR-AR DX+: >−0.25", top curve) versus a classifier score of less than or equal to −0.25 ("PR-AR DX−: <=−0.25", bottom curve).

Figure 18:
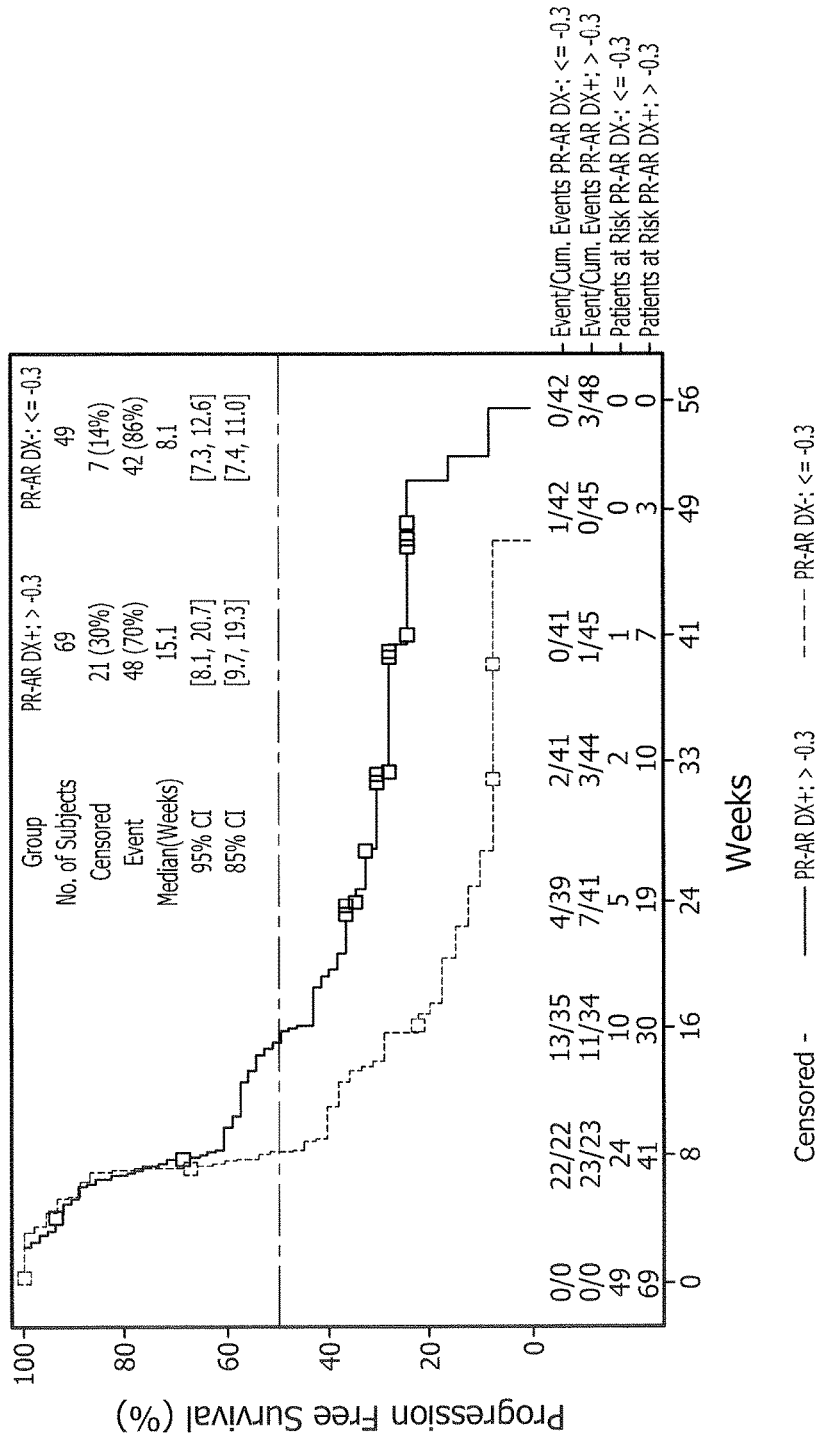

FIG. 18 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than −0.3 ("PR-AR DX+: >−0.3", top curve) versus a classifier score of less than or equal to −0.30 ("PR-AR DX−: <=−0.3", bottom curve).

Figure 19:
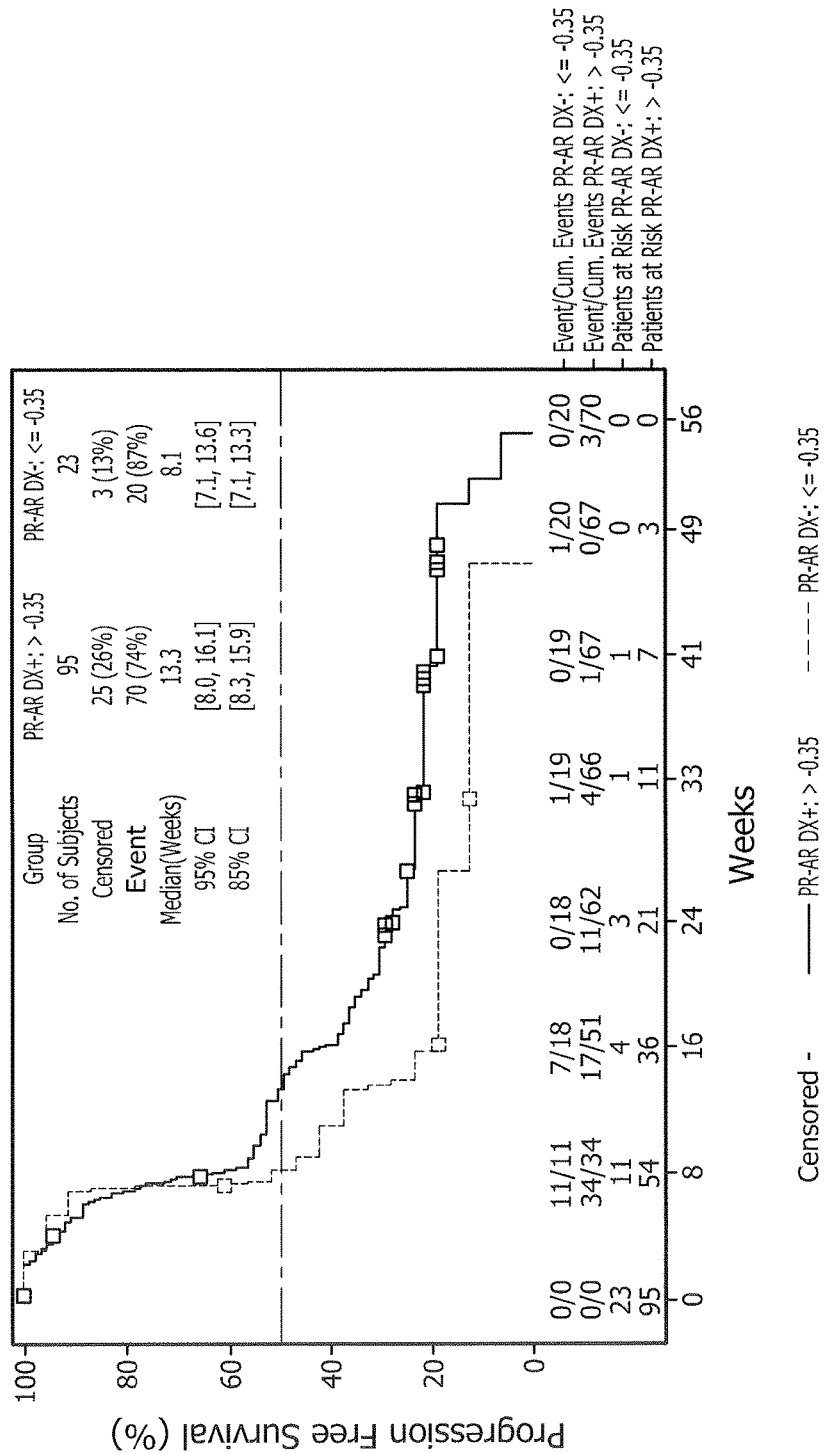

FIG. 19 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than −0.35 ("PR-AR DX+: >−0.35", top curve) versus a classifier score of less than or equal to −0.35 ("PR-AR DX−: <=−0.35", bottom curve).

Figure 20:
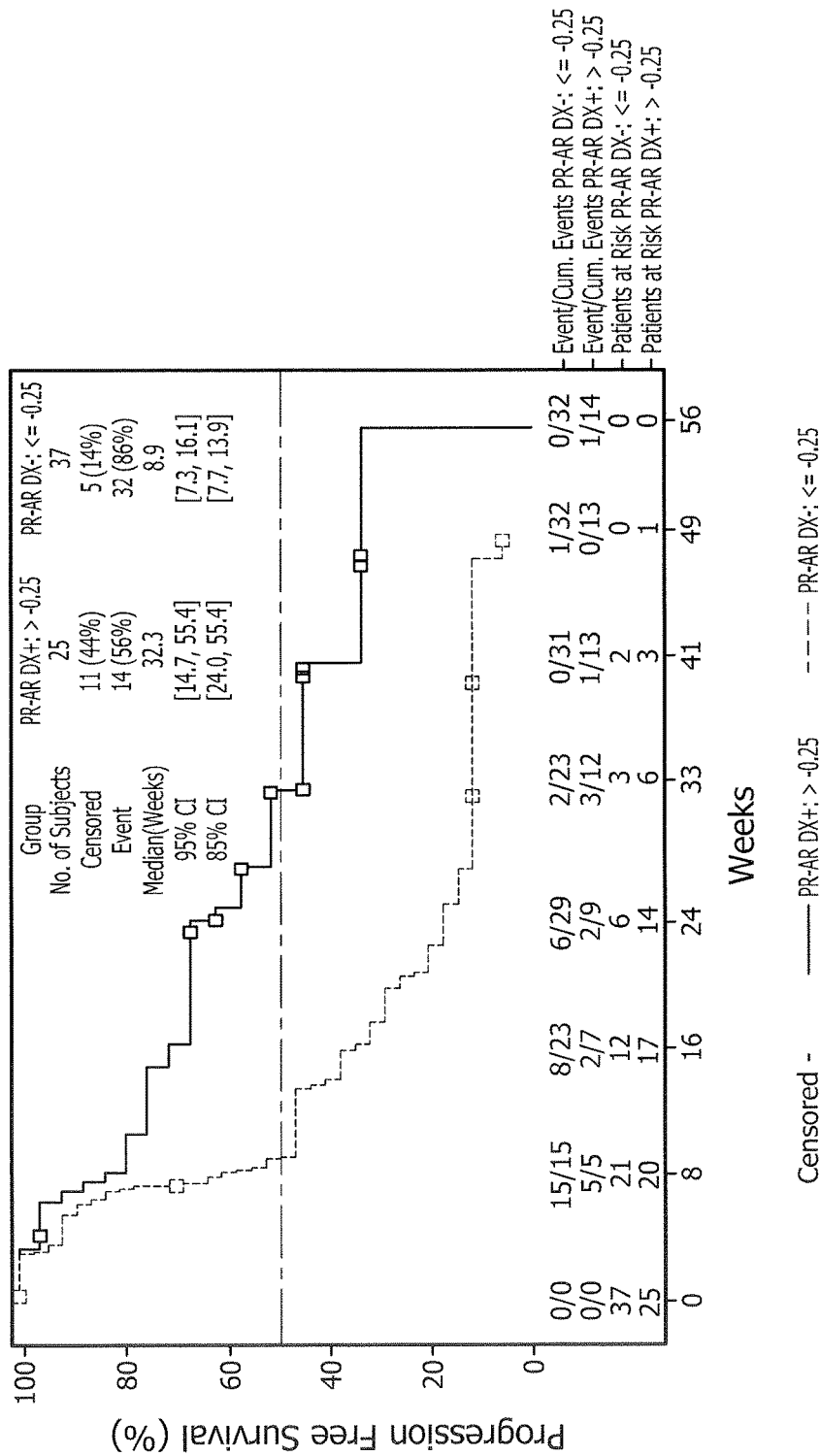

FIG. 20 is a Kaplan-Meier plot showing progression-free survival of patients treated with enzalutamide after receiving from zero to one prior therapies for treatment of TNBC with a drug other than an androgen receptor inhibitor. The curves correspond to patients that were identified as meeting the signature condition of a Weighted Basal and Luminal A classifier score of greater than −0.25 ("PR-AR DX+: >−0.25", top curve) versus a classifier score of less than or equal to −0.25 ("PR-AR DX−: <=−0.25", bottom curve).

Figure 21A:
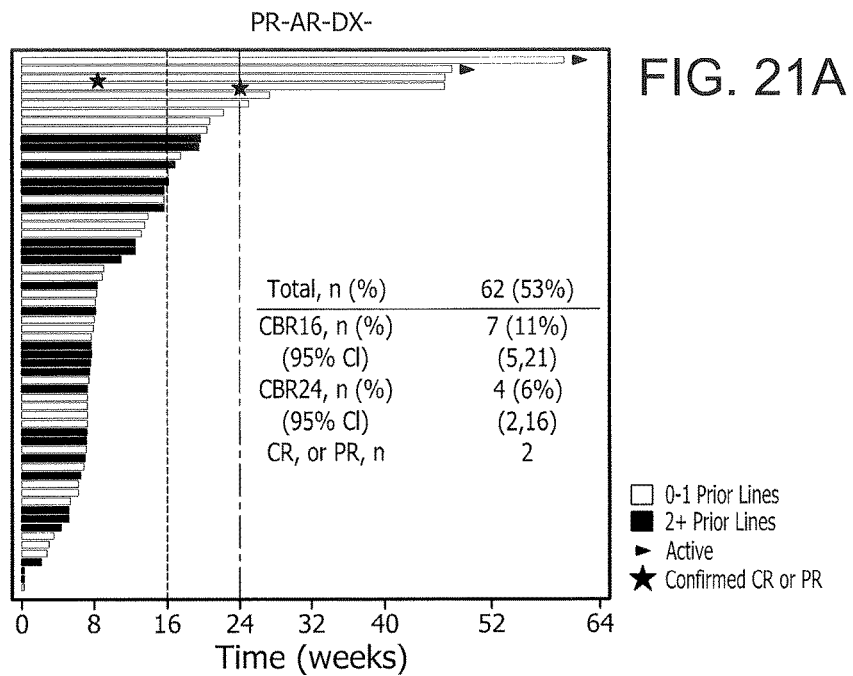
Figure 21B:
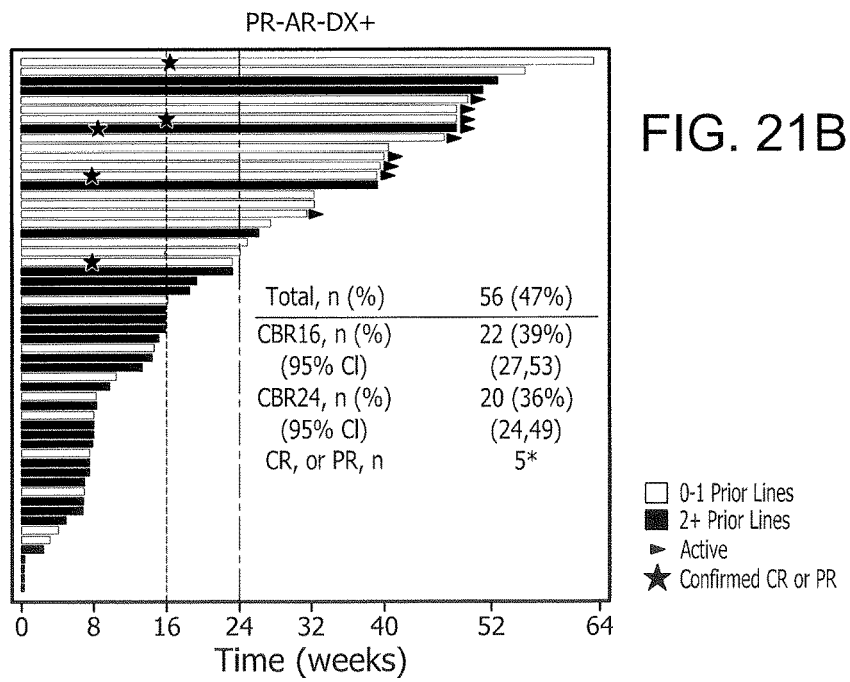

FIGS. 21A and 21B comprise graphs of the effect of the novel prognostic signature utilizing a Weighted Basal and Luminal A classifier score cut-off of >−0.25 as a predictor of response to AR inhibitor therapy in patients receiving zero or one (0-1 Prior Lines) or two or more (2+ Prior Lines) prior therapies for treatment of TNBC with a drug other than an androgen receptor inhibitor. The 56 patients of FIG. 21B were identified as meeting the signature condition of a Weighted Basal and Luminal A classifier score of greater than −0.25 The 62 study patients identified by a classifier score of less than or equal to −0.25 are identified in FIG. 21A. Each bar in the figures represents a single patient. Patient bars marked with a triangle ("Active") are active in the study. Patient bars marked with a star signify complete response (CR) or partial response (PR).

Figure 22A:
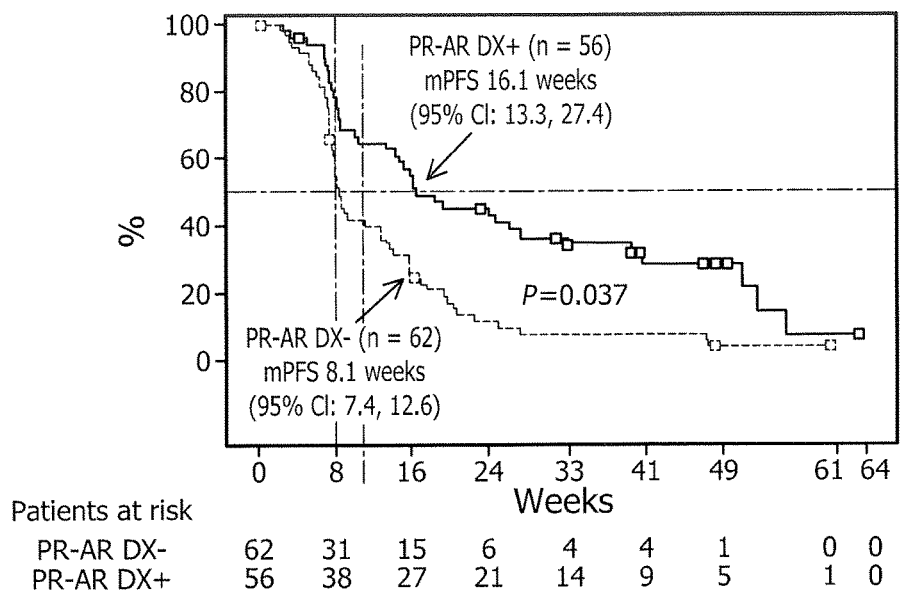
Figure 22B:
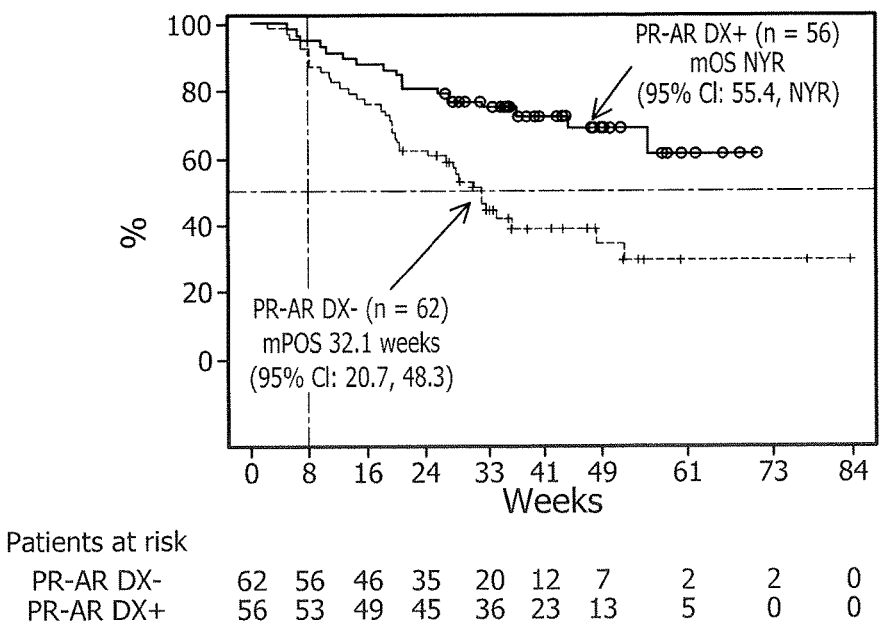

FIGS. 22A and 22B comprise Kaplan-Meier plots respectively showing median progression-free survival (FIG. 22A) (mPFS) and overall survival (mOS) of patients treated with enzalutamide as a function of time. The curves correspond to patients that were identified as meeting the signature condition of a Weighted Basal and Luminal A classifier score of greater than −0.25 ("PR-AR DX+", top curves) versus a classifier score of less than or equal to −0.25 ("PR-AR DX−", bottom curves). FIG. 22A: mPFS=16.1 weeks for patients meeting signature condition; mPFS=8.1 weeks for patients not meeting signature condition. FIG. 22B: mOS=NYR (not yet reached) at 84 weeks for patients meeting signature condition; mOS=32.1 weeks for patients not meeting signature condition.

Figure 23:
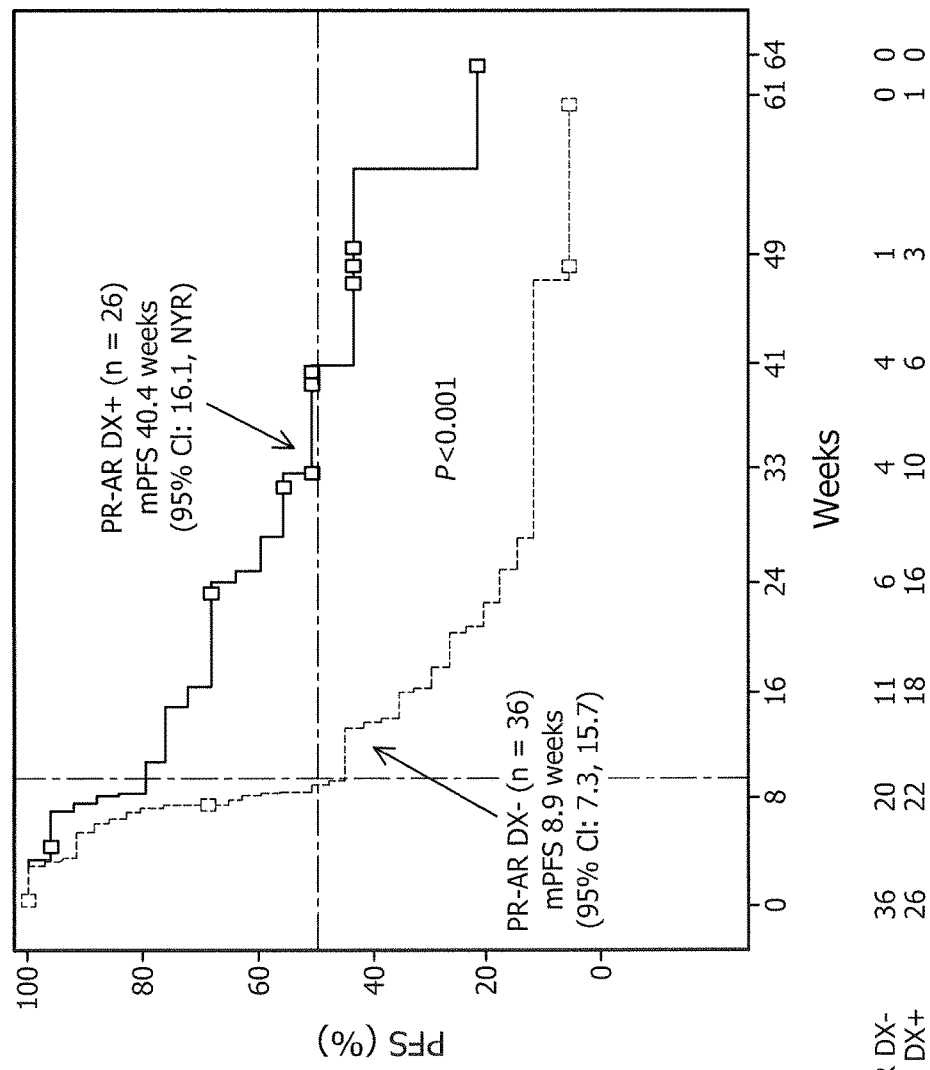

FIG. 23 is a Kaplan-Meier plot showing progression-free survival of patients treated with enzalutamide after receiving from zero to one prior therapies for treatment of TNBC with a drug other than an androgen receptor inhibitor. The curves correspond to patients that were identified as meeting the signature condition of a Weighted Basal and Luminal A classifier score of greater than −0.25 ("PR-AR DX+: >−0.25", top curve) versus a classifier score of less than or equal to −0.25 ("PR-AR DX−: <=−0.25", bottom curve). The data represents a continuation of the study of FIG. 20, taken beyond the 56 week interval of FIG. 20 to 64 weeks in FIG. 23. In FIG. 23, mPFS=40.4 weeks for patients meeting signature condition; mPFS=8.9 weeks for patients not meeting signature condition. "NYR" means "not yet reached" in the statement of the 95% confidence interval (CI) for the data represented by patients meeting the signature condition in FIG. 23.

Figure 24A:
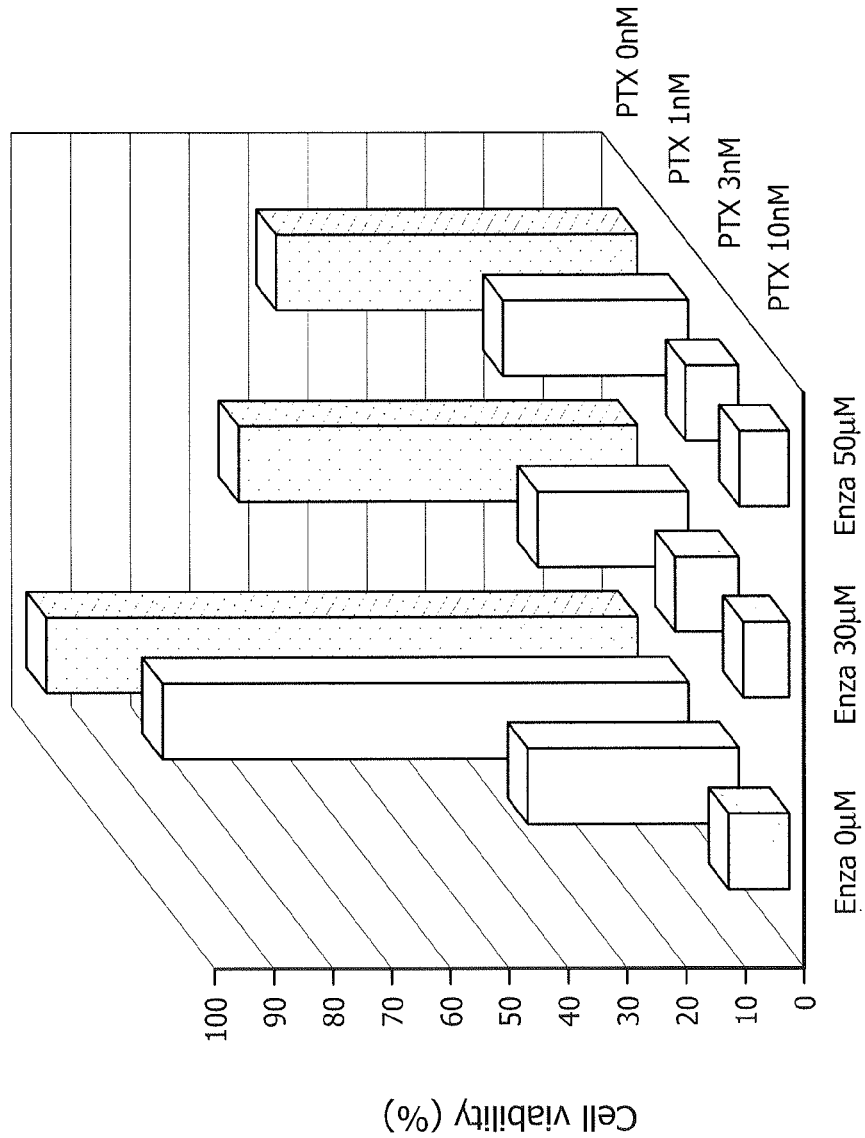
Figure 24B:
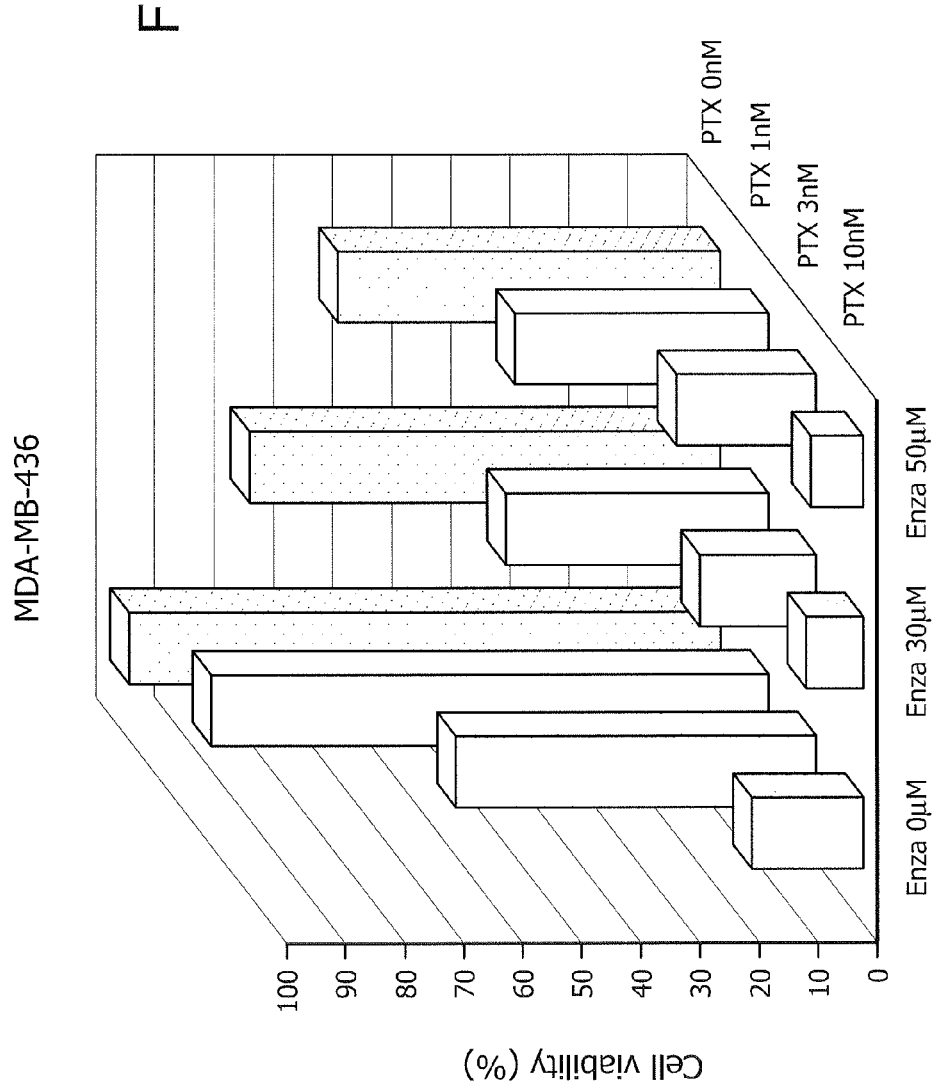
Figure 24C:
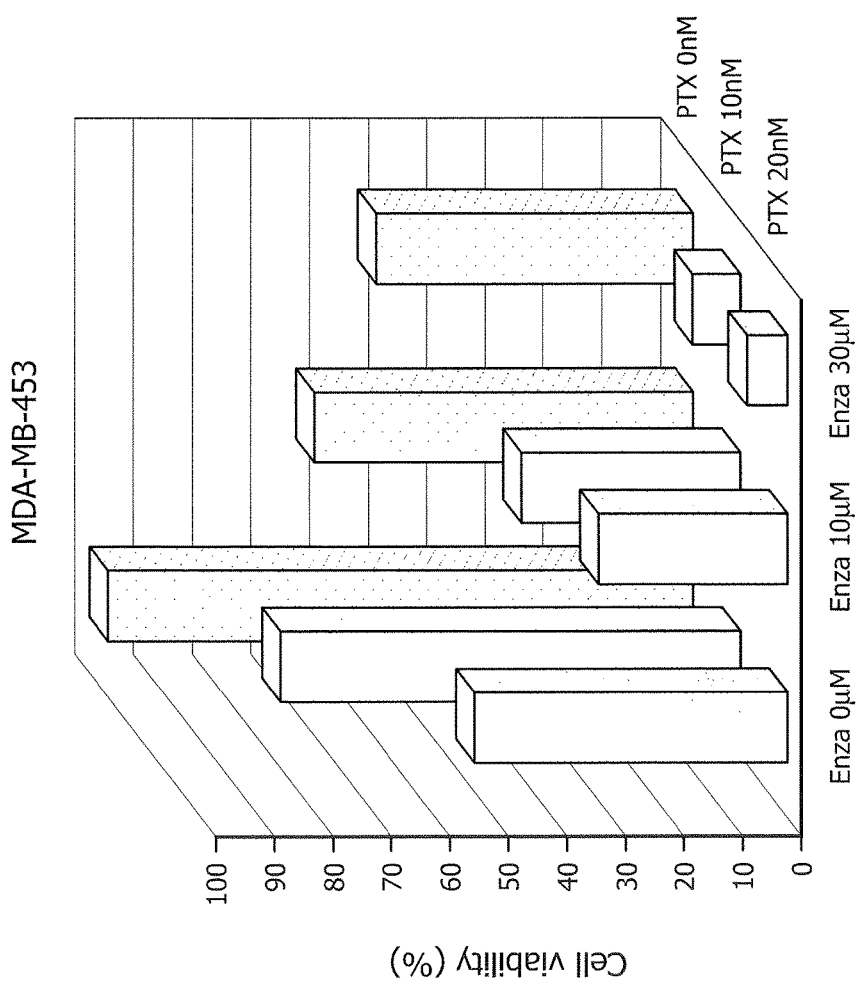

FIGS. 24A, 24B and 24C show the viability of TNBC cell lines BT549, MDA-MB-436 and MDA-MB-453, respectively, when treated with the indicated concentrations of enzalutamide (Enza), paclitaxel (PTX) or combinations thereof. Mean values are presented for each cell line (n=5).

Figure 25B:
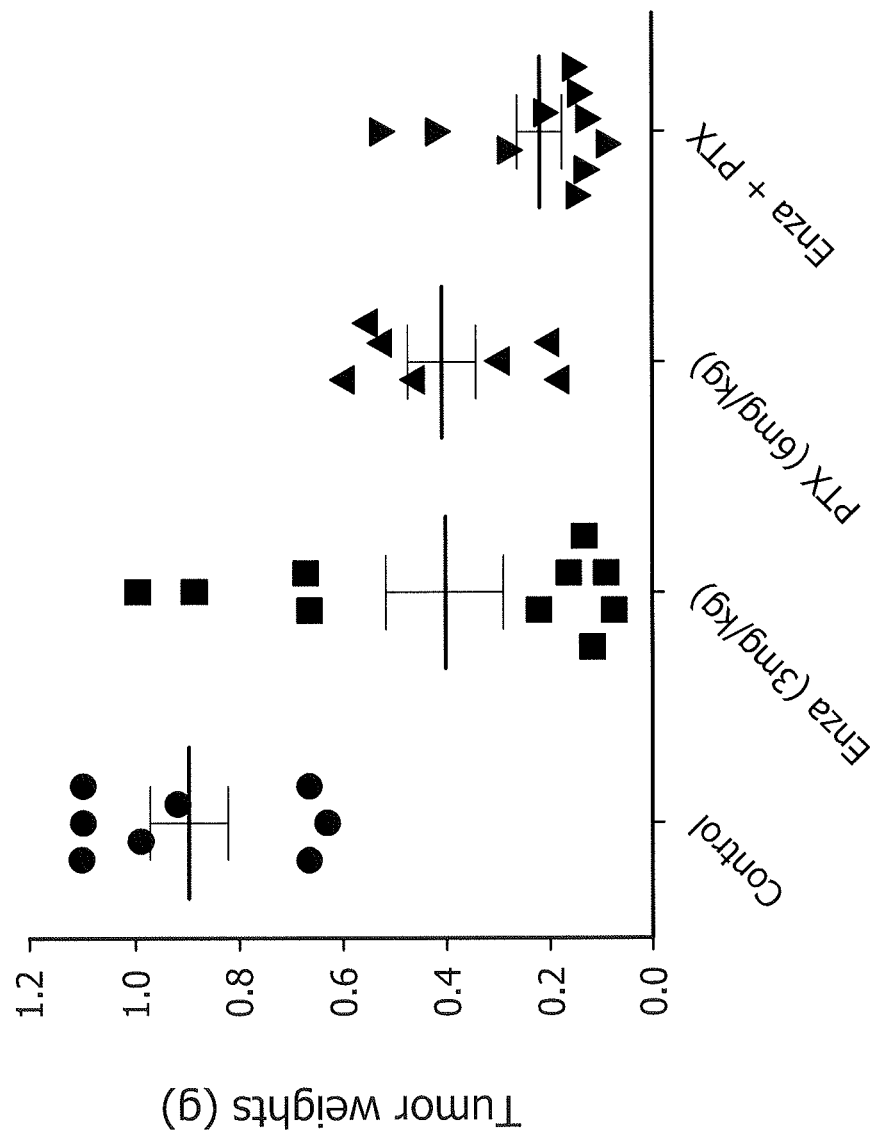

FIGS. 25A and 25B show the growth of tumors induced in NOD-SCID mice transplanted with cells of the TNBC cell line MDA-MB-453 following (i) oral gavage (PO) with enzalutamide (Enza) at 3 mg/kg/day (n=10), (ii) paclitaxel (PTX) at 6 mg/kg QMWF (IP) (n=7), or (iii) the combination of (i) and (ii) (n=10). Tumor volume was measured on the days indicated in FIG. 25A. Data points in FIG. 25A represent the average tumor volume for each group, and error bars reflect the SEM of the data. Tumor weights in FIG. 25B were determined at day 35.

DETAILED DESCRIPTION OF THE INVENTION

The present invention provides a method of treating TNBC in subjects afflicted with TNBC in which breast cancer cells of the TNBC-afflicted subject are characterized by a score derived from the expression by those cells of a certain set of intrinsic genes described more particularly below. The present invention also provides a method of assessing whether a TNBC treatment comprising an AR inhibitor is recommended (will likely be effective) for administration as a course of therapy for a patient afflicted with TNBC. Thus, the present invention provides in one embodiment a method of evaluating a treatment for triple negative breast cancer comprising the use of an androgen receptor inhibitor, the method comprising assaying a biological sample obtained from a subject to determine whether the biological sample obtained from the subject is classified as basal-like subtype or another subtype. If the biological sample is classified as other than a basal-like subtype, the breast cancer treatment comprising an androgen receptor inhibitor is more likely to be effective than if the sample were classified as basal-like subtype. Thus, the present invention provides in one embodiment a method of treating triple negative breast cancer in a subject having a cancer comprising breast cancer cells that have been previously classified as other than basal-like subtype. The method comprises administering a breast cancer treatment to the subject comprising an androgen receptor inhibitor, thereby treating the triple negative breast cancer in the subject.

The present invention further provides a method of treating TNBC by determining whether a TNBC patient should receive a treatment including AR inhibitor therapy, and then administering the optimal AR inhibitor treatment to the patient based on that determination. While the studies referenced herein were conducted on patient samples comprising tumor tissue staining positive by immunohistochemistry (IHC) for the AR receptor, the scope of the present invention is not so limited to the treatment and prognosis of AR(+) TNBC.

Studies of breast tumors based upon intrinsic gene analysis have identified five distinct subtypes of breast carcinomas: Luminal A (LumA), Luminal B (LumB), HER2-enriched (Her-2-E), Basal-like, and Normal-like (Perou et al. *Nature,* 406(6797):747-52 (2000); Sorlie et al. *PNAS,* 98(19):10869-74 (2001)). The HER2-enriched subtype may be referred to herein by "HER2", it being understood that the latter also means the HER2-enriched subtype. The Basal-like subtype may be referred to herein as "Basal", it being understood that the latter also means the Basal-like subtype. A breast cancer sample or cell is thus "classified" by assigning the cell or sample to an aforementioned subtype. A breast cancer sample or cell can also be considered "classified" in negative terms, i.e., a cell or sample may be classified as "non-Basal" or "other than Basal" upon determination that the cell or sample is of the LumA, LumB, HER2, or Normal-like sub-type.

We have unexpectedly found that the presence of the basal-like subtype is indicative of a likelihood of clinical non-response in TNBC to treatment with an AR inhibitor. We have found that a Basal Centroid classifier score of less than or equal to 0.9 is indicative of a likelihood of clinical response to an AR inhibitor. We have also unexpectedly found that an empirically determined weighted score based upon Basal-like and Luminal A subtype analysis conducted on biological samples from TNBC patients is indicative of a likelihood of clinical response to treatment with an AR inhibitor. Thus, in one embodiment, an assay is thus performed on a biological sample from a patient suffering from TNBC to determine the breast cancer subtype. In another embodiment, an assay is performed on a biological sample from a patient suffering from TNBC to determine the Basal Centroid classifier score, or both the Basal Centroid classifier score and the Luminal A classifier score.

The assay for determining whether the biological sample is classified as a subtype other than a basal-like subtype can comprise an assay for determining the presence of a basal-like subtype; a negative result indicates a non-basal subtype. Any assay capable of identifying the presence of a basal-like subtype may be utilized for this purpose. With approximately 70-90% of triple-negative carcinomas revealed to be basal-like breast carcinomas (Bertucci et al., *Int. J. Cancer* 2008, 123, 236-240; Wang et al., *Eur. J Clin. Invest.* 2008, 38, 438-446), the tripe negative phenotype has been used as a surrogate for the basal-like subtype. However, studies have shown that triple-negative and basal-like breast tumors are not synonymous. See, e.g., Choo and Nielsen, *Cancers* 2010, 2, 1040-1065. Thus, care must be exercised in selecting an assay for identifying the basal-like subtype.

Recently, an assay for basal-like subtype has been announced that relies on the following profile which has been found to be characteristic of the basal-like subtype: ER negative, HER2 negative, and cytokeratin 5/6 and/or HER1 positive. A panel of four antibodies (ER, HER1, HER2, and cytokeratin 5/6) has thus been proposed as an immunohistochemical profile for identifying breast basal-like tumors (Nielsen et al., *Clinical Cancer Research* 2014; 10:5367-5374).

The Basal-like and Luminal A subtype analysis is performed by means of a gene expression assay which utilizes expression of intrinsic genes as classifier genes for breast cancer classification. Intrinsic genes, as described in Perou et al. (2000) *Nature* 406:747-752, are statistically selected to have low variation in expression between biological sample replicates from the same individual and high variation in expression across samples from different individuals. The present invention utilizes the PAM50 gene expression assay (Parker et al. *J Clin Oncol.,* 27(8):1160-7 (2009) and U.S. Patent Application Publication No. 2011/0145176, both incorporated herein, by reference, in their entireties). The PAM50 gene expression assay can be used to identify intrinsic subtypes of breast cancer (Luminal A, Luminal B, HER2-enriched, Basal-like, and Normal-like) from standard biological samples, such as formalin fixed paraffin embedded tumor tissue. The PAM50 gene expression classifier is a supervised, centroid-based prediction method to classify breast cancers into one of the five aforesaid molecular subtypes using a 50-gene intrinsic gene signature.

As described in Parker et al. and in U.S. Patent Application Publication No. 2011/0145176, as well as in U.S. Patent application Publication No. 2013/0004482, the PAM50 gene expression assay method utilizes a supervised algorithm to classify subject samples according to breast cancer intrinsic subtype. This algorithm, referred to herein as the "PAM50 classification model" or "PAM50 classifier" is based on the gene expression profile of a defined subset of 50 intrinsic genes that has been identified for classifying breast cancer intrinsic subtypes. The subset of genes, along with primers specific for their detection, is provided in Table 1 of U.S. Patent Application Publication No. 2013/0004482 and reproduced below as Table 1 of this disclosure. Select sequences of the same 50 intrinsic genes are set forth in Table 2 below. The entire disclosure of Publication No. 2013/0004482, is incorporated herein by reference.

The detection and estimation of the expression of the set of 50 subtype predictor genes of Table 1 is performed by any suitable means.

The PAM50 gene expression classifier operates by using a supervised prediction algorithm developed based on the profiles of objectively-selected prototype samples for "training" the algorithm. The samples are selected and subtyped using an expanded intrinsic gene set according to the methods disclosed in U.S. Patent Publication No. 2009/0299640, the entire disclosure of which is incorporated herein by reference. After stratifying the training samples according to subtype, a centroid-based prediction algorithm is used to construct centroids for each molecular subtype based on the expression profile of the intrinsic gene set described in Table 1. The centroid is the average gene expression for each gene in each subtype (or "class") divided by the within-class standard deviation for that gene. Nearest centroid classification takes the gene expression profile of a new sample, and compares it to each of these class centroids. Subtype prediction is done by calculating the Spearman's rank correlation of each test case to the five centroids of the PAM50 subtypes, and assigning a sample to a subtype based on the nearest centroid.

According to one embodiment, which does not necessarily involve assigning the patient sample to a PAM50 subtype, the Spearman rank correlation to the basal-like gene expression centroid is determined. The Spearman rank correlation between the sample and the basal-like centroid is assigned as the "Basal Centroid classifier score". The Spearman rank correlation to the Luminal A gene expression centroid is determined. The Spearman rank correlation between the sample and the Luminal A centroid is assigned as the "Luminal A Centroid classifier score". Methods for utilizing the PAM50-based signature to provide a Basal Centroid classifier score and a Luminal A Centroid classifier score are known to those skilled in the art. See, for example, U.S. Patent Application Publication No. 2009/0299640; Parker et al., J Clin. Oncol., 27(8): 1160-7 (2009); U. S. Patent Application Publication No. 2011/0145176. Also see, for example, Prat et al., *British Journal of Cancer,* (2014) 111, 1532-1541, incorporated herein by reference.

We have found, as demonstrated by the clinical trial of TNBC patients treated with the AR inhibitor enzalutamide, that a Basal Centroid classifier score of less than or equal to 0.9 is indicative of a likelihood of clinical response to an AR inhibitor. In some embodiments, a Basal Centroid classifier scores of less than or equal to 0.9, from 0.2 to 0.8, from 0.4 to 0.7 are used to predict the likelihood of clinical response to an AR inhibitor. In one embodiment, a Basal Centroid classifier score of less than or equal to 0.6 is used to predict the likelihood of clinical response to an AR inhibitor.

We have further found that the Basal Centroid classifier score and Luminal A Centroid classifier score, when combined subject to certain empirically defined weighting factors, provides a score ("Weighted Basal and Luminal A classifier score") that can be used to further predict responsiveness to androgen receptor inhibitor therapy in an individual TNBC patient. The Weighted Basal and Luminal A classifier score is determined from the following equation:

Weighted Basal and Luminal A classifier score=
 −0.25(Basal Centroid classifier score)+0.27(Luminal A Centroid classifier score).

In some embodiments, the equation for determining the Weighted Basal and Luminal A classifier score takes the form:

Weighted Basal and Luminal A classifier score=
 −0.2468275(Basal Centroid classifier score)+
 0.2667110(Luminal A Centroid classifier score).

As demonstrated by the clinical trial of TNBC patients treated with the AR inhibitor enzalutamide, if the Weighted Basal and Luminal A classifier score is greater than −0.3, the patient is identified as one likely responsive to AR inhibitor therapy. Alternatively, if the Weighted Basal and Luminal A classifier score is greater than −0.2, the patient may also be identified as one likely responsive to AR inhibitor therapy. Increased accuracy is obtained by selecting −0.25 as the cut-off for predicting responsiveness to AR inhibitor therapy. Thus, in a preferred embodiment, if the Weighted Basal and Luminal A classifier score is greater than −0.25, the patient is identified as one likely responsive to AR inhibitor therapy. If the TNBC patient is identified through determination of the Weighted Basal and Luminal A classifier score as one who is likely responsive to AR inhibitor therapy for TNBC, an appropriate AR inhibitor therapy may then be administered to treat the TNBC condition in the patient.

The utility of the Weighted Basal and Luminal A classifier score for predicting patient response to AR inhibitor therapy is illustrated in FIGS. 14A-14D and FIG. 15. The figures comprise a representation of the response to enzalutamide of various TNBC patient subgroups treated with enzalutamide in the clinical trial. Patient responsiveness to enzalutamide therapy was correlated with Weighted Basal and Luminal A classifier score, applying a series of cut-offs of >−0.2 (FIG. 14A), >−0.25 (FIG. 14B), >−0.3 (FIG. 14C), and >−0.35 (FIG. 14D) to the Weighted Basal and Luminal A classifier score. "Diagnostic −" in FIGS. 14A-D and "PR-AR DX −" in FIG. 15 signify patients whose samples did not meet the indicated Weighted Basal and Luminal A classifier score threshold cut-off. "Diagnostic +" in FIGS. 14A-14D and "PR-AR DX +" in FIG. 15 signify patients whose samples did meet the indicated threshold cut-off. As is apparent from a consideration of the data, a Weighted Basal and Luminal A classifier score of greater than −0.25 provided the highest level of accuracy in predicting TNBC patient responsiveness to enzalutamide therapy, with the criteria of greater than −0.2, or greater than −0.3, also providing acceptable results.

The correlation between patient response and Weighted Basal and Luminal A classifier score is further illustrated in the Kaplan-Meier plot of FIGS. 16-19, showing progression-free survival of TNBC patients treated with enzalutamide, as a function of time to 56 weeks. The curves in FIG. 16 correspond to patients that were identified as meeting the signature condition of a Weighted Basal and Luminal A classifier score of greater than −0.2 ("PR-AR DX+: >−0.2", top curve) versus a classifier score of less than or equal to −0.2 ("PR-AR DX−: <=−0.2", bottom curve). FIGS. 17, 18 and 19 are similar to FIG. 16, where the signature conditions of greater than −0.25 (FIG. 17), greater than −0.3 (FIG. 18) and greater than −0.35 (FIG. 19) were imposed. It may be appreciated that the magnitude of the vertical separation between the respective curves on each individual plot is a measure of the accuracy of correlation between patient Weighted Basal and Luminal A classifier score and progression-free survival. On this basis, it may be further appreciated from a comparison of FIGS. 16-19 that applying the criterion of a Weighted Basal and Luminal A classifier score greater than −0.25 (FIG. 17) provides the most accuracy in correlating Weighted Basal and Luminal A classifier score to TNBC patient responsiveness to enzalutamide therapy, with the criteria of greater than −0.2 (FIG. 16) or greater than −0.3 (FIG. 18) also provided acceptable results.

It was also found that the novel Weighted Basal and Luminal A classifier score as a predictor of responsiveness to AR inhibitor therapy for TNBC achieves even greater accuracy in patients who have either received no prior TNBC therapy, or have received no more than one round of prior TNBC therapy. As may be appreciated from a comparison of FIG. 20 and FIG. 17, imposing the criterion of a Weighted Basal and Luminal A classifier score of greater than −0.25 in the zero to 1 prior therapy patient group (FIG. 20), versus the larger group of all trial patients (FIG. 17), resulted in increased accuracy in identifying patients responsive to enzalutamide therapy, as evidenced by the greater vertical separation between the curves in FIG. 20, versus the vertical separation of the curves in FIG. 17. The trend is further observed in FIG. 23, in which the progression-free survival time in the study subjects of FIG. 20 is shown beyond the 56 weeks in FIG. 20, to 64 weeks in FIG. 23.

This result is also illustrated in FIGS. 21A and 21B, showing the extent of time on treatment without progression of disease (progression-free survival) for 56 patients that were identified as meeting the signature condition of a Weighted Basal and Luminal A classifier score of greater than −0.25 (FIG. 21B) versus 62 patients identified by a classifier score of less than or equal to −0.25 (FIG. 21A). Each bar represents a patient. Patients received either zero or one prior TNBC therapy before enzalutamide treatment (0-1 Prior Lines) with a drug other than an androgen receptor inhibitor, or two or more prior therapies (2+ Prior Lines) with a drug other than an androgen receptor inhibitor. Patient bars marked with a triangle ("Active") are active in the study. Patient bars marked with a star signify complete response (CR) or partial response (PR). The best time on treatment without disease progression is apparent in responder patients who received one or no prior lines of therapy (FIG. 21B).

The correlation between patient response and Weighted Basal and Luminal A classifier score is further illustrated in the Kaplan-Meier plots of FIGS. 22A and 22B, comparing the endpoints of median progression-free survival (mPFS) (FIG. 22A) and median overall survival (mOS) (FIG. 22B) of study patients. The curves in FIGS. 22A and 22B correspond to patients that were identified as meeting the signature condition of a Weighted Basal and Luminal A classifier score of greater than −0.25 ("PR-AR DX+", top curves)

versus a classifier score of less than or equal to −0.25 ("PR-AR DX−", bottom curves). The results thus show that the Weighted Basal and Luminal A classifier of greater than −0.25 score correlates with overall survival, in addition to progression-free survival. The patients not meeting the prognostic signature condition were characterized by a median progression-free survival of 8.1 weeks and median overall survival of 32.1 weeks. In contrast, patients meeting the prognostic signature condition were characterized by a median progression-free survival of 16.1 weeks and median overall survival not yet reached (mOS NYR) at 84 weeks.

Gene Expression Detection

As the first step in determining the Basal Centroid Classifier Score or Weighted Basal and Luminal A classifier score of a TNBC patient, gene expression detection of the genes of the intrinsic gene set of Table 1 is carried out on patient samples by any method for determining the quantity or presence of an RNA transcript or its expression product of an intrinsic gene. Such methods are described in U.S. Patent Application Publication Nos. 2009/0299640 and 2013/0004482, incorporated herein by reference. They include, for example means, methods based on hybridization analysis of polynucleotides, methods based on sequencing of polynucleotides, immunohistochemistry methods, and proteomics-based methods. The methods generally detect expression products (e.g., mRNA) of the intrinsic genes listed in Table 1.

RNA sequencing as a method for assaying gene expression may be utilized in one embodiment. The assay for gene expression of the intrinsic gene set can also be performed by other technologies used to evaluate gene expression/quantification, including but not limited to real-time PCR, microarrays, microfluidic gene expression, and targeted gene sequencing. Such methods include, for example, hybridization analysis of polynucleotides, methods based on sequencing of polynucleotides, immunohistochemistry methods, and proteomics-based methods. PCR-based methods, such as reverse transcription PCR (RT-PCR) (Weis et al., *TIG* 8:263-64, 1992), and array-based methods such as microarray (Schena et al., *Science* 270:467-70, 1995) may be used.

General methods for RNA extraction are well known in the art and are disclosed in standard textbooks of molecular biology, including Ausubel et al., ed., *Current Protocols in Molecular Biology*, John Wiley & Sons, New York 1987-1999. Methods for RNA extraction from paraffin embedded tissues are disclosed, for example, in Rupp and Locker, *Lab Invest.* 56:A67, (1987); and De Andres et al., *Biotechniques* 18:42-44, (1995). Isolated RNA can be used in hybridization or amplification assays that include, but are not limited to, PCR analyses and probe arrays. Intrinsic gene expression product level determination in a sample may also involve nucleic acid amplification, for example, by RT-PCR (U.S. Pat. No. 4,683,202), ligase chain reaction, self-sustained sequence replication, transcriptional amplification, rolling circle replication, and other methods utilizing nucleic acid amplification method, followed by the detection of the amplified molecules using techniques well known to those of skill in the art.

Microarrays may be used for expression profiling. Each array includes a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316. High-density oligonucleotide arrays are particularly useful for determining the gene expression profile for a large number of RNAs in a sample.

Total RNA for analysis of the intrinsic gene set may be isolated from a biological sample, such as a tumor. If the source of RNA is a primary tumor, RNA (e.g., mRNA) can be extracted, for example, from frozen or archived paraffin-embedded and fixed (e.g., formalin-fixed) tissue samples (e.g., pathologist-guided tissue core samples).

Gene Analysis and Data Processing

Patient sample gene expression data from the intrinsic gene set may be pre-processed by known techniques to achieve sequence data alignment, data normalization and mean centering of data, for example. Methods of normalization include, for example, (i) global normalization that uses all genes on the array; (ii) housekeeping genes normalization that uses constantly expressed housekeeping/invariant genes; and (iii) internal controls normalization that uses known amount of exogenous control genes added during hybridization (Quackenbush *Nat. Genet.* 32 (Suppl.), 496-501 (2002)). Gene count estimates can also be normalized to a fixed quartile, such as a fixed upper quartile. The resulting normalized gene expression estimates may then be adjusted such that the median expression value of each gene is equivalent to the median of a known subset, such as a gene subset from TNBC patients.

According to one embodiment, patient sample expression data for processing by the PAM50 classifier is first pre-processed by alignment and data centering techniques. RNA-sequence data is first aligned to Human (*Homo sapiens*) genome sequence hg19 (https://genome.ucsc.edu/cgi-bin/hgGateway?db=hg19) (http://www.ncbi.nlm.nih.gov/assembly/GCF_000001405.25/) using, for example, MapSplice (Nucleic Acids Res. 2010 October; 38(18):e178. doi: 10.1093/nar/gkq622). Gene and isoform level counts may be estimated, for example, using RNA-Seq by Expectation-Maximization (RSEM) (deweylab.biostat.wisc.edu/rsem/). Gene count estimates are normalized to a fixed upper quartile. The resulting normalized gene expression estimates may then be adjusted such that the median expression value of each gene is equivalent to the median of the triple negative subset of the TCGA RNA-seq data reported in "Comprehensive Molecular Portraits of Human Breast Tumors", *The Cancer Genome Atlas Network, Nature* 490, 61-70 (Oct. 4, 2012) (www.nature.com/nature/journal/v490/n7418/full/nature11412.html.

Following pre-processing, the patient sample expression data from the PAM50 gene array is processed according to the known techniques for processing intrinsic gene set data. Complete instructions for processing of patient sample gene expression data from the PAM50 intrinsic gene set is described in detail in at least the following, and will not be detailed herein except by way of summary: Parker et al. J Clin Oncol., 27(8): 1160-7 (2009); U.S. Patent Application Publication No. 2011/0145176; and U.S. Patent Application Publication No. 2013/0004482. (U.S. Patent Application Publication No. 2013/0004482 describes the application of the PAM50 classifier for screening breast cancer subjects' possible responsiveness to anthracycline therapy relying on, inter alia, classification of the patient tumor into the HER2 subtype by the PAM50 classifier.) The Spearman rank correlation to the basal-like gene expression centroid is determined. The Spearman rank correlation between the sample and the basal-like centroid is assigned as the Basal Centroid classifier score. The Spearman rank correlation to the Luminal A gene expression centroid is determined. The Spearman rank correlation between the sample and the Luminal A centroid is assigned as the Luminal A Centroid classifier score. The Basal Centroid classifier score and Luminal A Centroid classifier score so determined are then inserted into the equation, Weighted Basal and Luminal A classifier score=
  −0.25(Basal Centroid classifier score)+0.27(Luminal A Centroid classifier score)

to provide the Weighted Basal and Luminal A classifier score for the patient sample.

Samples

Samples for analysis of intrinsic subtype classification may comprise a biological sample comprising a cancer cell or tissue, such as a breast tissue sample or a primary breast tumor tissue sample. In some embodiments, the biological sample comprises breast tissue or cells. By "biological sample" is intended any sampling of cells, tissues, or bodily fluids in which expression of an intrinsic gene can be detected. Examples of such biological samples include, but are not limited to, biopsies and smears. Bodily fluids useful in the present disclosure include blood, lymph, urine, saliva, nipple aspirates, fluid from ductal lavage, gynecological fluids, or any other bodily secretion or derivative thereof. Blood can include whole blood, plasma, serum, or any derivative of blood. In some embodiments, the biological sample includes breast cells, and may particularly comprise breast tissue from a biopsy, such as a breast tumor tissue sample. Biological samples may be obtained from a subject by a variety of techniques including, for example, by scraping or swabbing an area, by using a needle to aspirate cells or bodily fluids, or by removing a tissue sample (i.e., biopsy). Methods for collecting various biological samples are well known in the art. In some embodiments, a breast tissue sample is obtained by, for example, fine needle aspiration biopsy, core needle biopsy, or excisional biopsy. In another embodiment, fluid is obtained by ductal lavage. A thin catheter is inserted into the natural opening of the milk duct. A saline solution is then infused through the catheter to rinse the duct, which loosens cells from the duct lining. The solution containing the loosened cells is withdrawn through the catheter and biopsied. Fixative and staining solutions may be applied to the cells or tissues for preserving the specimen and for facilitating examination. In one embodiment, the biological sample is a formalin-fixed, paraffin-embedded breast tissue sample, particularly a primary breast tumor sample. In various embodiments, the tissue sample is obtained from a pathologist-guided tissue core sample.

Therapeutic Agents

Androgen receptor inhibitors directly or indirectly inhibit the androgen receptor (AR) signaling pathway. In one embodiment, direct inhibitors of the AR receptor include enzalutamide, bicalutamide (Casodex), flutamide, nilutamide, ARN509, and the like. In another embodiment, indirect inhibitors of AR include Cyp 17 inhibitors such as ketoconazole, abiraterone acetate, VN/124-1 (TOK-001), orteronel (TAK-700) and the like. In another embodiment, AR inhibitors include finasteride, galeterone, cyproterone acetate, and andarine, and the like. The antigen receptor inhibitor may result in complete or partial inhibition of the biological activity of the androgen receptor.

In a preferred embodiment, the AR inhibitor is enzalutamide (Xtandi®), which has the systematic (IUPAC) name 4-(3-(4-cyano-3-(trifluoromethyl)phenyl)-5,5-dimethyl-4-oxo-2-thioxoimidazolidin-1-yl)-2-fluoro-N-methylbenzamide, directly binds the androgen receptor (AR) and has three sites of activity. It inhibits binding of androgens to AR, inhibits nuclear translocation of AR, and inhibits AR-mediated DNA binding.

In certain embodiments, the breast cancer treatment comprising an androgen receptor inhibitor further comprises one or more other anti-cancer agents that is not an androgen receptor inhibitor. Such non-AR inhibitor anticancer agents that may also be administered to patients in conjunction with AR inhibitor therapy include, for example, cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserelin, goserelin, megestrol acetate, risedronate, pamidronate, ibandronate, alendronate, denosumab, zoledronate, trastuzumab, tykerb or bevacizumab, or combinations thereof.

In one embodiment, the non-AR inhibitor anticancer agent is paclitaxel. In one embodiment, the AR inhibitor is enzalutamide and the non-AR inhibitor anticancer agent is paclitaxel. As described hereinafter, it has been found that the combination of enzalutamide and paclitaxel results in enhanced cytotoxicity in tumor cells that are positive for the prognostic marker consisting of a Weighted Basal and Luminal A classifier score of greater than −0.25.

A therapeutically effective amount of one or more AR inhibitors is administered to the subject according to the present invention, to treat TNBC utilizing dosing and treatment regimens that are typically employed when administering AR inhibitors in the treatment of cancer. The AR inhibitor can be administered in the breast cancer treatments described herein, by the routes by which such agents are typically administered. A representative regimen for one such AR inhibitor, enzalutamide, is 160 mg/day orally, once daily. The dosage form may comprise, for example, a capsule. The daily dose may be administered, for example, in the form of a capsule comprising 160 mg enzalutamide. In another embodiment, four capsules, each comprising 40 mg enzalutamide, are administered. Lower or higher doses may be utilized. The non-AR inhibitor agents are administered according to well-known dosages and treatment regimens for such agents as used in the treatment of breast cancer.

TABLE 1

PAM50 Intrinsic Gene List

| Gene | Genbank Accession No. | Forward Primer | SEQ ID NO: | Reverse Primer | SEQ ID NO: |
|---|---|---|---|---|---|
| ACTR3B | NM_020445 NM_001040135 | AAAGATTCCTG GGACCTGA | 1 | TGGGGCAGTTC TGTATTACTTC | 51 |
| ANLN | NM_018685 | ACAGCCACTTTC AGAAGCAAG | 2 | CGATGGTTTTG TACAAGATTTC TC | 52 |
| BAG1 | NM_004323 | CTGGAAGAGTT GAATAAAGAGC | 3 | GCAAATCCTTG GGCAGA | 53 |
| BCL2 | NM_000633 | TACCTGAACCG GCACCTG | 4 | GCCGTACAGTT CCACAAAGG | 54 |
| BIRC5 | NM_001012271 | GCACAAAGCCA TTCTAAGTC | 5 | GACGCTTCCTA TCACTCTATTC | 55 |

TABLE 1-continued

PAM50 Intrinsic Gene List

| Gene | Genbank Accession No. | Forward Primer | SEQ ID NO: | Reverse Primer | SEQ ID NO: |
|---|---|---|---|---|---|
| BKVRA | BX647539 | GCTGGCTGAGCAGAAAG | 6 | TTCCTCCATCAAGAGTTCAACA | 56 |
| CCNB1 | NM_031966 | CTTTCGCCTGAGCCTATTT | 7 | GGGCACATCCAGATGTTT | 57 |
| CCNE1 | BC035498 | GGCCAAAATCGACAGGAC | 8 | GGGTCTGCACAGACTGCAT | 58 |
| CDC20 | BG256659 | CTGTCTGAGTGCCGTGGAT | 9 | TCCTTGTAATGGGGAGACCA | 59 |
| CDC6 | NM_001254 | GTAAATCACCTTCTGAGCCT | 10 | ACTTGGGATATGTGAATAAGACC | 60 |
| CDCA1 | NM_031423 | GGAGGCGGAAGAAACCAG | 11 | GGGGAAAGACAAAGTTTCCA | 61 |
| CDH3 | BC041846 | GACAAGGAGAATCAAAAGATCAGC | 12 | ACTGTCTGGGTCCATGGCTA | 62 |
| CENPF | NM_016343 | GTGGCAGCAGATCACAA | 13 | GGATTTCGTGGTGGGTTC | 63 |
| CEP55 | AB091343 | CCTCACGAATTGCTGAACTT | 14 | CCACAGTCTGTGATAAACGG | 64 |
| CXXC5 | BC006428 | CATGAAATAGTGCATAGTTTGCC | 15 | CCATCAACATTCTCTTTATGAACG | 65 |
| EGFR | NM_005228 | ACACAGAATCTATACCCACCAGAGT | 16 | ATCAACTCCCAAACGGTCAC | 66 |
| ERBB2 | NM_001005862 | GCTGGCTCTCACACTGATAG | 17 | GCCCTTACACATCGGAGAAC | 67 |
| ESR1 | NM_001122742 | GCAGGGAGAGGAGTTTGT | 18 | GACTTCAGGGTGCTGGAC | 68 |
| EXO1 | NM_130398 | CCCATCCATGTGAGGAAGTATAA | 19 | TGTGAAGCCAGCAATATGTATC | 69 |
| FGFR4 | AB209631 | CTTCTTGGACCTTGGCG | 20 | TATTGGGAGGCAGGAGGTTTA | 70 |
| FOXA1 | NM_004496 | GCTACTACGCAGACACG | 21 | CTGAGTTCATGTTGCTGACC | 71 |
| FOXC1 | NM_001453 | GATGTTCGAGTCACAGAGG | 22 | GACAGCTACTATTCCCGTT | 72 |
| GPR160 | AJ249248 | TTCGGCTGGAAGGAACC | 23 | TATGTGAGTAAGCTCGGAGAC | 73 |
| GRB7 | NM_005310 | CGTGGCAGATGTGAACGA | 24 | AGTGGGCATCCGTAGA | 74 |
| HSPC150 (UBE2T) | NM_014176 | GGAGATCCGTCAACTCCAAA | 25 | AGTGGACATGCGAGTGGAG | 75 |
| KIF2C | NM_006845 | TGGGTCGTGTCAGGAAAC | 26 | CACCGCTGGAAACTGAAC | 76 |
| KNTC2 | NM_006101 | CGCAGTCATCCAGAGATGT | 27 | CGTGCACATCCATGACCTT | 77 |
| KRT14 | BC042437 | ACTCAGTACAAGAAAGAACCG | 28 | GAGGAGATGACCTTGCC | 78 |
| KRT17 | AK095281 | GTTGGACCAGTCAACATCTCTG | 29 | GCCATAGCCACTGCCACT | 79 |
| KRT5 | M21389 | TGTGGCTCATTAGGCAAC | 30 | CTTCGACTGGACTCTGT | 80 |
| MAPT | NM_001123066 | GACTCCAAGCGCGAAAAC | 31 | CAGACATGTTGGTATTGCACATT | 81 |
| MDM2 | M92424 | CCAACAAAATATTCATGGTTCTTG | 32 | AGGCGATCCTGGGAAATTAT | 82 |
| MELK | NM_014791 | CCAGTAGCATTGTCCGAG | 33 | CCCATTTGTCTGTCTTCAC | 83 |
| MIA | BG765502 | GTCTCTGGTAATGCACACT | 34 | CTGATGGTTGAGGCTGTT | 84 |
| MK167 | NM_002417 | GTGGAATGCCTGCTGACC | 35 | CGCACTCCAGCACCTAGAC | 85 |
| MLPH | NM_024101 | AGGGGTGCCCTCTGAGAT | 36 | TCACAGGGTCAAACTTCCAGT | 86 |
| MMP11 | NM_005940 | CGAGATCGCCAAGATGTT | 37 | GATGGTAGAGTTCCAGTGATT | 87 |
| MYBL2 | BX647151 | AGGCGAACACACAACGTC | 38 | TCTGGTCACGCAGGGCAA | 88 |
| MYC | NM_002467 | AGCCTCGAACAATTGAAGA | 39 | ACACAGATGATGGGAGATGTC | 89 |
| NAT1 | BC013732 | ATCGACTGTGTAAACAACTAGAGAAGA | 40 | AGTAGCTACATCTCCAGGTTCTCTG | 90 |
| ORC6L | NM_014321 | TTTAAGAGGGCAATGGAAGG | 41 | CGGATTTTATCAACGATGCAG | 91 |
| PGR | NM_000926 | TGCCGCAGAACTCACTTG | 42 | CATTTGCCGTCCTTCATCG | 92 |
| PHGDH | AK093306 | CCTCAGATGATGCCTATCCA | 43 | GCAGGTCAAAACTCTCAAAG | 93 |
| PTTG1 | BE904476 | CAGCAAGCGATGGCATAGT | 44 | AGCGGGCTTCTGTAATCTGA | 94 |
| RRM2 | AK123010 | AATGCCACCGAAGCCTC | 45 | GCCTCAGATTTCAACTCGT | 95 |
| SFRP1 | BC036503 | TCGAACTGAAGGCTATTTACGAG | 46 | CTGCTGAGAATCAAAGTGGGA | 96 |
| SLC39A6 | NM_012319 | GTCGAAGCCGCAATTAGG | 47 | GGAACAAACTGCTCTGCCA | 97 |
| TMEM45B | AK098106 | CAAACGTGTGTTCTGGAAGG | 48 | ACAGCTCTTTAGCATTTGTGGA | 98 |
| TYMS | BQ056428 | TGCCCTGTATGATGTCAGGA | 49 | GGGACTATCAATGTTGGGTTCTC | 99 |
| UBE2C | BC032677 | GTGAGGGGTGTCAGCTCAGT | 50 | CACACAGTTCACTGCTCCACA | 100 |

TABLE 2

PAM50 Intrinsic Gene Sequences

| Gene | Genbank Accession No. | SEQ ID NO: |
|---|---|---|
| ACTR3B | NM_020445 | 101 |
|  | NM_001040135 | 102 |
| ANLN | NM_018685 | 103 |
| BAG1 | NM_004323 | 104 |
| BCL2 | NM_000633 | 105 |
| BIRC5 | NM_001012271 | 106 |
| BKVRA | BX647539 | 107 |
| CCNB1 | NM_031966 | 108 |
| CCNE1 | BC035498 | 109 |
| CDC20 | BG256659 | 110 |
| CDC6 | NM_001254 | 111 |
| CDCA1 | NM_031423 | 112 |
| CDH3 | BC041846 | 113 |
| CENPF | NM_016343 | 114 |
| CEP55 | AB091343 | 115 |
| CXXC5 | BC006428 | 116 |
| EGFR | NM_005228 | 117 |
| ERBB2 | NM_001005862 | 118 |
| ESR1 | NM_001122742 | 119 |
| EXO1 | NM_130398 | 120 |
| FGFR4 | AB209631 | 121 |
| FOXA1 | NM_004496 | 122 |
| FOXC1 | NM_001453 | 123 |
| GPR160 | AJ249248 | 124 |
| GRB7 | NM_005310 | 125 |
| HSPC150 (UBE2T) | NM_014176 | 126 |
| KIF2C | NM_006845 | 127 |
| KNTC2 | NM_006101 | 128 |
| KRT14 | BC042437 | 129 |
| KRT17 | AK095281 | 130 |
| KRT5 | M21389 | 131 |
| MAPT | NM_001123066 | 132 |
| MDM2 | M92424 | 133 |
| MELK | NM_014791 | 134 |
| MIA | BG765502 | 135 |
| MK167 | NM_002417 | 136 |
| MLPH | NM_024101 | 137 |
| MMP11 | NM_005940 | 138 |
| MYBL2 | BX647151 | 139 |
| MYC | NM_002467 | 140 |
| NAT1 | BC013732 | 141 |
| ORC6L | NM_014321 | 142 |
| PGR | NM_000926 | 143 |
| PHGDH | AK093306 | 144 |
| PTTG1 | BE904476 | 145 |
| RRM2 | AK123010 | 146 |
| SFRP1 | BC036503 | 147 |
| SLC39A6 | NM_012319 | 148 |
| TMEM45B | AK098106 | 149 |
| TYMS | BQ056428 | 150 |
| UBE2C | BC032677 | 151 |

The practice of the invention is illustrated by the following non-limiting examples.

EXAMPLES

Example 1

Clinical Study Protocol

A clinical trial was conducted to determine clinical benefit of enzalutamide treatment in patients whose tumors are androgen receptor-positive (AR+) and triple-negative. In this study, AR+ is defined as any nuclear AR staining by immunohistochemistry (IHC) and TNBC is defined as <1% staining by IHC for estrogen receptor (ER) and progesterone receptor (PgR), 0 or 1+ by IHC for human epidermal growth factor receptor 2 (HER2), or negative for HER2 amplification by in situ hybridization (ISH) for 2+ IHC disease. AR staining was carried out by IHC with two different antibodies each of which were individually optimized on breast cancer tissue. Enzalutamide (160 mg/day) was administered as four 40 mg soft gelatin capsules orally once daily with or without food. Patients received enzalutamide until disease progression per Response Evaluation Criteria in Solid Tumors version 1.1 (RECIST 1.1) was documented unless treatment was discontinued due to other reasons specified in the trial protocol. The study periods included prescreening (patients could sign consent to submit to tissue for testing for AR expression at any time in their disease course); screening (28 days before first dose of study drug); treatment (day 1 through discontinuation); safety follow-up (approximately 30 days after the last dose of study drug or before initiation of a new antitumor treatment, whichever occurs first); and long-term follow-up (assessment of subsequent breast cancer therapies and survival status every 3 to 6 months after treatment discontinuation). Objective response—complete response (CR) or partial response (PR)—was determined by investigators according to the RECIST 1.1.

The trial was a Simon 2-stage study where a minimum benefit was required in a pre-defined patient population prior to expanding the study to a larger size. In Stage 1, 42 patients enrolled into the study to obtain the pre-defined 26 Evaluable patients. The requisite clinical benefit to proceed to Stage 2 was observed in Stage 1 and an additional 76 patients were enrolled for a total of 118 patients overall. Patients who received prior treatment with an androgen receptor signaling inhibitor, who had central nervous system (CNS) metastases were excluded; there was no limit to number of prior therapies, and patients with patients measurable disease or bone-only nonmeasurable disease were eligible. Clinical Benefit Rate at 16 weeks (CBR16) was defined as the proportion of Evaluable Patients with a best response of complete remission (CR), partial response (PR) or stable disease (SD) ≥16 weeks (CBR16). The Clinical Benefit Rate at ≥24 weeks (CBR16) was also assessed.

In Stage 1, 42 patients were enrolled to get 26 Evaluable Patients (n=26). Evaluable patients were those who had both AR staining in ≥10% of tumor and at least 1 post-baseline tumor assessment. The Intent-To-Treat (ITT) population (n=42 in Stage 1) was defined as all enrolled patients who had centrally assessed AR+ TNBC and received at least 1 dose of study drug. Twenty-six (62%) of 42 ITT patients were Evaluable, while 16 of 42 were not Evaluable. Of the 16 not meeting the criteria for Evaluable, 10 had AR expression below 10%; 6 had AR expression ≥10% but did not have a post-baseline assessment (2 were discovered to have CNS metastases shortly after study entry and were withdrawn from treatment prior to having a post-baseline tumor assessment). More than 50% of the patients received enzalutamide as their first or second line of therapy, while >30% had ≥3 prior regimens before receiving enzalutamide.

Intrinsic Gene Expression Analysis

Human breast tumors from TNBC patients were obtained from the aforementioned clinical study of enzalutamide, an AR antagonist. The patient breast cancer tissue was stained for AR expression. The patient staining was graded by a pathologist on both the staining intensity (3+, 2+ and 1+) as well as the percentage of tumor cells stained as given in the standard operating procedure. AR staining was evaluated both in the nucleus and cytoplasm.

RNA-seq data utilized in this study were pre-processed as follows. The RNA-seq data was aligned to Human (*Homo sapiens*) genome sequence hg19 from the Human Genome Browser—hg19 Assembly created by the Genome Bioinformatics Group of UC Santa Cruz (genome.ucsc.edu/cgi-bin/hgGateway?db=hg19) (www.ncbi.nlm.nih.gov/assembly/GCF_000001405.25/) using MapSplice (Nucleic Acids Res.

2010 October; 38(18):e178. doi: 10.1093/nar/gkq622). Gene and isoform level counts were estimated using RNA-Seq by Expectation-Maximization (RSEM) (deweylab.biostat.wisc.edu/rsem/). Gene count estimates were normalized to a fixed upper quartile. The resulting normalized gene expression estimates were adjusted such that the median expression value of each gene was equivalent to the median of the triple negative subset of the TCGA RNA-seq data reported in "Comprehensive Molecular Portraits of Human Breast Tumors", The Cancer Genome Atlas Network, Nature 490, 61-70 (Oct. 4, 2012) (www.nature.com/nature/journal/v490/n7418/full/nature11412.html).

Intrinsic subtype classification was performed into the LumA, LumB, Basal, HER2 and Normal groups using the PAM50 classification model as described in Parker et al. J Clin Oncol., 27(8): 1160-7 (2009). The intrinsic subtype classification was carried out on genomic data obtained from RNA sequencing of RNA obtained from formalin fixed, paraffin embedded tissue collected from subjects' breast tumors. The data was pre-processed as indicated above. Subtype classification was performed on a "Training and Test" set and a further "Validation" set. The Training and Test set consisted of 122 patient samples out of which 42 patients were from the pre-screened population but not enrolled in the study and 80 patients samples were from the enrolled population in the clinical study. The Validation set consisted of 55 patient samples which had 15 patients from the pre-screened population not enrolled on the study and 40 samples from the enrolled population.

The data was analyzed according to the known methods for analyzing PAM50 intrinsic gene set data, as described by Parker et al. et al., supra. Essentially, the detection and estimation of the expression of the set of 50 subtype predictor genes of Table 1 from patient tumor samples was carried out. The expression profile of the set of 50 subtype predictor genes by the described method that provides Basal-like, HER2, LumA, LumB and Normal subtype classifications was analyzed. The Spearman correlation was calculated for each sample and PAM50 centroid. These values were used as continuous estimates of distance or similarity of a sample to each centroid. The subtype of each sample was assigned as the closest (largest positive correlation) centroid. The underlying measures of correlation to each subtype were used to classify a sample as one of 4 tumor subtypes (Basal-like, HER2, LumA and LumB) or Normal-like.

Further, the Spearman rank correlation to the Basal-like gene expression centroid was evaluated. The Spearman rank correlation between the sample and the Basal-like centroid was assigned as the "Basal Centroid classifier score". The Spearman rank correlation to the Luminal A gene expression centroid was evaluated. The Spearman rank correlation between the sample and the Luminal A centroid was assigned as the "Luminal A classifier score".

Figure 1:
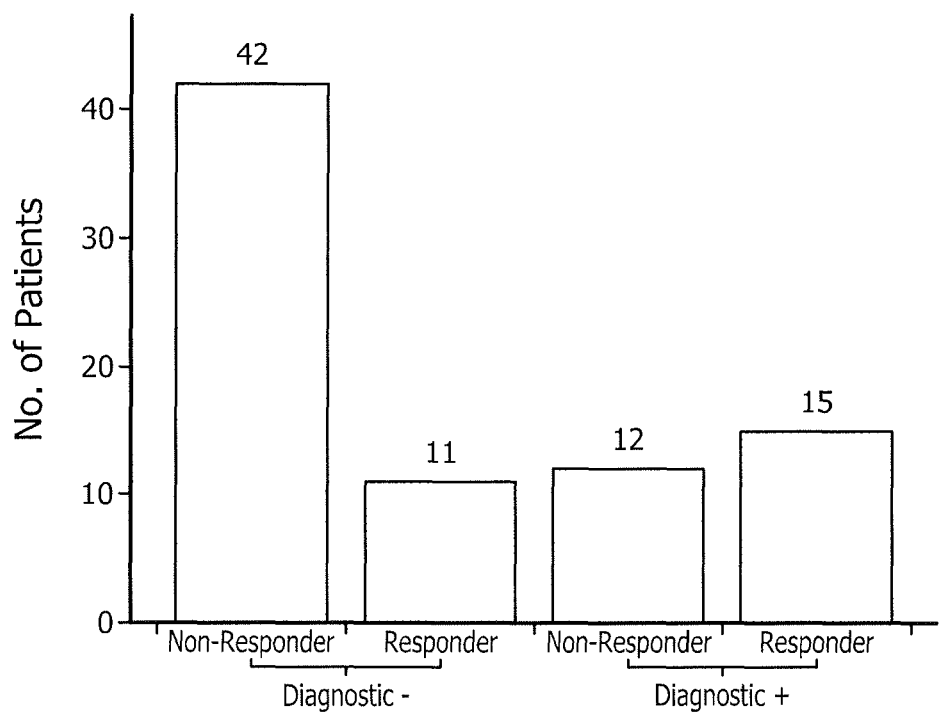
FIG. 1 is a graph of the results from some of the patients enrolled into either the prescreening or screening period of a clinical trial evaluating enzalutamide in patients whose TNBC also expressed AR. "Diagnostic −" represents patients having the Basal-like subtype, as determined by PAM50 gene breast cancer subtype classification. "Diagnostic +" represents the patients with Her2, LumA, LumB or Normal subtypes. Patients were scored as "Responder" or "Non-Responder" to the enzalutamide therapy according to the criteria set forth in Example 1.

In the enrolled patients (Intent-To-Treat (ITT) population, Basal-like subtype generally correlated with non-response to enzalutamide therapy, while existence of one of the other subtypes generally correlated with response to enzalutamide therapy. See FIG. 1, wherein "Diagnostic −" represents the Basal-like subtype patients and "Diagnostic +" represents the patients with Her2, LumA, LumB or Normal subtypes. Thus, a PAM50 gene expression classifier result indicating a non-Basal-like tumor type is a marker for predicting responsiveness to enzalutamide therapy in TNBC.

Example 2

The results of the clinical study of Example 1 were further analyzed utilizing the patient Basal Centroid classifier scores. The therapeutic response data was evaluated imposing a series of threshold cut-offs on the Basal Centroid classifier score. The enzalutamide response/non-response data was analyzed using Basal Centroid classifier score cut-offs of 0.2, 0.3, 0.4, 0.5, 0.6, 0.65, 0.7, 0.8 and 0.9. The data is set forth in FIGS. 2A/B through 10A/B. In each figure, "Diagnostic +" represents patients whose samples met the indicated prognostic signature comprising the indicted threshold cut-off. "Diagnostic −" represents patients whose samples did not meet the indicated threshold cut-off.

| | FIG. | | | | | | | | |
|---|---|---|---|---|---|---|---|---|---|
| | 2A/B | 3A/B | 4A/B | 5A/B | 6A/B | 7A/B | 8A/B | 9A/B | 10A/B |
| Basal Centroid classifier score | 0.2 | 0.3 | 0.4 | 0.5 | 0.6 | 0.65 | 0.7 | 0.8 | 0.9 |

Figure 2A:
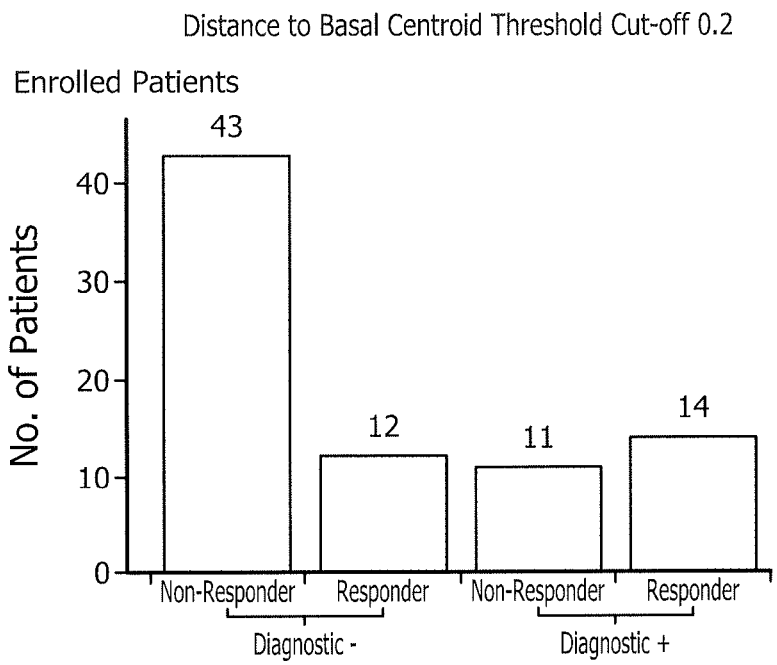
FIGS. 2A and 2B are graphs of results of the same TNBC clinical trial in which patient gene expression classifier scores for the Basal-like subtype were correlated with patient response. A threshold cut-off of 0.2 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 2B:
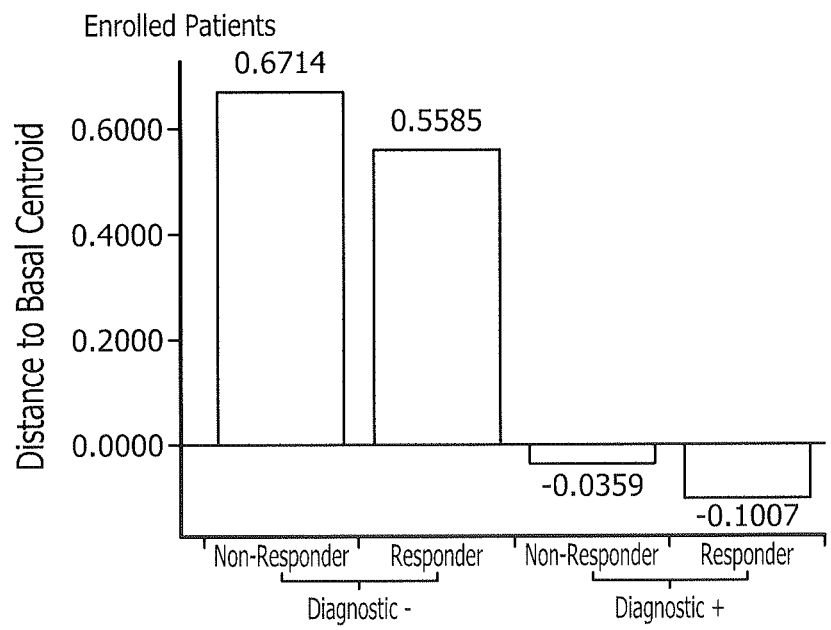
Figure 3A:
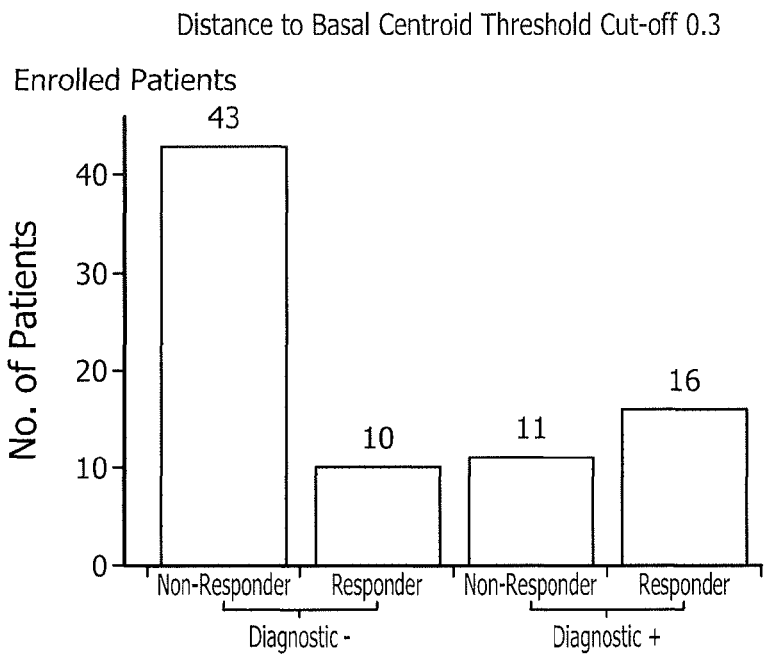
FIGS. 3A and 3B are graphs of results of the same TNBC clinical trial in which patient gene expression classifier scores for the Basal-like subtype were correlated with patient response. A threshold cut-off of 0.3 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 3B:
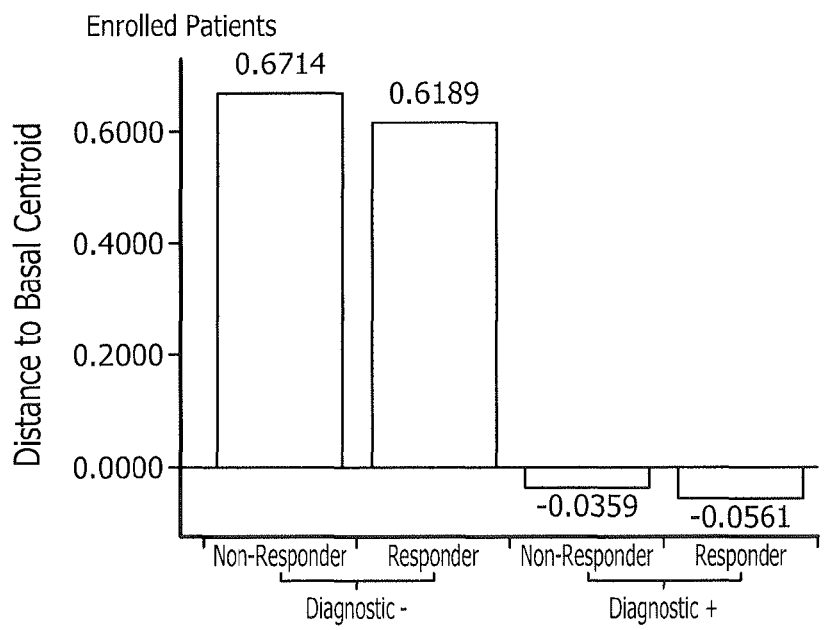
Figure 4A:
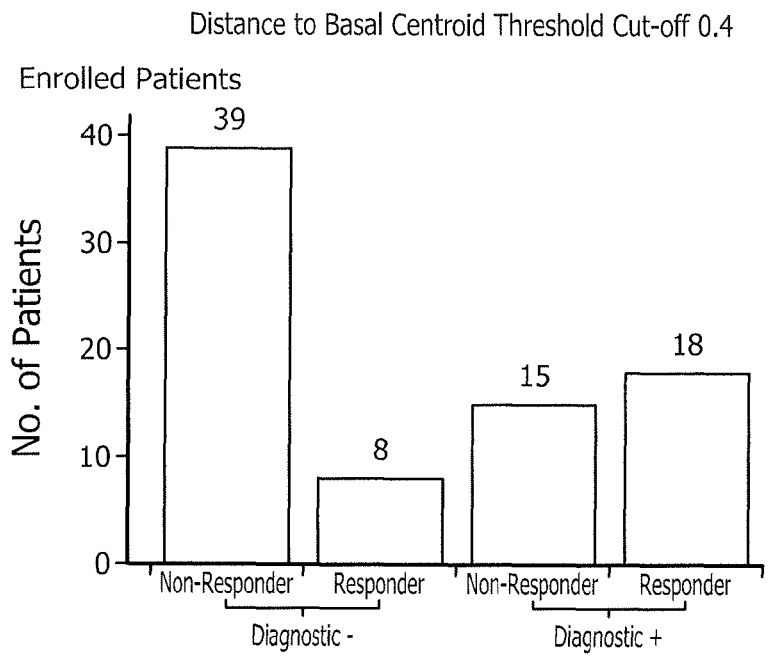
FIGS. 4A and 4B are graphs of results of the same TNBC clinical trial in which patient gene expression classifier scores for the Basal-like subtype were correlated with patient response. A threshold cut-off of 0.4 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 4B:
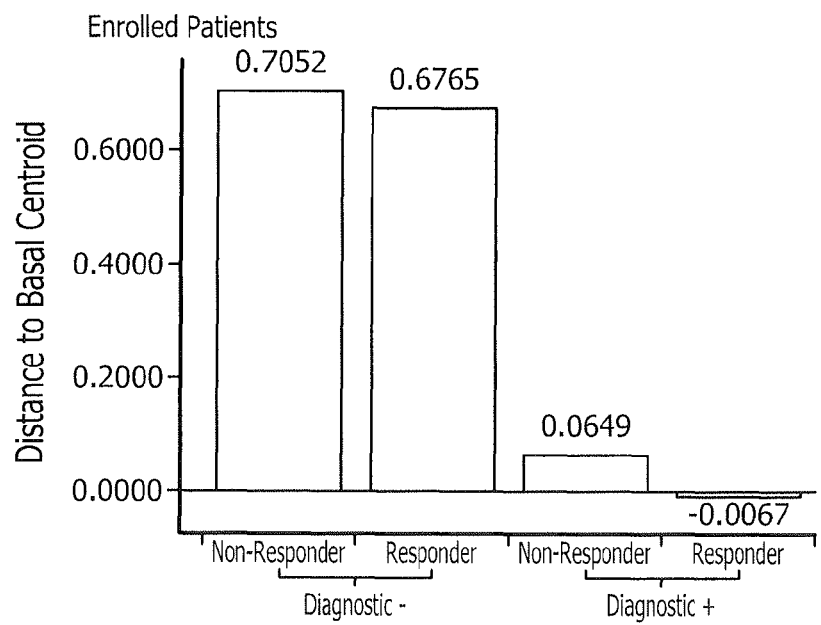
Figure 5A:
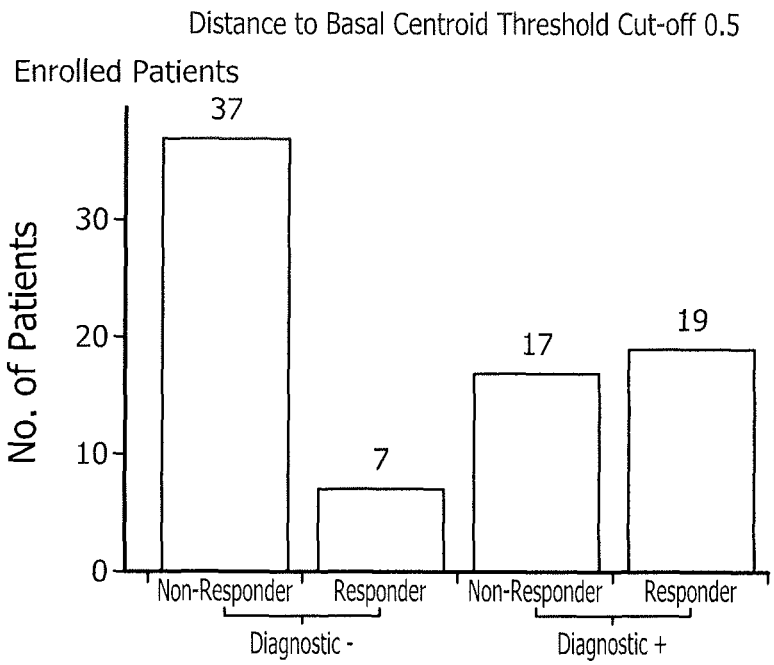
FIGS. 5A and 5B are graphs of results of the same TNBC clinical trial in which patient gene expression classifier scores for the Basal-like subtype were correlated with patient response. A threshold cut-off of 0.5 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 5B:
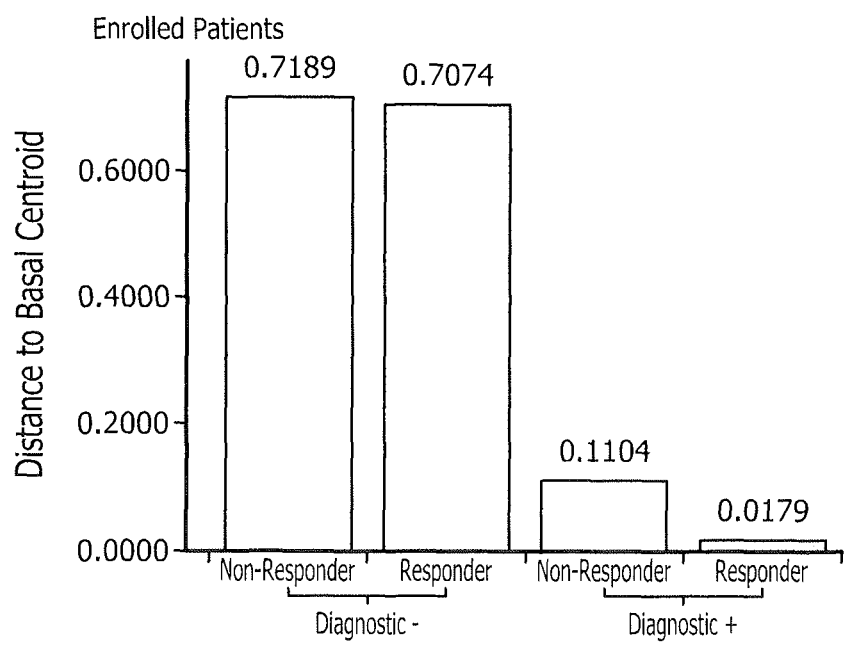
Figure 6A:
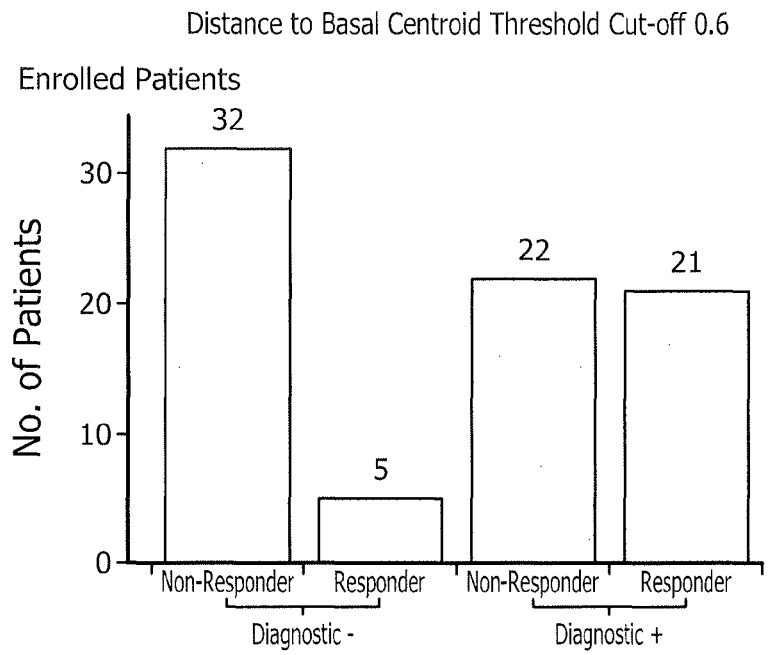
FIGS. 6A and 6B are graphs of results of the same TNBC clinical trial in which patient gene expression classifier scores for the Basal-like subtype were correlated with patient response. A threshold cut-off of 0.6 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 6B:
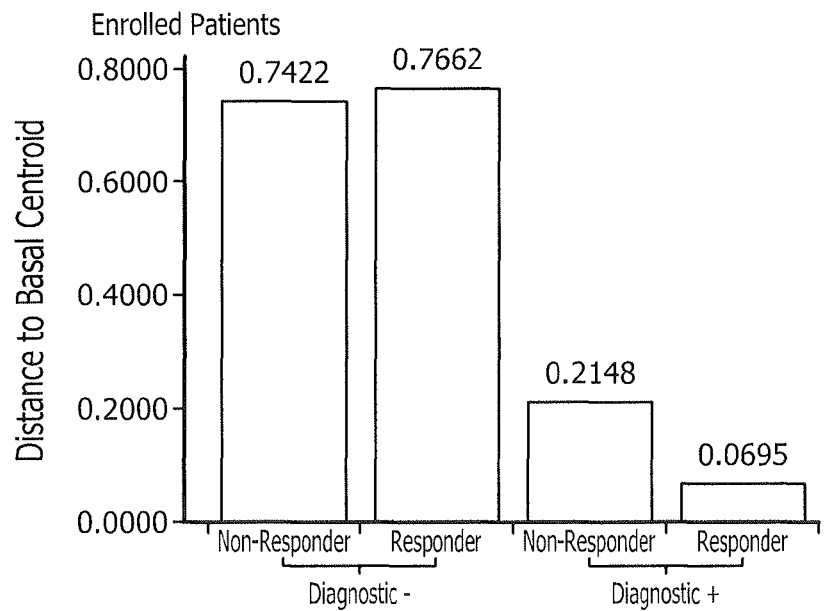
Figure 7A:
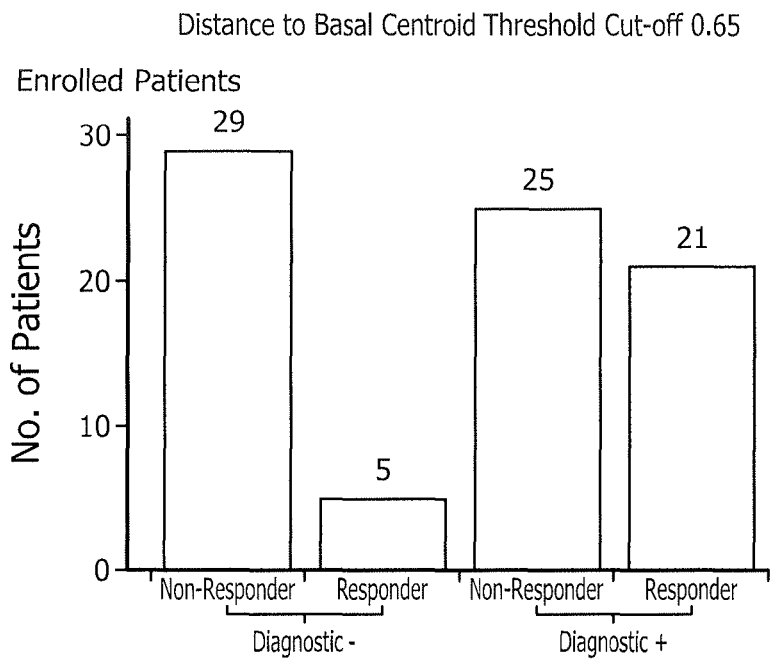
FIGS. 7A and 7B are graphs of results of the same TNBC clinical trial in which patient gene expression classifier scores for the Basal-like subtype were correlated with patient response. A threshold cut-off of 0.65 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 7B:
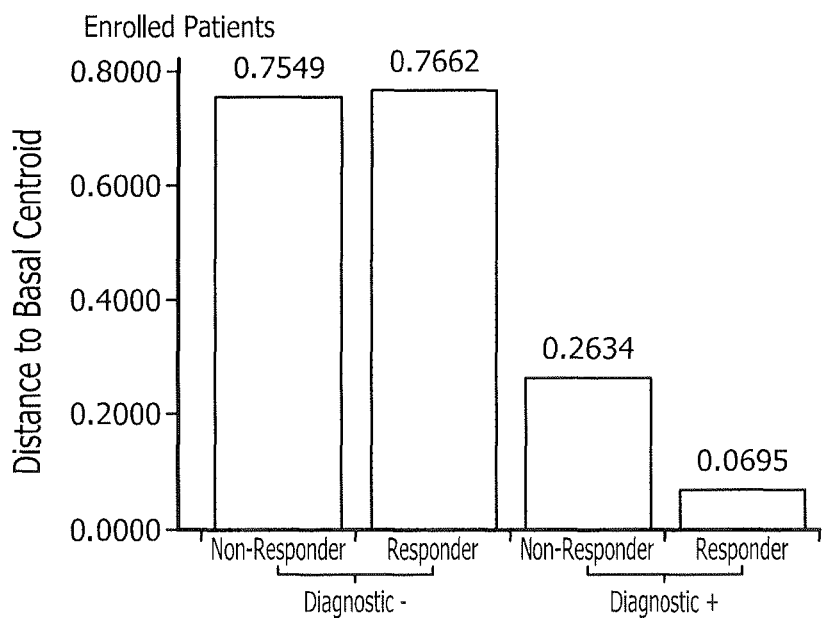
Figure 8A:
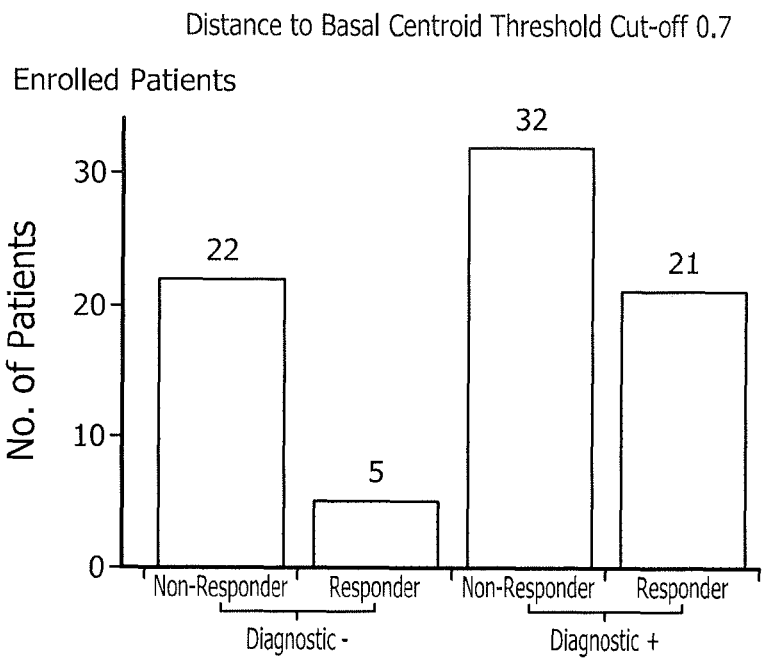
FIGS. 8A and 8B are graphs of results of the same TNBC clinical trial in which patient gene expression classifier scores for the Basal-like subtype were correlated with patient response. A threshold cut-off of 0.7 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 8B:
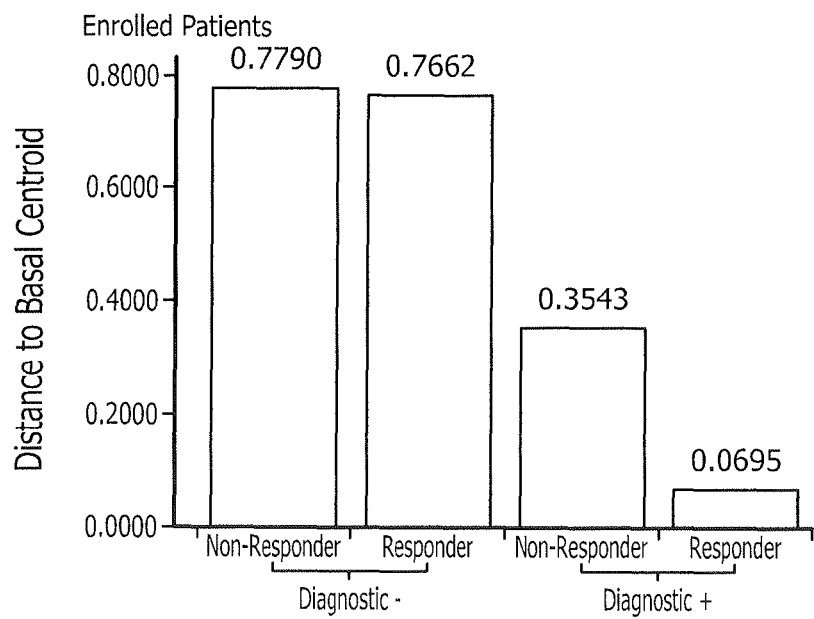
Figure 9A:
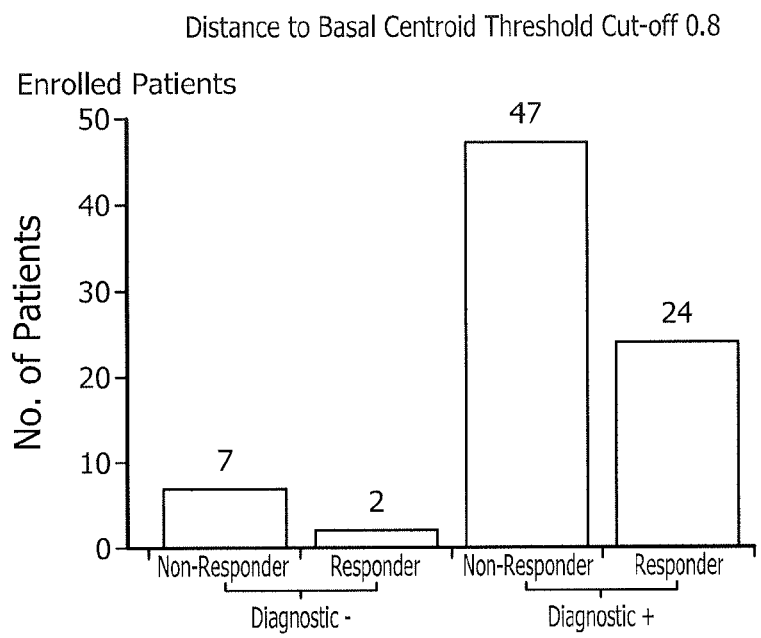
FIGS. 9A and 9B are graphs of results of the same TNBC clinical trial in which patient gene expression classifier scores for the Basal-like subtype were correlated with patient response. A threshold cut-off of 0.8 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 9B:
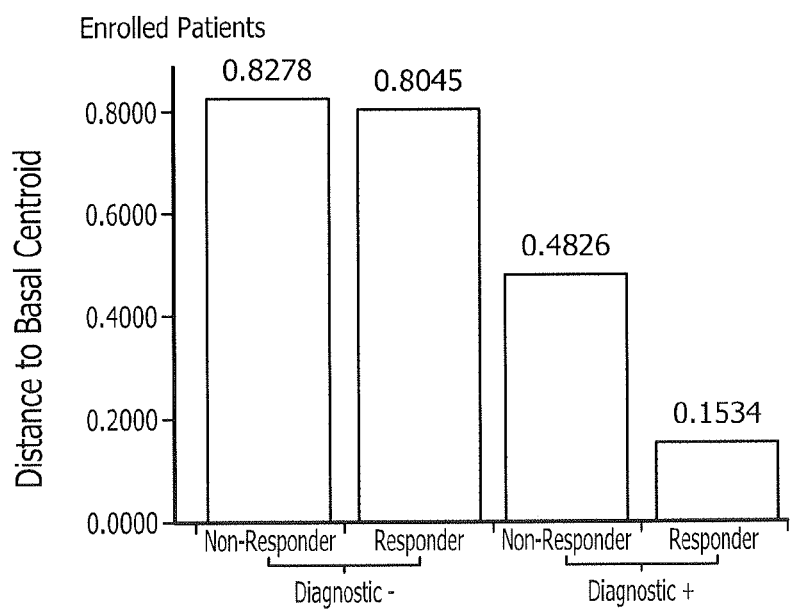
Figure 10A:
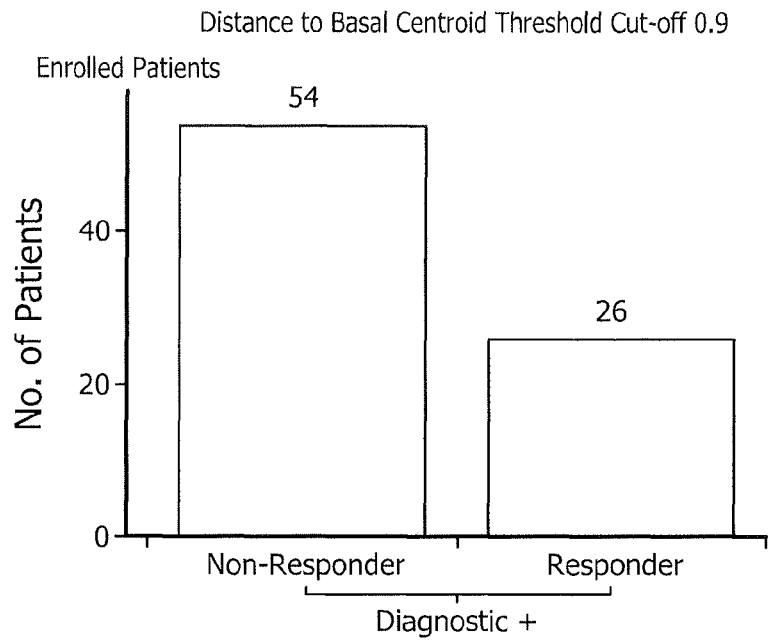
FIGS. 10A and 10B are graphs of results of the same TNBC clinical trial in which patient gene expression classifier scores for the Basal-like subtype were correlated with patient response. A threshold cut-off of 0.9 for the patient Basal Centroid classifier score was applied. "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 10B:
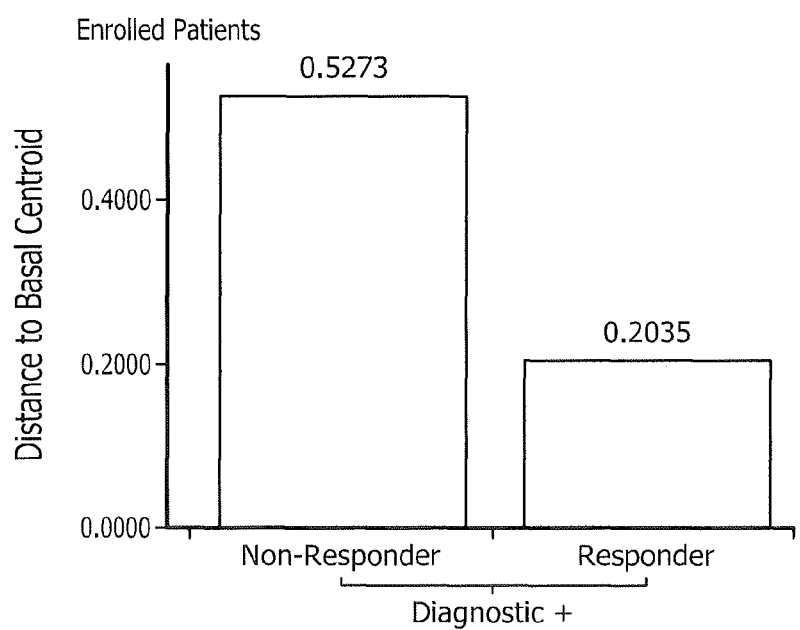

As shown in FIGS. 2A/B-10A/B, a target Basal Centroid classifier score of 0.6 or less for defining Dx+ and Dx− patients best correlated with response to enzalutamide therapy, while defining the Dx+ and Dx− based upon scores from 0.2 to 0.9 enriched the predictive value somewhat less. Thus, defining the population of responders and non-responders upon a Basal Centroid classifier cutoff score that is in the range of 0.2-0.9 is a further basis for predicting responsiveness to enzalutamide therapy in TNBC, with a sample's Basal Centroid classifier score of 0.6 or less being a preferred embodiment for a marker to predict responsiveness. As shown in FIG. 6A, defining Dx+ and Dx− pursuant to a relative Basal Centroid classifier score of 0.6 resulted in a prediction that yielded a large Diagnostic + population with most responders in the Diagnostic + population and high non-responders in the Diagnostic − population.

Example 3

Figure 11:
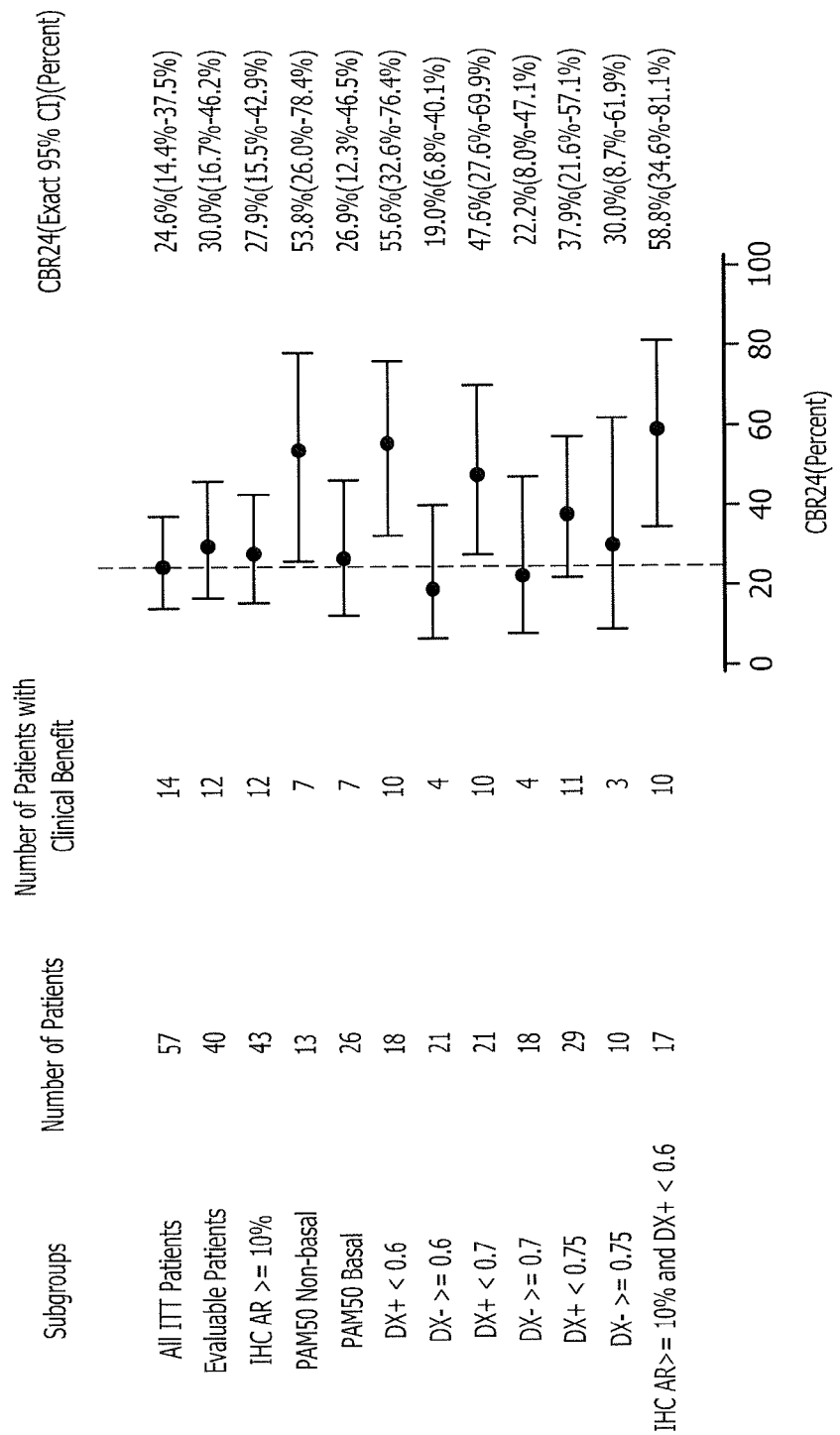
FIG. 11 comprises a representation of the response to enzalutamide of various patient subgroups treated with enzalutamide in the clinical trial. Response is shown in terms of Clinical Benefit Rate at ≥24 weeks (CBR24). The subgroups include Intent-To-Treat (ITT) patients; Evaluable Patients; patients with breast tumor tissue which was AR staining ≥10% (IHC AR>=10%); patients whose breast tumor tissue was classified as a non-Basal like subtype by the PAM50 subtype classifier (PAM50 non-basal); patients whose tumors were classified as Basal-like subtype (PAM50 basal); and patient samples analyzed by applying the indicated cut-offs of <0.6, ≥0.6, <0.7, ≥0.7, <0.75 and ≥0.75, from patient Basal Centroid classifier scores. "DX −" signifies patients whose samples did not meet the indicated threshold cut-off. "DX +" signifies patients whose samples did meet the indicated threshold cut-off. Also shown in FIG. 11 are data for the combined criteria IHC AR>=10% and DX+<0.6.

The results of the clinical study of Example 1 are further analyzed and summarized in FIG. 11, showing the response of various patient subgroups to enzalutamide therapy in terms of Clinical Benefit Rate at ≥24 weeks (CBR24). The subgroups include all Intent-To-Treat (ITT) patients; Evaluable Patients; patients with breast tumor tissue which was AR staining ≥10% (IHC AR>=10%); patients whose breast tumor tissue was classified as a non-Basal like subtype by the PAM50 subtype classifier (PAM50 non-basal); patients whose tumors were classified as Basal like subtype (PAM50 basal); and patient samples analyzed by applying the indicated cut-offs of <0.6, ≥0.6, <0.7, ≥0.7, <0.75 ≥0.75 to the Basal Centroid classifier score. "DX −" signifies patients whose samples did not meet the indicated threshold cut-off. "DX +" signifies patients whose samples did meet the indicated threshold cut-off. Also shown in FIG. 11 are data for the samples satisfying the combined criteria IHC AR>=10% and DX+<0.6, that is the sample met the criteria of (i) staining for AR of more than 10% and (ii) a PAM50 gene expression Basal Centroid classifier score of 0.6 or less.

Example 4

Figure 12:
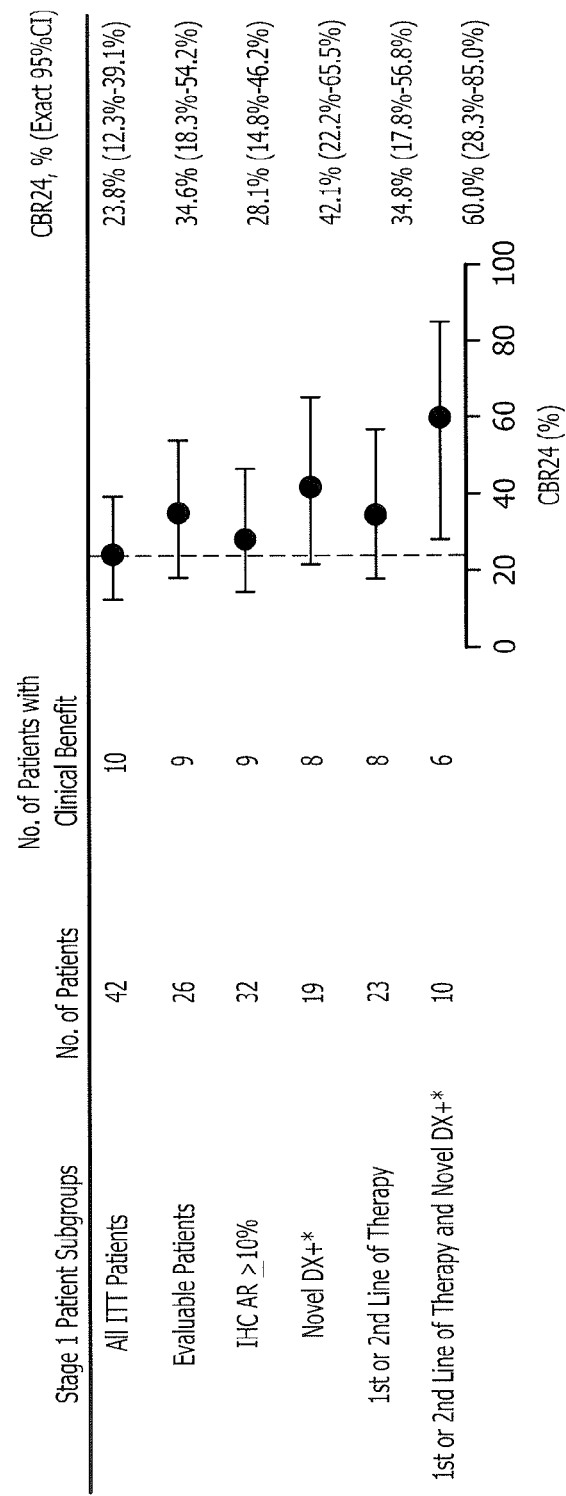
FIG. 12 is a further representation of the response to enzalutamide of various patient subgroups treated with enzalutamide in the clinical trial. Response is shown in terms of Clinical Benefit Rate at ≥24 weeks (CBR24). The subgroups include Intent-To-Treat (ITT) patients; Evaluable Patients; patients with breast tumor tissue which was AR staining ≥10% (IHC AR>=10%); and patients in which the enzalutamide therapy is administered as the first (1st line) or second (2nd line) of therapy. The subgroups further include a subgroup of patient samples analyzed by applying a <0.6 cut-off to Basal Centroid classifier scores ("Novel DX+"), and a subgroup comprising samples from 1st and 2nd line therapy, applying the <0.6 cut-off to Basal Centroid classifier scores.

The results of the clinical study of Example 1 are further analyzed and summarized in FIG. 12, showing the response of various patient subgroups to enzalutamide therapy in terms of Clinical Benefit Rate at ≥24 weeks (CBR24). The subgroups include all Intent-To-Treat (ITT) patients; Evaluable Patients; patients with breast tumor tissue which was AR staining ≥10% (IHC AR>=10%); and patients in which the enzalutamide therapy is the sole (1st line) or second (2nd line) of therapy. The subgroups further include subgroup of patient samples analyzed by applying a <0.6 Basal Centroid classifier score cut-off ("Novel DX+,"), and a subgroup comprising samples from 1st and 2nd line therapy, applying the <0.6 cut-off. A CBR of 42% using the prognostic Basal Centroid classifier score of <0.6 (and 60% when used in a group comprising both 1st line and 2nd line patients) exceeds typical benchmarks for predicting responsiveness to therapy in TNBC and is on a par with the predictive ability of models used to predict response to hormonal agent therapy in ER+/PgR+ breast cancer.

Example 5

Figure 13:
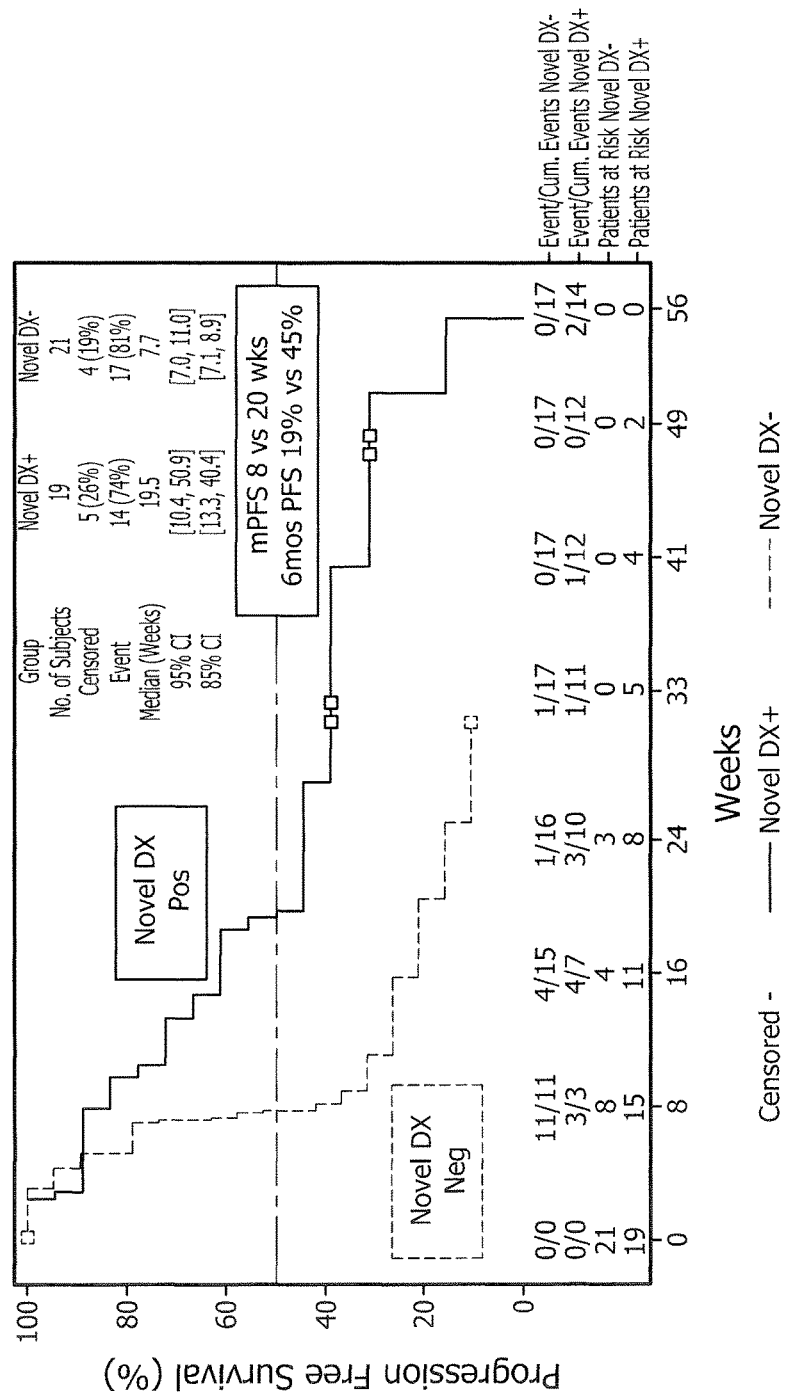
FIG. 13 is a Kaplan-Meier plot showing median progression-free survival (MPS) of patients treated with enzalutamide as a function of time. The curves correspond to patients that were identified as meeting the novel prognostic signature condition of a Basal Centroid classifier score of <0.6 ("Novel DX Pos") versus patients who did not meet the definition ("Novel DX Neg").

The effect of the novel prognostic signature utilizing a Basal Centroid classifier score of <0.6 as a predictor of response to AR inhibitor therapy is further illustrated in FIG. 13 with respect to patient progression-free survival time to 56 weeks. The results demonstrate a prolonged progression-free survival in patients that were identified as meeting the novel prognostic signature condition of a Basal Centroid classifier score of <0.6 ("Novel DX Pos") versus patients having a ≥0.6 distance score ("Novel DX Neg").

Example 6

The results of the clinical study of Example 1 were further analyzed utilizing the patient Basal Centroid classifier and Luminal A classifier scores. The classifier scores and response data were analyzed. As a result of analysis, a Weighted Basal and Luminal A classifier score was empirically devised that predicted responsiveness to androgen receptor inhibitor therapy in the clinical trial. The Weighted Basal and Luminal A classifier score of patient samples was determined from the following formula:

Weighted Basal and Luminal A classifier score=
−0.2468275(Basal Centroid classifier score)+
0.2667110(Luminal A Centroid classifier score).

The therapeutic response data was then evaluated imposing a series of threshold cut-offs on the Weighted Basal and Luminal A classifier score. Specifically, the enzalutamide response/non-response data was analyzed using Weighted Basal and Luminal A classifier score cut-offs of greater than −0.2, greater than −0.25, greater than −0.3 and greater than −0.35. The data is set forth in FIGS. 14A (>−0.2), 14B (>−0.25), 14C (>−0.3), and 14D (>−0.35). In each figure, "Diagnostic +" represents patients whose samples met the indicated prognostic signature comprising the indicted threshold cut-off. "Diagnostic −" represents patients whose samples did not meet the indicated threshold cut-off.

As shown in FIGS. 14A-14D, selecting a criterion of a Weighted Basal and Luminal A classifier of greater than x, with x in the range of −0.2 to −0.3, best correlated with response to enzalutamide therapy, with the criterion of a score of greater than −0.25 being optimal. Thus, defining the population of responders and non-responders based upon a Weighted Basal and Luminal A classifier score that is greater than −0.2, or greater than −0.3 is a basis for predicting responsiveness to enzalutamide therapy in TNBC, with a Weighted Basal and Luminal A classifier score of greater than −0.25 being a preferred embodiment of a criterion for predicting responsiveness.

Example 7

The results of the clinical study of Example 1 are further analyzed and summarized in FIG. 15, showing the response of various patient subgroups to enzalutamide therapy in terms of Clinical Benefit Rate at ≥24 weeks (CBR24). The subgroups include all Intent-To-Treat (ITT) patients; Evaluable Patients; patients whose breast tumor tissue samples were analyzed by applying the indicated cut-offs of >−0.2, >−0.25, >−0.3, and >−0.35, to the Weighted Basal and Luminal A classifier score. "PR-AR DX −" signifies patients whose samples did not meet the indicated threshold cut-off. "PR-AR DX +" signifies patients whose samples did meet the indicated threshold cut-off. Thus, for example, "PR-AR DX +>−0.25" indicates the patients whose samples met the criterion of a Weighted Basal and Luminal A classifier score greater than −0.25.

Also shown in FIG. 15 are data for samples from patients in the study receiving enzalutamide therapy (i) after having received from zero to one prior therapies for treatment of TNBC with a drug other than an androgen receptor inhibitor ("and 0-1 prior therapy") or (ii) after having received two or more prior therapies for treatment of TNBC with a drug other than an androgen receptor inhibitor ("and >=2 prior therapies"). A Weighted Basal and Luminal A classifier score cut-off of >−0.25 was applied to these patient samples.

Example 8

The effect of the novel prognostic signature utilizing a Weighted Basal and Luminal A classifier score cut-off of >−0.2 as a predictor of response to AR inhibitor therapy is further illustrated in FIG. 16 with respect to patient progression-free survival time to 56 weeks. The results demonstrate a prolonged progression-free survival in patients that were identified as meeting the prognostic signature condition of a Weighted Basal and Luminal A classifier score of greater than −0.2 ("PR-AR DX+: >−0.2", top curve) versus a classifier score of less than or equal to −0.2 ("PR-AR DX−: <=−0.2", bottom curve).

Example 9

The effect of the novel prognostic signature utilizing a Weighted Basal and Luminal A classifier score cut-off of >−0.25 as a predictor of response to AR inhibitor therapy is further illustrated in FIG. 17 with respect to patient progression-free survival time to 56 weeks. The results demonstrate a prolonged progression-free survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve).

Example 10

The effect of the novel prognostic signature utilizing a Weighted Basal and Luminal A classifier score cut-off of >−0.3 as a predictor of response to AR inhibitor therapy is further illustrated in FIG. 18 with respect to patient progression-free survival time to 56 weeks. The results demonstrate a prolonged progression-free survival in patients that were identified as meeting the prognostic signature condition of a Weighted Basal and Luminal A classifier score of greater than −0.3 ("PR-AR DX+: >−0.3", top curve) versus a classifier score of less than or equal to −0.3 ("PR-AR DX−: <=−0.3", bottom curve).

Example 11

The effect of the novel prognostic signature utilizing a Weighted Basal and Luminal A classifier score cut-off of >−0.35 as a predictor of response to AR inhibitor therapy is further illustrated in FIG. 19 with respect to patient progression-free survival time to 56 weeks. The results demonstrate a prolonged progression-free survival in patients that were identified as meeting the prognostic signature condition of a Weighted Basal and Luminal A classifier score of greater than −0.35 ("PR-AR DX+: >−0.35", top curve) versus less than or equal to −0.35 ("PR-AR DX−: <=−0.35", bottom curve).

Example 12

The effect of the novel prognostic signature utilizing a Weighted Basal and Luminal A classifier score cut-off of >−0.25 as a predictor of response to AR inhibitor therapy is further illustrated in FIG. 20 with respect to patient progression-free survival time to 56 weeks, in patients receiving from zero to one prior therapies for treatment of TNBC with a drug other than an androgen receptor inhibitor. The results demonstrate a prolonged progression-free survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve). It may be appreciated from a comparison of FIGS. 17 and 20, that the −0.25 cut-off was able to identify a longer duration of progression-free survival that characterized the zero to 1 prior therapy group (FIG. 20) versus the shorter duration of progression-free survival that characterized the population of all study patients (FIG. 17).

The effect of the novel prognostic signature utilizing a Weighted Basal and Luminal A classifier score cut-off of >−0.25 as a predictor of response to AR inhibitor therapy in patients receiving from zero to one prior therapies for treatment of TNBC with a drug other than an androgen receptor inhibitor is further shown in FIG. 23. FIG. 23 is similar to FIG. 20, except that the progression-free survival time in the study is determined beyond the 56 weeks in FIG. 20 to 64 weeks in FIG. 23.

Example 13

The effect of the novel prognostic signature utilizing a Weighted Basal and Luminal A classifier score cut-off of >−0.25 as a predictor of response to AR inhibitor therapy is further illustrated in FIGS. 21A and 21B, with respect to time on treatment without progression of patients receiving zero or one (0-1 Prior Lines), or two or more (2+ Prior Lines), prior therapies for treatment of TNBC with a drug other than an androgen receptor inhibitor. The 56 patients that were identified as meeting the signature condition of a Weighted Basal and Luminal A classifier score of greater than −0.25 are represented in FIG. 21B. The 62 study patients identified by a classifier score of less than or equal to −0.25 are identified in FIG. 21A. Each bar in the figures represents a single patient. The best time on treatment without disease progression is apparent in responder patients who received one or no prior lines of therapy (FIG. 21B). Patient bars marked with a triangle ("Active") are active on study. Patient bars marked with a star signify complete response (CR) or partial response (PR).

Example 14

The effect of the novel prognostic signature utilizing a Weighted Basal and Luminal A classifier score cut-off of >−0.25 as a predictor of response to AR inhibitor therapy is further illustrated in FIGS. 22A and 22B with respect to patient progression-free survival time to 64 weeks (FIG. 22A) and overall survival to 84 weeks (FIG. 22B). The results of FIG. 22A demonstrate a prolonged progression-free survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve). The results of FIG. 22B demonstrate a prolonged overall survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve). The patients not meeting the prognostic signature condition were characterized by a median progression-free survival of 8.1 weeks and median overall survival of 32.1 weeks. In contrast, patients meeting the prognostic signature condition were characterized by a median progression-free survival of 16.1 weeks and median overall survival not yet reached at 84 weeks.

Example 15

A Phase II clinical trial of the androgen receptor antagonist bicalutamide has been reported. Ayca et al., "Phase II Trial of Bicalutamide in Patients with Androgen Receptor Positive, Hormone Receptor Negative Metastatic Breast Cancer", *Clin Cancer Res* 19: 5505-5512 (Oct. 1, 2013). The trial was designed to study the effect of bicalutamide in treating metastatic breast cancer that is AR-positive, estrogen receptor (ER)-negative, and progesterone receptor (PgR)-negative.

Briefly, as described by Ayca et al., tumors from 452 patients with ER-negative/PgR-negative advanced breast cancer were tested centrally for AR by immunohistochemistry (IHC) (>10% nuclear staining considered positive). See Ayca et al., p. 5506 for additional eligibility criteria. If either the primary or a metastatic site was positive, patients were eligible to receive the AR antagonist bicalutamide at a dose of 150 mg daily. Twenty-eight patients were treated on study. Bicalutamide 150 mg was administered orally on a continuous daily schedule. Patients were treated until disease progression or unacceptable adverse events. A maximum of 2 dose reductions for grade ≥3 toxicity were allowed (100 and 50 mg). A maximum of 2 weeks was permitted for treatment delays due to toxicity. Two patients who initiated bicalutamide were removed from study, leaving 26 study participants with AR(+) ER/PgR(−) metastatic breast cancer. Five patients had stable disease >6 months (number of cycles completed: 6, 8, 10+, 13, 57+) as their best response on treatment. There were no confirmed complete or partial responses yielding a clinical benefit rate of 19% (95% CI, 7%-39%) in the target population (n=26). In an intention-to-treat analysis, a CBR of 18% (95% CI, 6%-37%) was observed. See Ayca et al., p. 5507.

Twenty-one of the 26 bicalutamide-treated study patients were determined to also be HER-2 negative, i.e., twenty-one patients had breast cancers that were triple negative (Her-2 (−), ER (−) and PgR(−)). Following the study, patient tumor samples from the twenty-one TNBC patients that received bicalutamide therapy were subjected to intrinsic subtype classification into the Luminal A, Luminal B, Basal-like, HER2-enriched and Normal-like groups using the PAM50 classification model. Each subtype score for each sample is listed in Table 3. Also set forth in Table 3 is the Weighted Basal and Luminal A classifier score of each sample. Based on the results obtained in Example 6 from the clinical trial of the AR-receptor antagonist enzalutamide, a greater than −0.25 Weighted Basal and Luminal A classifier score ("PR-AR DX +>−0.25") indicates that such patients are more likely to respond to the bicalutamide treatment than patients with a Weighted Basal and Luminal A classifier score of less than or equal to −0.25. Eight patients satisfied this criterion, and are designated in Table 3 as having a likely positive ("POS") prognosis on bicalutamide treatment. Each of the 21 patient samples displayed a confidence level of 1, except for sample No. 16, which had a confidence level of 0.99.

effects of enzalutamide alone or in combination with paclitaxel on androgen receptor signaling, cells (BT549, MDA-MB-436 or MDA-MB-453) were seeded on day one in 10% FBS. The cells were treated with enzalutamide or paclitaxel or the combination in 2% charcoal-stripped serum and were stimulated with 10 nM DHT for 4 hours. Cell fractionation was isolated for cytosolic and nuclear fractions. Protein expression levels were determined using a Western blotting method. The $IC_{50}$ for enzalutamide or paclitaxel for each cell line is shown in Table 4. Mean values are presented for each cell line (n=3). The prognostic marker-positive MDA-MB-453 cells exhibited greater sensitivity to enzalutamide compared to the prognostic marker-negative BT549 and MDA-MB-463 cells.

TABLE 4

| Cell Line | Enzalutamide $IC_{50}$ (µM) | Paclitaxel $IC_{50}$ (nM) |
|---|---|---|
| BT549 | 57.0 | 2.8 |
| MDA-MB-436 | 73.0 | 6.7 |
| MDA-MB-453 | 22.7 | 20.7 |

TABLE 3

| No. | Basal Score | Her2 Score | LumA Score | LumB Score | Normal Score | Weighted Basal/LumA Score | Prognosis |
|---|---|---|---|---|---|---|---|
| 1 | 0.542569 | −0.02857 | −0.59846 | 0.242161 | −0.25186 | −0.29354 | NEG |
| 2 | 0.405618 | −0.17714 | −0.11635 | −0.30343 | 0.296423 | −0.13115 | POS |
| 3 | 0.509628 | 0.038367 | −0.3915 | −0.20711 | 0.059208 | −0.23021 | POS |
| 4 | 0.753469 | 0.003025 | −0.59088 | −0.28912 | 0.055078 | −0.34357 | NEG |
| 5 | 0.766146 | −0.00543 | −0.69729 | −0.08581 | −0.07851 | −0.37508 | NEG |
| 6 | 0.638896 | −0.34665 | −0.22439 | −0.54103 | 0.447779 | −0.21755 | POS |
| 7 | 0.75078 | 0.112509 | −0.7188 | −0.01945 | −0.11001 | −0.37702 | NEG |
| 8 | 0.795342 | 0.039808 | −0.66511 | −0.22968 | 0.052293 | −0.37371 | NEG |
| 9 | 0.793421 | −0.06708 | −0.59818 | −0.372 | 0.158127 | −0.35538 | NEG |
| 10 | 0.699496 | −0.23275 | −0.43616 | −0.26617 | 0.192221 | −0.28898 | NEG |
| 11 | 0.634478 | −0.15333 | −0.33906 | −0.49273 | 0.304298 | −0.24704 | POS |
| 12 | 0.729556 | −0.15188 | −0.48984 | −0.35529 | 0.206531 | −0.31072 | NEG |
| 13 | 0.721104 | 0.015222 | −0.66387 | −0.074 | −0.03558 | −0.35505 | NEG |
| 14 | 0.747419 | −0.26098 | −0.42406 | −0.40687 | 0.255414 | −0.29758 | NEG |
| 15 | 0.702089 | −0.04 | −0.53719 | −0.25522 | 0.095414 | −0.31657 | NEG |
| 16 | 0.161104 | −0.10146 | −0.01647 | −0.29834 | 0.383721 | −0.04416 | POS |
| 17 | 0.571477 | −0.12826 | −0.27549 | −0.34146 | 0.260024 | −0.21453 | POS |
| 18 | 0.399184 | −0.03741 | −0.21268 | −0.22113 | 0.090708 | −0.15525 | POS |
| 19 | 0.622089 | −0.18588 | −0.31313 | −0.58329 | 0.431741 | −0.23706 | POS |
| 20 | 0.752797 | −0.13546 | −0.55064 | −0.40072 | 0.161008 | −0.33267 | NEG |
| 21 | 0.736567 | −0.1346 | −0.58339 | −0.24216 | 0.082737 | −0.3374 | NEG |

Example 16

The following study demonstrates the enhanced antitumor effect of the combination of enzalutamide plus paclitaxel in cells positive for the prognostic marker of a Weighted Basal and Luminal A classifier score greater than −0.25.

Triple negative breast cancer cell lines BT549, MDA-MB-436, MDA-MB-453 were selected for study. Messenger RNA datasets for the cell lines were down-loaded from the Cancer Cell Line Encyclopedia (CCLE) database. The Weighted Basal and Luminal A classifier score for each cell line was determined from the downloaded datasets. Applying a Weighted Basal and Luminal A classifier score of >−0.25 as a prognostic marker for responsiveness to AR inhibitor therapy, it was determined that MDA-MB-453, but not BT549 and MDA-MB-436, satisfied this criterion.

Cells were maintained in 10% FBS supplemented growth media. Viability assays were performed in 10% FBS, and measured by CellTiter-Glo reagent according to the manufacturer's protocol (Promega). To determine molecular Viability of the cells was measured in the presence of the concentrations of enzalutamide (Enza) and paclitaxel (PTX) in FIGS. 24A-C. Mean values are presented for each cell line (n=5). In the prognostic marker-positive MDA-MB-453 cell line, the combination of enzalutamide plus paclitaxel resulted in enhanced cytotoxicity. See FIG. 24C.

Example 17

To generate a mouse xenograft model, 5- to 6-week-old female NOD-SCID mice were injected orthotopically into the mammary gland with $6.0 \times 10^6$ MDA-MB-453 cells. DHT (10.5 mg in a 60-day release pellet) or control pellets were implanted into animals. When tumor size reached ~100 mm³, mice were treated by (i) oral gavage (PO) with enzalutamide ("Enza") at 3 mg/kg/day (n=10), (ii) paclitaxel ("PTX") at 6 mg/kg QMWF (IP) (n=7), or (iii) the combination of (i) and (ii) (n=10). A control group of mice (n=8) was treated with vehicle (0.5% Methocel solution). Tumor size was measured by caliper. Tumor weights were determined at day 35. The results are shown in FIG. 25A (tumor volume vs. time) and FIG. 25B (tumor weight). Data points in FIG. 25A represent the average tumor volume for each group, and error bars reflect the SEM of the data. The student T-Test was used to calculate p values: FIG. 25A: control v. enzalutamide, 0.007; control v. paclitaxel, 0.0007; enzalutamide vs. enzalutamide plus paclitaxel, 0.074; paclitaxel vs. enzalutamide plus paclitaxel, 0.013. FIG. 25B: control v. enzalutamide, 0.001; control v. paclitaxel, 0.0001; enzalutamide vs. enzalutamide plus paclitaxel, 0.08; paclitaxel vs. enzalutamide plus paclitaxel, 0.017. The data demonstrates that the combination of enzalutamide plus paclitaxel results in enhanced antitumor effect compared to either drug alone.

Representative tumors from each treated group were selected to perform immunohistochemistry against AR, Ki67 or p-AKT. Immunohistochemistry staining for Ki67 or AKT phosphorylation was significantly reduced in the enzalutamide plus paclitaxel tumors compared to the enzalutamide or paclitaxel single treated group (data not shown).

The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

The invention claimed is:

1. A method of treating triple negative breast cancer in a subject, said subject having a breast cancer comprising breast cancer cells that have been classified as other than basal-like subtype, said method comprising:
   testing the subject to determine the Weighted Basal and Luminal A classifier score of breast cancer cells of the subject; and
   administering a breast cancer treatment to the subject comprising an androgen receptor inhibitor, thereby treating the triple negative breast cancer in the subject;
   wherein the breast cancer cells of the subject are characterized by a Weighted Basal and Luminal A classifier score greater than −0.3 according to the formula:

Weighted Basal and Luminal A classifier score= −0.25(Basal Centroid classifier score)+0.27(Luminal A Centroid classifier score)

wherein said Basal Centroid classifier score and said Luminal A Centroid classifier score are determined for the breast cancer cells of the subject from the expression by said cells of the set of intrinsic genes listed in Table 1.

2. The method according to claim 1, wherein the breast cancer cells of the subject are characterized by a Weighted Basal and Luminal A classifier score greater than −0.2.

3. The method according to claim 1, wherein the breast cancer cells of the subject are characterized by a Weighted Basal and Luminal A classifier score greater than −0.25.

4. The method according to claim 1, wherein the breast cancer of the subject is characterized by the presence of androgen receptor-positive tumor cells.

5. The method according to claim 1, wherein the androgen receptor inhibitor is selected from the group consisting of enzalutamide, bicalutamide, flutamide, nilutamide, ARN509, ketoconazole, abiraterone acetate, VN/124-1 (TOK-001), orteronel (TAK-700), finasteride, galeterone, cyproterone acetate, andarine, and combinations thereof.

6. The method according to claim 5, wherein the androgen receptor inhibitor is enzalutamide.

7. The method according to claim 1, wherein the androgen receptor inhibitor is enzalutamide.

8. The method according to claim 2, wherein the androgen receptor inhibitor is enzalutamide.

9. The method according to claim 3, wherein the androgen receptor inhibitor is enzalutamide.

10. The method according to claim 6, wherein the enzalutamide is orally administered once daily at a dose of 160 mg.

11. The method according to claim 10, wherein the enzalutamide is administered as a single capsule comprising 160 mg enzalutamide.

12. The method according to claim 10, wherein the enzalutamide is administered as four capsules, each capsule comprising 40 mg enzalutamide.

13. The method according to claim 1, wherein the breast cancer treatment comprising an androgen receptor inhibitor further comprises one or more other anti-cancer agents that is not an androgen receptor inhibitor.

14. The method according to claim 13, wherein the other anti-cancer agent that is not an androgen receptor inhibitor is selected from the group consisting of cyclophosphamide, fluorouracil, 5-fluorouracil, methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserelin, goserelin, megestrol acetate, risedronate, pamidronate, ibandronate, alendronate, denosumab, zoledronate, trastuzumab, tykerb, bevacizumab, and combinations thereof.

15. The method according to claim 14 wherein the other anti-cancer agent hat is not an androgen receptor inhibitor is paclitaxel.

16. The method according to claim 1, further comprising a step of testing the subject to determine whether the subject has a breast cancer comprising breast cancer cells that are other than basal-like subtype.

17. The method according to claim 3, wherein the subject has received zero or one round of prior treatment with an anti-cancer agent, other than an androgen receptor inhibitor, for treatment of triple negative breast cancer.

18. A method of treating triple negative breast cancer in a subject in need of such treatment comprising:
   (a) providing a biological sample from the subject;
   (b) assaying the biological sample to determine whether the biological sample is classified as a basal-like subtype or another subtype; and
   (c) if the biological sample is classified as other than a basal-like subtype, administering a breast cancer treatment to the subject comprising an androgen receptor inhibitor, thereby treating the breast cancer in the subject.

19. The method of claim 18, wherein assaying the biological sample to determine whether the biological sample is classified as a basal-like subtype or another subtype is performed by detecting the expression of the intrinsic genes listed in Table 1.

20. The method according to claim 19, comprising:
(a) determining the Basal Centroid classifier score and the Luminal A Centroid classifier score of the sample from the expression of the set of intrinsic genes listed in Table 1; and
(b) calculating a Weighted Basal and Luminal A classifier score from the Basal Centroid classifier score and the Luminal A Centroid classifier score according to the following equation:

Weighted Basal and Luminal A classifier score =−0.25(Basal Centroid classifier score)+ 0.27(Luminal A Centroid classifier score); and wherein the breast cancer treatment is administered to the subject if the Weighted Basal and Luminal A classifier score is greater than −0.3.

21. The method according to claim 20, wherein the breast cancer treatment is administered if the Weighted Basal and Luminal A classifier score is greater than −0.2.

22. The method according to claim 20, wherein the breast cancer treatment is administered if the Weighted Basal and Luminal A classifier score is greater than −0.25.

23. The method according to claim 19, comprising determining the Basal Centroid classifier score of the sample from the expression of the set of intrinsic genes listed in Table 1, wherein the breast cancer treatment is administered if the Basal Centroid classifier score is less than or equal to 0.9.

24. The method according to claim 23 wherein the breast cancer treatment is administered if the Basal Centroid classifier score is less than or equal to 0.6.

25. The method according to claim 23, wherein a breast cancer treatment is administered to the subject if the Basal Centroid classifier score is in the range from 0.2 to 0.8.

26. The method according to claim 22, wherein a breast cancer treatment is administered to the subject if the Basal Centroid classifier score is in the range from 0.4 to 0.7.

27. The method according to claim 18, wherein the breast cancer of the subject is characterized by the presence of androgen receptor-positive tumor cells.

28. The method according to claim 18, wherein the androgen receptor inhibitor is selected from the group consisting of enzalutamide, bicalutamide, flutamide, nilutamide, ARN509, ketoconazole, abiraterone acetate, VN/124-1 (TOK-001), orteronel (TAK-700) finasteride, galeterone, cyproterone acetate, andirine, and combinations thereof.

29. The method according to claim 28, wherein the androgen receptor inhibitor is enzalutamide.

30. The method according to claim 20 wherein the androgen receptor inhibitor is enzalutamide.

31. The method according to claim 21, wherein the androgen receptor inhibitor is enzalutamide.

32. The method according to claim 22, wherein the androgen receptor inhibitor is enzalutamide.

33. The method according to claim 29, wherein the enzalutamide is orally administered once daily at a dose of 160 mg.

34. The method according to claim 33, wherein the enzalutamide is administered as a single capsule comprising 160 mg enzalutamide.

35. The method according to claim 33, wherein the enzalutamide is administered as four capsules, each capsule comprising 40 mg enzalutamide.

36. The method according to claim 18, wherein the breast cancer treatment comprising an androgen receptor inhibitor further comprises one or more other anti-cancer agents that is not an androgen receptor inhibitor.

37. The method according to claim 36, wherein the other anti-cancer agent that is not an androgen receptor inhibitor is selected from the group consisting of cyclophosphamide, fluorouracil, 5-fluorouracil, methotrexate, ethotrexate, thiotepa, carboplatin, cisplatin, taxanes, paclitaxel, protein; bound paclitaxel, docetaxel, vinorelbine, tamoxifen, raloxifene, toremifene, fulvestrant, gemcitabine, irinotecan, ixabepilone, temozolmide, topotecan, vincristine, vinlblastine, eribulin, irautamycin, capecitabine, anastrozole, exemestane, letrozole, leuprolide, abarelix, buserelin, goserelin, megestrol acetate, risedronate, parnidronate, ibandronate, alendronate, denosumab, zoledronate, trastuzumab, tykerb, bevacizumab, and combinations thereof.

38. The method according to claim 37 wherein the other anti-cancer agent that is not an androgen receptor inhibitor is paclitaxel.

39. The method according to claim 18, wherein the biological sample is selected from the group consisting of a cell, tissue, and bodily fluid.

40. The method according to claim 39, wherein the biological sample comprises breast tissue or cells.

41. The method of claim 40, wherein the tissue is obtained from a biopsy.

42. The method of claim 40, wherein the bodily fluid is selected from the group consisting of blood, lymph, urine, saliva, fluid from ductal lavage, and nipple aspirate.

43. The method according to claim 22, wherein the subject has received zero or one round of prior treatment with an anti-cancer agent, other than an androgen receptor inhibitor, for treatment of triple negative breast cancer.

44. The method according to claim 20, wherein the androgen receptor inhibitor is selected from the group consisting of enzalutamide, bicalutamide flutamide, nilutamide, ARN509, ketoconazole, abiraterone acetate, VN/124-1 (TOK-001), orteronel (TAK-700), finasteride, galeterone, cyproterone acetate, andarine, and combinations thereof.

45. The method according to claim 21, wherein the androgen receptor inhibitor is selected from the group consisting of enzalutamide, bicalutamide, flutamide, nilutamide, ARN509, ketoconazole, abiraterone acetate, VN/124-1 (TOK-001), orteronel (TAK-700), finasteride, galeterone, cyproterone acetate, andarine, and combinations thereof.

46. The method according to claim 23, wherein the androgen receptor inhibitor is selected from the group consisting of enzalutainide, bicalutamide, flutamide, nilutamide, ARN509, ketoconazole, abiraterone acetate, VN/124-1 (TOK-001), orteronel (TAK-700), finasteride, galeterone, cyproterone acetate, andarine, and combinations thereof.

47. The method according to claim 23, wherein the androgen receptor inhibitor is enzalutamide.

48. The method according to claim 26, wherein the androgen receptor inhibitor is selected from the group consisting of enzalutamide, hicalutamide, flutamide, nilutamide, ARN509, ketoconazole, abiraterone acetate, VN/124-1 (TOK-001), orteronel (TAK-700), finasteride, galeterone, cyproterone acetate, andarine, and combinations thereof.

49. The method according to claim 26, wherein the androgen receptor inhibitor is enzalutamide.

50. The method according to claim 20, wherein the breast cancer treatment comprising an androgen receptor inhibitor further comprises one or more other anti-cancer agents that is not an androgen receptor inhibitor.

51. The method according to claim 21, wherein the breast cancer treatment comprising an androgen receptor inhibitor further comprises one or more other anti-cancer agents that is not an androgen receptor inhibitor.

52. The method according to claim 23, wherein the breast cancer treatment comprising an androgen receptor inhibitor further comprises one or more other anti-cancer agents that is not an androgen, receptor inhibitor.

53. The method according to claim 26, wherein the breast cancer treatment comprising an androgen receptor inhibitor further comprises one or more other anti-cancer agents that is not an androgen receptor inhibitor.

54. The method according to claim 50, wherein the other anti-cancer agent that is not an androgen receptor inhibitor is selected from the group consisting cyclophosphamide, fluorouracil, 5-fluorouracil, methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserelin, goserelin, megestrol acetate, risedronate, pamidronate, ibandronate, alendronate, denosumab, zoledronate, trastuzumab, tykerb, bevacizumab, and combinations thereof.

55. The method according to claim 51, wherein the other anti-cancer agent that is not an androgen receptor inhibitor is selected from the group consisting of cyclophosphamide, fluorouracil, 5-fluorouracil, methotrexate, thiotepa, carboplatin, cisplatin, taxanes, paclitaxel, protein-bound paclitaxel, docetaxel, vinorelbine, tamoxifen, raloxifene, toremifene, fulvestrant, gemeitabine, irinotecan, ixabepilone, temozolmide, topotecan, vincristine, vinblastine, eribulin, mutamycin, capecitabine, anastrozole, exemestane, letrozole, leuprolide, abarelix, buserelin, goserelin, megestrol acetate, risedronate, pamidronate, ibandronate, alendronate, denosumab, zoledronate, trastuzumab, tykerb, bevacizumab, and combinations thereof.

56. The method according to claim 52, wherein the other anti-cancer agent that is not an androgen receptor inhibitor is selected from the group consisting of cyclophosphamide, fluorouracil, 5-fluorouracil, methotrexate, thiotepa, carboplatin, cisplatin, taxanes, paclitaxel, protein-bound paclitaxel, docetaxel, vinorelbine, tamoxifen, raloxifene, torernifene, fulvestrant, gemcitabine, irinotecan, ixabepilone, ternozolmide, topotecan, vincristine, vinblastine, eribulin, mutamycin, capecitabine, anastrozole, exemestane, letrozole, leuprolide, abarelix, buserelin, goserelin, megestrol acetate, risedronate, pamidronate, ibandronate, alendronate, denosumab, zoledronate, trastuzumab, tykerb, bevacizumab, and combinations thereof.

57. The method according to claim 53, wherein the other anti-cancer agent that is not an androgen receptor inhibitor is selected from the group consisting of cyclophosphamide, fluorouracil, 5-fluorouracil, methotrexate, thiotepa, carboplatin, cisplatin, taxanes, paclitaxel, protein-bound paclitaxel, docetaxel, vinoreibine, tamoxifen, raloxifene, toremifene, fulvestrant, gemcitabine, irinotecan, ixabepilone, temozolmide, topotecan, vincristine, vinblastine, mutamycin, capecitabine, anastrozole, exemestane, letrozole, leuprolide, abarelix, buserelin, goserelin, megestrol acetate, risedronate, pamidronate, ibandronate, alendronate, denosumab, zoledronate, trasutzumab, tykerb, bevacizumab, and combinations thereof.

58. The method according to claim 20, wherein the breast cancer treatment comprising an androgen receptor inhibitor further comprises one or more other anti-cancer agents that is not an androgen receptor inhibitor, wherein the androgen receptor inhibitor is enzalutamide.

59. The method according to claim 21, wherein the breast cancer treatment comprising an androgen receptor inhibitor further comprises one or more other anti-cancer agents that is not an androgen receptor inhibitor, wherein the androgen receptor inhibitor is enzalutamide.

60. The method according to claim 23, wherein the breast cancer treatment comprising an androgen receptor inhibitor further comprises one or more other anti-cancer agents that is not an androgen receptor inhibitor, wherein the androgen receptor inhibitor is enzalutamide.

61. The method according to claim 26, wherein the breast cancer treatment comprising an androgen receptor inhibitor further comprises one or more other anti-cancer agents that is not an, androgen receptor inhibitor, wherein the androgen receptor inhibitor is enzalutamide.

* * * * *

```
                        SEQUENCE LISTING

<160> NUMBER OF SEQ ID NOS: 151

<210> SEQ ID NO 1
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 1
aaagattcct gggacctga                                                    19

<210> SEQ ID NO 2
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 2
acagccactt tcagaagcaa g                                                 21

<210> SEQ ID NO 3
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 3
ctggaagagt tgaataaaga gc                                                22

<210> SEQ ID NO 4
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 4
tacctgaacc ggcacctg                                                     18

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized primer
```

```
<400> SEQUENCE: 5
gcacaaagcc attctaagtc                                                    20

<210> SEQ ID NO 6
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 6
gctggctgag cagaaag                                                       17

<210> SEQ ID NO 7
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 7
ctttcgcctg agcctattt                                                     19

<210> SEQ ID NO 8
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 8
ggccaaaatc gacaggac                                                      18

<210> SEQ ID NO 9
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 9
ctgtctgagt gccgtggat                                                     19

<210> SEQ ID NO 10
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 10
gtaaatcacc ttctgagcct                                                    20

<210> SEQ ID NO 11
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 11
ggaggcggaa gaaaccag                                                      18

<210> SEQ ID NO 12
<211> LENGTH: 24
```

```
<212> TYPE: DNA
<213> ORGANISM: Artificial Sequence
<220> FEATURE:
<223> OTHER INFORMATION: Chemically synthesized primer

<400> SEQUENCE: 12
gacaaggaga atcaaaagat cagc                                              24

<210> SEQ ID NO 13
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 13
gtggcagcag atcacaa                                                      17

<210> SEQ ID NO 14
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 14
cctcacgaat tgctgaactt                                                   20

<210> SEQ ID NO 15
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 15
catgaaatag tgcatagttt gcc                                               23

<210> SEQ ID NO 16
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 16
acacagaatc tatacccacc agagt                                             25

<210> SEQ ID NO 17
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 17
gctggctctc acactgatag                                                   20

<210> SEQ ID NO 18
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 18
```
gcagggagag gagtttgt                                                  18

<210> SEQ ID NO 19
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 19
cccatccatg tgaggaagta taa                                            23

<210> SEQ ID NO 20
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 20
cttcttggac cttggcg                                                   17

<210> SEQ ID NO 21
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 21
gctactacgc agacacg                                                   17

<210> SEQ ID NO 22
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 22
gatgttcgag tcacagagg                                                 19

<210> SEQ ID NO 23
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 23
ttcggctgga aggaacc                                                   17

<210> SEQ ID NO 24
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 24
cgtggcagat gtgaacga                                                  18

<210> SEQ ID NO 25
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 25
ggagatccgt caactccaaa                                               20

<210> SEQ ID NO 26
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 26
tgggtcgtgt caggaaac                                                 18

<210> SEQ ID NO 27
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 27
cgcagtcatc cagagatgtg                                               20

<210> SEQ ID NO 28
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 28
actcagtaca agaaagaacc g                                             21

<210> SEQ ID NO 29
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 29
gttggaccag tcaacatctc tg                                            22

<210> SEQ ID NO 30
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 30
tgtggctcat taggcaac                                                 18

<210> SEQ ID NO 31
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 31
gactccaagc gcgaaaac                                                 18

<210> SEQ ID NO 32
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 32
ccaacaaaat attcatggtt cttg                                    24

<210> SEQ ID NO 33
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 33
ccagtagcat tgtccgag                                           18

<210> SEQ ID NO 34
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 34
gtctctggta atgcacact                                          19

<210> SEQ ID NO 35
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 35
gtggaatgcc tgctgacc                                           18

<210> SEQ ID NO 36
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 36
aggggtgccc tctgagat                                           18

<210> SEQ ID NO 37
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 37
cgagatcgcc aagatgtt                                           18

<210> SEQ ID NO 38
<211> LENGTH: 18
<212> TYPE: DNA
<213> ORGANISM: Artificial Sequence
<220> FEATURE:
<223> OTHER INFORMATION: Chemically synthesized primer

```
<400> SEQUENCE: 38
aggcgaacac acaacgtc                                              18

<210> SEQ ID NO 39
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 39
agcctcgaac aattgaaga                                             19

<210> SEQ ID NO 40
<211> LENGTH: 27
<212> TYPE: DNA
<213> ORGANISM: Artificial Sequence
<220> FEATURE:
<223> OTHER INFORMATION: Chemically synthesized primer

<400> SEQUENCE: 40
atcgactgtg taaacaacta gagaaga                                    27

<210> SEQ ID NO 41
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 41
tttaagaggg caatggaagg                                            20

<210> SEQ ID NO 42
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 42
tgccgcagaa ctcacttg                                              18

<210> SEQ ID NO 43
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 43
cctcagatga tgcctatcca                                            20

<210> SEQ ID NO 44
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 44
cagcaagcga tggcatagt                                             19

<210> SEQ ID NO 45
```

```
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 45
aatgccaccg aagcctc                                                    17

<210> SEQ ID NO 46
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 46
tcgaactgaa ggctatttac gag                                             23

<210> SEQ ID NO 47
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 47
gtcgaagccg caattagg                                                   18

<210> SEQ ID NO 48
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 48
caaacgtgtg ttctggaagg                                                 20

<210> SEQ ID NO 49
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 49
tgccctgtat gatgtcagga                                                 20

<210> SEQ ID NO 50
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 50 gtgagggtg tcagctcagt                                                  20

<210> SEQ ID NO 51
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 51
```

```
tggggcagtt ctgtattact tc                                                  22

<210> SEQ ID NO 52
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 52
cgatggtttt gtacaagatt tctc                                                24

<210> SEQ ID NO 53
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 53
gcaaatcctt gggcaga                                                        17

<210> SEQ ID NO 54
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 54
gccgtacagt tccacaaagg                                                     20

<210> SEQ ID NO 55
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 55
gacgcttcct atcactctat tc                                                  22

<210> SEQ ID NO 56
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 56
ttcctccatc aagagttcaa ca                                                  22

<210> SEQ ID NO 57
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 57
gggcacatcc agatgttt                                                       18

<210> SEQ ID NO 58
<211> LENGTH: 19
<212> TYPE: DNA
```

```
<213> ORGANISM: Artificial Sequence
<220> FEATURE:
<223> OTHER INFORMATION: Chemically synthesized primer

<400> SEQUENCE: 58
gggtctgcac agactgcat                                                    19

<210> SEQ ID NO 59
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 59
tccttgtaat ggggagacca                                                   20

<210> SEQ ID NO 60
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 60
acttgggata tgtgaataag acc                                               23

<210> SEQ ID NO 61
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 61
ggggaaagac aaagtttcca                                                   20

<210> SEQ ID NO 62
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 62
actgtctggg tccatggcta                                                   20

<210> SEQ ID NO 63
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 63
ggatttcgtg gtgggttc                                                     18

<210> SEQ ID NO 64
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 64
ccacagtctg tgataaacgg                                                   20
```

<210> SEQ ID NO 65
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 65
ccatcaacat tctctttatg aacg                                          24

<210> SEQ ID NO 66
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 66
atcaactccc aaacggtcac                                               20

<210> SEQ ID NO 67
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 67
gcccttacac atcggagaac                                               20

<210> SEQ ID NO 68
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 68
gacttcaggg tgctggac                                                 18

<210> SEQ ID NO 69
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 69
tgtgaagcca gcaatatgta tc                                            22

<210> SEQ ID NO 70
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 70
tattgggagg caggaggttt a                                             21

<210> SEQ ID NO 71
<211> LENGTH: 20
<212> TYPE: DNA
<213> ORGANISM: Artificial Sequence
<220> FEATURE:

```
<223> OTHER INFORMATION: Chemically synthesized primer

<400> SEQUENCE: 71
ctgagttcat gttgctgacc                                               20

<210> SEQ ID NO 72
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 72
gacagctact attcccgtt                                                19

<210> SEQ ID NO 73
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 73
tatgtgagta agctcggaga c                                             21

<210> SEQ ID NO 74
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 74
agtgggcatc ccgtaga                                                  17

<210> SEQ ID NO 75
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 75
agtggacatg cgagtggag                                                19

<210> SEQ ID NO 76
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 76
caccgctgga aactgaac                                                 18

<210> SEQ ID NO 77
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 77
cgtgcacatc catgacctt                                                19
```

```
<210> SEQ ID NO 78
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 78
gaggagatga ccttgcc                                                    17

<210> SEQ ID NO 79
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 79
gccatagcca ctgccact                                                   18

<210> SEQ ID NO 80
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 80
cttcgactgg actctgt                                                    17

<210> SEQ ID NO 81
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 81
cagacatgtt ggtattgcac att                                             23

<210> SEQ ID NO 82
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 82
aggcgatcct gggaaattat                                                 20

<210> SEQ ID NO 83
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 83
cccatttgtc tgtcttcac                                                  19

<210> SEQ ID NO 84
<211> LENGTH: 18
<212> TYPE: DNA
<213> ORGANISM: Artificial Sequence
<220> FEATURE:
<223> OTHER INFORMATION: Chemically synthesized primer
```

<400> SEQUENCE: 84
ctgatggttg aggctgtt                                                 18

<210> SEQ ID NO 85
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 85
cgcactccag cacctagac                                                19

<210> SEQ ID NO 86
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 86
tcacagggtc aaacttccag t                                             21

<210> SEQ ID NO 87
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 87
gatggtagag ttccagtgat t                                             21

<210> SEQ ID NO 88
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 88
tctggtcacg cagggcaa                                                 18

<210> SEQ ID NO 89
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 89
acacagatga tggagatgtc                                               20

<210> SEQ ID NO 90
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 90
agtagctaca tctccaggtt ctctg                                         25

<210> SEQ ID NO 91
<211> LENGTH: 21

```
<212> TYPE: DNA
<213> ORGANISM: Artificial Sequence
<220> FEATURE:
<223> OTHER INFORMATION: Chemically synthesized primer

<400> SEQUENCE: 91 cggatttat caacgatgca g                                              21

<210> SEQ ID NO 92
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 92
catttgccgt ccttcatcg                                                19

<210> SEQ ID NO 93
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 93
gcaggtcaaa actctcaaag                                               20

<210> SEQ ID NO 94
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 94
agcgggcttc tgtaatctga                                               20

<210> SEQ ID NO 95
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 95
gcctcagatt tcaactcgt                                                19

<210> SEQ ID NO 96
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 96
ctgctgagaa tcaaagtggg a                                             21

<210> SEQ ID NO 97
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 97
```
ggaacaaact gctctgcca                                                19

<210> SEQ ID NO 98
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 98
acagctcttt agcatttgtg ga                                            22

<210> SEQ ID NO 99
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 99
gggactatca atgttgggtt ctc                                           23

<210> SEQ ID NO 100
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 100
cacacagttc actgctccac a                                             21

<210> SEQ ID NO 101
<211> LENGTH: 2199
<212> TYPE: DNA
<213> ORGANISM: Homo sapiens

<400> SEQUENCE: 101
cagcggcgct gcggcggctc gcgggagacg ctgcgcgcgg ggctagcggg cggcggagcg      60
gacggcgacg gggcgctctc gggctgccgg cggggccgag cgccgcgcgt cccgagcatg     120
gcaggctccc tgcctcccta cgtggtggac tgtggcaccg ggtataccaa gcttggctac     180
gcaggcaaca ctgagcccca gttcattatt ccttcatgta ttgccatcag agagtcagca     240
aaggtagttg accaagctca aaggagagtg ttgaggggag ttgatgacct tgactttttc     300
ataggagatg aagccatcga taaacctaca tatgctacaa agtggccgat acgacatgga     360
atcattgaag actgggatct tatggaaagg ttcatggagc aagtggtttt taaatatctt     420
cgagctgaac ctgaggacca ttatttttta atgacagaac ctccactcaa tacaccagaa     480
aacagagagt atcttgcaga aattatgttt gaatcattta cgtaccagg actctacatt     540
gcagttcagg cagtgctggc cttggcggca tcttggacat ctcgacaagt gggtgaacgt     600
acgttaacgg ggatagtcat tgacagcgga gatgagtca cccatgttat cccagtggca     660
gaaggttatg taattggaag ctgcatcaaa cacatcccga ttgcaggtag agatattacg     720
tatttcattc aacagctgct aagggagagg gaggtgggaa tccctcctga gcagtcactg     780
gagaccgcaa aagccattaa ggagaaatac tgttacattt gccccgatat agtcaaggaa     840
tttgccaagt atgatgtgga tcccggaag tggatcaaac agtacacggg tatcaatgcg     900
atcaaccaga gaagtttgt tatagacgtt ggttacgaaa gattcctggg acctgaaata     960
ttctttcacc cggagtttgc caacccagac tttatggagt ccatctcaga tgttgttgat    1020

```
gaagtaatac agaactgccc catcgatgtg cggcgcccgc tgtataagaa tgtcgtactc    1080
tcaggaggct ccaccatgtt cagggatttc ggacgccgac tgcagaggga tttgaagaga    1140
gtggtggatg ctaggctgag gctcagcgag gagctcagcg gcgggaggat caagccgaag    1200
cctgtggagg tccaggtggt cacgcatcac atgcagcgct acgccgtgtg gttcggaggc    1260
tccatgctgg cctcgactcc cgagttcttt caggtctgcc acaccaagaa ggactatgaa    1320
gagtacgggc ccagcatctg ccgccacaac cccgtctttg gagtcatgtc ctagtgtctg    1380
cctgaacgcg tcgttcgatg gtgtcacgtt ggggaacaag tgtccttcag aacccagaga    1440
aggccgccgt tctgtaaata gcgacgtcgg tgttgctgcc cagcagcgtg cttgcattgc    1500
cggtgcatga ggcgcggcgc gggccccttca gtaaaagcca tttatccgtg tgccgaccgc    1560
tgtctgccag cctcctcctt ctcccgccct cctcaccctc gctctccctc ctcctcctcc    1620
tccgagctgc tagctgacaa atacaattct gaaggaatcc aaatgtgact ttgaaaattg    1680
ttagagaaaa caacattaga aaatggcgca aaatcgttag gtcccaggag agaatgtggg    1740
ggcgcaaacc cttttcctcc cagcctattt ttgtaaataa aatgtttaaa cttgaaatac    1800
aaatcgatgt ttatatttcc tatcattttg tattttatgg tatttggtac aactggctga    1860
tactaagcac gaatagatat tgatgttatg gagtgctgta atccaaagtt tttaattgtg    1920
aggcatgttc tgatatgttt ataggcaaac aaataaaaca gcaaactttt ttgccacatg    1980
tttgctagaa aatgattata ctttattgga gtgacatgaa gtttgaacac taaacagtaa    2040
tgtatgagaa ttactacaga tacatgtatc ttttagtttt ttttgtttga actttctgga    2100
gctgttttat agaagatgat ggtttgttgt cggtgagtgt tggatgaaat acttccttgc    2160
accattgtaa taaaagctgt tagaatattt gtaaatatc                          2199
```

<210> SEQ ID NO 102
<211> LENGTH: 1989
<212> TYPE: DNA
<213> ORGANISM: Homo sapiens

<400> SEQUENCE: 102

```
cagcggcgct gcggcggctc gcgggagacg ctgcgcgcgg ggctagcggg cggcggagcg      60
gacggcgacg gggcgctctc gggctgccgg cggggccgag cgccgcgcgt cccgagcatg     120
gcaggctccc tgcctcccctg cgtggtggac tgtggcaccg ggtataccaa gcttggctac     180
gcaggcaaca ctgagcccca gttcattatt ccttcatgta ttgccatcag agagtcagca     240
aaggtagttg accaagctca aaggagagtg ttgagggggag ttgatgacct tgactttttc     300
ataggagatg aagccatcga taaacctaca tatgctacaa agtggccgat acgacatgga     360
atcattgaag actgggatct tatggaaagg ttcatggagc aagtggtttt taaatatctt     420
cgagctgaac ctgaggacca ttattttta atgacagaac ctccactcaa tacaccagaa     480
aacagagagt atcttgcaga aattatgttt gaatcattta acgtaccagg actctacatt     540
gcagttcagg cagtgctggc cttggcggca tcttggacat ctcgacaagt gggtgaacgt     600
acgttaacgg ggatagtcat tgacagcgga gatggagtca cccatgttat cccagtggca     660
gaaggttatg taattggaag ctgcatcaaa cacatcccga ttgcaggtag agatattacg     720
tatttcattc aacagctgct aagggagagg gaggtgggaa tccctcctga gcagtcactg     780
gagaccgcaa aagccattaa ggagaaatac tgttacattt gccccgatat agtcaaggaa     840
tttgccaagt atgatgtgga tccccggaag tggatcaaac agtacacggg tatcaatgcg     900
```

| | | | | |
|---|---|---|---|---|
| atcaaccaga | agaagtttgt | tatagacgtt | ggttacgaaa | gattcctggg | acctgaaata | 960 |
| ttctttcacc | cggagtttgc | caacccagac | tttatggagt | ccatctcaga | tgttgttgat | 1020 |
| gaagtaatac | agaactgccc | catcgatgtg | cggcgcccgc | tgtataagcc | cgagttcttt | 1080 |
| caggtctgcc | acaccaagaa | ggactatgaa | gagtacgggc | ccagcatctg | ccgccacaac | 1140 |
| cccgtctttg | gagtcatgtc | ctagtgtctg | cctgaacgcg | tcgttcgatg | gtgtcacgtt | 1200 |
| ggggaacaag | tgtccttcag | aacccagaga | aggccgccgt | tctgtaaata | gcgacgtcgg | 1260 |
| tgttgctgcc | cagcagcgtg | cttgcattgc | cggtgcatga | ggcgcggcgc | gggcccttca | 1320 |
| gtaaaagcca | tttatccgtg | tgccgaccgc | tgtctgccag | cctcctcctt | ctcccgccct | 1380 |
| cctcaccctc | gctctccctc | ctcctcctcc | tccgagctgc | tagctgacaa | atacaattct | 1440 |
| gaaggaatcc | aaatgtgact | ttgaaaattg | ttagagaaaa | caacattaga | aaatggcgca | 1500 |
| aaatcgttag | gtcccaggag | agaatgtggg | ggcgcaaacc | cttttcctcc | cagcctattt | 1560 |
| ttgtaaataa | aatgtttaaa | cttgaaatac | aaatcgatgt | ttatatttcc | tatcattttg | 1620 |
| tattttatgg | tatttggtac | aactggctga | tactaagcac | gaatagatat | tgatgttatg | 1680 |
| gagtgctgta | atccaaagtt | tttaattgtg | aggcatgttc | tgatatgttt | ataggcaaac | 1740 |
| aaataaaaca | gcaaacttttt | tgccacatg | tttgctagaa | aatgattata | ctttattgga | 1800 |
| gtgacatgaa | gtttgaacac | taaacagtaa | tgtatgagaa | ttactacaga | tacatgtatc | 1860 |
| ttttagtttt | ttttgtttga | actttctgga | gctgttttat | agaagatgat | ggtttgttgt | 1920 |
| cggtgagtgt | tggatgaaat | acttccttgc | accattgtaa | taaaagctgt | tagaatattt | 1980 |
| gtaaatatc | | | | | 1989 |

<210> SEQ ID NO 103
<211> LENGTH: 4786
<212> TYPE: DNA
<213> ORGANISM: Homo sapiens

<400> SEQUENCE: 103

| | | | | |
|---|---|---|---|---|
| ctcggcgctg | aaattcaaat | ttgaacggct | gcagaggccg | agtccgtcac | tggaagccga | 60 |
| gaggagagga | cagctggttg | tgggagagtt | cccccgcctc | agactcctgg | ttttttccag | 120 |
| gagacacact | gagctgagac | tcactttttct | cttcctgaat | ttgaaccacc | gtttccatcg | 180 |
| tctcgtagtc | cgacgcctgg | ggcgatggat | ccgtttacgg | agaaactgct | ggagcgaacc | 240 |
| cgtgccaggc | gagagaatct | tcagagaaaa | atggctgaga | ggcccacagc | agctccaagg | 300 |
| tctatgactc | atgctaagcg | agctagacag | ccactttcag | aagcaagtaa | ccagcagccc | 360 |
| ctctctggtg | gtgaagagaa | atcttgtaca | aaaccatcgc | catcaaaaaa | acgctgttct | 420 |
| gacaacactg | aagtagaagt | ttctaacttg | gaaaataaac | aaccagttga | gtcgacatct | 480 |
| gcaaaatctt | gttctccaag | tcctgtgtct | cctcaggtgc | agccacaagc | agcagatacc | 540 |
| atcagtgatt | ctgttgctgt | cccggcatca | ctgctgggca | tgaggagagg | gctgaactca | 600 |
| agattggaag | caactgcagc | ctcctcagtt | aaaacacgta | tgcaaaaact | tgcagagcaa | 660 |
| cggcgccgtt | gggataatga | tgatatgaca | gatgacattc | ctgaaagctc | actcttctca | 720 |
| ccaatgccat | cagaggaaaa | ggctgcttcc | cctcccagac | ctctgctttc | aaatgcctcg | 780 |
| gcaactccag | ttggcagaag | gggccgtctg | gccaatcttg | ctgcaactat | ttgctcctgg | 840 |
| gaagatgatg | taaatcactc | atttgcaaaa | caaacagtg | tacaagaaca | gcctggtacc | 900 |
| gcttgtttat | ccaaattttc | ctctgcaagt | ggagcatctg | ctaggatcaa | tagcagcagt | 960 |
| gttaagcagg | aagctacatt | ctgttcccaa | agggatggcg | atgcctcttt | gaataaagcc | 1020 |

-continued

```
ctatcctcaa gtgctgatga tgcgtctttg gttaatgcct caatttccag ctctgtgaaa    1080
gctacttctc cagtgaaatc tactacatct atcactgatg ctaaaagttg tgagggacaa    1140
aatcctgagc tacttccaaa aactcctatt agtcctctga aacgggggt atcgaaacca     1200 attgtgaagt caactttatc ccagacagtt ccatccaagg gagaattaag tagagaaatt    1260
tgtctgcaat ctcaatctaa agacaaatct acgacaccag gaggaacagg aattaagcct    1320
ttcctggaac gctttggaga gcgttgtcaa gaacatagca agaaagtcc agctcgtagc     1380 acaccccaca gaaccccat tattactcca aatacaaagg ccatccaaga aagattattc     1440
aagcaagaca catcttcatc tactacccat ttagcacaac agctcaagca ggaacgtcaa    1500
aaagaactag catgtcttcg tggccgattt gacaagggca atatatggag tgcagaaaaa    1560
ggcggaaact caaaaagcaa acaactagaa accaaacagg aaactcactg tcagagcact    1620
cccctcaaaa aacaccaagg tgtttcaaaa actcagtcac ttccagtaac agaaaaggtg    1680
accgaaaacc agataccagc caaaaattct agtacagaac ctaaaggttt cactgaatgc    1740
gaaatgacga aatctagccc tttgaaaata acattgtttt tagaagagga caaatcctta    1800
aaagtaacat cagacccaaa ggttgagcag aaaattgaag tgatacgtga aattgagatg    1860
agtgtggatg atgatgatat caatagttcg aaagtaatta atgacctctt cagtgatgtc    1920
ctagaggaag gtgaactaga tatggagaag agccaagagg agatggatca agcattagca    1980
gaaagcagcg aagaacagga gatgcactg aatatctcct caatgtcttt acttgcacca     2040
ttggcacaaa cagttggtgt ggtaagtcca gagagtttag tgtccacacc tagactggaa    2100
ttgaaagaca ccagcagaag tgatgaaagt ccaaaaccag gaaaattcca agaactcgt     2160 gtccctcgag ctgaatctgg tgatagcctt ggttctgaag atcgtgatct tctttacagc    2220
attgatgcat atagatctca aagattcaaa gaaacagaac gtccatcaat aaagcaggtg    2280
attgttcgga aggaagatgt tacttcaaaa ctggatgaaa aaataatgc ctttccttgt     2340 caagttaata tcaaacagaa aatgcaggaa ctcaataacg aaataaatat gcaacagaca    2400
gtgatctatc aagctagcca ggctcttaac tgctgtgttg atgaagaaca tggaaaaggg    2460
tccctagaag aagctgaagc agaaagactt cttctaattg caactgggaa gagaacactt    2520
ttgattgatg aattgaataa attgaagaac gaaggacctc agaggaagaa taaggctagt    2580
ccccaaagtg aatttatgcc atccaaagga tcagttactt tgtcagaaat ccgcttgcct    2640
ctaaaagcag attttgtctg cagtacggtt cagaaaccag atgcagcaaa ttactattac    2700
ttaattatac taaaagcagg agctgaaaat atggtagcca caccattagc aagtacttca    2760
aactctctta acggtgatgc tctgacattc actactacat ttactctgca agatgtatcc    2820
aatgactttg aaataaatat tgaagtttac agcttggtgc aaaagaaaga tccctcaggc    2880
cttgataaga agaaaaaaac atccaagtcc aaggctatta ctccaaagcg actcctcaca    2940
tctataacca caaaaagcaa cattcattct tcagtcatgg ccagtccagg aggtcttagt    3000
gctgtgcgaa ccagcaactt cgcccttgtt ggatcttaca cattatcatt gtcttcagta    3060
ggaaatacta agtttgttct ggacaaggtc cctttttat cttctttgga aggtcatatt      3120
tatttaaaaa taaaatgtca agtgaattcc agtgttgaag aaagaggttt tctaaccata    3180
tttgaagatg ttagtggttt tggtgcctgg catcgaagat ggtgtgttct ttctggaaac    3240
tgtatatctt attggactta tccagatgat gagaaacgca agaatcccat aggaaggata    3300
aatctggcta attgtaccag tcgtcagata gaaccagcca acagagaatt ttgtgcaaga    3360
```

```
cgcaacactt ttgaattaat tactgtccga ccacaaagag aagatgaccg agagactctt    3420
gtcagccaat gcagggacac actctgtgtt accaagaact ggctgtctgc agatactaaa    3480
gaagagcggg atctctggat gcaaaaactc aatcaagttc ttgttgatat tcgcctctgg    3540
caacctgatg cttgctacaa acctattgga aagccttaaa ccgggaaatt tccatgctat    3600
ctagaggttt tgatgtcat cttaagaaac acacttaaga gcatcagatt tactgattgc     3660
attttatgct ttaagtacga aagggtttgt gccaatattc actacgtatt atgcagtatt    3720
tatatctttt gtatgtaaaa ctttaactga tttctgtcat tcatcaatga gtagaagtaa    3780
atacattata gttgattttg ctaaatctta atttaaaagc ctcatttttcc tagaaatcta   3840 attattcagt tattcatgac aatatttttt taaaagtaag aaattctgag ttgtcttctt    3900
ggagctgtag tcttgaagc agcaacgtct tcaggggtt ggagacagaa acccattctc      3960
caatctcagt agttttttcg aaaggctgtg atcatttatt gatcgtgata tgacttgtta    4020
ctagggtact gaaaaaaatg tctaaggcct tacagaaac attttagta atgaggatga      4080 gaactttttc aaatagcaaa tatatattgg cttaaagcat gaggctgtct tcagaaaagt    4140
gatgtggaca taggaggcaa tgtgtgagac ttgggggttc aatatttat atagaagagt     4200 taataagcac atggtttaca tttactcagc tactatatat gcagtgtggt gcacattttc    4260
acagaattct ggcttcatta agatcattat ttttgctgcg tagcttacag acttagcata    4320
ttagtttttt ctactcctac aagtgtaaat tgaaaaatct ttatattaaa aaagtaaact    4380
gttatgaagc tgctatgtac taataatact ttgcttgcca aagtgtttgg gttttgttgt    4440
tgtttgtttg tttgttgtt tttggttcat gaacaacagt gtctagaaac ccatttttgaa    4500 agtggaaaat tattaagtca cctatcacct ttaaacgcct ttttttaaaa ttataaaata    4560
ttgtaaagca gggtctcaac ttttaaatac actttgaact tcttctctga attattaaag    4620
ttctttatga cctcatttat aaacactaaa ttctgtcacc tcctgtcatt ttattttta    4680 ttcattcaaa tgtattttt cttgtgcata ttataaaaat atattttatg agctcttact     4740
caaataaata cctgtaaatg tctaaaggaa aaaaaaaaa aaaaaa                    4786

<210> SEQ ID NO 104
<211> LENGTH: 3885
<212> TYPE: DNA
<213> ORGANISM: Homo sapiens

<400> SEQUENCE: 104
aggccggggc ggggctggga agtagtcggg cggggttgtg agacgccgcg ctcagcttcc      60
atcgctgggc ggtcaacaag tgcgggcctg gctcagcgcg ggggggcgcg gagaccgcga    120
ggcgaccggg agcggctggg ttcccggctg cgcgccctcc ggccaggccg ggagccgcgc    180
cagtcggagc ccccggccca gcgtggtccg cctccctctc ggcgtccacc tgcccggagt    240
actgccagcg ggcatgaccg acccaccagg ggcgccgccg ccggcgctcg caggccgcgg    300
atgaagaaga aaacccggcg ccgctcgacc cggagcgagg agttgacccg gagcgaggag    360
ttgaccctga gtgaggaagc gacctggagt gaagaggcga cccagagtga ggaggcgacc    420
cagggcgaag agatgaatcg gagccaggag gtgacccggg acgaggagtc gacccggagc    480
gaggaggtga ccagggagga aatggcggca gctgggctca ccgtgactgt caccccacagc   540 aatgagaagc acgaccttca tgttacctcc cagcagggca gcagtgaacc agttgtccaa    600
gacctggccc aggttgttga agaggtcata ggggttccac agtctttttca gaaactcata   660 tttaagggaa aatctctgaa ggaaatggaa acaccgttgt cagcacttgg aatacaagat    720
```

```
ggttgccggg tcatgttaat tgggaaaaag aacagtccac aggaagaggt tgaactaaag    780
aagttgaaac atttggagaa gtctgtggag aagatagctg accagctgga agagttgaat    840
aaagagctta ctggaatcca gcagggtttt ctgcccaagg atttgcaagc tgaagctctc    900
tgcaaacttg ataggagagt aaaagccaca atagagcagt ttatgaagat cttggaggag    960
attgacacac tgatcctgcc agaaaatttc aaagacagta gattgaaaag gaaaggcttg   1020
gtaaaaaagg ttcaggcatt cctagccgag tgtgacacag tggagcagaa catctgccag   1080
gagactgagc ggctgcagtc tacaaacttt gccctggccg agtgaggtgt agcagaaaaa   1140
ggctgtgctg ccctgaagaa tggcgccacc agctctgccg tctctggagc ggaatttacc   1200
tgatttcttc agggctgctg ggggcaactg gccatttgcc aattttccta ctctcacact   1260
ggttctcaat gaaaaatagt gtctttgtga ttttgagtaa agctcctatc tgttttctcc   1320
ttctgtctct gtggttgtac tgtccagcaa tccaccttt ctggagaggg ccacctctgc   1380
ccaaattttc ccagctgttt ggacctctgg gtgctttctt tgggctggtg agagctctaa   1440
tttgccttgg gccagtttca ggtttatagg cccctcagt cttcagatac atgagggctt   1500
ctttgctctt gtgatcgtgt agtcccatag ctgtaaaacc agaatcacca ggaggttgca   1560
cctagtcagg aatattggga atggcctaga acaaggtgtt tggcacataa gtagaccact   1620
tatccctcat tgtgacctaa ttccagcaga tctggctggg ttgttgggtt ctagactttg   1680
tcctcacctc ccagtgaccc tgactagcca caggccatga gataccaggg ggccgttcct   1740
tggatggagc ctgtggttga tgcaaggctt ccttgtcccc aagcaagtct tcagaaggtt   1800
agaacccagt gttgactgag tctgtgcttg aaaccaggcc agagccatgg attaggaagg   1860
gcaaagagaa ggcaccagaa tgagtaaagc aggcaggtgg tgaagccaac cataaacttc   1920
tcaggagtga catgtgcttc cttcaaaggc attttttgtta accatatcct tctgagttct   1980
atgtttcctt cacagctgtt ctatccattt tgtggactgt ccccaccccc cacccccatca   2040 ttgttttttaa aaaattaagg cctggcgcag cagctcatgc ctataatccc agcactttgg   2100
gaggctgagg cgggcggatc acttgaggcc aggagtttga ccagcccca ggcaacatag   2160 caaaaccca ttctgcttta aaaaaaaaaa aaaaaaaaat tagcttggcg tagtggcatg   2220
tgcctataat cccagctact ggggaggctg aggcacaaga atcatttgaa cctgggaggt   2280
agaggttgct gtgagccgag attacgcccc tgcactccag cctgggtcac agagtgagac   2340
tccatctcag aaaaaaaaaa aattgagtca ggtgcagtag ctccttcctg tagtcccagc   2400
tacttgggag gctgaggcta gaggatcact tgagcccagg agtttgagtc tagtctgggc   2460
aacatagcaa gaccccatct ctaaaattta agtaagtaaa agtagataaa taaaaagaaa   2520
aaaaaactgt ttatgtgctc atcataaagt agaagagtgg tttgcttttt ttttttttt   2580 tggattaatg aggaaatcat tctgtggctc tagtcataat ttatgcttaa taacattgat   2640
agtagccctt tgcgctataa ctctacctaa agactcacat catttggcag agagagagtc   2700
gttgaagtcc caggaattca ggactgggca ggttaagacc tcagacaagg tagtagaggt   2760
agacttgtgg acaaggctcg ggtcccagcc caccgcaccc caactttaat cagagtggtt   2820
cactattgat ctattttgt gtgatagctg tgtggcgtgg gccacaacat ttaatgagaa   2880
gttactgtgc accaaactgc cgaacaccat tctaaactat tcatatatat tagtcattta   2940
attcttacat aacttgagag gtagacagat atccttattt tagagatgag gaaaccaaga   3000
gaacttaggt cattagcgca aggttgtaga gtaagcggca aagccaagac acaaagctgg   3060
```

| | |
|---|---|
| gtggtttggt ttcagagcca gtgcttttcc cctctactgt actgcctctc aaccaacaca | 3120 |
| gggttgcaca ggcccattct ctgattttt tcctcttgtc ctctgcctct ccctctagct | 3180 |
| cccacttcct ctctgctcta gttcattttc tttagagcag cccgagtgat catgaagtgc | 3240 |
| aaatcttgcc atgtcagtcc cctgcttaga accctccaat ggctcacttt ctctttaggc | 3300 |
| aaaagtcttt accccatgcc ttctcccatc tcatctcaac ccctcatttt gttggctgtc | 3360 |
| tgctgtcagc cactcttctt tcaggtcctc agatgcactg caccctctcc tgcctggggg | 3420 |
| tctttgctcc tgctactacc tctgcttgaa cagctcctca ccttccttcc tccaaccta | 3480 |
| cccttgtata ggtgactttt gttcatcctt cagaattcaa ctcacatgtc tcttgcatgg | 3540 |
| agaaccctca cctactgtgt tgagaccctg tccagccccc aggtgggatc ctctctcgac | 3600 |
| ttcccataca tttctttcac agcatttaca tagtccatga tagtttactt gtgggattat | 3660 |
| ttggttaatc tttgccttta acaccagggt tccttgggtg aaggagcttc tttatcttgg | 3720 |
| taacagcatt atttcaagca taacttgtaa tatagttata ttacatatat aacatatata | 3780 |
| tatataacat aacatatata acatatataa caagcataac ttgttatata gtcttgtata | 3840 |
| tagtaagacc tcaataaata tttggagaac aaaaaaaaaa aaaaa | 3885 |

<210> SEQ ID NO 105
<211> LENGTH: 6492
<212> TYPE: DNA
<213> ORGANISM: Homo sapiens

<400> SEQUENCE: 105

| | |
|---|---|
| tttctgtgaa gcagaagtct gggaatcgat ctggaaatcc tcctaatttt tactccctct | 60 |
| ccccgcgact cctgattcat tgggaagttt caaatcagct ataactggag agtgctgaag | 120 |
| attgatggga tcgttgcctt atgcatttgt tttggtttta caaaaggaa acttgacaga | 180 |
| ggatcatgct gtacttaaaa aatacaacat cacagaggaa gtagactgat attaacaata | 240 |
| cttactaata ataacgtgcc tcatgaaata aagatccgaa aggaattgga ataaaaattt | 300 |
| cctgcatctc atgccaaggg ggaaacacca gaatcaagtg ttccgcgtga ttgaagacac | 360 |
| cccctcgtcc aagaatgcaa agcacatcca ataaaatagc tggattataa ctcctcttct | 420 |
| ttctctgggg gccgtggggt gggagctggg gcgagaggtg ccgttggccc ccgttgcttt | 480 |
| tcctctggga aggatggcgc acgctgggag aacagggtac gataaccggg agatagtgat | 540 |
| gaagtacatc cattataagc tgtcgcagag gggctacgag tgggatgcgg gagatgtggg | 600 |
| cgccgcgccc ccgggggccg cccccgcacc gggcatcttc tcctcccagc ccgggcacac | 660 |
| gccccatcca gccgcatccc gggacccggt cgccaggacc tcgccgctgc agaccccggc | 720 |
| tgccccggc gccgccgcgg ggcctgcgct cagcccggtg ccacctgtgg tccacctgac | 780 |
| cctccgccag gccggcgacg acttctcccg ccgctaccgc cgcgacttcg ccgagatgtc | 840 |
| cagccagctg cacctgacgc ccttcaccgc gcggggacgc tttgccacgg tggtggagga | 900 |
| gctcttcagg gacggggtga actgggggag gattgtggcc ttctttgagt tcggtggggt | 960 |
| catgtgtgtg gagagcgtca accgggagat gtcgcccctg gtggacaaca tcgccctgtg | 1020 |
| gatgactgag tacctgaacc ggcacctgca cacctggatc caggataacg gaggctggga | 1080 |
| tgcctttgtg gaactgtacg gccccagcat gcggcctctg tttgatttct cctggctgtc | 1140 |
| tctgaagact ctgctcagtt tggggcctgg gggagcttgc atcaccctgg gtgcctatct | 1200 |
| gggccacaag tgaagtcaac atgcctgccc caaacaaata tgcaaaaggt tcactaaagc | 1260 |
| agtagaaaata atatgcattg tcagtgatgt accatgaaac aaagctgcag gctgtttaag | 1320 |

```
aaaaaataac acacatataa acatcacaca cacagacaga cacacacaca cacaacaatt    1380
aacagtcttc aggcaaaacg tcgaatcagc tatttactgc caaagggaaa tatcatttat    1440
tttttacatt attaagaaaa aaagattat ttatttaaga cagtcccatc aaaactcctg     1500
tctttggaaa tccgaccact aattgccaag caccgcttcg tgtggctcca cctggatgtt    1560
ctgtgcctgt aaacatagat tcgctttcca tgttgttggc cggatcacca tctgaagagc    1620
agacggatgg aaaaaggacc tgatcattgg ggaagctggc tttctggctg ctggaggctg    1680
gggagaaggt gttcattcac ttgcatttct ttgccctggg ggctgtgata ttaacagagg    1740
gagggttcct gtgggggaa gtccatgcct ccctggcctg aagaagagac tctttgcata     1800
tgactcacat gatgcatacc tggtgggagg aaaagagttg gaacttcag atggacctag     1860 tacccactga gatttccacg ccgaaggaca gcgatgggaa aaatgccctt aaatcatagg    1920
aaagtatttt tttaagctac caattgtgcc gagaaaagca ttttagcaat ttatacaata    1980
tcatccagta ccttaagccc tgattgtgta tattcatata ttttggatac gcacccccca    2040
actcccaata ctggctctgt ctgagtaaga aacagaatcc tctggaactt gaggaagtga    2100
acatttcggt gacttccgca tcaggaaggc tagagttacc cagagcatca ggccgccaca    2160
agtgcctgct tttaggagac cgaagtccgc agaacctgcc tgtgtcccag cttggaggcc    2220
tggtcctgga actgagccgg ggccctcact ggcctcctcc agggatgatc aacagggcag    2280
tgtggtctcc gaatgtctgg aagctgatgg agctcagaat tccactgtca agaaagagca    2340
gtagaggggt gtggctgggc ctgtcaccct ggggccctcc aggtaggccc gttttcacgt    2400
ggagcatggg agccacgacc cttcttaaga catgtatcac tgtagaggga aggaacagag    2460
gccctgggcc cttcctatca gaaggacatg gtgaaggctg ggaacgtgag gagaggcaat    2520
ggccacggcc cattttggct gtagcacatg gcacgttggc tgtgtggcct tggcccacct    2580
gtgagtttaa agcaaggctt taaatgactt tggagagggt cacaaatcct aaaagaagca    2640
ttgaagtgag gtgtcatgga ttaattgacc cctgtctatg gaattacatg taaaacatta    2700
tcttgtcact gtagtttggt tttatttgaa aacctgacaa aaaaaaagtt ccaggtgtgg    2760
aatatggggg ttatctgtac atcctggggc attaaaaaaa aatcaatgg tggggaacta    2820 taaagaagta acaaaagaag tgacatcttc agcaaataaa ctaggaaatt ttttttttctt    2880 ccagtttaga atcagccttg aaacattgat ggaataactc tgtggcatta ttgcattata    2940
taccatttat ctgtattaac tttggaatgt actctgttca atgtttaatg ctgtggttga    3000
tatttcgaaa gctgctttaa aaaaatacat gcatctcagc gttttttttgt ttttaattgt    3060 atttagttat ggcctataca ctatttgtga gcaaggtga tcgttttctg tttgagattt       3120
ttatctcttg attcttcaaa agcattctga gaaggtgaga taagccctga gtctcagcta    3180
cctaagaaaa acctggatgt cactggccac tgaggagctt tgtttcaacc aagtcatgtg    3240
catttccacg tcaacagaat tgtttattgt gacagttata tctgttgtcc ctttgacctt    3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggtttga ccttttagaga gttgctttac gtggcctgtt    3480
tcaacacaga cccacccaga gccctcctgc cctccttccg cgggggcttt ctcatggctg    3540
tccttcaggt tcttcctgaa atgcagtggt gcttacgctc caccaagaaa gcaggaaacc    3600
tgtggtatga agccagacct ccccggcggg cctcaggaa cagaatgatc agacctttga     3660
```

```
atgattctaa tttttaagca aaatattatt ttatgaaagg tttacattgt caaagtgatg    3720
aatatggaat atccaatcct gtgctgctat cctgccaaaa tcattttaat ggagtcagtt    3780
tgcagtatgc tccacgtggt aagatcctcc aagctgcttt agaagtaaca atgaagaacg    3840
tggacgtttt taatataaag cctgttttgt cttttgttgt tgttcaaacg ggattcacag    3900
agtatttgaa aaatgtatat atattaagag gtcacggggg ctaattgctg gctggctgcc    3960
ttttgctgtg gggttttgtt acctggtttt aataacagta aatgtgccca gcctcttggc    4020
cccagaactg tacagtattg tggctgcact tgctctaaga gtagttgatg ttgcattttc    4080
cttattgtta aaaacatgtt agaagcaatg aatgtatata aaagcctcaa ctagtcattt    4140
ttttctcctc ttctttttt tcattatatc taattatttt gcagttgggc aacagagaac    4200
catccctatt ttgtattgaa gagggattca catctgcatc ttaactgctc tttatgaatg    4260
aaaaaacagt cctctgtatg tactcctctt tacactggcc agggtcagag ttaaatagag    4320
tatatgcact ttccaaattg gggacaaggg ctctaaaaaa agccccaaaa ggagaagaac    4380
atctgagaac ctcctcggcc ctcccagtcc ctcgctgcac aaatactccg caagagaggc    4440
cagaatgaca gctgacaggg tctatggcca tcgggtcgtc tccgaagatt tggcaggggc    4500
agaaaactct ggcaggctta agatttggaa taaagtcaca gaattaagga agcacctcaa    4560
tttagttcaa acaagacgcc aacattctct ccacagctca cttacctctc tgtgttcaga    4620
tgtggccttc catttatatg tgatctttgt tttattagta aatgcttatc atctaaagat    4680
gtagctctgg cccagtggga aaaattagga agtgattata atcgagagg agttataata    4740 atcaagatta aatgtaaata atcagggcaa tcccaacaca tgtctagctt tcacctccag    4800
gatctattga gtgaacagaa ttgcaaatag tctctatttg taattgaact tatcctaaaa    4860
caaatagttt ataaatgtga acttaaactc taattaattc caactgtact tttaaggcag    4920
tggctgtttt tagactttct tatcacttat agttagtaat gtacacctac tctatcagag    4980
aaaaacagga aaggctcgaa atacaagcca ttctaaggaa attagggagt cagttgaaat    5040
tctattctga tcttattctg tggtgtcttt tgcagcccag acaaatgtgg ttacacactt    5100
tttaagaaat acaattctac attgtcaagc ttatgaaggt tccaatcaga tctttattgt    5160
tattcaattt ggatctttca gggattttt ttttaaatta ttatgggaca aaggacattt    5220
gttggagggg tgggagggag gaagaatttt taaatgtaaa acattcccaa gtttggatca    5280
gggagttgga agttttcaga ataaccagaa ctaagggtat gaaggacctg tattggggtc    5340
gatgtgatgc ctctgcgaag aaccttgtgt gacaaatgag aaacattttg aagtttgtgg    5400
tacgaccttt agattccaga gacatcagca tggctcaaag tgcagctccg tttggcagtg    5460
caatggtata aatttcaagc tggatatgtc taatgggtat ttaaacaata aatgtgcagt    5520
tttaactaac aggatattta atgacaacct tctggttggt agggacatct gtttctaaat    5580
gtttattatg tacaatacag aaaaaaattt tataaaatta agcaatgtga aactgaattg    5640
gagagtgata atacaagtcc tttagtctta cccagtgaat cattctgttc catgtctttg    5700
gacaaccatg accttggaca atcatgaaat atgcatctca ctggatgcaa agaaaatcag    5760
atggagcatg aatggtactg taccggttca tctggactgc cccagaaaaa taacttcaag    5820
caaacatcct atcaacaaca aggttgttct gcataccaag ctgagcacag aagatgggaa    5880
cactggtgga ggatggaaag gctcgctcaa tcaagaaaat tctgagacta ttaataaata    5940
agactgtagt gtagatactg agtaaatcca tgcacctaaa ccttttggaa aatctgccgt    6000
gggccctcca gatagctcat ttcattaagt ttttccctcc aaggtagaat ttgcaagagt    6060
```

-continued

```
gacagtggat tgcatttctt ttggggaagc tttcttttgg tggttttgtt tattatacct      6120
tcttaagttt tcaaccaagg tttgcttttg ttttgagtta ctggggttat ttttgtttta      6180
aataaaaata agtgtacaat aagtgttttt gtattgaaag cttttgttat caagattttc      6240
atacttttac cttccatggc tcttttttaag attgatactt ttaagaggtg gctgatattc     6300
tgcaacactg tacacataaa aaatacggta aggatacttt acatggttaa ggtaaagtaa      6360
gtctccagtt ggccaccatt agctataatg cactttgtt tgtgttgttg gaaaaagtca       6420
cattgccatt aaactttcct tgtctgtcta gttaatattg tgaagaaaaa taaagtacag      6480
tgtgagatac tg                                                          6492
```

<210> SEQ ID NO 106
<211> LENGTH: 2724
<212> TYPE: DNA
<213> ORGANISM: Homo sapiens

<400> SEQUENCE: 106

```
cccagaaggc cgcgggggt ggaccgccta agagggcgtg cgctcccgac atgccccgcg        60
gcgcgccatt aaccgccaga tttgaatcgc gggacccgtt ggcagaggtg gcggcggcgg      120
catgggtgcc ccgacgttgc cccctgcctg gcagcccttt ctcaaggacc accgcatctc      180
tacattcaag aactgccct tcttggaggg ctgcgcctgc accccggagc ggatggccga       240
ggctggcttc atccactgcc ccactgagaa cgagccagac ttggcccagt gtttcttctg      300
cttcaaggag ctggaaggct gggagccaga tgacgacccc attgggccgg gcacggtggc      360
ttacgcctgt aataccagca ctttgggagg ccgaggcggg cggatcacga gagaggaaca      420
taaaaagcat tcgtccggtt gcgctttcct ttctgtcaag aagcagtttg aagaattaac      480
ccttggtgaa ttttttgaaac tggacagaga aagagccaag aacaaaattg caaggaaac      540 caacaataag aagaaagaat ttgaggaaac tgcggagaaa gtgcgccgtg ccatcgagca      600
gctggctgcc atggattgag gcctctggcc ggagctgcct ggtcccagag tggctgcacc      660
acttccaggg tttattccct ggtgccacca gccttcctgt gggcccctta gcaatgtctt      720
aggaaaggag atcaacattt tcaaattaga tgtttcaact gtgctcttgt tttgtcttga      780
aagtggcacc agaggtgctt ctgcctgtgc agcgggtgct gctggtaaca gtggctgctt      840
ctctctctct ctctcttttt tgggggctca ttttttgctgt tttgattccc gggcttacca     900
ggtgagaagt gagggaggaa gaaggcagtg tcccttttgc tagagctgac agctttgttc      960
gcgtgggcag agccttccac agtgaatgtg tctggacctc atgttgttga ggctgtcaca     1020
gtcctgagtg tggacttggc aggtgcctgt tgaatctgag ctgcaggttc cttatctgtc     1080
acacctgtgc ctcctcagag gacagttttt ttgttgttgt gtttttttgt tttttttttt     1140
ttggtagatg catgacttgt gtgtgatgag agaatggaga cagagtccct ggctcctcta     1200
ctgtttaaca acatggcttt cttatttttgt ttgaattgtt aattcacaga atagcacaaa    1260
ctacaattaa aactaagcac aaagccattc taagtcattg gggaaacggg gtgaacttca     1320
ggtggatgag gagacagaat agagtgatag gaagcgtctg gcagatactc cttttgccac     1380
tgctgtgtga ttagacaggc ccagtgagcc gcggggcaca tgctggccgc tcctccctca     1440
gaaaaaggca gtggcctaaa tccttttttaa atgacttggc tcgatgctgt gggggactgg    1500
ctgggctgct gcaggccgtg tgtctgtcag cccaaccttc acatctgtca cgttctccac     1560
acggggagga gacgcagtcc gcccaggtcc ccgctttctt tggaggcagc agctcccgca    1620
```

```
gggctgaagt ctggcgtaag atgatggatt tgattcgccc tcctccctgt catagagctg    1680
cagggtggat tgttacagct tcgctggaaa cctctggagg tcatctcggc tgttcctgag    1740
aaataaaaag cctgtcattt caaacactgc tgtggaccct actgggtttt taaaatattg    1800
tcagtttttc atcgtcgtcc ctagcctgcc aacagccatc tgcccagaca gccgcagtga    1860
ggatgagcgt cctggcagag acgcagttgt ctctgggcgc ttgccagagc cacgaacccc    1920
agacctgttt gtatcatccg ggctccttcc gggcagaaac aactgaaaat gcacttcaga    1980
cccacttatt tctgccacat ctgagtcggc ctgagataga cttttccctc taaactggga    2040
gaatatcaca gtggttttg ttagcagaaa atgcactcca gcctctgtac tcatctaagc    2100
tgcttatttt tgatatttgt gtcagtctgt aaatggatac ttcactttaa taactgttgc    2160
ttagtaattg gctttgtaga gaagctggaa aaaaatggtt ttgtcttcaa ctcctttgca    2220
tgccaggcgg tgatgtggat ctcggcttct gtgagcctgt gctgtgggca gggctgagct    2280
ggagccgccc ctctcagccc gcctgccacg gcctttcctt aaaggccatc cttaaaacca    2340
gaccctcatg gctaccagca cctgaaagct tcctcgacat ctgttaataa agccgtaggc    2400
ccttgtctaa gtgcaaccgc ctagactttt tttcagatac atgtccacat gtccattttt    2460
caggttctct aagttggagt gggagtctggg aagggttgtg aatgaggctt ctgggctatg    2520
ggtgaggttc caatggcagg ttagagcccc tcgggccaac tgccatcctg gaaagtagag    2580
acagcagtgc ccgctgccca gaagagacca gcaagccaaa ctggagcccc cattgcaggc    2640
tgtcgccatg tggaaagagt aactcacaat tgccaataaa gtctcatgtg gttttatcta    2700
aaaaaaaaaa aaaaaaaaaa aaaa                                           2724

<210> SEQ ID NO 107
<211> LENGTH: 4934
<212> TYPE: DNA
<213> ORGANISM: Homo sapiens

<400> SEQUENCE: 107
aatgagggta tttataaact acttaaatta taaaagaat gagacatcag acttacagtt      60
ttggatacta attttttttca cttaacgttc attatgtgat aggagttttc catcctatta    120
taccgctgtg cgatctgatc ttgggcacgt taaccaacct cttgttgcct cgattttctc    180
acctgtaaaa gtgggggtaa tcataatgct tacttagtag gatagccctg aagaataagt    240
gacttagcga acataaatag cttacaatag ggttttcagc atgggaagga ttcagtaaat    300
gttagctgtc atcatcacca cctacaaagg aagcaatact gtgctgaaag ttttccatc    360 attaatgtaa tttctatagt acgattccca agaagatatt aaaattatgg aaataaaggt    420
attggtatat tcctaattat ttcctaaaag attgtattga taaatatgct catccttccc    480
ttaacgggat gcattccaga aaaacaagtc aaatgttaga caaagtatca gaagggaaat    540
tctgtagcca gagagctaaa aattacaata gggtctctaa ttatacttca acttttttag    600
gaataattct cagtgtgttt tcccacattt catatgtaat tttttttttt tttttttttt    660
gagacagagc ctcgccctgt caccaggctg gagtacagtg gcgcgatctc ggctcactgc    720
aacttccacc tgctgggttc aagcaattct tctgacctca ggtgatccac cgcctcggc     780 ctcccaaagt gctgggatta acaggcgt ggcatgagtc accgcgcccg gccgatcttt      840
acttttttat tctttgtacc ccctgcctat ccagttagca tgtgattaaa gtcaaagatt    900
tgccactttg ggccacatct attaattttc atctttgtta taattgtatt tagttttga     960 tctacactgc ttattactcc cagtcatttt ttatagaact gaaaatctgg taaaatactc    1020
```

```
aaaattgcac tgacttctat gtagaggcga cactccatca gaaccgtggg ctgacaggga     1080
atcccactgt gcaggagctg cgcgcatttt catttctgat tctctttggc gtatccagga     1140
ctctgatgac atgatcatat atttatcagt agtaacaggt tgggccattt gttttttgtg     1200
gtaaatcata tatttaagat tttagaaata agttgatagc catgtatttt ggaatttgaa     1260
aaagacattg cattactcag cttcaaatta agctttaatc aaatagtgaa actttccatt     1320 aatgacagt gtatacctt tgtgtattt aaaaaaaaa acactgaata tagtgccttt         1380
gtgacagggg agcttggttc ctgacaatgt cctcttgagc ctttttttt tttttgagat      1440 ggagtctcac tgtgtcaccc aggctggagt gcagtggcgc catcttggct cactgcaacc    1500 tccgcccct gggttcaagt gattctcatt cctcagcttc ctaagtagct gggattacag     1560
gcacgcacca ccatgaccag ctaattttta tactttttagt agagacaggg ttttgccatg  1620
ttggctaggt tggtctcgaa ctcctgacct caagtaatcc acccaccatg gcctccccaa    1680
agtgctggga ttacaggcgt gagccatttc acccggcctc tcttccgtct ttgagctgtg    1740
aggaaatagc tacattacat gagctgctag atctgcctta tggtcagaaa tgaaggttga    1800
actctcagga acagtgacat atatacacac tgatatttcc aaagtacaat gccccaaatt    1860
gatccacaaa ggaattaagg tcatttgcaa caaaatcaca gaatagtaac aaataaatag   1920
aagataaata tggccaggga tgctgcaaac tgatatactg ccaagtttat cagttgggaa   1980
tcccaacagt gaaaagcata aaatgaaag gaattttaag gagacttttt atagaagagt     2040
gggaaggatt ggaggagcca acaagtgatg gtgaggcaca cagggaagag cttcagtggg    2100
caccatcccc tctctggttt gaaggggtag ggaggggacc agagctggga ggaggggct    2160 ggaatactgc tggaggagcc actcccttcc agacctgctg tggccatcac agaatgcagc    2220
cactgccaga gcagcagccc gaggaaccag gcaggggag cacaagtacc ctagcctctc     2280
tctttctgtt tcttgcctgc cgatctcctc cactggctaa cccagctgg atgctaagag    2340 tacagtcagc ctgcctgctg aggagggacc accagggacc accatcagca agggatccaa    2400 tgtcttctg cctctgcaga atgaaggttg gggcgcgggg ggcgctctac ttcttaggga    2460
tattgtggga ataaaaggaa ataggcaaaa aatgtttttg aaaaacaaag cacatactgc    2520
gcacccgtgg gccactactg cttttgaccc ctggctctgt tcatgaagt aatgtcgtgt     2580 cattctcttt ttaggtgcta caggatttct ttaggttttgt tttctgtcca ccatatttca    2640
actcatgtgt gctgtttgtt gtgctaaaac aaatatttgc tgatgcctga gtgaatagtt    2700
gaatatttta tataagtcaa atttatacgt aatgattttt cttgtaacttt agccgtttct   2760 cttttacaaa ctcagaaaac ctcagacttt gaaaaggcct tgaagttcct cacctgaaat    2820
ctgagaactt ggagcgcctt aaaaaatcta aggaaaaca aaacagtgaa agaacatgat    2880
atagtcagtg tagagaataa aattatttat gtaattaata ttgaggatgc agataacaca    2940
ttgtgaaatc ttgcttgtaa aaaatctcga tctgctgaag aaagatgttc tctctagaga    3000
tctttgaaag cataattatt gagcttttaa aatgttagaa acaaagtta gacccacaca    3060 tattctggcg tgtggaagat ttgcattcct tcccctgccc gccccgcccc cacacttgtg    3120
agttgtgcct gtgtacgcag ttcctgtagc actcggctgg gcagaaatca tctttcagca    3180
ctaagggaac atagttatga tctggacctt ctgggagtgg tcagtgccca agaacaggta    3240
tgggactcca gaaagttctg ctctcaaccc tattttgaaa tagagttaca cattgttcta    3300
caattatttg agttaataag cagctctttt caaacgtgat tatgcccttc caagtttaaa    3360
```

-continued

```
tacactagac tttagtgaaa gtaattgacc tcatctcatt tctctcctgt tatattaaga    3420
tcactttcag taaaaggtag aagcttttga agtggtgagg aggaggtaga ggagggacat    3480
agagcagata ggggctggaa agtggggtga ggaagagagt ggcttctctt tggcagagta    3540
ccaaggaaaa gccctatctg tacagaacct ttgtgcctgg gaacttgatg gctgcaacct    3600
gagcctcaac ctagtttgct tgcggagcca gaagagaagc taaaaacctt cagttaacca    3660
agccagacac caagaaagtt aaaccgaaag agaaccccccc acccccgca aaaaaagaa     3720
gtaaagtggg ttaaagtgat atcatgttag cacagaaaga gaacataagg gtcatctaag    3780
ttcatctgcc ccctcttcta tttcaaggtg cagaaactaa ggcacaaggg accccgtgtc    3840
ctgctcttga tcacatagct agtgggtgcc aagccaggtc tagaactctg ttctctgggg    3900
tcacaggctg gctcttcatc cctctagaga gatagctcat ctgtgtgcac ctgagcccgt    3960
tgtgtttcgg agtcaaagca aataaaggct caaactccaa gactgttttg cagaccggct    4020
gcagtagata tgggggagg agaaacctgc tttaaattgc ttcaagcaag ttgtttctgc     4080
aaaggtgttg acttttttct ttcaacttc tagtgagtca ctgcagcctg agctgttatt     4140
tgtcattatg caataattca ggaactaact caagattctt ctttttaaat tatttgttta    4200
tttagagaca gagtcttgct ctgttgccca ggctggagtg cagtggtgtg atctcggctc    4260
actgcagcct ctgcctcctg ggttcaagca attctcatgt ctcagcctcc cgaatagctg    4320
gtattgcagg ctcgtgccac caccccctgc taatttttgt aatttagtg gagacacggt     4380
ttcgccatgt tggccgggct cgtcttgagc tcctggcctc aggtgatccg cccgcctcgg    4440
cctcccaaag tgctgggatt gcagccgtga gcctccacac ccggcctatt tatttatttt    4500
taaattggct gctcttagaa aggcatacca tgtttctgga tgggaaggct tattaattca    4560
ccctaattta atgtataaat ttgatgcaat catagtcaca gtcccagtgg aattttttaa    4620
cttggtaaga tgttctaaaa ttaatgagag aacttgaatt accaggtatt gaaacactgt    4680
aaagccacaa tcatgtaaac agtatgttat aaccatggga atagaggtct gtgatacagc    4740
agaaaaagt gaaaaaaga ataactgtat tcataaaaat ttaaatgtgg agtcactggg      4800
ggaaaggatt aaatattcga taatgtgaaa acaactcaac tatttggaga aatgtaaatt    4860
tagagcctta tctcatgcca tataccaaaa tactatttag atttgattaa aaaataaaaa    4920
aaaaaaaaaa aaaa                                                      4934
```

<210> SEQ ID NO 108
<211> LENGTH: 2177
<212> TYPE: DNA
<213> ORGANISM: Homo sapiens

<400> SEQUENCE: 108

```
cgaacgcctt cgcgcgatcg ccctggaaac gcattctctg cgaccggcag ccgccaatgg      60
gaagggagtg agtgccacga acaggccaat aaggagggag cagtgcgggg tttaaatctg     120
aggctaggct ggctcttctc ggcgtgctgc ggcggaacgg ctgttggttt ctgctgggtg     180
taggtccttg gctggtcggg cctccggtgt tctgcttctc cccgctgagc tgctgcctgg    240
tgaagaggaa gccatggcgc tccgagtcac caggaactcg aaaattaatg ctgaaaataa    300
ggcgaagatc aacatggcag gcgcaaagcg cgttcctacg gcccctgctg caacctccaa    360
gcccggactg aggccaagaa cagctcttgg ggacattggt aacaaagtca gtgaacaact    420
gcaggccaaa atgcctatga agaaggaagc aaaaaccttca gctactggaa aagtcattga    480
taaaaaacta ccaaaacctc ttgaaaaggt acctatgctg gtgccagtgc cagtgtctga    540
```

```
gccagtgcca gagccagaac ctgagccaga acctgagcct gttaaagaag aaaaactttc      600
gcctgagcct attttggttg atactgcctc tccaagccca atggaaacat ctggatgtgc      660
ccctgcagaa gaagacctgt gtcaggcttt ctctgatgta attcttgcag taaatgatgt      720
ggatgcagaa gatggagctg atccaaacct ttgtagtgaa tatgtgaaag atatttatgc      780
ttatctgaga caacttgagg aagagcaagc agtcagacca aaatacctac tgggtcggga      840
agtcactgga aacatgagag ccatcctaat tgactggcta gtacaggttc aaatgaaatt      900
caggttgttg caggagacca tgtacatgac tgtctccatt attgatcggt tcatgcagaa      960
taattgtgtg cccaagaaga tgctgcagct ggttggtgtc actgccatgt ttattgcaag     1020
caaatatgaa gaaatgtacc ctccagaaat tggtgacttt gcttttgtga ctgacaacac     1080
ttatactaag caccaaatca gacagatgga aatgaagatt ctaagagctt aaactttgg      1140 tctgggtcgg cctctacctt tgcacttcct tcggagagca tctaagattg gagaggttga     1200
tgtcgagcaa catactttgg ccaaataccct gatggaacta actatgttgg actatgacat    1260
ggtgcacttt cctccttctc aaattgcagc aggagctttt tgcttagcac tgaaaattct     1320
ggataatggt gaatggacac caactctaca acattacctg tcatatactg aagaatctct    1380
tcttccagtt atgcagcacc tggctaagaa tgtagtcatg gtaaatcaag gacttacaaa     1440
gcacatgact gtcaagaaca gtatgccac atcgaagcat gctaagatca gcactctacc      1500
acagctgaat tctgcactag ttcaagattt agccaaggct gtggcaaagg tgtaacttgt     1560
aaacttgagt tggagtacta tatttacaaa taaaattggc accatgtgcc atctgtacat     1620
attactgttg catttacttt taataaagct tgtggcccct tttacttttt tatagcttaa     1680
ctaatttgaa tgtggttact tcctactgta gggtagcgga aaagttgtct taaaaggtat    1740
ggtggggata tttttaaaaa ctccttttgg tttacctggg gatccaattg atgtatatgt     1800
ttatatactg ggttcttgtt ttatatacct ggcttttact ttattaatat gagttactga     1860
aggtgatgga ggtatttgaa aattttactt ccataggaca tactgcatgt aagccaagtc     1920
atggagaatc tgctgcatag ctctatttta agtaaaagt ctaccaccga atccctagtc      1980
cccctgtttt ctgtttcttc ttgtgattgc tgccataatt ctaagttatt tacttttacc    2040
actatttaag ttatcaactt tagctagtat cttcaaactt tcactttgaa aaatgagaat    2100
tttatattct aagccagttt tcattttggt tttgtgtttt ggttaataaa acaatactca    2160
aatacaaaaa aaaaaaa                                                    2177

<210> SEQ ID NO 109
<211> LENGTH: 2011
<212> TYPE: DNA
<213> ORGANISM: Homo sapiens

<400> SEQUENCE: 109
gcggccgcca gcgcggtgta gggggcaggc gcggatcccg ccaccgccgc gcgctcggcc       60
cgccgactcc cggcgccgcc gccgccactg ccgtcgccgc cgccgcctgc cgggactgga      120
gcgcgccgtc cgccgcggac aagaccctgg cctcaggccg gagcagcccc atcatgccga      180
gggagcgcag ggagcgggat gcgaaggagc gggacaccat gaaggaggac ggcggcgcgg      240
agttctcggc tcgctccagg aagaggaagg caaacgtgac cgttttttg caggatccag       300 atgaagaaat ggccaaaatc gacaggacg cgagggacca gtgtgggagc cagccttggg       360
acaataatgc agtctgtgca gacccctgct ccctgatccc cacacctgac aaagaagatg      420
```

| | |
|---|---|
| atgaccgggt ttacccaaac tcaacgtgca agcctcggat tattgcacca tccagaggct | 480 |
| ccccgctgcc tgtactgagc tgggcaaata gagaggaagt ctggaaaatc atgttaaaca | 540 |
| aggaaaagac atacttaagg gatcagcact ttcttgagca cacccctctt ctgcagccaa | 600 |
| aaatgcgagc aattcttctg gattggttaa tggaggtgtg tgaagtctat aaacttcaca | 660 |
| gggagacctt ttacttggca caagatttct ttgaccggta tatggcgaca caagaaaatg | 720 |
| ttgtaaaaac tcttttacag cttattggga tttcatcttt atttattgca gccaaacttg | 780 |
| aggaaatcta tcctccaaag ttgcaccagt ttgcgtatgt gacagatgga gcttgttcag | 840 |
| gagatgaaat tctcaccatg gaattaatga ttatgaaggc ccttaagtgg cgtttaagtc | 900 |
| ccctgactat tgtgtcctgg ctgaatgtat acatgcaggt tgcatatcta aatgacttac | 960 |
| atgaagtgct actgccgcag tatccccagc aaatctttat acagattgca gagctgttgg | 1020 |
| atctctgtgt cctggatgtt gactgccttg aatttcctta tggtatactt gctgcttcgg | 1080 |
| ccttgtatca tttctcgtca tctgaattga tgcaaaaggt ttcagggtat cagtggtgcg | 1140 |
| acatagagaa ctgtgtcaag tggatggttc catttgccat ggttataagg gagacgggga | 1200 |
| gctcaaaact gaagcacttc aggggcgtcg ctgatgaaga tgcacacaac atacagaccc | 1260 |
| acagagacag cttggatttg ctggacaaag cccgagcaaa gaaagccatg ttgtctgaac | 1320 |
| aaaatagggc ttctcctctc cccagtgggc tcctcacccc gccacagagc ggtaagaagc | 1380 |
| agagcagcgg gccggaaatg gcgtgaccac cccatccttc tccaccaaag acagttgcgc | 1440 |
| gcctgctcca cgttctcttc tgtctgttgc agcggaggcg tgcgtttgct tttacagata | 1500 |
| tctgaatgga gagtgttttc ttccacaaca gaagtatttc tgtggatggc atcaaacagg | 1560 |
| gcaaagtgtt ttttattgaa tgcttatagg ttttttttaa ataagtgggt caagtacacc | 1620 |
| agccacctcc agacaccagt gcgtgctccc gatgctgcta tggaaggtgc tacttgacct | 1680 |
| aagggactcc cacaacaaca aaagcttgaa gctgtggagg ccacggtgg cgtggctctc | 1740 |
| ctcgcaggtg ttctgggctc cgttgtacca agtggagcag gtggttgcgg gcaagcgttg | 1800 |
| tgcagagccc atagccagct gggcaggggg ctgccctctc acattatca gttgacagtg | 1860 |
| tacaatgcct tgatgaact gttttgtaag tgctgctata tctatccatt ttttaataaa | 1920 |
| gataatactg ttttgaaaa aaaaaaaaa aaaaaaaaa aaaaaaaaa aaaaaaaaa | 1980 |
| aaaaaaaaaa aaaaaaaaa aaaaaaaaa a | 2011 |

<210> SEQ ID NO 110
<211> LENGTH: 1737
<212> TYPE: DNA
<213> ORGANISM: Homo sapiens

<400> SEQUENCE: 110

| | |
|---|---|
| gagggcacgg gctccgtagg caccaactgc aaggacccct ccccctgcgg gcgctcccat | 60 |
| ggcacagttc gcgttcgaga gtgacctgca ctcgctgctt cagctggatg cacccatccc | 120 |
| caatgcaccc cctgcgcgct ggcagcgcaa agccaaggaa gccgcaggcc cggccccctc | 180 |
| acccatgcgg gccgccaacc gatcccacag cgccggcagg actccgggcc gaactcctgg | 240 |
| caaatccagt tccaaggttc agaccactcc tagcaaacct ggcggtgacc gctatatccc | 300 |
| ccatcgcagt gctgcccaga tggaggtggc cagcttcctc ctgagcaagg agaaccagcc | 360 |
| tgaaaacagc cagacgccca ccaagaagga acatcagaaa gcctgggctt tgaacctgaa | 420 |
| cggttttgat gtagaggaag ccaagatcct tcggctcagt ggaaaaacca caaaatgcg | 480 |
| ccagagggtt atcacgaaca gactgaaagt actctacagc caaaaggcca ctcctggctc | 540 |

```
cagccggaag acctgccgtt tacattcctt ccctgccaag accgtatcct ggatgcgcct      600
gaaatcgaat gactattaac tgaacctgtg ggactggcag tccggggaat gtccgggccg      660
ggccacggcc acgaggtgtt ccgtgtggag tgcaagctgg acacaccgt gccgcttgtg       720 cacagggcca cgcggggaaa taatcccggg gcgcgcaaag cggcactggc gagagccgca      780
cgggccggtg ctggggggtgg tacaacaggc caaaacaaca cacaaggcca acaagacata    840
cgcgcgctga caccacggtg caaagcgctc agacgagtag taaccggcac tgtggttgct     900
gcctccccac ctctcccgct ctcagcgtaa gataaaagaa agaagagcaa aaagcaaaga     960
aagaagacga gacgagacac acaggaacga acagtaaagc aagctaaagc aaacgcaaga   1020
ccagacaaca gaaatagaaa gaaccaacag agaggagaca gaacaggacg ccagcaacat   1080
agcaacaaac gaacagaaga gagcactaaa caaaagcagc agcaagacga gacaggagag   1140
aaggaggaag gagggccgag cgagcaggga gcgcgagcag cgaggcgaag cagcagacaa   1200
gggcaggcga agggcaacga gaggaggcac cacacaaaaa ggagaggga caggagaagc    1260 agcgagagaa gcggaggagc aacaaggaga agaaaggag agggagagga gggagagagc    1320
ggaaggagga agaaacagca cgaggcgacg aaggggggag acgcggggc aggaaaagac    1380 acaggaaggc agcgcggagg aggagaaggg gaagcaggaa ggagacggaa ggagaagagg   1440
gagaggacag cgcaagagag cgcgcgcggc gacagcgagg gacggagcga gagagaggaa   1500
acggaaagcg agagggaaga ggagaggcaa cgcagcgaac caaccgaaaa cagcagaaag   1560
agaggagaag gacgcgcaaa gaggcaagcg caagacgaca ggaaacgaag cgagagacga   1620
gaagccggtg acgagcagga gaaagggaag gcaggagaca ggacaggcgg aagagagaca   1680
cgcgagacgc aaagagtgag cagaacgaag cgaagagcaa cgcacgagag aaacgac      1737

<210> SEQ ID NO 111
<211> LENGTH: 3053
<212> TYPE: DNA
<213> ORGANISM: Homo sapiens

<400> SEQUENCE: 111
gagcgcggct ggagtttgct gctgccgctg tgcagtttgt tcaggggctt gtggtggtga       60
gtccgagagg ctgcgtgtga gagacgtgag aaggatcctg cactgaggag gtggaaagaa     120
gaggattgct cgaggaggcc tggggtctgt gaggcagcgg agctgggtga aggctgcggg     180
ttccggcgag gcctgagctg tgctgtcgtc atgcctcaaa cccgatccca ggcacaggct     240
acaatcagtt ttccaaaaag gaagctgtct cgggcattga acaaagctaa aaactccagt     300
gatgccaaac tagaaccaac aaatgtccaa accgtaacct gttctcctcg tgtaaaagcc     360
ctgcctctca gccccaggaa acgtctgggc gatgacaacc tatgcaacac tccccattta     420
cctccttgtt ctccaccaaa gcaaggcaag aaagagaatg gtccccctca ctcacataca    480
cttaagggac gaagattggt atttgacaat cagctgacaa ttaagtctcc tagcaaaaga    540
gaactagcca agttcaccca aaacaaaata ctttcttcag ttagaaaaag tcaagagatc    600
acaacaaatt ctgagcagag atgtccactg aagaaagaat ctgcatgtgt gagactattc    660
aagcaagaag gcacttgcta ccagcaagca agctggtcc tgaacacagc tgtcccagat     720
cggctgcctg ccagggaaag ggagatggat gtcatcagga atttcttgag ggaacacatc    780
tgtgggaaaa aagctggaag cctttacctt tctggtgctc ctggaactgg aaaaactgcc    840
tgcttaagcc ggattctgca agacctcaag aaggaactga aaggctttaa aactatcatg    900
```

```
ctgaattgca tgtccttgag gactgcccag gctgtattcc cagctattgc tcaggagatt    960
tgtcaggaag aggtatccag gccagctggg aaggacatga tgaggaaatt ggaaaaacat   1020
atgactgcag agaagggccc catgattgtg ttggtattgg acgagatgga tcaactggac   1080
agcaaaggcc aggatgtatt gtacacgcta tttgaatggc catggctaag caattctcac   1140
ttggtgctga ttggtattgc taatacccty gatctcacag atagaattct acctaggctt   1200
caagctagag aaaaatgtaa gccacagctg ttgaacttcc caccttatac cagaaatcag   1260
atagtcacta ttttgcaaga tcgacttaat caggtatcta gagatcaggt tctggacaat   1320
gctgcagttc aattctgtgc ccgcaaagtc tctgctgttt caggagatgt tcgcaaagca   1380
ctggatgttt gcaggagagc tattgaaatt gtagagtcag atgtcaaaag ccagactatt   1440
ctcaaaccac tgtctgaatg taaatcacct tctgagcctc tgattcccaa gagggttggt   1500
cttattcaca tatcccaagt catctcagaa gttgatggta acaggatgac cttgagccaa   1560
gaaggagcac aagattcctt ccctcttcag cagaagatct tggtttgctc tttgatgctc   1620
ttgatcaggc agttgaaaat caagagggtc actctgggga agttatatga agcctacagt   1680
aaagtctgtc gcaaacagca ggtggcggct gtggaccagt cagagtgttt gtcactttca   1740
gggctcttgg aagccagggg cattttagga ttaaagagaa acaaggaaac ccgttttgaca  1800
aaggtgtttt tcaagattga agagaaagaa atagaacatg ctctgaaaga taaagcttta   1860
attggaaata tcttagctac tggattgcct taaattcttc tcttacaccc cacccgaaag   1920
tattcagctg gcatttagag agctacagtc ttcattttag tgctttacac attcgggcct   1980
gaaaacaaat atgacctttt ttacttgaag ccaatgaatt ttaatctata gattctttaa   2040
tattagcaca gaataatatc tttgggtctt actatttta cccataaaag tgaccaggta    2100
gacccttttt aattacattc actacttcta ccacttgtgt atctctagcc aatgtgcttg   2160
caagtgtaca gatctgtgta gaggaatgtg tgtatattta cctcttcgtt tgctcaaaca   2220
tgagtgggta ttttttttgtt tgtttttttt gttgttgttg ttttttgaggc gcgtctcacc  2280
ctgttgccca ggctggagtg caatggcgcg ttctctgctc actacagcac ccgcttccca   2340
ggttgaagtg attctcttgc ctcagcctcc cgagtagctg ggattacagg tgcccaccac   2400
cgcgcccagc taatttttta atttttagta gagacagggt tttaccatgt tggccaggct   2460
ggtcttgaac tcctgaccct caagtgatct gcccaccttg gcctccctaa gtgctgggat   2520
tataggcgtg agccaccatg ctcagccatt aaggtatttt gttaagaact ttaagtttag   2580
ggtaagaaga atgaaaatga tccagaaaaa tgcaagcaag tccacatgga gatttggagg   2640
acactggtta aagaatttat ttctttgtat agtatactat gttcatggtg cagatactac   2700
aacattgtgg cattttagac tcgttgagtt tcttgggcac tcccaagggc gttgggtca    2760
taaggagact ataactctac agattgtgaa tatatttatt ttcaagttgc attctttgtc   2820
tttttaagca atcagatttc aagagagctc aagctttcag aagtcaatgt gaaaattcct   2880
tcctaggctg tcccacagtc tttgctgccc ttagatgaag ccacttgttt caagatgact   2940
actttggggt tgggttttca tctaaacaca ttttttccagt cttattagat aaattagtcc   3000
atatggttgg ttaatcaaga gccttctggg tttggtttgg tggcattaaa tgg          3053
```

<210> SEQ ID NO 112
<211> LENGTH: 1843
<212> TYPE: DNA
<213> ORGANISM: Homo sapiens

<400> SEQUENCE: 112

-continued

```
gcggaatggg gcgggacttc cagtaggagg cggcaagttt gaaaagtgat gacggttgac      60
gtttgctgat ttttgacttt gcttgtagct gctccccgaa ctcgccgtct tcctgtcggc     120
ggccggcact gtagattaac aggaaacttc aagatggaa actttgtctt tccccagata     180
taatgtagct gagattgtga ttcatattcg caataagatc ttaacaggag ctgatggtaa     240
aaacctcacc aagaatgatc tttatccaaa tccaaagcct gaagtcttgc acatgatcta     300
catgagagcc ttacaaatag tatatggaat tcgactggaa catttttaca tgatgccagt     360
gaactctgaa gtcatgtatc cacatttaat ggaaggcttc ttaccattca gcaatttagt     420
tactcatctg gactcatttt tgcctatctg ccgggtgaat gactttgaga ctgctgatat     480
tctatgtcca aaagcaaaac ggacaagtcg ttttttaagt ggcattatca actttattca     540
cttcagagaa gcatgccgtg aaacgtatat ggaatttctt tggcaatata aatcctctgc     600
ggacaaaatg caacagttaa acgccgcaca ccaggaggca ttaatgaaac tggagagact     660
tgattctgtt ccagttgaag agcaagaaga gttcaagcag ctttcagatg gaattccagga    720 gctacaacaa tcactaaatc aggattttca tcaaaaaacg atagtgctgc aagagggaaa     780
ttcccaaaag aagtcaaata tttcagagaa aaccaagcgt ttgaatgaac taaaattgtc     840
ggtggtttct ttgaaagaaa tacaagagag tttgaaaaca aaaattgtgg attctccaga     900
gaagttaaag aattataaag aaaaaatgaa agatacggtc cagaagctta aaaatgccag     960
acaagaagtg gtggagaaat atgaaatcta tggagactca gttgactgcc tgccttcatg    1020
tcagttggaa gtgcagttat atcaaaagaa aatacaggac ctttcagata atagggaaaa    1080
attagccagt atcttaaagg agagcctgaa cttggaggac caaattgaga gtgatgagtc    1140
agaactgaag aaattgaaga ctgaagaaaa ttcgttcaaa agactgatga ttgtgaagaa    1200
ggaaaaactt gccacagcac aattcaaaat aaataagaag catgaagatg ttaagcaata    1260
caaacgcaca gtaattgagg attgcaataa agttcaagaa aaaagaggtg ctgtctatga    1320
acgagtaacc acaattaatc aagaaatcca aaaaattaaa cttggaattc aacaactaaa    1380
agatgctgct gaaagggaga aactgaagtc ccaggaaata tttctaaact tgaaaactgc    1440
tttggagaaa taccacgacg gtattgaaaa ggcagcagag gactcctatg ctaagataga    1500
tgagaagaca gctgaactga agaggaagat gttcaaaatg tcaacctgat taacaaaatt    1560
acatgtcttt ttgtaaatgg cttgccatct tttaattttc tatttagaaa gaaagttga    1620 agcgaatgga agtatcagaa gtaccaaata atgttggctt catcagtttt tatacactct    1680
cataagtagt taataagatg aatttaatgt aggcttttat taatttataa ttaaaataac    1740
ttgtgcagct attcatgtct ctactctgcc ccttgttgta aatagtttga gtaaaacaaa    1800
actagttacc tttgaaatat atatatttt ttctgttact atc                       1843
```

<210> SEQ ID NO 113
<211> LENGTH: 3686
<212> TYPE: DNA
<213> ORGANISM: Homo sapiens

<400> SEQUENCE: 113

```
ggctagcgcg ggaggtggag aaagaggctt gggcggcccc gctgtagccg cgtgtgggag      60
gacgcacggg cctgcttcaa agctttggga taacagcgcc tccggggat aatgaatgcg     120 gagcctccgt tttcagtcga cttcagatgt gtctccactt ttttccgctg tagccgcaag    180
gcaaggaaac atttctcttc ccgtactgag gaggctgagg agtgcactgg gtgttctttt    240
```

```
ctcctctaac ccagaactgc gagacagagg ctgagtccct gtaaagaaca gctccagaaa        300
agccaggaga gcgcaggagg gcatccggga ggccaggagg ggttcgctgg ggcctcaacc        360
gcacccacat cggtcccacc tgcgaggggg cgggacctcg tggcgctgga ccaatcagca        420
cccacctgcg ctcacctggc ctcctcccgc tggctcccgg gggctgcggt gctcaaaggg        480
gcaagagctg agcggaacac cggcccgccg tcgcggcagc tgcttcaccc ctctctctgc        540
agccatgggg ctccctcgtg gacctctcgc gtctctcctc cttctccagg tttgctggct        600
gcagtgcgcg gcctccgagc cgtgccgggc ggtcttcagg gaggctgaag tgaccttgga        660
ggcgggaggc gcggagcagg agcccggcca ggcgctgggg aaagtattca tgggctgccc        720
tgggcaagag ccagctctgt ttagcactga taatgatgac ttcactgtgc ggaatggcga        780
gacagtccag gaaagaaggt cactgaagga aggaatccca ttgaagatct tcccatccaa        840
acgtatctta cgaagacaca agagagattg ggtggttgct ccaatatctg tccctgaaaa        900
tggcaagggt cccttccccc agagactgaa tcagctcaag tctaataaag atagagacac        960
caagattttc tacagcatca cggggccggg ggcagacagc cccctgaggg tgtcttcgc       1020 tgtagagaag gagacaggct ggttgttgtt gaataagcca ctggaccggg aggagattgc       1080
caagtatgag ctctttggcc acgctgtgtc agagaatggg gcctcagtgg aggaccccat       1140
gaacatctcc atcatagtga ccgaccagaa tgaccacaag cccaagttta cccaggacac       1200
cttccgaggg agtgtcttag agggagtcct accaggtact tctgtgatgc agatgacagc       1260
cacagatgag gatgatgcca tctacaccta caatggggtg gttgcttact ccatccatag       1320
ccaagaacca aaggacccac acgacctcat gttcacaatt accggagca caggcaccat       1380 cagcgtcatc tccagtggcc tggaccggga aaaagtccct gagtacacac tgaccatcca       1440
ggccacagac atggatgggg acggctccac caccacggca gtggcagtag tggagatcct       1500
tgatgccaat gacaatgctc ccatgtttga cccccagaag tacgaggccc atgtgcctga       1560
gaatgcagtg ggccatgagg tgcagaggct gacggtcact gatctggacg cccccaactc       1620
accagcgtgg cgtgccacct accttatcat gggcggtgac gacggggacc atttaccat       1680 caccaccccac cctgagagca accagggcat cctgacaacc aggaagggtt tggattttga       1740
ggccaaaaac cagcacaccc tgtacgttga agtgaccaac gaggcccctt ttgtgctgaa       1800
gctcccaacc tccacagcca ccatagtggt ccacgtggag gatgtgaatg aggcacctgt       1860
gtttgtccca ccctccaaag tcgttgaggt ccaggagggc atccccactg ggagcctgt       1920 gtgtgtctac actgcagaag accctgacaa ggagaatcaa aagatcagct accgcatcct       1980
gagagaccca gcagggtggc tagccatgga cccagacagt gggcaggtca cagctgtggg       2040
caccctcgac cgtgaggatg agcagtttgt gaggaacaac atctatgaag tcatggtctt       2100
ggccatggac aatggaagcc ctcccaccac tggcacggga acccttctgc taacactgat       2160
tgatgtcaac gaccatggcc cagtccctga gcccgtcag atcaccatct gcaaccaaag       2220
ccctgtgcgc caggtgctga acatcacgga caaggacctg tctccccaca cctcccttt       2280 ccaggcccag ctcacagatg actcagacat ctactggacg cagaggtca acgaggaagg       2340 tgacacagtg gtcttgtccc tgaagaagtt cctgaagcag gatacatatg acgtgcacct       2400
ttctctgtct gaccatggca acaaagagca gctgacggtg atcagggcca ctgtgtgcga       2460
ctgccatggc catgtcgaaa cctgccctgg accctggaaa ggaggtttca tcctccctgt       2520 gctggggct gtcctggctc tgctgttcct cctgctggtg ctgcttttgt tggtgagaaa       2580
gaagcggaag atcaaggagc ccctcctact cccagaagat gacacccgtg acaacgtctt       2640
```

```
ctactatggc gaagaggggg gtggcgaaga ggaccaggac tatgacatca cccagctcca    2700
ccgaggtctg gaggccaggc cggaggtggt tctccgcaat gacgtggcac caaccatcat    2760
cccgacaccc atgtaccgtc ctaggccagc caacccagat gaaatcggca actttataat    2820
tgagaacctg aaggcggcta acacagaccc cacagcccg ccctacgaca ccctcttggt     2880
gttcgactat gagggcagcg gctccgacgc cgcgtccctg agctccctca cctcctccgc    2940
ctccgaccaa gaccaagatt acgattatct gaacgagtgg ggcagccgct tcaagaagct    3000
ggcagacatg tacggtggcg gggaggacga ctaggcggcc tgcctgcagg gctggggacc    3060
aaacgtcagg ccacagagca tctccaaggg gtctcagttc ccccttcagc tgaggacttc    3120
ggagcttgtc aggaagtggc cgtagcaact ggcggagac aggctatgag tctgacgtta     3180
gagtggttgc ttccttagcc tttcaggatg aggaatgtg ggcagtttga cttcagcact     3240
gaaaacctct ccacctgggc cagggttgcc tcagaggcca agtttccaga agcctcttac    3300
ctgccgtaaa atgctcaacc ctgtgtcctg ggcctgggcc tgctgtgact gacctacagt    3360
ggactttctc tctggaatgg aaccttctta ggcctcctgg tgcaacttaa ttttttttt     3420 taatgctatc ttcaaaacgt tagagaaagt tcttcaaaag tgcagcccag agctgctggg    3480
cccactggcc gtcctgcatt tctggtttcc agaccccaat gcctcccatt cggatggatc    3540
tctgcgtttt tatactgagt gtgcctaggt tgccccttat tttttatttt ccctgttgcg    3600
ttgctataga tgaagggtga ggacaatcgt gtatatgtac tagaacttt ttattaaaga     3660 aactttccc aaaaaaaaaa aaaaaa                                           3686

<210> SEQ ID NO 114
<211> LENGTH: 10316
<212> TYPE: DNA
<213> ORGANISM: Homo sapiens

<400> SEQUENCE: 114
gagaccagaa gcgggcgaat tgggcaccgg tggcggctgc gggcagtttg aattagactc      60
tgggctccag cccgccgaag ccgcgccaga actgtactct ccgagaggtc gttttcccgt     120
ccccgagagc aagtttattt acaaatgttg gagtaataaa gaaggcagaa caaaatgagc     180
tgggctttgg aagaatggaa agaagggctg cctacaagag ctcttcagaa aattcaagag    240
cttgaaggac agcttgacaa actgaagaag gaaaagcagc aaaggcagtt tcagcttgac    300
agtctcgagg ctgcgctgca gaagcaaaaa cagaaggttg aaaatgaaaa aaccgagggt    360
acaaacctga aagggagaa tcaaagattg atggaaatat gtgaaagtct ggagaaaact     420
aagcagaaga tttctcatga acttcaagtc aaggagtcac aagtgaattt ccaggaagga    480
caactgaatt caggcaaaaa acaaatagaa aaactggaac aggaacttaa aaggtgtaaa    540
tctgagcttg aaagaagcca acaagctgcg cagtctgcag atgtctctct gaatccatgc    600
aatacaccac aaaaaatttt tacaactcca ctaacaccaa gtcaatatta tagtggttcc    660
aagtatgaag atctaaaaga aaaatataat aaagaggttg aagaacgaaa aagattagag    720
gcagaggtta aagccttgca ggctaaaaaa gcaagccaga ctcttccaca agccaccatg    780
aatcaccgcg acattgcccg gcatcaggct tcatcatctg tgttctcatg gcagcaagag    840 aagacccaa gtcatctttc atctaattct caaagaactc caattaggag agatttctct    900
gcatcttact tttctgggga acaagaggtg actccaagtc gatcaacttt gcaaataggg    960
aaaagagatg ctaatagcag tttctttgac aattctagca gtcctcatct tttggatcaa    1020
```

```
ttaaaagcgc agaatcaaga gctaagaaac aagattaatg agttggaact acgcctgcaa   1080
ggacatgaaa aagaaatgaa aggccaagtg aataagtttc aagaactcca actccaactg   1140
gagaaagcaa aagtggaatt aattgaaaaa gagaaagttt tgaacaaatg tagggatgaa   1200
ctagtgagaa caacagcaca atacgaccag gcgtcaacca agtatactgc attggaacaa   1260
aaactgaaaa aattgacgga agatttgagt tgtcagcgac aaaatgcaga aagtgccaga   1320
tgttctctgg aacagaaaat taaggaaaaa gaaaaggagt ttcaagagga gctctcccgt   1380
caacagcgtt ctttccaaac actggaccag gagtgcatcc agatgaaggc cagactcacc   1440
caggagttac agcaagccaa gaatatgcac aacgtcctgc aggctgaact ggataaactc   1500
acatcagtaa agcaacagct agaaaacaat ttggaagagt ttaagcaaaa gttgtgcaga   1560
gctgaacagg cgttccaggc gagtcagatc aaggagaatg agctgaggag aagcatggag   1620
gaaatgaaga aggaaaacaa cctccttaag agtcactctg agcaaaaggc cagagaagtc   1680
tgccacctgg aggcagaact caagaacatc aaacagtgtt taaatcagag ccagaatttt   1740
gcagaagaaa tgaaagcgaa gaatacctct caggaaacca tgttaagaga tcttcaagaa   1800
aaaataaatc agcaagaaaa ctcccttgact ttagaaaaac tgaagcttgc tgtggctgat   1860
ctggaaaagc agcgagattg ttctcaagac cttttgaaga aaagagaaca tcacattgaa   1920
caacttaatg ataagttaag caagacagag aaagagtcca aagccttgct gagtgcttta   1980
gagttaaaaa agaaagaata tgaagaattg aaagaagaga aaactctgtt ttcttgttgg   2040
aaaagtgaaa acgaaaaact tttaactcag atggaatcag aaaaggaaaa cttgcagagt   2100
aaaattaatc acttggaaac ttgtctgaag acacagcaaa taaaaagtca tgaatacaac   2160
gagagagtaa gaacgctgga gatggacaga gaaaacctaa gtgtcgagat cagaaaccctt   2220 cacaacgtgt tagacagtaa gtcagtggag gtagagaccc agaaactagc ttatatggag   2280
ctacagcaga aagctgagtt ctcagatcag aaacatcaga aggaaataga aaatatgtgt   2340
ttgaagactt ctcagcttac tgggcaagtt gaagatctag aacacaagct tcagttactg   2400
tcaaatgaaa taatggacaa agaccggtgt taccaagact tgcatgccga atatgagagc   2460
ctcagggatc tgctaaaatc caagatgct tctctggtga caaatgaaga tcatcagaga   2520
agtcttttgg cttttgatca gcagcctgcc atgcatcatt cctttgcaaa tataattgga   2580
gaacaaggaa gcatgccttc agagaggagt gaatgtcgtt tagaagcaga ccaaagtccg   2640
aaaaattctg ccatcctaca aaatagagtt gattcacttg aattttcatt agagtctcaa   2700
aaacagatga actcagacct gcaaaagcag tgtgaagagt tggtgcaaat caaaggagaa   2760
atagaagaaa atctcatgaa agcagaacag atgcatcaaa gttttgtggc tgaaacaagt   2820
cagcgcatta gtaagttaca ggaagacact tctgctcacc agaatgttgt tgctgaaacc   2880
ttaagtgccc ttgagaacaa ggaaaaagag ctgcaacttt taaatgataa ggtagaaact   2940
gagcaggcag agattcaaga attaaaaaag agcaaccatc tacttgaaga ctctctaaag   3000
gagctacaac ttttatccga aaccctaagc ttggagaaga agaaatgag ttccatcatt   3060 tctctaaata aagggaaat tgaagagctg acccaagaga atgggactct taaggaaatt   3120
aatgcatcct taaatcaaga gaagatgaac ttaatccaga aaagtgagag ttttgcaaac   3180
tatatagatg aaagggagaa aagcatttca gagttatctg atcagtacaa gcaagaaaaa   3240 cttatttttac tacaaagatg tgaagaaacc ggaaatgcat atgaggatct tagtcaaaaa   3300
tacaaagcag cacaggaaaa gaattctaaa ttagaatgct tgctaaatga atgcactagt   3360
ctttgtgaaa ataggaaaaa tgagttggaa cagctaaagg aagcatttgc aaaggaacac   3420
```

```
caagaattct taacaaaatt agcatttgct gaagaaagaa atcagaatct gatgctagag    3480
ttggagacag tgcagcaagc tctgagatct gagatgacag ataaccaaaa caattctaag    3540
agcgaggctg gtggtttaaa gcaagaaatc atgactttaa aggaagaaca aaacaaaatg    3600
caaaaggaag ttaatgactt attacaagag aatgaacagc tgatgaaggt aatgaagact    3660
aaacatgaat gtcaaaatct agaatcagaa ccaattagga actctgtgaa agaaagagag    3720
agtgagagaa atcaatgtaa ttttaaacct cagatggatc ttgaagttaa agaaatttct    3780
ctagatagtt ataatgcgca gttggtgcaa ttagaagcta tgctaagaaa taaggaatta    3840
aaacttcagg aaagtgagaa ggagaaggag tgcctgcagc atgaattaca gacaattaga    3900
ggagatcttg aaaccagcaa tttgcaagac atgcagtcac aagaaattag tggccttaaa    3960
gactgtgaaa tagatgcgga agaaaagtat atttcagggc ctcatgagtt gtcaacaagt    4020
caaaacgaca atgcacacct tcagtgctct ctgcaaacaa caatgaacaa gctgaatgag    4080
ctagagaaaa tatgtgaaat actgcaggct gaaaagtatg aactcgtaac tgagctgaat    4140
gattcaaggt cagaatgtat cacagcaact aggaaaatgg cagaagaggt agggaaacta    4200
ctaaatgaag ttaaaatatt aaatgatgac agtggtcttc tccatggtga gttagtggaa    4260
gacataccag gaggtgaatt tggtgaacaa ccaaatgaac agcaccctgt gtctttggct    4320
ccattggacg agagtaattc ctacgagcac ttgacattgt cagacaaaga agttcaaatg    4380
cactttgccg aattgcaaga gaaattctta tctttacaaa gtgaacacaa aattttacat    4440
gatcagcact gtcagatgag ctctaaaatg tcagagctgc agacctatgt tgactcatta    4500
aaggccgaaa atttggtctt gtcaacgaat ctgagaaact ttcaaggtga cttggtgaag    4560
gagatgcagc tgggcttgga ggaggggctc gttccatccc tgtcatcctc ttgtgtgcct    4620
gacagctcta gtcttagcag tttgggagac tcctcctttt acagagctct tttagaacag    4680
acaggagata tgtctctttt gagtaattta aaggggctg tttcagcaaa ccagtgcagt    4740
gtagatgaag tattttgcag cagtctgcag gaggagaatc tgaccaggaa agaaaccccct   4800 tcggccccag cgaagggtgt tgaagagctt gagtccctct gtgaggtgta ccggcagtcc    4860
ctcgagaagc tagaagagaa aatggaaagt caagggatta tgaaaaataa ggaaattcaa    4920
gagctcgagc agttattaag ttctgaaagg caagagcttg actgccttag gaagcagtat    4980
ttgtcagaaa atgaacagtg gcaacagaag ctgacaagcg tgactctgga gatggagtcc    5040
aagttggcgg cagaaaagaa acagacggaa caactgtcac ttgagctgga agtagcacga    5100
ctccagctac aaggtctgga cttaagttct cggtctttgc ttggcatcga cacagaagat    5160
gctattcaag gccgaaatga gagctgtgac atatcaaaag aacatacttc agaaactaca    5220
gaaagaacac caaagcatga tgttcatcag atttgtgata agatgctcca gcaggacctc    5280
aatctagaca ttgagaaaat aactgagact ggtgcagtga acccacagg agagtgctct    5340 ggggaacagt ccccagatac caattatgag cctccagggg aagataaaac ccagggctct    5400
tcagaatgca tttctgaatt gtcatttct ggtcctaatg ctttggtacc tatggatttc    5460
ctggggaatc aggaagatat ccataatctt caactgcggg taaaagagac atcaaatgag    5520
aatttgagat tacttcatgt gatagaggac cgtgacagaa aagttgaaag tttgctaaat    5580
gaaatgaaag aattagactc aaaactccat ttacaggagg tacaactaat gaccaaaatt    5640
gaagcatgca tagaattgga aaaaatagtt ggggaactta agaaagaaaa ctcagattta    5700
agtgaaaaat tggaatattt ttcttgtgat caccaggagt tactccagag agtagaaact    5760
```

```
tctgaaggcc tcaattctga tttagaaatg catgcagata aatcatcacg tgaagatatt    5820
ggagataatg tggccaaggt gaatgacagc tggaaggaga gatttcttga tgtggaaaat    5880
gagctgagta ggatcagatc ggagaaagct agcattgagc atgaagccct ctacctggag    5940
gctgacttag aggtagttca aacagagaag ctatgtttag aaaaagacaa tgaaaataag    6000
cagaaggtta ttgtctgcct tgaagaagaa ctctcagtgg tcacaagtga gagaaaccag    6060
cttcgtggag aattagatac tatgtcaaaa aaaccacgg cactggatca gttgtctgaa    6120
aaaatgaagg agaaaacaca agagcttgag tctcatcaaa gtgagtgtct ccattgcatt    6180
caggtggcag aggcagaggt gaaggaaaag acggaactcc ttcagacttt gtcctctgat    6240
gtgagtgagc tgttaaaaga caaaactcat ctccaggaaa agctgcagag tttggaaaag    6300
gactcacagg cactgtcttt gacaaaatgt gagctggaaa accaaattgc acaactgaat    6360
aaagagaaag aattgcttgt caaggaatct gaaagcctgc aggccagact gagtgaatca    6420
gattatgaaa agctgaatgt ctccaaggcc ttggaggccg cactggtgga aaaggtgag    6480 ttcgcattga ggctgagctc aacacaggag gaagtgcatc agctgagaag aggcatcgag    6540
aaactgagag ttcgcattga ggccgatgaa aagaagcagc tgcacatcgc agagaaactg    6600
aaagaacgcg agcgggagaa tgattcactt aaggataaag ttgagaacct gaaagggaa    6660 ttgcagatgt cagaagaaaa ccaggagcta gtgattcttg atgccgagaa ttccaaagca    6720
gaagtagaga ctctaaaaac acaaatagaa gagatggcca gaagcctgaa gttttttgaa    6780
ttagaccttg tcacgttaag gtctgaaaaa gaaaatctga caaaacaaat acaagaaaaa    6840
caaggtcagt tgtcagaact agacaagtta ctctcttcat ttaaagtct gttagaagaa    6900 aaggagcaag cagagataca gatcaaagaa gaatctaaaa ctgcagtgga gatgcttcag    6960
aatcagttaa aggagctaaa tgaggcagta gcagccttgt gtggtgacca agaaattatg    7020
aaggccacag aacagagtct agacccacca atagaggaag agcatcagct gagaaatagc    7080
attgaaaagc tgagagcccg cctagaagct gatgaaaaga agcagctctg tgtcttacaa    7140
caactgaagg aaagtgagca tcatgcagat ttacttaagg gtagagtgga gaaccttgaa    7200
agagagctag atagccagg acaaaccaa gagcatgcag ctcttgaggc agagaattcc    7260
aaaggagagg tagagaccct aaaagcaaaa atagaaggga tgacccaaag tctgagaggt    7320
ctggaattag atgttgttac tataaggtca gaaaaagaaa atctgacaaa tgaattacaa    7380
aaagagcaag agcgaatatc tgaattagaa ataataaatt catcatttga aaatattttg    7440
caagaaaaag agcaagagaa agtacagatg aaagaaaaat caagcactgc catggagatg    7500
cttcaaacac aattaaaaga gctcaatgag agagtggcag ccctgcataa tgaccaagaa    7560
gcctgtaagg ccaaagagca gaatcttagt agtcaagtag agtgtcttga acttgagaag    7620
gctcagttgc tacaaggcct tgatgaggcc aaaaataatt atattgtttt gcaatcttca    7680
gtgaatggcc tcattcaaga agtagaagat ggcaagcaga aactggagaa aaggatgaa    7740 gaaatcagta gactgaaaaa tcaaattcaa gaccaagagc agcttgtctc taaactgtcc    7800
caggtggaag gagagcacca actttggaag gagcaaaact agaactgag aaatctgaca    7860 gtggaattgg agcagaagat ccaagtgcta caatccaaaa atgcctcttt gcaggacaca    7920
ttagaagtgc tgcagagttc ttacaagaat ctagagaatg agcttgaatt gacaaaaatg    7980
gacaaaatgt cctttgttga aaagtaaac aaaatgactg caaaggaaac tgagctgcag    8040
agggaaatgc atgagatggc acagaaaaca gcagagctgc aagaagaact cagtggagag    8100
aaaaataggc tagctggaga gttgcagtta ctgttggaag aaataaagag cagcaaagat    8160
```

```
caattgaagg agctcacact agaaaatagt gaattgaaga agagcctaga ttgcatgcac    8220
aaagaccagg tggaaaagga agggaaagtg agagaggaaa tagctgaata tcagctacgg    8280
cttcatgaag ctgaaaagaa acaccaggct ttgcttttgg acacaaacaa acagtatgaa    8340
gtagaaatcc agacataccg agagaaattg acttctaaag aagaatgtct cagttcacag    8400
aagctggaga tagaccttt aaagtctagt aaagaagagc tcaataattc attgaaagct    8460
actactcaga ttttggaaga attgaagaaa accaagatgg acaatctaaa atatgtaaat    8520
cagttgaaga aggaaaatga acgtgcccag gggaaaatga agttgttgat caaatcctgt    8580
aaacagctgg aagaggaaaa ggagatactg cagaaagaac tctctcaact tcaagctgca    8640
caggagaagc agaaaacagg tactgttatg gataccaagg tcgatgaatt aacaactgag    8700
atcaaagaac tgaaagaaac tcttgaagaa aaaaccaagg aggcagatga atacttggat    8760
aagtactgtt ccttgcttat aagccatgaa aagttagaga agctaaaga gatgttagag    8820 acacaagtgg cccatctgtg ttcacagcaa tctaaacaag attcccgagg gtctcctttg    8880
ctaggtccag ttgttccagg accatctcca atcccttctg ttactgaaaa gaggttatca    8940
tctggccaaa ataaagcttc aggcaagagg caaagatcca gtggaatatg ggagaatggt    9000
agaggaccaa cacctgctac cccagagagc ttttctaaaa aaagcaagaa agcagtcatg    9060
agtggtattc accctgcaga agacacgaa ggtactgagt ttgagccaga gggacttcca    9120
gaagttgtaa agaaagggtt tgctgacatc ccgacaggaa agactagccc atatatcctg    9180
cgaagaacaa ccatggcaac tcggaccagc ccccgcctgg ctgcacagaa gttagcgcta    9240
tccccactga gtctcggcaa agaaaatctt gcagagtcct ccaaaccaac agctggtggc    9300
agcagatcac aaaaggtcaa agttgctcag cggagcccag tagattcagg caccatcctc    9360
cgagaaccca ccacgaaatc cgtcccagtc aataatcttc ctgagagaag tccgactgac    9420
agccccagag agggcctgag ggtcaagcga ggccgacttg tccccagccc caaagctgga    9480
ctggagtcca acggcagtga gaactgtaag gtccagtgaa ggcactttgt gtgtcagtac    9540
ccctgggagg tgccagtcat tgaatagata aggctgtgcc tacaggactt ctctttagtc    9600
agggcatgct ttattagtga ggagaaaaca attccttaga agtcttaaat atattgtact    9660
ctttagatct cccatgtgta ggtattgaaa aagtttggaa gcactgatca cctgttagca    9720
ttgccattcc tctactgcaa tgtaaatagt ataaagctat gtatataaag cttttggta    9780 atatgttaca attaaaatga caagcactat atcacaatct ctgtttgtat gtgggttta    9840 cactaaaaaa atgcaaaaca cattttattc ttctaattaa cagctcctag gaaaatgtag    9900
acttttgctt tatgatattc tatctgtagt atgaggcatg gaatagtttt gtatcgggaa    9960
tttctcagag ctgagtaaaa tgaaggaaaa gcatgttatg tgttttttaag gaaaatgtgc   10020 acacatatac atgtaggagt gtttatcttt ctcttacaat ctgttttaga catctttgct   10080
tatgaaacct gtacatatgt gtgtgtgggt atgtgtttat ttccagtgag ggctgcaggc   10140
ttcctagagg tgtgctatac catgcgtctg tcgttgtgct ttttctgtt tttagaccaa   10200 tttttacag ttcttggta agcattgtcg tatctggtga tggattaaca tatagccttt   10260
gttttctaat aaaatagtcg ccttcgtttt ctgtaaaaaa aaaaaaaaaa aaaaaa       10316
```

<210> SEQ ID NO 115
<211> LENGTH: 2639
<212> TYPE: DNA
<213> ORGANISM: Homo sapiens

<400> SEQUENCE: 115

```
ggcacgaggg gccgacgcga gcgccgcgct tcgcttcagc tgctagctgg cccaagggag      60
gcgaccgcgg agggtggcga ggggcggcca ggacccgcag ccccggggcc gggccggtcc     120
ggaccgccag ggagggcagg tcagtgggca gatcgcgtcc gcgggattca atctctgccc     180
gctctgataa cagtccttttt ccctggcgct cacttcgtgc ctggcacccg gctgggcgcc     240
tcaagaccgt tgtctcttcg atcgcttctt tggacttggc gaccatttca gagatgtctt     300
ccagaagtac caaagattta attaaaagta agtggggatc gaagcctagt aactccaaat     360
ccgaaactac attagaaaaa ttaaagggag aaattgcaca cttaaagaca tcagtggatg     420
aaatcacaag tgggaaagga agctgactg ataaagagag cacagactt ttggagaaaa      480
ttcgagtcct tgaggctgag aaggagaaga atgcttatca actcacagag aaggacaaag     540
aaatacagcg actgagagac caactgaagg ccagatatag tactaccgca ttgcttgaac     600
agctggaaga caacgagaa gaaggagaaa ggagggagca ggtgttgaaa gccttatctg      660
aagagaaaga cgtattgaaa caacagttgt ctgctgcaac ctcacgaatt gctgaacttg     720
aaagcaaaac caatacactc cgtttatcac agactgtggc tccaaactgc ttcaactcat     780
caataaataa tattcatgaa atggaaatac agctgaaaga tgctctggag aaaaatcagc     840
agtggctcgt gtatgatcag cagcgggaag tctatgtaaa aggacttta gcaaagatct      900
ttgagttgga aagaaaacg gaaacagctg ctcattcact cccacagcag acaaaaaagc      960
ctgaatcaga aggttatctt caagaagaga agcagaaatg ttacaacgat ctcttggcaa    1020
gtgcaaaaaa agatcttgag gttgaacgac aaaccataac tcagctgagt tttgaactga    1080
gtgaatttcg aagaaaatat gaagaaaccc aaaagaagt tcacaattta aatcagctgt    1140
tgtattcaca agaagggca gatgtgcaac atctggaaga tgataggcat aaaacagaga    1200
agatacaaaa actcagggaa gagaatgata ttgctagggg aaaacttgaa gaagagaaga    1260
agagatccga agagctctta tctcaggtcc agtttctta cacatctctg ctaaagcagc    1320
aagaagaaca aacaagggta gctctgttgg aacaacagat gcaggcatgt actttagact    1380
ttgaaaatga aaaactcgac cgtcaacatg tgcagcatca attgcatgta attcttaagg    1440
agctccgaaa agcaagaaat caaataacac agttggaatc cttgaaacag cttcatgagt    1500
ttgccatcac agagccatta gtcactttcc aaggagagac tgaaaacaga gaaaagttg    1560
ccgcctcacc aaaaagtccc actgctgcac tcaatgaaag cctggtggaa tgtcccaagt    1620
gcaatataca gtatccagcc actgagcatc gcgatctgct tgtccatgtg gaatactgtt    1680
caaagtagca aaataagtat ttgttttgat attaaaagat tcaatactgt attttctgtt    1740
agcttgtggg catttgaat tatatatttc acattttgca taaaactgcc tatctacctt    1800
tgacactcca gcatgctagt gaatcatgta tcttttaggc tgctgtgcat ttctcttggc    1860
agtgatacct ccctgacatg gttcatcatc aggctgcaat gacagaatgt ggtgagcagc    1920
gtctactgag actactaaca tttgtgcactg tcaaaatact tggtgaggaa aagatagctc    1980
aggttattgc taatgggtta atgcaccagc aagcaaaata ttttatgttt tgggggtttg    2040
aaaaatcaaa gataattaac caaggatctt aactgtgttc gcatttttta tccaagcact    2100
tagaaaacct acaatcctaa ttttgatgtc cattgttaag aggtggtgat agatactatt    2160
ttttttttca tattgtatag cggttattag aaaagttggg gattttcttg atctttattg    2220
ctgcttacca ttgaaactta acccagctgt gttccccaac tctgttctgc gcacgaaaca    2280
gtatctgttt gaggcataat cttaagtggc cacacacaat gttttctctt atgttatctg    2340
```

```
gcagtaactg taacttgaat tacattagca cattctgctt agctaaaatt gttaaaataa    2400
actttaataa acccatgtag ccctctcatt tgattgacag tattttagtt attttttggca    2460 ttcttaaagc tgggcaatgt aatgatcaga tctttgtttg tctgaacagg tattttttata    2520 catgctttt gtaaaccaaa aacttttaaa tttcttcagg ttttctaaca tgcttaccac    2580
tgggctactg taaatgagaa aagaataaaa ttatttaatg tttaaaaaa aaaaaaaaa    2639
```

<210> SEQ ID NO 116
<211> LENGTH: 2632
<212> TYPE: DNA
<213> ORGANISM: Homo sapiens

<400> SEQUENCE: 116

```
ggcggctgag cctgagcggg gatgtagagg cggcggcagc agaggcggca ctggcggcaa      60
gagcagacgc ccgagccgag cgagaagagc ggcagagcct tatcccctga agccgggccc     120
cgcgtcccag ccctgcccag cccgcgccca gccatgcgcg ccgcctgctg agtccgggcg     180
ccgcacgctg agccctccgc ccgcgagccg cgctcagctc ggggggtgatt agttgctttt    240 tgttgttttt taatttgggc cgcggggagg gggaggaggg gcaggtgctg caggctcccc    300
cccctccccg cctcgggcca gccgcggcgg cgcgactcgg gctccggacc cgggcactgc    360
tggcggctgg agcggagcgc accgcggcgg tggtgcccag agcggagcgc agctccctgc    420
cccgcccctc ccctcggcc tcgcggcgac ggcggcggtg gcggcttgga cgactcggag    480
agccgagtga agacatttcc acctggacac ctgaccatgt gcctgccctg agcagcgagg    540
cccaccaggc atctctgttg tgggcagcag ggccaggtcc tggtctgtgg accctcggca    600
gttggcaggc tccctctgca gtggggtctg ggcctcggcc ccaccatgtc gagcctcggc    660
ggtggctccc aggatgccgg cggcagtagc agcagcagca ccaatggcag cggtggcagt    720
ggcagcagtg gcccaaaggc aggagcagca gacaagagtg cagtggtggc tgccgccgca    780
ccagcctcag tggcagatga cacaccaccc cccgagcgtc ggaacaagag cggtatcatc    840
agtgagcccc tcaacaagag cctgcgccgc tcccgcccgc tctcccacta ctcttctttt    900
ggcagcagtg gtggtagtgg cggtggcagc atgatgggcg gagagtctgc tgacaaggcc    960
actgcggctg cagccgctgc ctccctgttg gccaatgggc atgacctggc ggcggccatg    1020
gcggtggaca aaagcaaccc tacctcaaag cacaaaagtg gtgctgtggc cagcctgctg    1080
agcaaggcag agcgggccac ggagctggca gccgagggac agctgacgct gcagcagttt    1140
gcgcagtcca cagagatgct gaagcgcgtg gtgcaggagc atctcccgct gatgagcgag    1200
gcgggtgctg gcctgcctga catggaggct gtggcaggtg ccgaagccct caatggccag    1260
tccgacttcc cctacctggg cgcttttccc atcaacccag gctcttcat tatgaccccg    1320 gcaggtgtgt tcctggccga gagcgcgctg cacatggcgg gcctggctga gtaccccatg    1380
cagggagagc tggcctctgc catcagctcc ggcaagaaga gcggaaacg ctgcggcatg    1440 tgcgcgccct gccggcggcg catcaactgc gagcagtgca gcagttgtag gaatcgaaag    1500
actggccatc agatttgcaa attcagaaaa tgtgaggaac tcaaaagaa gccttccgct    1560 gctctggaga aggtgatgct tccgacggga gccgccttcc ggtggtttca gtgacggcgg    1620
cggaacccaa agctgccctc tccgtgcaat gtcactgctc gtgtggtctc cagcaaggga    1680
ttcgggcgaa gacaaacgga tgcacccgtc tttagaacca aaaatattct ctcacagatt    1740
tcattcctgt tttatatat atattttttg ttgtcgtttt aacatctcca cgtccctagc    1800
```

| | |
|---|---|
| ataaaaagaa aaagaaaaaa atttaaactg cttttttcgga agaacaacaa caaaaaagag | 1860 |
| gtaaagacga atctataaag taccgagact tcctgggcaa agaatggaca atcagtttcc | 1920 |
| ttcctgtgtc gatgtcgatg ttgtctgtgc aggagatgca gttttttgtgt agagaatgta | 1980 |
| aattttctgt aacctttga aatctagtta ctaataagca ctactgtaat ttagcacagt | 2040 |
| ttaactccac cctcatttaa acttcctttg attcttttccg accatgaaat agtgcatagt | 2100 |
| ttgcctggag aatccactca cgttcataaa gagaatgttg atggcgccgt gtagaagccg | 2160 |
| ctctgtatcc atccacgcgt gcagagctgc cagcagggag ctcacagaag gggagggagc | 2220 |
| accaggccag ctgagctgca cccacagtcc cgagactggg atccccccacc ccaacagtga | 2280 |
| ttttggaaaa aaaaatgaaa gttctgttcg tttatccatt gcgatctggg gagccccatc | 2340 |
| tcgatatttc caatcctggc tactttttctt agagaaaata agtccttttt ttctggcctt | 2400 |
| gctaatggca acagaagaaa gggcttcttt gcgtggtccc ctgctggtgg gggtgggtcc | 2460 |
| ccagggggcc ccctgcggcc tgggcccccc tgcccacggc cagcttcctg ctgatgaaca | 2520 |
| tgctgtttgt attgttttag gaaaccaggc tgttttgtga ataaaacgaa tgcatgtttg | 2580 |
| tgtcacgaaa aaaaaaaaaa aaaaaaaaaa aaaaaaaaaa aaaaaaaaaa aa | 2632 |

<210> SEQ ID NO 117
<211> LENGTH: 5616
<212> TYPE: DNA
<213> ORGANISM: Homo sapiens

<400> SEQUENCE: 117

| | |
|---|---|
| cccccggcgca gcgcggccgc agcagcctcc gcccccccgca cggtgtgagc gcccgacgcg | 60 |
| gccgaggcgg ccggagtccc gagctagccc cggcggccgc cgccgcccag accggacgac | 120 |
| aggccacctc gtcggcgtcc gcccgagtcc ccgcctcgcc gccaacgcca caaccaccgc | 180 |
| gcacggcccc ctgactccgt ccagtattga tcgggagagc cggagcgagc tcttcgggga | 240 |
| gcagcgatgc gaccctccgg gacggccggg gcagcgctcc tggcgctgct ggctgcgctc | 300 |
| tgcccggcga gtcgggctct ggaggaaaag aaagtttgcc aaggcacgag taacaagctc | 360 |
| acgcagttgg gcacttttga agatcatttt ctcagcctcc agaggatgtt caataactgt | 420 |
| gaggtggtcc ttgggaattt ggaaattacc tatgtgcaga ggaattatga tctttccttc | 480 |
| ttaaagacca tccaggaggt ggctggttat gtcctcattg ccctcaacac agtgagcga | 540 |
| attcctttgg aaaacctgca gatcatcaga ggaaatatgt actacgaaaa ttcctatgcc | 600 |
| ttagcagtct tatctaacta tgatgcaaat aaaaccggac tgaaggagct gcccatgaga | 660 |
| aatttacagg aaatcctgca tggcgccgtg cggttcagca caaccctgc cctgtgcaac | 720 |
| gtggagagca tccagtggcg ggacatagtc agcagtgact ttctcagcaa catgtcgatg | 780 |
| gacttccaga accacctggg cagctgccaa aagtgtgatc caagctgtcc caatgggagc | 840 |
| tgctggggtg caggagagga gaactgccag aaactgacca aaatcatctg tgcccagcag | 900 |
| tgctccgggc gctgccgtgg caagtccccc agtgactgct gccacaacca gtgtgctgca | 960 |
| ggctgcacag gccccgggga gagcgactgc ctggtctgcc gcaaattccg agacgaagcc | 1020 |
| acgtgcaagg acacctgccc cccactcatg ctctacaacc ccaccacgta ccagatggat | 1080 |
| gtgaaccccg agggcaaata cagctttggt gccacctgcg tgaagaagtg tccccgtaat | 1140 |
| tatgtggtga cagatcacgg ctcgtgcgtc cgagcctgtg gggccgacag ctatgagatg | 1200 |
| gaggaagacg gcgtccgcaa gtgtaagaag tgcgaagggc cttgccgcaa agtgtgtaac | 1260 |
| ggaataggta ttggtgaatt taaagactca ctctccataa atgctacgaa tattaaacac | 1320 |

```
ttcaaaaact gcacctccat cagtggcgat ctccacatcc tgccggtggc atttaggggt    1380
gactccttca cacatactcc tcctctggat ccacaggaac tggatattct gaaaaccgta    1440
aaggaaatca cagggttttt gctgattcag gcttggcctg aaaacaggac ggacctccat    1500
gcctttgaga acctagaaat catacgcggc aggaccaagc aacatggtca gttttctctt    1560
gcagtcgtca gcctgaacat aacatccttg ggattacgct ccctcaagga gataagtgat    1620
ggagatgtga taatttcagg aaacaaaaat ttgtgctatg caaatacaat aaactggaaa    1680
aaactgtttg ggacctccgg tcagaaaacc aaaattataa gcaacagagg tgaaaacagc    1740
tgcaaggcca caggccaggt ctgccatgcc ttgtgctccc ccgagggctg ctggggcccg    1800
gagcccaggg actgcgtctc ttgccggaat gtcagccgag cagggaatg cgtggacaag    1860 tgcaaccttc tggagggtga gccaaggag tttgtggaga actctgagtg catacagtgc    1920
cacccagagt gcctgcctca ggccatgaac atcacctgca caggacgggg accagacaac    1980
tgtatccagt gtgcccacta cattgacggc ccccactgcg tcaagacctg cccggcagga    2040
gtcatgggag aaaacaacac cctggtctgg aagtacgcag acgccggcca tgtgtgccac    2100
ctgtgccatc caaactgcac ctacggatgc actgggccag tcttgaagg ctgtccaacg    2160 aatgggccta agatcccgtc catcgccact gggatggtgg gggcctcct cttgctgctg    2220 gtggtggccc tggggatcgg cctcttcatg cgaaggcgcc acatcgttcg gaagcgcacg    2280
ctgcggaggc tgctgcagga gagggagctt gtggagcctc ttacacccag tggagaagct    2340
cccaaccaag ctctcttgag gatcttgaag gaaactgaat tcaaaaagat caaagtgctg    2400
ggctccggtg cgttcggcac ggtgtataag ggactctgga tcccagaagg tgagaaagtt    2460
aaaattcccg tcgctatcaa ggaattaaga gaagcaacat ctccgaaagc caacaaggaa    2520
atcctcgatg aagcctacgt gatggccagc gtggacaacc cccacgtgtg ccgcctgctg    2580
ggcatctgcc tcacctccac cgtgcagctc atcacgcagc tcatgccctt cggctgcctc    2640
ctggactatg tccgggaaca caaagacaat attggctccc agtacctgct caactggtgt    2700
gtgcagatcg caaagggcat gaactacttg gaggaccgtc gcttggtgca ccgcgacctg    2760
gcagccagga acgtactggt gaaaacaccg cagcatgtca agatcacaga ttttgggctg    2820
gccaaactgc tgggtgcgga agagaaagaa taccatgcag aaggaggcaa agtgcctatc    2880
aagtggatgg cattggaatc aattttacac agaatctata cccaccagag tgatgtctgg    2940
agctacgggg tgaccgtttg ggagttgatg acctttggat ccaagccata tgacggaatc    3000
cctgccagcg agatctcctc catcctggag aaaggagaac gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc agggggatga aagaatgcat ttgccaagtc ctacagactc caacttctac    3240
cgtgccctga tggatgaaga agacatggac gacgtggtgg atgccgacga gtacctcatc    3300
ccacagcagg gcttcttcag cagcccctcc acgtcacgga ctcccctcct gagctctctg    3360
agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcagag acccacacta ccaggacccc cacagcactg cagtgggcaa ccccgagtat    3660
```

| | |
|---|---|
| ctcaacactg tccagcccac ctgtgtcaac agcacattcg acagccctgc ccactgggcc | 3720 |
| cagaaaggca gccaccaaat tagcctggac aaccctgact accagcagga cttctttccc | 3780 |
| aaggaagcca agccaaatgg catctttaag ggctccacag ctgaaaatgc agaataccta | 3840 |
| agggtcgcgc cacaaagcag tgaatttatt ggagcatgac cacggaggat agtatgagcc | 3900 |
| ctaaaaatcc agactctttc gatacccagg accaagccac agcaggtcct ccatcccaac | 3960 |
| agccatgccc gcattagctc ttagacccac agactggttt tgcaacgttt acaccgacta | 4020 |
| gccaggaagt acttccacct cgggcacatt ttgggaagtt gcattccttt gtcttcaaac | 4080 |
| tgtgaagcat ttacagaaac gcatccagca agaatattgt cccttt gagc agaaatttat | 4140 |
| ctttcaaaga ggtatatttg aaaaaaaaaa aaagtatatg tgaggatttt tattgattgg | 4200 |
| ggatcttgga gtttttcatt gtcgctattg attttta ctt caatgggctc ttccaacaag | 4260 |
| gaagaagctt gctggtagca cttgctaccc tgagttcatc caggcccaac tgtgagcaag | 4320 |
| gagcacaagc cacaagtctt ccagaggatg cttgattcca gtggttctgc ttcaaggctt | 4380 |
| ccactgcaaa acactaaaga tccaagaagg ccttcatggc cccagcaggc cggatcggta | 4440 |
| ctgtatcaag tcatggcagg tacagtagga taagccactc tgtcccttcc tgggcaaaga | 4500 |
| agaaacggag gggatggaat tcttccttag acttactttt gtaaaaatgt ccccacggta | 4560 |
| cttactcccc actgatggac cagtggtttc cagtcatgag cgttagactg acttgtttgt | 4620 |
| cttccattcc attgttttga aactcagtat gctgcccctg tcttgctgtc atgaaatcag | 4680 |
| caagagagga tgacacatca ataataact cggattccag cccacattgg attcatcagc | 4740 |
| atttggacca atagcccaca gctgagaatg tggaatacct aaggatagca ccgcttttgt | 4800 |
| tctcgcaaaa acgtatctcc taatttgagg ctcagatgaa atgcatcagg tcctttgggg | 4860 |
| catagatcag aagactacaa aaatgaagct gctctgaaat ctcctttagc catcaccca | 4920 |
| accccccaaa attagtttgt gttacttatg gaagatagtt ttctcctttt acttcacttc | 4980 |
| aaaagctttt tactcaaaga gtatatgttc cctccaggtc agctgccccc aaacccctc | 5040 |
| cttacgcttt gtcacacaaa aagtgtctct gccttgagtc atctattcaa gcacttacag | 5100 |
| ctctggccac aacagggcat tttacaggtg cgaatgacag tagcattatg agtagtgtgg | 5160 |
| aattcaggta gtaaatatga aactagggtt tgaaattgat aatgctttca caacatttgc | 5220 |
| agatgtttta gaaggaaaaa agttccttcc taaaataatt tctctacaat tggaagattg | 5280 |
| gaagattcag ctagttagga gcccaccttt tttcctaatc tgtgtgtgcc ctgtaacctg | 5340 |
| actggttaac agcagtcctt tgtaaacagt gttttaaact ctcctagtca atatccaccc | 5400 |
| catccaattt atcaaggaag aaatggttca gaaaatattt tcagcctaca gttatgttca | 5460 |
| gtcacacaca catacaaaat gttccttttg cttttaaagt aattttttgac tcccagatca | 5520 |
| gtcagagccc ctacagcatt gttaagaaag tatttgattt ttgtctcaat gaaaataaaa | 5580 |
| ctatattcat ttccactcta aaaaaaaaaa aaaaaa | 5616 |

<210> SEQ ID NO 118
<211> LENGTH: 4816
<212> TYPE: DNA
<213> ORGANISM: Homo sapiens

<400> SEQUENCE: 118

| | |
|---|---|
| gttcccggat ttttgtgggc gcctgccccg cccctcgtcc ccctgctgtg tccatatatc | 60 |
| gaggcgatag ggttaaggga aggcggacgc ctgatgggat aatgagcaaa ctgaagtgtt | 120 |
| ttccatgatc ttttttgagt cgcaattgaa gtaccacctc ccgagggtga ttgcttcccc | 180 |

```
atgcgggta gaacctttgc tgtcctgttc accactctac ctccagcaca gaatttggct    240
tatgcctact caatgtgaag atgatgagga tgaaaacctt tgtgatgatc cacttccact    300
taatgaatgg tggcaaagca aagctatatt caagaccaca tgcaaagcta ctccctgagc    360
aaagagtcac agataaaacg gggcaccag tagaatggcc aggacaaacg cagtgcagca    420
cagagactca gaccctggca gccatgcctg cgcaggcagt gatgagagtg acatgtactg    480
ttgtggacat gcacaaaagt gagtgtgcac cggcacagac atgaagctgc ggctccctgc    540
cagtcccgag acccacctgg acatgctccg ccacctctac cagggctgcc aggtggtgca    600
gggaaacctg gaactcacct acctgccccac caatgccagc ctgtccttcc tgcaggatat    660
ccaggaggtg cagggctacg tgctcatcgc tcacaaccaa gtgaggcagg tcccactgca    720
gaggctgcgg attgtgcgag gcacccagct ctttgaggac aactatgccc tggccgtgct    780
agacaatgga gacccgctga caataccac ccctgtcaca ggggcctccc caggaggcct    840
gcgggagctg cagcttcgaa gcctcacaga gatcttgaaa ggaggggtct tgatccagcg    900 gaaccccag ctctgctacc aggacacgat tttgtggaag acatcttcc acaagaacaa    960 ccagctggct ctcacactga tagacaccaa ccgctctcgg gcctgccacc cctgttctcc   1020
gatgtgtaag ggctcccgct gctggggaga gagttctgag gattgtcaga gcctgacgcg   1080
cactgtctgt gccggtggct gtgcccgctg caaggggcca ctgccactg actgctgcca   1140 tgagcagtgt gctgccggct gcacgggccc caagcactct gactgcctgg cctgcctcca   1200
cttcaaccac agtggcatct gtgagctgca ctgcccagcc ctggtcacct acaacacaga   1260
cacgtttgag tccatgccca atcccgaggg ccggtataca ttcggcgcca gctgtgtgac   1320
tgcctgtccc tacaactacc tttctacgga cgtgggatcc tgcacccctcg tctgccccct   1380 gcacaaccaa gaggtgacag cagaggatgg aacacagcgg tgtgagaagt gcagcaagcc   1440
ctgtgcccga gtgtgctatg gtctgggcat ggagcacttg cgagaggtga gggcagttac   1500
cagtgccaat atccaggagt ttgctggctg caagaagatc tttgggagcc tggcatttct   1560
gccggagagc tttgatgggg acccagcctc caacactgcc ccgctccagc cagagcagct   1620
ccaagtgttt gagactctgg aagagatcac aggttaccta tacatctcag catggccgga   1680
cagcctgcct gacctcagcg tcttccagaa cctgcaagta atccggggac gaattctgca   1740
caatggcgcc tactcgctga ccctgcaagg gctgggcatc agctggctgg gctgcgctc   1800 actgagggaa ctgggcagtg actggcccct catccaccat aacacccacc tctgcttcgt   1860
gcacacggtg ccctgggacc agctctttcg gaacccgcac caagctctgc tccacactgc   1920
caaccggcca gaggacgagt gtgtgggcga gggcctggcc tgccaccagc tgtgcgcccg   1980
agggcactgc tgggtccag ggcccaccca gtgtgtcaac tgcagccagt ccttcgggg   2040 ccaggagtgc gtggaggaat gccgagtact gcaggggctc cccagggagt atgtgaatgc   2100
caggcactgt ttgccgtgcc accctgagtg tcagccccag aatggctcag tgacctgttt   2160
tggaccggag gctgaccagt gtgtggcctg tgcccactat aaggaccctc ccttctgcgt   2220
ggcccgctgc cccagcggtg tgaaacctga cctctcctac atgcccatct ggaagtttcc   2280
agatgaggag ggcgcatgcc agccttgccc catcaactgc acccactcct gtgtggacct   2340
ggatgacaag ggctgccccg ccgagcagag agccagccct ctgacgtcca tcatctctgc   2400
ggtggttggc attctgctgg tcgtggtctt ggggtggtc tttgggatcc tcatcaagcg   2460
acggcagcag aagatccgga agtacacgat gcggagactg ctgcaggaaa cggagctggt   2520
```

```
ggagccgctg acacctagcg gagcgatgcc caaccaggcg cagatgcgga tcctgaaaga    2580
gacggagctg aggaaggtga aggtgcttgg atctggcgct tttggcacag tctacaaggg    2640
catctggatc cctgatgggg agaatgtgaa aattccagtg gccatcaaag tgttgaggga    2700
aaacacatcc cccaaagcca acaaagaaat cttagacgaa gcacgcgtga tggctggtgt    2760
gggctcccca tatgtctccc gccttctggg catctgcctg acatccacgg tgcagctggt    2820
gacacagctt atgccctatg ctgcctctt  agaccatgtc cgggaaaacc gcggacgcct     2880
gggctcccag gacctgctga actggtgtat gcagattgcc aaggggatga gctacctgga    2940
ggatgtgcgg ctcgtacaca gggacttggc cgctcggaac gtgctggtca agagtcccaa    3000
ccatgtcaaa attacagact cgggctggc  tcggctgctg acattgacg  agacagagta     3060 ccatgcagat gggggcaagg tgcccatcaa gtggatggcg ctggagtcca ttctccgccg    3120
gcggttcacc caccagagtg atgtgtggag ttatggtgtg actgtgtggg agctgatgac    3180
ttttggggcc aaaccttacg atgggatccc agcccgggag atccctgacc tgctggaaaa    3240
gggggagcgg ctgcccccagc ccccccatctg caccattgat gtctacatga tcatggtcaa   3300
atgttggatg attgactctg aatgtcggcc aagattccgg gagttggtgt ctgaattctc    3360
ccgcatggcc agggaccccc agcgctttgt ggtcatccag aatgaggact gggcccagc     3420 cagtcccttg gacagcacct tctaccgctc actgctggag gacgatgaca tgggggacct    3480
ggtggatgct gaggagtatc tggtacccca gcagggcttc ttctgtccag accctgcccc    3540
gggcgctggg ggcatggtcc accacaggca ccgcagctca tctaccagga gtggcggtgg    3600
ggacctgaca ctagggctgg agccctctga agaggaggcc cccaggtctc cactggcacc    3660
ctccgaaggg gctggctccg atgtatttga tggtgacctg ggaatggggg cagccaaggg    3720
gctgcaaagc ctccccacac atgaccccag ccctctacag cggtacagtg aggaccccac    3780
agtacccctg ccctctgaga ctgatggcta cgttgccccc ctgacctgca gccccagcc    3840 tgaatatgtg aaccagccag atgttcggcc ccagccccct tcgccccgag agggccctct    3900
gcctgctgcc cgacctgctg gtgccactct ggaaaggccc aagactctct ccccagggaa    3960
gaatggggtc gtcaaagacg ttttttgcctt tgggggtgcc gtggagaacc ccgagtactt    4020 gacacccag ggaggagctg cccctcagcc ccaccctcct cctgccttca gcccagcctt     4080
cgacaacctc tattactggg accaggaccc accagagcgg ggggctccac ccagcacctt    4140
caaagggaca cctacggcag agaacccaga gtacctgggt ctggacgtgc cagtgtgaac    4200
cagaaggcca agtccgcaga agccctgatg tgtcctcagg gagcagggaa ggcctgactt    4260
ctgctggcat caagaggtgg agggccctc  cgaccacttc caggggaacc tgccatgcca     4320
ggaacctgtc ctaaggaacc ttccttcctg cttgagttcc cagatggctg aagggggtcc    4380
agcctcgttg gaagaggaac agcactgggg agtctttgtg gattctgagg ccctgcccaa    4440
tgagactcta gggtccagtg gatgccacag cccagcttgg ccctttcctt ccagatcctg    4500
ggtactgaaa gccttaggga agctggcctg agaggggaag cggccctaag ggagtgtcta    4560
agaacaaaag cgacccattc agagactgtc cctgaaacct agtactgccc cccatgagga    4620
aggaacagca atggtgtcag tatccaggct ttgtacagag tgcttttctg tttagttttt    4680 acttttttt  tttgtttttt ttaaagatga aataaagacc caggggagaa atgggtgttg      4740 tatgggagg caagtgtggg gggtccttct ccacacccac tttgtccatt tgcaaatata     4800
ttttggaaaa cagcta                                                   4816
```

```
<210> SEQ ID NO 119
<211> LENGTH: 6466
<212> TYPE: DNA
<213> ORGANISM: Homo sapiens

<400> SEQUENCE: 119
atggtcataa cagcctcctg tctaccgact cagaacggat tttaccaaaa ctgaaaatgc      60
aggctccatg ctcagaagct ctttaacagg ctcgaaaggt ccatgctcct ttctcctgcc     120
cattctatag cataagaaga cagtctctga gtgataatct tctcttcaag aagaagaaaa     180
ctaggaagga gtaagcacaa agatctcttc acattctccg ggactgcggt accaaatatc     240
agcacagcac ttcttgaaaa aggatgtaga ttttaatctg aactttgaac catcactgag     300
gtggcccgcc ggtttctgag ccttctgccc tgcggggaca cggtctgcac cctgcccgcg     360
gccacggacc atgaccatga ccctccacac caaagcatct gggatggccc tactgcatca     420
gatccaaggg aacgagctgg agccctgaa ccgtccgcag ctcaagatcc cctggagcg      480
gcccctgggc gaggtgtacc tggacagcag caagcccgcc gtgtacaact accccgaggg     540
cgccgcctac gagttcaacg ccgcggccgc cgccaacgcg caggtctacg tcagaccgg      600
cctcccctac ggccccgggt ctgaggctgc ggcgttcggc tccaacggcc tgggggttt      660
ccccccactc aacagcgtgt ctccgagccc gctgatgcta ctgcacccgc cgccgcagct     720
gtcgcctttc ctgcagcccc acggccagca ggtgccctac tacctggaga cgagcccag      780
cggctacacg gtgcgcgagg ccggcccgcc ggcattctac aggccaaatt cagataatcg     840
acgccagggt ggcagagaaa gattggccag taccaatgac aagggaagta tggctatgga     900
atctgccaag gagactcgct actgtgcagt gtgcaatgac tatgcttcag gctaccatta     960
tggagtctgg tcctgtgagg gctgcaaggc cttcttcaag agaagtattc aaggacataa    1020
cgactatatg tgtccagcca ccaaccagtg caccattgat aaaaacagga ggaagagctg    1080
ccaggcctgc cggctccgca atgctacgaa gtgggaatg atgaaggtg ggatacgaaa      1140
agaccgaaga ggagggagaa tgttgaaaca caagcgccag agagatgatg gggagggcag    1200
gggtgaagtg gggtctgctg gagacatgag agctgccaac cttggccaa gcccgctcat      1260
gatcaaacgc tctaagaaga acagcctggc cttgtccctg acggccgacc agatggtcag    1320
tgccttgttg gatgctgagc cccatact ctattccgag tatgatccta ccagaccctt      1380
cagtgaagct tcgatgatgg gcttactgac caacctggca gacagggagc tggttcacat    1440
gatcaactgg gcgaagaggg tgccaggctt tgtggatttg accctccatg atcaggtcca    1500
ccttctagaa tgtgcctggc tagagatcct gatgattggt ctcgtctggc gctccatgga    1560
gcacccaggg aagctactgt ttgctcctaa cttgctcttg acaggaacc agggaaaatg     1620
tgtagagggc atggtggaga tcttcgacat gctgctggct acatcatctc ggttccgcat    1680
gatgaatctg cagggagagg agtttgtgtg cctcaaatct attattttgc ttaattctgg    1740
agtgtacaca tttctgtcca gcaccctgaa gtctctggaa gagaaggacc atatccaccg    1800
agtcctggac aagatcacag acactttgat ccacctgatg gccaaggcag cctgaccct      1860
gcagcagcag caccagcggc tggcccagct cctcctcatc ctctcccaca tcaggcacat    1920
gagtaacaaa ggcatggagc atctgtacag catgaagtgc aagaacgtgg tgcccctcta    1980
tgacctgctg ctggagatgc tggacgccca ccgcctacat gcgcccacta gccgtggagg    2040
ggcatccgtg gaggagacgg accaaagcca cttggccact gcgggctcta cttcatcgca    2100
ttccttgcaa aagtattaca tcacggggga ggcagagggt ttccctgcca cggtctgaga    2160
```

```
gctccctggc tcccacacgg ttcagataat ccctgctgca ttttacccte atcatgcacc    2220 actttagcca aattctgtct cctgcataca ctccggcatg catccaacac caatggcttt    2280
ctagatgagt ggccattcat ttgcttgctc agttcttagt ggcacatctt ctgtcttctg    2340
ttgggaacag ccaaagggat tccaaggcta aatctttgta acagctctct ttccccettg    2400 ctatgttact aagcgtgagg attcccgtag ctcttcacag ctgaactcag tctatgggtt    2460
ggggctcaga taactctgtg catttaagct acttgtagag acccaggcct ggagagtaga    2520
cattttgcct ctgataagca cttttttaaat ggctctaaga ataagccaca gcaaagaatt    2580
taaagtggct cctttaattg gtgacttgga gaaagctagg tcaagggttt attatagcac    2640
cctcttgtat tcctatggca atgcatcctt ttatgaaagt ggtacacctt aaagctttta    2700
tatgactgta gcagagtatc tggtgattgt caattcattc ccctatagg aatacaaggg    2760 gcacacaggg aaggcagatc ccctagttgg caagactatt ttaacttgat acactgcaga    2820
ttcagatgtg ctgaaagctc tgcctctggc tttccggtca tgggttccag ttaattcatg    2880
cctcccatgg acctatggag agcagcaagt tgatcttagt taagtctccc tatatgaggg    2940
ataagttcct gattttttgtt tttatttttg tgttacaaaa gaaagccctc cctccctgaa    3000
cttgcagtaa ggtcagcttc aggacctgtt ccagtgggca ctgtacttgg atcttcccgg    3060
cgtgtgtgtg ccttacacag gggtgaactg ttcactgtgg tgatgcatga tgagggtaaa    3120
tggtagttga aggagcagg ggccctggtg ttgcatttag ccctggggca tggagctgaa    3180
cagtacttgt gcaggattgt tgtggctact agagaacaag agggaaagta gggcagaaac    3240
tggatacagt tctgaggcac agccagactt gctcagggtg gccctgccac aggctgcagc    3300
tacctaggaa cattccttgc agacccgca ttgccctttg ggggtgccct gggatccctg    3360
gggtagtcca gctcttcttc atttcccagc gtggccctgg ttggaagaag cagctgtcac    3420
agctgctgta gacagctgtg ttcctacaat tggcccagca ccctggggca cgggagaagg    3480
gtggggaccg ttgctgtcac tactcaggct gactggggcc tggtcagatt acgtatgccc    3540
ttggtggttt agagataatc caaaatcagg gtttggtttg gggaagaaaa tcctcccct    3600 tcctccccg ccccgttccc taccgcctcc actcctgcca gctcatttcc ttcaatttcc    3660
tttgacctat aggctaaaaa agaaaggctc attccagcca cagggcagcc ttccctgggc    3720 cttttgcttct ctagcacaat tatgggttac ttcctttttc ttaacaaaaa agaatgtttg    3780
atttcctctg ggtgacctta ttgtctgtaa ttgaaaccct attgagaggt gatgtctgtg    3840
ttagccaatg acccaggtga gctgctcggg cttctcttgg tatgtcttgt ttggaaaagt    3900
ggatttcatt catttctgat tgtccagtta agtgatcacc aaaggactga gaatctggga    3960
gggcaaaaaa aaaaaaaaag ttttttatgtg cacttaaatt tggggacaat tttatgtatc    4020
tgtgttaagg atatgtttaa gaacataatt cttttgttgc tgtttgttta agaagcacct    4080
tagtttgttt aagaagcacc ttatatagta taatatatat ttttttgaaa ttacattgct    4140
tgtttatcag acaattgaat gtagtaattc tgttctggat ttaatttgac tgggttaaca    4200
tgcaaaaacc aaggaaaaat atttagttttt tttttttttt tttgtatact tttcaagcta    4260
ccttgtcatg tatacagtca tttatgccta aagcctggtg attattcatt taaatgaaga    4320
tcacatttca tatcaacttt tgtatccaca gtagacaaaa tagcactaat ccagatgcct    4380
attgttggat actgaatgac agacaatctt atgtagcaaa gattatgcct gaaaaggaaa    4440
attattcagg gcagctaatt ttgctttac caaaatatca gtagtaatat ttttggacag    4500
tagctaatgg gtcagtgggt tctttttaat gtttatactt agattttctt ttaaaaaaat    4560
```

```
taaaataaaa caaaaaaaaa tttctaggac tagacgatgt aataccagct aaagccaaac    4620
aattatacag tggaaggttt tacattattc atccaatgtg tttctattca tgttaagata    4680
ctactacatt tgaagtgggc agagaacatc agatgattga aatgttcgcc caggggtctc    4740
cagcaacttt ggaaatctct ttgtattttt acttgaagtg ccactaatgg acagcagata    4800
ttttctggct gatgttggta ttgggtgtag aacatgatt taaaaaaaaa ctcttgcctc     4860
tgctttcccc cactctgagg caagttaaaa tgtaaaagat gtgatttatc tgggggctc    4920 aggtatggtg gggaagtgga ttcaggaatc tggggaatgg caaatatatt aagaagagta    4980
ttgaaagtat ttggaggaaa atggttaatt ctgggtgtgc accagggttc agtagagtcc    5040
acttctgccc tggagaccac aaatcaacta gctccattta cagccatttc taaaatggca    5100
gcttcagttc tagagaagaa agaacaacat cagcagtaaa gtccatggaa tagctagtgg    5160
tctgtgtttc ttttcgccat tgcctagctt gccgtaatga ttctataatg ccatcatgca    5220
gcaattatga gaggctaggt catccaaaga gaagaccta tcaatgtagg ttgcaaaatc    5280 taaccctaa ggaagtgcag tctttgattt gatttccta gtaaccttgc agatatgttt     5340
aaccaagcca tagcccatgc cttttgaggg ctgaacaaat aagggactta ctgataattt    5400
acttttgatc acattaaggt gttctcacct tgaaatctta tacactgaaa tggccattga    5460
tttaggccac tggcttagag tactccttcc cctgcatgac actgattaca aatactttcc    5520
tattcatact ttccaattat gagatggact gtgggtactg ggagtgatca ctaacaccat    5580
agtaatgtct aatattcaca ggcagatctg cttggggaag ctagttatgt gaaaggcaaa    5640
tagagtcata cagtagctca aaaggcaacc ataattctct ttggtgcagg tcttgggagc    5700
gtgatctaga ttacactgca ccattcccaa gttaatcccc tgaaaactta ctctcaactg    5760
gagcaaatga actttggtcc caaatatcca tcttttcagt agcgttaatt atgctctgtt    5820
tccaactgca tttcctttcc aattgaatta aagtgtggcc tcgtttttag tcatttaaaa    5880
ttgttttcta agtaattgct gcctctatta tggcacttca attttgcact gtcttttgag    5940
attcaagaaa aatttctatt ctttttttg catccaattg tgcctgaact tttaaaatat     6000
gtaaatgctg ccatgttcca aacccatcgt cagtgtgtgt gtttagagct gtgcacccta    6060
gaaacaacat attgtcccat gagcaggtgc ctgagacaca gaccccttg cattcacaga     6120 gaggtcattg gttatagaga cttgaattaa taagtgacat tatgccagtt tctgttctct    6180
cacaggtgat aaacaatgct ttttgtgcac tacatactct tcagtgtaga gctcttgttt    6240
tatgggaaaa ggctcaaatg ccaaattgtg tttgatggat taatatgccc ttttgccgat    6300
gcatactatt actgatgtga ctcggttttg tcgcagcttt gctttgttta atgaaacaca    6360
cttgtaaacc tcttttgcac tttgaaaaag aatccagcgg gatgctcgag cacctgtaaa    6420
caattttctc aacctatttg atgttcaaat aaagaattaa actaaa              6466
```

<210> SEQ ID NO 120
<211> LENGTH: 3478
<212> TYPE: DNA
<213> ORGANISM: Homo sapiens

<400> SEQUENCE: 120

```
aaattgaaag gtcagccttt cgcgcgctgt gtaggcaagt tacccgtgtt ctgcgttgcc      60
ggccgtgggt gctctggcca cagtgagtta ggggcgtcgg agcgggtttc tccaaccgca    120
atcggctccg ctcaagggga ggaggagagt cccttctcgg aaggcctaag gaaacgtgtc    180
```

```
gtctggaatg ggcttggggg ccacgcctgc acatctccgc gagacagagg gataaagtga    240
agatggtgct gttattgtta cctcgagtgc cacatgcgac ctctgagata tgtacacagt    300
cattcttact atcgcactca gccattctta ctacgctaaa gaagaaataa ttattcgagg    360
atatttgcct ggcccagaag aaacttatgt aaatttcatg aactattata tccgttttcc    420
tcggagtgag agaaaactct ttttagatat catctgagag aactagtgaa tcccagtcac    480
tgagtggagt tgagagtcta agaacctctg aaatttgaga actgctggac cagagccttt    540
agagctctga taaggtgtca acagggtagt taatttggca ccatggggat acagggattg    600 ctacaatttta tcaaagaagc ttcagaaccc atccatgtga ggaagtataa agggcaggta    660
gtagctgtgg atacatattg ctggcttcac aaaggagcta ttgcttgtgc tgaaaaacta    720
gccaaaggtg aacctactga taggtatgta ggattttgta tgaaatttgt aaatatgtta    780
ctatctcatg ggatcaagcc tattctcgta tttgatggat gtactttacc ttctaaaaag    840
gaagtagaga gatctagaag agaaagacga caagccaatc ttcttaaggg aaagcaactt    900
cttcgtgagg ggaaagtctc ggaagctcga gagtgtttca cccggtctat caatatcaca    960
catgccatgg cccacaaagt aattaaagct gcccggtctc agggggtaga ttgcctcgtg   1020
gctccctatg aagctgatgc gcagttggcc tatcttaaca aagcgggaat tgtgcaagcc   1080
ataattacag aggactcgga tctcctagct tttggctgta aaaaggtaat tttaaagatg   1140
gaccagtttg gaaatggact tgaaattgat caagctcggc taggaatgtg cagacagctt   1200
ggggatgtat tcacggaaga gaagtttcgt tacatgtgta ttcttttcagg ttgtgactac   1260 ctgtcatcac tgcgtgggat tggattagca aaggcatgca aagtcctaag actagccaat   1320
aatccagata tagtaaaggt tatcaagaaa attggacatt atctcaagat gaatatcacg   1380
gtaccagagg attacatcaa cgggtttatt cgggccaaca ataccttcct ctatcagcta   1440 gttttttgatc ccatcaaaag gaaacttatt cctctgaacg cctatgaaga tgatgttgat   1500
cctgaaacac taagctacgc tgggcaatat gttgatgatt ccatagctct tcaaatagca   1560
cttggaaata agatatataa tacttttgaa cagatcgatg actacaatcc agacactgct   1620
atgcctgccc attcaagaag tcatagttgg gatgacaaaa catgtcaaaa gtcagctaat   1680
gttagcagca tttggcatag gaattactct cccagaccag agtcgggtac tgtttcagat   1740
gccccacaat tgaaggaaaa tccaagtact gtgggagtgg aacgagtgat tagtactaaa   1800
gggttaaatc tcccaaggaa atcatccatt gtgaaaagac caagaagtgc agagctgtca   1860
gaagatgacc tgttgagtca gtattctctt tcatttacga agaagaccaa gaaaaatagc   1920
tctgaaggca ataaatcatt gagcttttct gaagtgtttg tgcctgacct ggtaaatgga   1980
cctactaaca aaaagagtgt aagcactcca cctaggacga gaaataaatt tgcaacattt   2040
ttacaaagga aaaatgaaga agtggtgca gttgtggttc cagggaccag aagcaggttt   2100
ttttgcagtt cagattctac tgactgtgta tcaaacaaag tgagcatcca gcctctggat   2160
gaaactgctg tcacagataa agagaacaat ctgcatgaat cagagtatgg agaccaagaa   2220
ggcaagagac tggttgacac agatgtagca cgtaattcaa gtgatgacat tccgaataat   2280
catattccag gtgatcatat tccagacaag gcaacagtgt ttacagatga agagtcctac   2340
tcttttgaga gcagcaaatt tacaaggacc atttcaccac ccactttggg aacactaaga   2400
agttgtttta gttggtctgg aggtcttgga gattttcaa gaacgccgag cccctctcca   2460
agcacagcat tgcagcagtt ccgaagaaag agcgattccc ccacctcttt gcctgagaat   2520
aatatgtctg atgtgtcgca gttaaagagc gaggagtcca gtgacgatga gtctcatccc   2580
```

```
ttacgagaag aggcatgttc ttcacagtcc caggaaagtg gagaattctc actgcagagt    2640
tcaaatgcat caaagctttc tcagtgctct agtaaggact ctgattcaga ggaatctgat    2700
tgcaatatta agttacttga cagtcaaagt gaccagacct ccaagctacg tttatctcat    2760
ttctcaaaaa aagacacacc tctaaggaac aaggttcctg ggctatataa gtccagttct    2820
gcagactctc tttctacaac caagatcaaa cctctaggac ctgccagagc cagtgggctg    2880
agcaagaagc cggcaagcat ccagaagaga agcatcata atgccgagaa caagccgggg    2940
ttacagatca aactcaatga gctctggaaa aactttggat ttaaaaaaga ttctgaaaag    3000
cttcctcctt gtaagaaacc cctgtcccca gtcagagata acatccaact aactccagaa    3060
gcggaagagg atatatttaa caaacctgaa tgtggccgtg ttcaaagagc aatattccag    3120
taaatgcaga ctgctgcaaa gcttttgcct gcaagagaat ctgatcaatt tgaagtccct    3180
gtttgggaat gaggcactta tcagcatgaa gaatttttc tcattctgtg ccattttaaa    3240
aatagaatac attttgtata ttaactttat aattgggttg tggttttttt gctcagcttt    3300 ttatatttt ataagaagct aaatagaaga ataattgtat ctctgacagg ttttggagg    3360 ttttagtgtt aattgggaaa atcctctgga gtttataaaa gtctactcta aatatttctg    3420
taatgttgtc aagtagaaag atagtaaatg gagaaactac aaaaaaaaaa aaaaaaaa    3478

<210> SEQ ID NO 121
<211> LENGTH: 5192
<212> TYPE: DNA
<213> ORGANISM: Homo sapiens

<400> SEQUENCE: 121
ccatgacctg ccttgagaag gggcagggga agccagatgg actggaagtg gagtggcagt      60
gaccaaggag gaggaggtgt gataggcttc ccacgcaggg tagatccaga gacaccagtg     120
ccacccatag gcccctagga ctgcagtggt caccgattc ctttgtccca gctgagactc      180
agttctgagt gttctatttt ggggaacaga ggcgtccttg gtagcatttg gaagaggata     240
gccagctggg gtgtgtgtac atcacagcct gacagtaaca gcatccgaac cagaggtgac     300
tggctaaggg cagacccagg gcaacaggtt aaccgttcta gggccgggca cagggaggag     360
aacattccaa cactctgtgt gcccagtgcc gacgcacgtt ctctctttta tcctcaaaac     420
agtcctatga ggatataagc cagagagaga cagagacaag gaattacaag ttggtgagag     480
tcaggatttg aacttggctc tggcagatgg aaaattaggg tctgtattct ttacaaaacc     540
gtgtgtgcct cagatggagt tggtgcataa caagcagagg tatccagggt cgcggtcctg     600
cttgccacgg aaggggccgc cttgtcagtt gtgaccaccc agccctggaa atgtcagtaa     660
tgctgtaagg agtggggatc ggatcagatg ccatccagat gctgaagttt gaccttgtgt     720 cattttcac tttctttttt ggctcttctg caatcaattc atttatttag caaaaagaa      780 attatgtgtg ccgagagcat gcagaagata tgtctccgtt ctctgcttcc ctccaaaaa     840 gaatcccaaa actgctttct gtgaacgtgt gccagggtcc cagcaggact cagggagagc     900
aggaagccca gcccagaccc cttgcacaac ctaccgtggg gaggccttag gctctggcta     960
ctacagagct ggttccagtc tgcactgcca cagcctggcc agggacttgg acacatctgc    1020
tggccacttc ctgtctcagt ttccttatct gcaaaataag ggaaaagccc ccacaaaggt    1080
gcacgtgtag caggagctct tttccctccc tatttttagga aggcagttgg tgggaagtcc    1140
agcttgggtc cctgagagct gtgagaagga gatgcggctg ctgctggccc tgttgggggt    1200
```

```
cctgctgagt gtgcctgggc ctccagtctt gtccctggag gcctctgagg aagtggagct    1260
tggtatggct tctgaggtgg gagagggtgg caggggtggg aagagtgggc accaggaggg    1320
ggctgctggg ctgagcaaag ctggaaagga tccttgccca ggccctgaga aggtggcggc    1380
agggcagggc tcaaccactg agactcagtc agtgcctggc ttccagcaag cattcatcta    1440
tcactgtgtc tgcgagagag gactggcctt gcagggcgca gggccctaag ctgggctgca    1500
gagctggtgg tgagctcctt gcctgggtgt gtgtgcgtgt gtgtgtgtgt tctgtgcact    1560
gggtgtgtga cctaggaggt ccaggcagca tgtgtggtat aagcattatg agggtgatat    1620
gccccggtgc agcatgaccc tgtatgtggc accaacagca tgtgccttgt gtgtgtgtgt    1680
gtccgtatgt gtgtgtgtgt atgcgtgtgt gtgtgtgtgt gtgtgtgtct tggccactgt    1740
catgtgcact aaatgctgtg tgtgtgacat gccccaagag tgtggcattt gccctgggtg    1800
tggcatccgc agcatgtggc tgtgtgggtg tcaaggagtg gtggctcctt cagcatgcgt    1860
tgcgaagtgc ttgtgccctg catgtgcggt gtgttctctg tacacaggag gctgcctcag    1920
atggggctgc ggggtctgct gacctctgcc ctctgcccac agagccctgc ctggctccca    1980
gcctggagca gcaagagcag gagctgacag tagcccttgg gcagcctgtg cggctgtgct    2040
gtgggcgggc tgagcgtggt ggccactggt acaaggaggg cagtcgcctg gcacctgctg    2100
gccgtgtacg gggctggagg ggccgcctag agattgccag cttcctacct gaggatgctg    2160
gccgctacct ctgcctggca cgaggctcca tgatcgtcct gcagaatctc accttgatta    2220
caggtgactc cttgacctcc agcaacgatg atgaggaccc caagtcccat agggacctct    2280
cgaataggca cagttacccc cagcaaggtc agtaggtctc caaggacttg tgtccccgct    2340
gctgctcatc tgatcactga aagaggagg cctgtgtggg aacacacggt cattctaggg    2400
gccttcccct gccctccagc accctactgg acacacccc agcgcatgga gaagaaactg    2460
catgcagtac ctgcggggaa caccgtcaag ttccgctgtc cagctgcagg caaccccacg    2520
cccaccatcc gctggcttaa ggatggacag gcctttcatg gggagaaccg cattggaggc    2580
attcggctgc gccatcagca ctggagtctc gtgatggaga gcgtggtgcc ctcggaccgc    2640
ggcacataca cctgcctggt agagaacgct gtgggcagca tccgttataa ctacctgcta    2700
gatgtgctgg agcggtcccc gcaccggccc atcctgcagg ccgggctccc ggccaacacc    2760
acagccgtgg tgggcagcga cgtggagctg ctgtgcaagg tgtacagcga tgcccagccc    2820
cacatccagt ggctgaagca catcgtcatc aacggcagca gcttcggagc cgacggtttc    2880
ccctatgtgc aagtcctaaa gactgcagac atcaatagct cagaggtgga ggtcctgtac    2940
ctgcggaacg tgtcagccga ggacgcaggc gagtacacct gcctcgcagg caattccatc    3000
ggcctctcct accagtctgc ctggctcacg gtgctgccag gtgagcacct gaagggccag    3060
gagatgctgc gagatgcccc tctgggccag cagtggggc tgtggcctgt tgggtggtca    3120
gtctctgttg gcctgtgggg tctggcctgg ggggcagtgt gtggatttgt gggtttgagc    3180
tgtatgacag cccctctgtg cctctccaca cgtggccgtc catgtgaccg tctgctgagg    3240
tgtgggtgcc tgggactggg cataactaca gcttcctccg tgtgtgtccc cacatatgtt    3300
gggagctggg agggactgag ttagggtgca cggggcggcc agtctcacca ctgaccagtt    3360
tgtctgtctg tgtgtgtcca tgtgcgaggg cagaggagga ccccacatgg accgcagcag    3420
cgcccgaggc caggtatacg gacatcatcc tgtacgcgtc gggctccctg gccttggctg    3480
tgctcctgct gctggccagg ctgtatcgag ggcaggcgct ccacggccgg caccccgcc    3540
cgcccgccac tgtgcagaag ctctcccgct tccctctggc ccgacagttc tccctggagt    3600
```

```
caggctcttc cggcaagtca agctcatccc tggtacgagg cgtgcgtctc tcctccagcg   3660
gccccgcctt gctcgccggc ctcgtgagtc tagatctacc tctcgaccca ctatgggagt   3720
tcccccggga caggctggtg cttgggaagc ccctaggcga gggctgcttt ggccaggtag   3780
tacgtgcaga ggcctttggc atggaccctg cccggcctga ccaagccagc actgtggccg   3840
tcaagatgct caaagacaac gcctctgaca aggacctggc cgacctggtc tcggagatgg   3900
aggtgatgaa gctgatcggc cgacacaaga acatcatcaa cctgcttggt gtctgcaccc   3960
aggaagggcc cctgtacgtg atcgtggagt gcgccgccaa gggaaacctg cgggagttcc   4020
tgcgggcccg gcgccccca ggccccgacc tcagccccga cggtcctcgg agcagtgagg    4080
ggccgctctc cttcccagtc ctggtctcct gcgcctacca ggtggcccga ggcatgcagt   4140
atctggagtc ccggaagtgt atccaccggg acctggctgc ccgcaatgtg ctggtgactg   4200
aggacaatgt gatgaagatt gctgactttg gctggcccg cggcgtccac cacattgact    4260
actataagaa aaccagcaac ggccgcctgc ctgtgaagtg gatggcgccc gaggccttgt   4320
ttgaccgggt gtacacacac cagagtgacg tgtggtcttt tgggatcctg ctatgggaga   4380
tcttcaccct cggggctcc ccgtatcctg gcatcccggt ggaggagctg ttctcgctgc    4440
tgcgggaggg acatcggatg gaccgacccc cacactgccc cccagagctg tacgggctga   4500
tgcgtgagtg ctggcacgca gcgccctccc agaggcctac cttcaagcag ctggtggagg   4560
cgctggacaa ggtcctgctg gccgtctctg aggagtacct cgacctccgc ctgaccttcg   4620
gaccctattc cccctctggt ggggacgcca gcagcacctg ctcctccagc gattctgtct   4680
tcagccacga cccctgcca ttgggatcca gctccttccc cttcgggtct ggggtgcaga    4740
catgagcaag gctcaaggct gtgcaggcac ataggctggt ggccttgggc cttgggctc    4800
agccacagcc tgacacagtg ctcgaccttg atagcatggg gcccctggcc cagagttgct   4860
gtgccgtgtc caagggccgt gcccttgccc ttggagctgc cgtgcctgtg tcctgatggc   4920
ccaaatgtca gggttctgct cggcttcttg gaccttggcg cttagtcccc atcccgggtt   4980
tggctgagcc tggctggaga gctgctatgc taaacctcct gcctcccaat accagcagga   5040
ggttctgggc ctctgaaccc cctttcccca cacctcccc tgctgctgct gccccagcgt    5100
cttgacggga gcattggccc ctgagcccag agaagctgga agcctgccga aaacaggagc   5160
aaatggcgtt ttataaatta ttttttttgaa at                                5192

<210> SEQ ID NO 122
<211> LENGTH: 3124
<212> TYPE: DNA
<213> ORGANISM: Homo sapiens

<400> SEQUENCE: 122
taagatccac atcagctcaa ctgcacttgc ctcgcagagg cagcccgctc acttcccgcg     60
gaggcgctcc ccggcgccgc gctcgcggc agcgcctgc ccccggcgct gccccgcccc     120
gccgcgccgc cgccgccgcc gcgcacgccg cgcccgcag ctctgggctt cctcttcgcc    180
cgggtggcgt tgggcccgcg cgggcgctcg ggtgactgca gctgctcagc tcccctcccc    240
cgccccgcgc gcgcggccg cccgtcgctt cgcacagggc tggatggttg tattgggcag    300
ggtggctcca ggatgttagg aactgtgaag atggaagggc atgaaaccag cgactggaac   360
agctactacg cagacacgca ggaggcctac tcctccgtcc cggtcagcaa catgaactca   420
ggcctgggct ccatgaactc catgaacacc tacatgacca tgaacaccat gactacgagc   480
```

```
ggcaacatga ccccggcgtc cttcaacatg tcctatgcca acccgggcct aggggccggc    540
ctgagtcccg gcgcagtagc cggcatgccg gggggctcgg cggcgcgcat gaacagcatg    600
actgcggccg gcgtgacggc catgggtacg gcgctgagcc cgagcggcat gggcgccatg    660
ggtgcgcagc aggcggcctc catgaatggc ctgggcccct acgcgccgcc catgaacccg    720
tgcatgagcc ccatggcgta cgcgccgtcc aacctgggcc gcagccgcgc gggcggcggc    780
ggcgacgcca agacgttcaa gcgcagctac ccgcacgcca agccgcccta ctcgtacatc    840
tcgctcatca ccatggccat ccagcaggcg cccagcaaga tgctcacgct gagcgagatc    900
taccagtgga tcatggacct cttcccctat taccggcaga accagcagcg ctggcagaac    960
tccatccgcc actcgctgtc cttcaatgac tgcttcgtca aggtggcacg ctccccggac   1020
aagccgggca agggctccta ctggacgctg caccccggact ccggcaacat gttcgagaac   1080
ggctgctact tgcgccgcca gaagcgcttc aagtgcgaga agcagccggg ggccggcggc   1140
gggggcggga gcgaagcgg gggcagcggc gccaagggcg gccctgagag ccgcaaggac   1200
ccctctggcg cctctaaccc cagcgccgac tcgcccctcc atcggggtgt gcacgggaag   1260
accggccagc tagagggcgc gccggccccc gggcccgccg ccagcccca gactctggac    1320 cacagtgggg cgacggcgac aggggggccgc tcggagttga agactccagc ctcctcaact   1380 gcgccccca taagctccgg gcccggggcg ctggcctctg tgcccgcctc tcacccggca   1440
cacggcttgg caccccacga gtcccagctg cacctgaaag gggaccccca ctactccttc    1500
aaccacccgt tctccatcaa caacctcatg tcctcctcgg agcagcagca taagctggac   1560
ttcaaggcat acgaacaggc actgcaatac tcgccttacg gctctacgtt gcccgccagc   1620
ctgcctctag gcagcgcctc ggtgaccacc aggagcccca tcgagccctc agccctggag   1680
ccggcgtact accaaggtgt gtattccaga cccgtcctaa acacttccta gctcccggga   1740 ctgggggggtt tgtctggcat agccatgctg gtagcaagag agaaaaaatc aacagcaaac   1800
aaaaccacac aaaccaaacc gtcaacagca taataaaatc ccaacaacta ttttattttc    1860 attttttcatg cacaaccttt ccccagtgc aaaagactgt actttatta ttgtattcaa    1920 aattcattgt gtatattact acaaagacaa ccccaaacca atttttttcc tgcgaagttt    1980
aatgatccac aagtgtatat atgaaattct cctccttcct tgccccctc tctttcttcc    2040 ctcttttcccc tccagacatt ctagtttgtg gagggttatt taaaaaaaca aaaaggaag    2100 atggtcaagt ttgtaaaata tttgtttgtg cttttttcccc ctccttacct gacccctac    2160 gagtttacag gtctgtggca atactcttaa ccataagaat tgaaatggtg aagaaacaag   2220
tatacactag aggctcttaa aagtattgaa agacaatact gctgttatat agcaagacat   2280
aaacagatta taaacatcag agccatttgc ttctcagttt acatttctga tacatgcaga   2340
tagcagatgt ctttaaatga aatacatgta tattgtgtat ggacttaatt atgcacatgc   2400
tcagatgtgt agacatcctc cgtatattta cataacatat agaggtaata gataggtgat   2460
atacatgata cattctcaag agttgcttga ccgaaagtta caaggacccc aacccctttg   2520
tcctctctac ccacagatgg ccctgggaat caattcctca ggaattgccc tcaagaactc   2580
tgcttcttgc tttgcagagt gccatggtca tgtcattctg aggtcacata acacataaaa   2640
ttagtttcta tgagtgtata ccatttaaag aatttttttt tcagtaaaag ggaatattac   2700
aatgttggag gagagataag ttatagggag ctggatttca aaacgtggtc caagattcaa   2760
aaatcctatt gatagtggcc attttaatca ttgccatcgt gtgcttgttt catccagtgt   2820
tatgcacttt ccacagttgg acatggtgtt agtatagcca gacgggtttc attattattt   2880
```

```
ctctttgctt tctcaatgtt aatttattgc atggtttatt cttttctttt acagctgaaa    2940
ttgctttaaa tgatggttaa aattacaaat taaattgtta attttatca atgtgattgt    3000 aattaaaaat attttgattt aaataacaaa aataatacca gattttaagc cgtggaaaat    3060
gttcttgatc atttgcagtt aaggacttta aataaatcaa atgttaacaa aaaaaaaaaa    3120
aaaa                                                                3124

<210> SEQ ID NO 123
<211> LENGTH: 3452
<212> TYPE: DNA
<213> ORGANISM: Homo sapiens

<400> SEQUENCE: 123
atgcaggcgc gctactccgt gtccagcccc aactccctgg gagtggtgcc ctacctcggc      60
ggcgagcaga gctactaccg cgcggcggcc gcggcggccg ggggcggcta caccgccatg     120 ccggcccca tgagcgtgta ctcgcaccct gcgcacgccg agcagtaccc gggcggcatg      180
gcccgcgcct acgggcccta cacgccgcag ccgcagccca aggacatggt gaagccgccc     240
tatagctaca tcgcgctcat caccatggcc atccagaacg ccccggacaa gaagatcacc     300
ctgaacggca tctaccagtt catcatggac cgcttcccct tctaccggga caacaagcag     360
ggctggcaga acagcatccg ccacaacctc tcgctcaacg agtgcttcgt caaggtgccg     420
cgcgacgaca agaagccggg caagggcagc tactggacgc tggacccgga ctcctacaac     480
atgttcgaga acggcagctt cctgcggcgg cggcggcgct tcaagaagaa ggacgcggtg     540
aaggacaagg aggagaagga caggctgcac ctcaaggagc cgccccgcc cggccgccag      600 cccccgcccg cgccgccgga gcaggccgac ggcaacgcgc ccgtccgca gccgccgccc      660 gtgcgcatcc aggacatcaa gaccgagaac ggtacgtgcc cctcgccgcc ccagcccctg     720
tccccggccg ccgcccctggg cagcggcagc gccgccgcgg tgcccaagat cgagagcccc     780
gacagcagca gcagcagcct gtccagcggg agcagccccc cgggcagcct gccgtcggcg     840
cggccgctca gcctggacgg tgcggattcc gcgccgccgc cgcccgcgcc ctccgccccg     900
ccgccgcacc atagccaggg cttcagcgtg gacaacatca tgacgtcgct gcgggggtcg     960
ccgcagagcg cggccgcgga gctcagctcc ggccttctgg cctcggcggc cgcgtcctcg    1020
cgcgcgggga tcgcaccccc gctggcgctc ggcgcctact cgcccggcca gagctccctc    1080
tacagctccc cctgcagcca gacctccagc gcgggcagct cgggcggcgg cggcggcggc    1140
gcgggggccg cggggggcgc gggcggcgcc gggacctacc actgcaacct gcaagccatg    1200
agcctgtacg cggccggcga gcgcgggggc cacttgcagg gcgcgcccgg gggcgcgggc    1260
ggctcggccg tggacgaccc cctgcccgac tactctctgc ctccggtcac cagcagcagc    1320
tcgtcgtccc tgagtcacgg cggcggcggc ggcggcggcg gggaggcca ggaggccggc    1380 caccaccctg cggcccacca aggccgcctc acctcgtggt acctgaacca ggcgggcgga    1440
gacctgggcc acttggcgag cgcggcggcg cggcggcggg ccgcaggcta cccgggccag    1500
cagcagaact ccactcggt gcgggagatg ttcgagtcac agaggatcgg cttgaacaac    1560
tctccagtga acgggaatag tagctgtcaa atggccttcc cttccagcca gtctctgtac    1620
cgcacgtccg gagctttcgt ctacgactgt agcaagtttt gacacaccct caaagccgaa    1680
ctaaatcgaa ccccaaagca ggaaaagcta aggaaccca tcaaggcaaa atcgaaacta    1740
aaaaaaaaaa atccaattaa aaaaaaccccc tgagaatatt caccacacca gcgaacagaa    1800
```

-continued

| | |
|---|---|
| tatccctcca aaaattcagc tcaccagcac cagcacgaag aaaactctat tttcttaacc | 1860 |
| gattaattca gagccacctc cactttgcct tgtctaaata aacaaacccg taaactgttt | 1920 |
| tatacagaga cagcaaaatc ttggtttatt aaaggacagt gttactccag ataacacgta | 1980 |
| agtttcttct tgcttttcag agacctgctt tcccctcctc ccgtctcccc tctcttgcct | 2040 |
| tcttccttgc ctctcacctg taagatatta ttttatccta tgttgaaggg aggggggaaag | 2100 |
| tccccgttta tgaaagtcgc tttcttttta ttcatggact tgttttaaaa tgtaaattgc | 2160 |
| aacatagtaa tttatttta atttgtagtt ggatgtcgtg gaccaaacgc cagaaagtgt | 2220 |
| tcccaaaacc tgacgttaaa ttgcctgaaa ctttaaattg tgctttttt ctcattataa | 2280 |
| aaagggaaac tgtattaatc ttattctatc ctcttttctt tcttttgtt gaacatattc | 2340 |
| attgtttgtt tattaataaa ttaccattca gtttgaatga gacctatatg tctggatact | 2400 |
| ttaatagagc tttaattatt acgaaaaaag atttcagaga taaaacacta gaagttaccta | 2460 |
| attctccacc taaatctctg aaaaatggag aaaccctctg actagtccat gtcaaatttt | 2520 |
| actaaaagtc ttttgttta gatttatttt cctgcagcat cttctgcaaa atgtactata | 2580 |
| tagtcagctt gctttgaggc tagtaaaaag atattttct aaacagattg gagttggcat | 2640 |
| ataaacaaat acgttttctc actaatgaca gtccatgatt cggaaatttt aagcccatga | 2700 |
| atcagccgcg gtcttaccac ggtgatgcct gtgtgccgag agatgggact gtgcggccag | 2760 |
| atatgcacag ataaatattt ggcttgtgta ttccatataa aattgcagtg catattatac | 2820 |
| atccctgtga gccagatgct gaatagatat tttcctatta tttcagtcct ttataaaagg | 2880 |
| aaaaataaac cagttttaa atgtatgtat ataattctcc cccatttaca atccttcatg | 2940 |
| tattacatag aaggattgct ttttaaaaa tatactgcgg gttggaaagg gatatttaat | 3000 |
| cttgagaaa ctatttaga aaatatgttt gtagaacaat tattttgaa aaagatttaa | 3060 |
| agcaataaca agaaggaagg cgagaggagc agaacatttt ggtctagggt ggtttctttt | 3120 |
| taaaccattt tttcttgtta atttacagtt aaacctaggg gacaatccgg attggccctc | 3180 |
| cccctttgt aaataaccca ggaaatgtaa taaattcatt atcttagggt gatctgccct | 3240 |
| gccaatcaga ctttggggag atggcgattt gattacagac gttcgggggg gtgggggct | 3300 |
| tgcagtttgt tttggagata atacagtttc ctgctatctg ccgctcctat ctagaggcaa | 3360 |
| cacttaagca gtaattgctg ttgcttgttg tcaaatttg atcattgtta aaggattgct | 3420 |
| gcaaataaat acacttaat ttcagtcaaa aa | 3452 |

<210> SEQ ID NO 124
<211> LENGTH: 1749
<212> TYPE: DNA
<213> ORGANISM: Homo sapiens

<400> SEQUENCE: 124

| | |
|---|---|
| gtggcctcga ggtggtggca gggccgcccc ctgcagtccg gagacgaacg cacggaccgg | 60 |
| gcctccggag gcaggttcgg ctggaaggaa ccgctctcgc ttcgtcctac acttgcgcaa | 120 |
| atgtctccga gcttactcac atagcatatt ggtatatcaa aatgaaatgc aaggaaccaa | 180 |
| aaataacata attgaaggca gtaaaagtga aattaaatag gaagatcatc agtcaaggaa | 240 |
| gacccactgg agaggacaga aaatgaagca gtgttttatc atgtgtattt cagcaggtct | 300 |
| tcttgaaatt taactaaaaa tatgactgct ctctcttcag agaactgctc ttttcagtac | 360 |
| cagttacgtc aaacaaacca gccctagac gttaactatc tgctattctt gatcatactt | 420 |
| gggaaaatat tattaaatat ccttacacta ggaatgagaa gaaaaaacac ctgtcaaaat | 480 |

```
tttatggaat attttttgcat ttcactagca ttcgttgatc tttttacttt tggtaaacatt      540 tccattatat tgtatttcag ggattttgta cttttaagca ttaggttcac taaataccac       600
atctgcctat ttactcaaat tatttccttt acttatggct ttttgcatta tccagttttc       660
ctgacagctt gtatagatta ttgcctgaat ttctctaaaa caaccaagct ttcatttaag       720
tgtcaaaaat tattttattt ctttacagta attttaattt ggatttcagt ccttgcttat       780
gttttgggag acccagccat ctaccaaagc ctgaaggcac agaatgctta ttctcgtcac       840
tgtcctttct atgtcagcat tcagagttac tggctgtcat ttttcatggt gatgatttta      900
tttgtagctt tcataacctg ttgggaagaa gttactactt tggtacaggc tatcaggata      960
acttcctata tgaatgaaac tatcttatat tttcctttt catcccactc cagttatact       1020
gtgagatcta aaaaaatatt cttatccaag ctcattgtct gttttctcag tacctggtta      1080
ccatttgtac tacttcaggt aatcattgtt ttacttaaag ttcagattcc agcatatatt      1140
gagatgaata ttccctggtt atactttgtc aatagttttc tcattgctac agtgtattgg      1200
tttaattgtc acaagcttaa tttaaaagac attggattac ctttggatcc atttgtcaac      1260
tggaagtgct gcttcattcc acttacaatt cctaatcttg agcaaattga aaagcctata      1320
tcaataatga tttgttaata ttattaatta aaagttacag ctgtcataag atcataattt      1380
tatgaacaga aagaactcag gacatattaa aaaataaact gaactaaaac aacttttgcc      1440
ccctgactga tagcatttca gaatgtgtct tttgaagggc tataccagtt attaaatagt      1500
gtttattttt aaaaacaaaa taattccaag aagttttat agttattcag ggacactata      1560
ttacaaatat tactttgtta ttaacacaaa aagtgataag agttaacatt tggctatact      1620
gatgtttgtg ttactcaaaa aaactactgg atgcaaactg ttatgtaaat ctgagatttc      1680
actgacaact ttaagatatc aacctaaaca tttttattaa atgttcaaat gtaagcaaga      1740
aaaaaaaa                                                              1749

<210> SEQ ID NO 125
<211> LENGTH: 2285
<212> TYPE: DNA
<213> ORGANISM: Homo sapiens

<400> SEQUENCE: 125
acccgccccc atctgcccaa gataatttta gtttccttgg gcctggaatc tggacacaca       60
gggctccccc ccgcctctga cttctctgtc cgaagtcggg acaccctcct accacctgta      120
gagaagcggg agtggatctg aaataaaatc caggaatctg ggggttccta gacggagcca      180
gacttcggaa cgggtgtcct gctactcctg ctggggctcc tccaggacaa gggcacacaa      240
ctggttccgt taagcccctc tctcgctcag acgccatgga gctggatctg tctccacctc      300
atcttagcag ctctccggaa gaccctttgcc cagcccctgg gaccectcct gggactcccc      360 ggccccctga taccectctg cctgaggagg taaagaggtc ccagcctctc ctcatcccaa      420
ccaccggcag gaaacttcga gaggaggaga ggcgtgccac ctccctcccc tctatcccca      480
accccttccc tgagctctgc agtcctccct cacagagccc aattctcggg ggcccctcca      540
gtgcaagggg gctgctcccc cgcgatgcca gccgccccca tgtagtaaag gtgtacagtg      600
aggatggggc ctgcaggtct gtggaggtgg cagcaggtgc cacagctcgc cacgtgtgtg      660
aaatgctggt gcagcgagct cacgccttga gcgacgagac ctggggggctg gtggagtgcc      720 accccccacct agcactggag cggggtttgg aggaccacga gtccgtggtg gaagtgcagg      780
```

```
ctgcctggcc cgtgggcgga gatagccgct tcgtcttccg gaaaaacttc gccaagtacg    840
aactgttcaa gagctcccca cactcccgt tcccagaaaa aatggtctcc agctgtctcg     900
atgcacacac tggtatatcc catgaagacc tcatccagaa cttcctgaat gctggcagct    960
ttcctgagat ccagggcttt ctgcagctgc ggggttcagg acggaagctt tggaaacgct   1020
ttttctgctt cttgcgccga tctggcctct attactccac caagggcacc tctaaggatc   1080
cgaggcacct gcagtacgtg gcagatgtga acgagtccaa cgtgtacgtg gtgacgcagg   1140
gccgcaagct ctacgggatg cccactgact tcggtttctg tgtcaagccc aacaagcttc   1200
gaaatggcca aaggggcttt cggatcttct gcagtgaaga tgagcagagc cgcacctgct   1260
ggctggctgc cttccgcctc ttcaagtacg gggtgcagct gtacaagaat taccagcagg   1320
cacagtctcg ccatctgcat ccatcttgtt tgggctcccc acccttgaga agtgcctcag   1380 ataatacccct ggtggccatg gacttctctg gccatgctgg gcgtgtcatt gagaaccccc   1440
gggaggctct gagtgtggcc ctggaggagg cccaggcctg gaggaagaag acaaaccacc   1500
gcctcagcct gcccatgcca gcctccggca cgagcctcag tgcagccatc caccgcaccc   1560
aactctggtt ccacgggcgc atttcccgtg aggagagcca gcggcttatt ggacagcagg   1620
gcttggtaga cggcctgttc ctggtccggg agagtcagcg gaaccccag ggctttgtcc    1680 tctctttgtg ccacctgcag aaagtgaagc attatctcat cctgccgagc gaggaggagg   1740
gccgcctgta cttcagcatg gatgatggcc agacccgctt cactgacctg ctgcagctcg   1800
tggagttcca ccagctgaac cgcggcatcc tgccgtgctt gctgcgccat gctgcacgc    1860 gggtggccct ctgaccaggc cgtggactgg ctcatgcctc agcccgcctt caggctgccc   1920
gccgcccctc cacccatcca gtggactctg gggcgcggcc acaggggacg ggatgaggag   1980
cgggagggtt ccgccactcc agttttctcc tctgcttctt tgcctccctc agatagaaaa   2040
cagcccccac tccagtccac tcctgacccc tctcctcaag ggaaggcctt gggtggcccc   2100
ctctccttct cctagctctg gaggtgctgc tctagggcag ggaattatgg gagaagtggg   2160
ggcagcccag gcggtttcac gccccacact ttgtacagac cgagaggcca gttgatctgc   2220 tctgtttat actagtgaca ataaagatta tttttgata caaaaaaaaa aaaaaaaaa     2280 aaaaa                                                              2285
```

```
<210> SEQ ID NO 126
<211> LENGTH: 935
<212> TYPE: DNA
<213> ORGANISM: Homo sapiens

<400> SEQUENCE: 126
agtcagaggt cgcgcaggcg ctggtacccc gttggtccgc gcgttgctgc gttgtgaggg     60
gtgtcagctc agtgcatccc aggcagctct tagtgtggag cagtgaactg tgtgtggttc    120
cttctacttg gggatcatgc agagagcttc acgtctgaag agagagctgc acatgttagc    180
cacagagcca cccccaggca tcacatgttg gcaagataaa gaccaaatgg atgacctgcg    240
agctcaaata ttaggtggag ccaacacacc ttatgagaaa ggtgttttta agctagaagt    300
tatcattcct gagaggtacc catttgaacc tcctcagatc cgatttctca ctccaattta    360
tcatccaaac attgattctg ctggaaggat ttgtctggat gttctcaaat tgccaccaaa    420
aggtgcttgg agaccatccc tcaacatcgc aactgtgttg acctctattc agctgctcat    480
gtcagaaccc aaccctgatg acccgctcat ggctgacata tcctcagaat ttaaatataa    540
taagccagcc ttcctcaaga atgccagaca gtggacagag aagcatgcaa gacagaaaca    600
```

| | |
|---|---|
| aaaggctgat gaggaagaga tgcttgataa tctaccagag gctggtgact ccagagtaca | 660 |
| caactcaaca cagaaaagga aggccagtca gctagtaggc atagaaaaga aatttcatcc | 720 |
| tgatgtttag gggacttgtc ctggttcatc ttagttaatg tgttctttgc caaggtgatc | 780 |
| taagttgcct accttgaatt tttttttaaa tatatttgat gacataattt ttgtgtagtt | 840 |
| tatttatctt gtacatatgt attttgaaat cttttaaacc tgaaaaataa atagtcattt | 900 |
| aatgttgaaa aaaaaaaaaa aaaaaaaaaa aaaaa | 935 |

<210> SEQ ID NO 127
<211> LENGTH: 2896
<212> TYPE: DNA
<213> ORGANISM: Homo sapiens

<400> SEQUENCE: 127

| | |
|---|---|
| acgcttgcgc gcgggattta aactgcggcg gtttacgcgg cgttaagact tcgtagggtt | 60 |
| agcgaaattg aggtttcttg gtattgcgcg tttctcttcc ttgctgactc tccgaatggc | 120 |
| catggactcg tcgcttcagg cccgcctgtt tcccggtctc gctatcaaga tccaacgcag | 180 |
| taatggttta attcacagtg ccaatgtaag gactgtgaac ttggagaaat cctgtgtttc | 240 |
| agtggaatgg gcagaaggag gtgccacaaa gggcaaagag attgattttg atgatgtggc | 300 |
| tgcaataaac ccagaactct tacagcttct tcccttacat ccgaaggaca atctgccctt | 360 |
| gcaggaaaat gtaacaatcc agaaacaaaa acggagatcc gtcaactcca aaattcctgc | 420 |
| tccaaaagaa agtcttcgaa gccgctccac tcgcatgtcc actgtctcag agcttcgcat | 480 |
| cacggctcag gagaatgaca tggaggtgga gctgcctgca gctgcaaact cccgcaagca | 540 |
| gttttcagtt cctcctgccc ccactaggcc ttcctgccct gcagtggctg aaataccatt | 600 |
| gaggatggtc agcgaggaga tggaagagca agtccattcc atccgaggca gctcttctgc | 660 |
| aaaccctgtg aactcagttc ggaggaaatc atgtcttgtg aaggaagtgg aaaaaatgaa | 720 |
| gaacaagcga aagagaaga aggcccagaa ctctgaaatg agaatgaaga gagctcagga | 780 |
| gtatgacagt agttttccaa actgggaatt tgcccgaatg attaaagaat tcgggctac | 840 |
| tttggaatgt catccactta ctatgactga tcctatcgaa gagcacagaa tatgtgtctg | 900 |
| tgttaggaaa cgcccactga ataagcaaga attggccaag aaagaaattg atgtgatttc | 960 |
| cattcctagc aagtgtctcc tcttggtaca tgaacccaag ttgaaagtgg acttaacaaa | 1020 |
| gtatctggag aaccaagcat tctgctttga cttttgcattt gatgaaacag cttcgaatga | 1080 |
| agttgtctac aggttcacag caaggccact ggtacagaca atctttgaag gtggaaaagc | 1140 |
| aacttgtttt gcatatggcc agacaggaag tggcaagaca catactatgg gcggagacct | 1200 |
| ctctggaaa gcccagaatg catccaaagg gatctatgcc atggcctccc gggacgtctt | 1260 |
| cctcctgaag aatcaaccct gctaccggaa gttgggcctg gaagtctatg tgacattctt | 1320 |
| cgagatctac aatgggaagc tgtttgacct gctcaacaag aaggccaagc tgcgcgtgct | 1380 |
| ggaggacggc aagcaacagg tgcaagtggt ggggctgcag gagcatctgg ttaactctgc | 1440 |
| tgatgatgtc atcaagatga tcgacatggg cagcgcctgc agaacctctg gcagacatt | 1500 |
| tgccaactcc aattcctccc gctcccacgc gtgcttccaa attattcttc gagctaaagg | 1560 |
| gagaatgcat ggcaagttct ctttggtaga tctggcaggg aatgagcgag gcgcggacac | 1620 |
| ttccagtgct gaccggcaga cccgcatgga gggcgcagaa atcaacaaga gtctcttagc | 1680 |
| cctgaaggag tgcatcaggg ccctgggaca gaacaaggct cacacccgt tccgtgagag | 1740 |

```
caagctgaca caggtgctga gggactcctt cattggggag aactctagga cttgcatgat    1800
tgccacgatc tcaccaggca taagctcctg tgaatatact ttaaacaccc tgagatatgc    1860
agacagggtc aaggagctga gcccccacag tgggcccagt ggagagcagt tgattcaaat    1920
ggaaacagaa gagatggaag cctgctctaa cggggcgctg attccaggca atttatccaa    1980
ggaagaggag gaactgtctt cccagatgtc cagctttaac gaagccatga ctcagatcag    2040
ggagctggag gagaaggcta tggaagagct caaggagatc atacagcaag gaccagactg    2100
gcttgagctc tctgagatga ccgagcagcc agactatgac ctggagacct tgtgaacaa     2160 agcggaatct gctctggccc agcaagccaa gcatttctca gccctgcgag atgtcatcaa    2220
ggccttgcgc ctggccatgc agctggaaga gcaggctagc agacaaataa gcagcaagaa    2280
acggccccag tgacgactgc aaataaaaat ctgtttggtt tgacacccag cctcttccct    2340
ggccctcccc agagaacttt gggtacctgg tgggtctagg cagggtctga gctgggacag    2400
gttctggtaa atgccaagta tgggggcatc tgggcccagg gcagctgggg aggggggtcag   2460 agtgacatgg gacactcctt ttctgttcct cagttgtcgc cctcacgaga ggaaggagct    2520
cttagttacc cttttgtgtt gcccttcttt ccatcaaggg gaatgttctc agcatagagc    2580
tttctccgca gcatcctgcc tgcgtggact ggctgctaat ggagagctcc ctggggttgt    2640
cctggctctg gggagagaga cggagccttt agtacagcta tctgctggct ctaaaccttc    2700 tacgccttg ggccgagcac tgaatgtctt gtactttaaa aaaatgtttc tgagacctct     2760
ttctacttta ctgtctccct agagatccta gaggatccct actgttttct gttttatgtg    2820
tttatacatt gtatgtaaca ataaagagaa aaaataaatc agctgtttaa gtgtgtggaa    2880
aaaaaaaaaa aaaaaa                                                    2896

<210> SEQ ID NO 128
<211> LENGTH: 2209
<212> TYPE: DNA
<213> ORGANISM: Homo sapiens

<400> SEQUENCE: 128
actgcgcgcg tcgtgcgtaa tgacgtcagc gccggcggag aatttcaaat tcgaacggct     60
ttggcgggcc gaggaaggac ctggtgtttt gatgaccgct gtcctgtcta gcagatactt    120
gcacggttta cagaaattcg gtccctgggt cgtgtcagga aactggaaaa aaggtcataa    180
gcatgaagcg cagttcagtt tccagcggtg gtgctggccg cctctccatg caggagttaa    240
gatcccagga tgtaaataaa caaggcctct atacccctca aaccaaagag aaaccaacct    300
ttggaaagtt gagtataaac aaaccgacat ctgaaagaaa agtctcgcta tttggcaaaa    360
gaactagtgg acatggatcc cggaatagtc aacttggtat attttccagt tctgagaaaa    420
tcaaggaccc gagaccactt aatgacaaag cattcattca gcagtgtatt cgacaactct    480
gtgagtttct tacagaaaat ggttatgcac ataatgtgtc catgaaatct ctacaagctc    540
cctctgttaa agacttcctg aagatcttca catttcttta tggcttcctg tgcccctcat    600
acgaacttcc tgcacacaaag tttgaagaag aggttccaag aatctttaaa gaccttgggt    660 atcctttgc actatccaaa agctccatgt acacagtggg ggctcctcat acatggcctc     720
acattgtggc agccttagtt tggctaatag actgcatcaa gatacatact gccatgaaag    780
aaagctcacc tttatttgat gatgggcagc cttggggaga agaaactgaa gatggaatta    840
tgcataataa gttgttttg gactacacca taaaatgcta tgagttttt atgagtggtg      900 ccgacagctt tgatgagatg aatgcagagc tgcagtcaaa actgaaggat ttatttaatg    960
```

```
tggatgcttt taagctggaa tcattagaag caaaaaacag agcattgaat gaacagattg    1020
caagattgga acaagaaaga gaaaagaac cgaatcgtct agagtcgttg agaaaactga    1080
aggcttcctt acaaggagat gttcaaaagt atcaggcata catgagcaat ttggagtctc    1140
attcagccat tcttgaccag aaattaaatg gtctcaatga ggaaattgct agagtagaac    1200
tagaatgtga acaataaaa caggagaaca ctcgactaca gaatatcatt gacaaccaga    1260
agtactcagt tgcagacatt gagcgaataa atcatgaaag aaatgaattg cagcagacta    1320
ttaataaatt aaccaaggac ctggaagctg aacaacagaa gttgtggaat gaggagttaa    1380
aatatgccag aggcaaagaa gcgattgaaa cacaattagc agagtatcac aaattggcta    1440
gaaaattaaa acttattcct aaaggtgctg agaattccaa aggttatgac tttgaaatta    1500
agtttaatcc cgaggctggt gccaactgcc ttgtcaaata cagggctcaa gtttatgtac    1560
ctcttaagga actcctgaat gaaactgaag aagaaattaa taaagcccta aataaaaaaa    1620
tgggtttgga ggatacttta gaacaattga atgcaatgat aacagaaagc aagagaagtg    1680
tgagaactct gaaagaagaa gttcaaaagc tggatgatct ttaccaacaa aaaattaagg    1740
aagcagagga agaggatgaa aaatgtgcca gtgagcttga gtccttggag aaacacaagc    1800
acctgctaga aagtactgtt aaccaggggc tcagtgaagc tatgaatgaa ttagatgctg    1860
ttcagcggga ataccaacta gttgtgcaaa ccacgactga agaaagacga aaagtgggaa    1920
ataacttgca acgtctgtta gagatggttg ctacacatgt tgggtctgta gagaaacatc    1980
ttgaggagca gattgctaaa gttgatagag aatatgaaga atgcatgtca gaagatctct    2040
cggaaaatat taaagagatt agagataagt atgagaagaa agctactcta attaagtctt    2100
ctgaagaatg aagataaaat gttgatcatg tatatatatc catagtgaat aaaattgtct    2160
cagtaaagtg taaaaaaaaa aaaaaaaaaa aaaaaaaaaa aaaaaaaa              2209

<210> SEQ ID NO 129
<211> LENGTH: 1740
<212> TYPE: DNA
<213> ORGANISM: Homo sapiens

<400> SEQUENCE: 129
ctccctcctc tgcaccatga ctacctgcag ccgccagttc acctcctcca gctccatgaa      60
gggctcctgc ggcatcgggg gcggcatcgg gggcggctcc agccgcatct cctccgtcct     120
ggccggaggg tcctgccgcg cccccagcac ctacgggggc ggcctgtctg tctcatcctc     180
ccgcttctcc tctggggag cctatgggtt gggggggcggc tatggcggtg gcttcagcag     240
cagcagcagc agctttggta gtggcttggg ggaggatat ggtggtggcc ttggtgctgg     300
cttgggtggt ggctttggtg gtggcttgc tggtggtgat gggcttctgg tgggcagtga     360
gaaggtgacc atgcagaacc tcaacgaccg cctggcctcc tacctggaca aggtgcgtgc     420
tctggaggag gccaacgccg acctggaagt gaagatccgt gactggtacc agaggcagcg     480
gcctgctgag atcaaagact acagtcccta cttcaagacc attgaggacc tgaggaacaa     540
gattctcaca gccacagtgg acaatgccaa tgtccttctg cagattgaca atgcccgtct     600
ggccgcggat gacttccgca ccaagtatga gacagagttg aacctgcgca tgagtgtgga     660
agccgacatc aatggcctgc gcagggtgct ggacgaactg acctggcca gagctgacct     720 ggagatgcag attgagagcc tgaaggagga gctggcctac ctgaagaaga accacgagga     780
ggagatgaat gcccctgagag gccaggtggg tgagatgtc aatgtgggaga tggacgctgc     840
```

```
acctggcgtg gacctgagcc gcattctgaa cgagatgcgt gaccagtatg agaagatggc      900
agagaagaac cgcaaggatg ccgaggaatg gttcttcacc aagacagagg agctgaaccg      960
cgaggtggcc accaacagcg agctggtgca gagcggcaag agcgagatct cggagctccg     1020
gcgcaccatg cagaacctgg agattgagct gcagtcccag ctcagcatga agcatccct     1080 ggagaacagc ctggaggaga ccaaaggtcg ctactgcatg cagctggccc agatccagga    1140
gatgattggc agcgtggagg agcagctggc ccagctccgc tgcgagatgg agcagcagaa    1200
ccaggagtac aagatcctgc tggacgtgaa gacgcggctg gagcaggaga tcgccaccta    1260
ccgccgcctg ctggagggcg aggacgccca cctctcctcc tcccagttct cctctggatc    1320
gcagtcatcc agagatgtga cctcctccag ccgccaaatc cgcaccaagg tcatggatgt    1380
gcacgatggc aaggtggtgt ccacccacga gcaggtcctt cgcaccaaga actgaggctg    1440
cccagccccg ctcaggccta ggaggccccc cgtgtggaca cagatcccac tggaagatcc    1500
cctctcctgc ccaagcactt cacagctgga ccctgcttca ccctcacccc ctcctggcaa    1560
tcaatacagc ttcattatct gagttgcata aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaaa aaaaaaaaaa aaaaaaaaaa aaaaaaaaaa aaaaaaaaaa aaaaaaaaaa    1740

<210> SEQ ID NO 130
<211> LENGTH: 2895
<212> TYPE: DNA
<213> ORGANISM: Homo sapiens

<400> SEQUENCE: 130
ctcttttgca ggggccgttc ctcggggcat gacgctggct cctgcacaga tcctgctcct      60
ctgtggcctt cctgggctgc cctcccctcc tccgggactg ctctggactg acactgctca    120
ggttcggatt ccctcaaaga ctttgggaga caagacttgg tccccttttt acaaacaagg    180
gaacggaggc tctagaactg acttcctgaa aggcttggat ccaaagctcc ctcagttcag    240
cggccacgtc tatttccctc agacacaggg atccttgaac ctgtgggctg tatctccccg    300
cggacttgga agaatcccaa gagagtgggg ctcccacagg ctggagtgca atggtgtgat    360
ctcggctcac tgcaacctcc acctcccagg ttcaagctat tctcctgcct cagcctcctg    420
agtagctggg attacagatc ctggtggctg tggtcggtaa ttccagcttc gtgctggcta    480
caggtggatg atgcccacct ggctgccgat gacctctgca ccaagtgagg ctgggtctct    540
ggagctgccc caggggctgg acaagctgac cctggccggg ccaacctgg agatgcagat     600 tgagaacctc aaggaggacc tggtctacct gaagaagaac cacaagcagg aaatgaacgt    660
cctttgaggt caggtggatg aggatgtcag tgtgaagatg gacactgtgc ctggagtgaa    720
cctgagctgc atcctgaatg agatgcgtga ccaggacaag acattggtgg agaagagctg    780
caaggatgcc gagggctggt tcttcagcat ggtgggtggc cgtgcgtaag caggtgtgta    840
cacgtgtggg cacatgtgct gcatgctggt gcagctggag cactggcaga tccacaggct    900
gtcccagttg gaaggacttt tggaaaccag ttggaccagc cctcatgttt ttagatgtaa    960
aacgtgaggc tcagagagga ctcaagctca cacagccctt cactgtggcc tgcaaaatag   1020
atccaggtct ctacaagtct ggtcttgggt ttccaccaca gctgtttaca ggatgtgcgt    1080
atttgaatac atatgtatac ccttggcaag cacaggctga gtatctccgg tatcctaggg    1140
acagcaacag gcgcaaaaga ataacaccca gtgcctgtct ttgaggtgct gcagttcagt    1200
aggaaaaaga aatgcaaatg accgcagagc aggctgaatt cctccaagtt ccaatgtggg    1260
```

```
tgcagaggct ctctgtgtgc agaaagaggg gctgaactgc gaggtggcca ccaacacaga    1320
ggccctgcag agtggctgga tagagatatg gagctctacg tctctgtgca gaacctgagc    1380
cgtcccagct cagcaagaaa gcatcgctgg agggcagcct ggtggagatg gaggtgtgtt    1440
acaggaccct gccggcccag ctgcaggggc ttaacagaag catggagcag cagctgtgcg    1500
agctctgctg cgacacggag caccaggacc acaagcacag gtccttctgg acgtgaagac    1560
gtggctggag caggagatcg ccacctaccg ccgcttgctg gaggttgagg acgcccagag    1620
gtgatactga cgatgcaggc tggagtctgg ctgaggagcc ttgaatgcca agttaaagcg    1680
tctggactag atcacgtagg caatggggag ccatggaggg atttggagca ggagagtgaa    1740
atgaacatca agagatttta gaacattcac tctggctgca gagggagaaa tggatcagag    1800
gggtcagggc ggggccagag agatgtgtca ggggctgga gcaggagtc tggccagaga     1860 agtcccgtgc ggtggtgggt agtggggcag gggaaggaag gtggtgcacg cagaagagag    1920
gttatagctc aaaacagcgg gactggatgc ctggatctcg gggtaagcat ggctcacagt    1980
caggactcag taagtgtcgg gagaacacat gaaggagcag gcattgatgg ccctgggttt    2040
ctggttctga tgactgtgtg agtggtgaag agcaaggtgg gtggtggttg ggtttgcagt    2100
tgggaagggt gatcaggcct tcagctgaga gtgtcccgga gtctccatgc ttagtcacac    2160
gttgcagctt tttgctcccc ggaaatggtg aagtccatct atagtctaac aacagtctct    2220
cctgctttaa ttgggtctat ttgttgggcc ctctgggtta tggaaaaacc acttgctcag    2280
cttctccttg taaattcctg gtgagtagcc acagagtgcc gccagaccta ctgctgtgct    2340
gtttcttttt cttcttcctg ctgtgctgaa cccctgccct ttcattcttg ggcctgcgct    2400
aatttctgtg cattcccaac tgtgattttt caccaattta ggggaacctc ctctgccagg    2460
gcctacttct ccccagcagt gcttgcaggt gcctgggctg gctggcatcc ctgggctgat    2520
gggtgcttct ctccctgcag gctggccact cagtactcct tgtccctggc ctcgcagccc    2580
acccgggaag ccacagtgac cagccaccag gtgtgccatc gtggaggaag tccaggttgg    2640
agaggtggtc ttcttctgtg agcaggtcca cttctccacc cactgagacc cctttctgtc    2700
tgcgacagcc ccacctcgag ggccacggca cagccatcag ctccagctcc cagcatgcta    2760
ctgccacgcc ccgagtgtcc gtctgggccc cggtgcatgg cctgttgtct ttctgtatct    2820
actttctgca gccctcact gaggaggcct cctgggtttg tccagtgcct actattaaag    2880
ctttgctcca agttc                                                    2895
```

<210> SEQ ID NO 131
<211> LENGTH: 2529
<212> TYPE: DNA
<213> ORGANISM: Homo sapiens

<400> SEQUENCE: 131

```
gcatcctttt tgggctgctc acagccccca gcctctatgg tgaagacata cttgctagca     60
gcgtcaccaa cttgctgcca agagatcagt gctgcaaggc aaggttattt ctaactgagc    120
agagcctgcc aggaagaaag cgtttgcacc ccacaccact gtgcaggtgt gaccggtgag    180
ctcacagctg cccccaggc atgcccagcc cacttaatca ttcacagctc gacagctctc     240
tcgcccagcc cagttctgga agggataaaa agggggcatc accgttcctg ggtaacagag    300
ccaccttctg cgtcctgctg agctctgttc tctccagcac ctcccaaccc actagtgcct    360
ggttctcttg ctccaccagg aacaagccac catgtctcgc cagtcaagtg tgtccttccg    420
```

```
gagcgggggc agtcgtagct tcagcaccgc ctctgccatc accccgtctg tctcccgcac    480
cagcttcacc tccgtgtccc ggtccggggg tggcggtggt ggtggcttcg gcagggtcag    540
ccttgcgggt gcttgtggag tgggtggcta tggcagccgg agcctctaca acctgggggg    600
ctccaagagg atatccatca gcactagagg aggcagcttc aggaaccggt ttggtgctgg    660
tgctggaggc ggctatggct ttggaggtgg tgccggtagt ggatttggtt tcggcggtgg    720
agctggtggt ggctttgggc tcggtggcgg agctggcttt ggaggtggct tcggtggccc    780
tggctttcct gtctgccctc ctggaggtat ccaagaggtc actgtcaacc agagtctcct    840
gactcccctc aacctgcaaa tcgacccccag catccagagg gtgaggaccg aggagcgcga    900
gcagatcaag accctcaaca ataagtttgc ctccttcatc gacaaggtgc ggttcctgga    960
gcagcagaac aaggttctgg acaccaagtg gaccctgctg caggagcagg gcaccaagac   1020
tgtgaggcag aacctggagc cgttgttcga gcagtacatc aacaacctca ggaggcagct   1080
ggacagcatc gtgggggaac ggggccgcct ggactcagag ctgagaaaca tgcaggacct   1140
ggtggaagac ttcaagaaca gtatgaggga tgaaatcaac aagcgtacca ctgctgagaa   1200
tgagtttgtg atgctgaaga aggatgtaga tgctgcctac atgaacaagg tggagctgga   1260
ggccaaggtt gatgcactga tggatgagat taacttcatg aagatgttct ttgatgcgga   1320
gctgtcccag atgcagacgc atgtctctga cacctcagtg gtcctctcca tggacaacaa   1380
ccgcaacctg gacctggata gcatcatcgc tgaggtcaag gcccagtatg aggagattgc   1440
caaccgcagc cggacagaag ccgagtcctg gtatcagacc aagtatgagg agctgcagca   1500
gacagctggc cggcatggcg atgacctccg caacaccaag catgagatca cagagatgaa   1560
ccggatgatc cagaggctga gagccgagat tgacaatgtc aagaaacagt gcgccaatct   1620
gcagaacgcc attgcggatg ccgagcagcg tggggagctg gccctcaagg atgccaggaa   1680
caagctggcc gagctggagg aggccctgca gaaggccaag caggacatgg cccggctgct   1740
gcgtgagtac caggagctca tgaacaccaa gctggccctg gacgtggaga tcgccactta   1800
ccgcaagctg ctggagggcg aggaatgcag actcagtgga gaaggagttg gaccagtcaa   1860
catctctgtt gtcacaagca gtgtttcctc tggatatggc agtggcagtg gctatggcgg   1920
tggcctcggt ggaggtcttg gcggcggcct cggtggaggt cttgccggag gtagcagtgg   1980
aagctactac tccagcagca gtgggggtgt cggcctaggt ggtgggctca gtgtgggggg   2040
ctctggcttc agtgcaagca gtggccgagg gctggggtg ggctttggca gtggcggggg   2100
tagcagctcc agcgtcaaat ttgtctccac cacctcctcc tcccggaaga gcttcaagag   2160
ctaagaacct gctgcaagtc actgccttcc aagtgcagca acccagccca tggagattgc   2220
ctcttctagg cagttgctca agccatgttt tatccttttc tggagagtag tctagaccaa   2280
gccaattgca gaaccacatt ctttggttcc caggagagcc ccattcccag cccctggtct   2340
cccgtgccgc agttctatat tctgcttcaa atcagccttc aggtttccca cagcatggcc   2400
cctgctgaca cgagaaccca aagttttccc aaatctaaat catcaaaaca gaatccccac   2460
cccaatccca aattttgttt tggttctaac tacctccaga atgtgttcaa taaaatgctt   2520
ttataatat                                                           2529
```

<210> SEQ ID NO 132
<211> LENGTH: 6816
<212> TYPE: DNA
<213> ORGANISM: Homo sapiens

<400> SEQUENCE: 132

```
ggacggccga gcggcagggc gctcgcgcgc gcccactagt ggccggagga gaaggctccc    60
gcggaggccg cgctgccgc ccctccccct ggggaggctc gcgttccgc tgctcgcgcc    120 tgcgccgccc gccggcctca ggaacgcgcc ctcttcgccg gcgcgcgccc tcgcagtcac   180
cgccacccac cagctccggc accaacagca gcgccgctgc caccgccac cttctgccgc    240 cgccaccaca gccaccttct cctcctccgc tgtcctctcc cgtcctcgcc tctgtcgact   300
atcaggtgaa ctttgaacca ggatggctga gccccgccag gagttcgaag tgatggaaga   360
tcacgctggg acgtacgggt tgggggacag gaaagatcag gggggctaca ccatgcacca   420
agaccaagag ggtgacacgg acgctggcct gaaagaatct cccctgcaga cccccactga   480
ggacggatct gaggaaccgg gctctgaaac ctctgatgct aagagcactc aacagcgga    540 agatgtgaca gcacccttag tggatgaggg agctcccggc aagcaggctg ccgcgcagcc   600
ccacacggag atcccagaag gaaccacagc tgaagaagca ggcattggag acaccccag    660 cctggaagac gaagctgctg gtcacgtgac ccaagagcct gaaagtggta aggtggtcca   720
ggaaggcttc ctccgagagc caggccccc aggtctgagc caccagctca tgtccggcat    780
gcctggggct cccctcctgc ctgagggcc cagagaggcc acacgccaac cttcggggac    840
aggacctgag gacacagagg gcggccgcca cgcccctgag ctgctcaagc accagcttct   900
aggagacctg caccaggagg ggccgccgct gaaggggca ggggcaaag agaggccggg    960 gagcaaggag gaggtggatg aagaccgcga cgtcgatgag tcctcccccc aagactcccc   1020
tccctccaag gcctcccag cccaagatgg gcggcctccc cagacagccg ccagagaagc   1080
caccagcatc ccaggcttcc cagcggaggg tgccatcccc ctccctgtgg atttcctctc   1140
caaagttccc acagagatcc cagcctcaga gcccgacggg cccagtgtag ggcgggccaa   1200
agggcaggat gcccccctgg agttcacgtt tcacgtggaa atcacaccca acgtgcagaa   1260
ggagcaggcg cactcggagg agcatttggg aagggctgca tttccagggg ccctgggaga   1320
ggggccagag gcccggggcc cctcttggg agaggacaca aaagaggctg accttccaga   1380
gccctctgaa aagcagcctg ctgctgctcc gcggggaag cccgtcagcc gggtccctca   1440
actcaaagct cgcatggtca gtaaaagcaa agacgggact ggaagcgatg acaaaaaagc   1500
caagacatcc acacgttcct ctgctaaaac cttgaaaaat aggccttgcc ttagccccaa   1560 acacccact cctggtagct cagaccctct gatccaaccc tccagccctg ctgtgtgccc   1620
agagccacct tcctctccta aatacgtctc ttctgtcact tcccgaactg gcagttctgg   1680
agcaaaggag atgaaactca gggggcga tggtaaaacg aagatcgcca caccgcgggg   1740
agcagcccct ccaggccaga agggccaggc caacgccacc aggattccag caaaaacccc   1800
gccgctccaa aagacaccac ccagctctgc gactaagcaa gtccagagaa gaccacccc   1860 tgcagggccc agatctgaga gaggtgaacc tccaaaatca ggggatcgca gcggctacag   1920
cagccccggc tccccaggca ctcccggcag ccgctcccgc accccgtccc ttccaacccc   1980
acccacccgg gagcccaaga aggtggcagt ggtccgtact ccacccaagt cgccgtcttc   2040
cgccaagagc cgcctgcaga cagccccgt gccatgcca gacctgaaga atgtcaagtc   2100
caagatcggc tccactgaga acctgaagca ccagccggga ggcgggaagg tgcagataat   2160
taataagaag ctggatctta gcaacgtcca gtccaagtgt ggctcaaagg ataatatcaa   2220
acacgtcccg ggaggcggca gtgtgcaaat agtctacaaa ccagttgacc tgagcaaggt   2280
gacctccaag tgtggctcat taggcaacat ccatcataaa ccaggaggtg ccaggtggaa   2340
```

```
agtaaaatct gagaagcttg acttcaagga cagagtccag tcgaagattg ggtccctgga    2400
caatatcacc cacgtccctg gcggaggaaa taaaaagatt gaaacccaca agctgacctt    2460
ccgcgagaac gccaaagcca agacagacca cggggcggag atcgtgtaca agtcgccagt    2520
ggtgtctggg gacacgtctc cacggcatct cagcaatgtc tcctccaccg gcagcatcga    2580
catggtagac tcgccccagc tcgccacgct agctgacgag gtgtctgcct ccctggccaa    2640
gcagggtttg tgatcaggcc cctggggcgg tcaataattg tggagaggag agaatgagag    2700
agtgtggaaa aaaaaagaat aatgacccgg cccccgccct ctgccccccag ctgctcctcg    2760
cagttcggtt aattggttaa tcacttaacc tgcttttgtc actcggcttt ggctcgggac    2820
ttcaaaatca gtgatgggag taagagcaaa tttcatcttt ccaaattgat gggtgggcta    2880
gtaataaaat atttaaaaaa aaacattcaa aaacatggcc acatccaaca tttcctcagg    2940
caattccttt tgattctttt ttcttccccc tccatgtaga agagggagaa ggagaggctc    3000
tgaaagctgc ttctggggga tttcaaggga ctggggtgc caaccacctc tggccctgtt    3060
gtgggggtgt cacagaggca gtggcagcaa caaaggattt gaaacttggt gtgttcgtgg    3120
agccacaggc agacgatgtc aaccttgtgt gagtgtgacg ggggttgggg tgggcgggga    3180
ggccacgggg gaggccgagg cagggctggg gcagagggga gaggaagcac aagaagtggg    3240
agtgggagag gaagccacgt gctggagagt agacatcccc ctccttgccg ctgggagagc    3300
caaggcctat gccacctgca gcgtctgagc ggccgcctgt ccttggtggc cggggtgggg    3360
ggcctgctgt gggtcagtgt gccaccctct gcagggcagc ctgtgggaga agggacagcg    3420
ggtaaaaaga gaaggcaagc tggcaggagg gtggcacttc gtggatgacc tccttagaaa    3480
agactgacct tgatgtcttg agagcgctgg cctcttcctc cctccctgca gggtaggggg    3540
cctgagttga ggggcttccc tctgctccac agaaaccctg ttttattgag ttctgaaggt    3600
tggaactgct gccatgattt tggccacttt gcagacctgg gactttaggg ctaaccagtt    3660
ctctttgtaa ggacttgtgc ctcttgggag acgtccaccc gtttccaagc ctgggccact    3720
ggcatctctg gagtgtgtgg gggtctggga ggcaggtccc gagcccctg tccttcccac    3780
ggccactgca gtcaccccgt ctgcgccgct gtgctgttgt ctgccgtgag agcccaatca    3840
ctgcctatac ccctcatcac acgtcacaat gtcccgaatt cccagcctca ccaccccttc    3900
tcagtaatga ccctggttgg ttgcaggagg tacctactcc atactgaggg tgaaattaag    3960
ggaaggcaaa gtccaggcac aagagtggga ccccagcctc tcactctcag ttccactcat    4020
ccaactggga ccctcaccac gaatctcatg atctgattcg gttccctgtc tcctcctccc    4080
gtcacagatg tgagccaggg cactgctcag ctgtgaccct aggtgtttct gccttgttga    4140
catggagaga gccctttccc ctgagaaggc ctggccccctt cctgtgctga gcccacagca    4200
gcaggctggg tgtcttggtt gtcagtggtg gcaccaggat ggaagggcaa ggcacccagg    4260
gcaggcccac agtcccgctg tcccccactt gcacccctagc ttgtagctgc caacctccca    4320
gacagcccag cccgctgctc agctccacat gcatagtatc agccctccac acccgacaaa    4380
ggggaacaca ccccccttgga aatggttctt ttcccccagt cccagctgga agccatgctg    4440
tctgttctgc tggagcagct gaacatatac atagatgttg ccctgccctc cccatctgca    4500
ccctgttgag ttgtagttgg atttgtctgt ttatgcttgg attcaccaga gtgactatga    4560
tagtgaaaag aaaaaaaaaa aaaaaaaagg acgcatgtat cttgaaatgc ttgtaaagag    4620
gtttctaacc caccctcacg aggtgtctct caccccaca ctgggactcg tgtggcctgt    4680
gtggtgccac cctgctgggg cctcccaagt tttgaaaggc tttcctcagc acctgggacc    4740
```

```
caacagagac cagcttctag cagctaagga ggccgttcag ctgtgacgaa ggcctgaagc    4800
acaggattag gactgaagcg atgatgtccc cttccctact tccccttggg gctccctgtg    4860
tcagggcaca gactaggtct tgtggctggt ctggcttgcg gcgcgaggat ggttctctct    4920
ggtcatagcc cgaagtctca tggcagtccc aaaggaggct acaactcct gcatcacaag    4980 aaaaaggaag ccactgccag ctgggggat ctgcagctcc cagaagctcc gtgagcctca    5040
gccacccctc agactgggtt cctctccaag ctcgccctct ggaggggcag cgcagcctcc    5100
caccaagggc cctgcgacca cagcagggat tgggatgaat tgcctgtcct ggatctgctc    5160
tagaggccca agctgcctgc ctgaggaagg atgacttgac aagtcaggag acactgttcc    5220
caaagccttg accagagcac ctcagcccgc tgaccttgca caaactccat ctgctgccat    5280 gagaaaggg aagccgcctt tgcaaaacat tgctgcctaa agaaactcag cagcctcagg    5340
cccaattctg ccacttctgg tttgggtaca gttaaaggca accctgaggg acttggcagt    5400
agaaatccag ggcctcccct ggggctggca gcttcgtgtg cagctagagc tttacctgaa    5460
aggaagtctc tgggcccaga actctccacc aagagcctcc ctgccgttcg ctgagtccca    5520
gcaattctcc taagttgaag ggatctgaga aggagaagga aatgtggggt agatttggtg    5580
gtggttagag atatgccccc ctcattactg ccaacagttt cggctgcatt tcttcacgca    5640
cctcggttcc tcttcctgaa gttcttgtgc cctgctcttc agcaccatgg gccttcttat    5700
acggaaggct ctgggatctc cccttgtgg ggcaggctct tggggccagc ctaagatcat    5760
ggtttagggt gatcagtgct ggcagataaa ttgaaaaggc acgctggctt gtgatcttaa    5820
atgaggacaa tcccccagg gctgggcact cctccctcc cctcacttct cccacctgca    5880
gagccagtgt ccttgggtgg gctagatagg atatactgta tgccggctcc ttcaagctgc    5940
tgactcactt tatcaatagt tccatttaaa ttgacttcag tggtgagact gtatcctgtt    6000
tgctattgct tgttgtgcta tgggggagg ggaggaat gtgtaagata gttaacatgg    6060
gcaaagggag atcttggggt gcagcactta aactgcctcg taaccctttt catgatttca    6120
accacatttg ctagagggag ggagcagcca cggagttaga ggcccttggg gtttctcttt    6180
tccactgaca ggctttccca ggcagctggc tagttcattc cctccccagc caggtgcagg    6240
cgtaggaata tggacatctg gttgctttgg cctgctgccc tctttcaggg gtcctaagcc    6300
cacaatcatg cctccctaag accttggcat ccttccctct aagccgttgg cacctctgtg    6360
ccacctctca cactggctcc agacacacag cctgtgcttt tggagctgag atcactcgct    6420
tcaccctcct catctttgtt ctccaagtaa agccacgagg tcgggcgag gcagaggtg    6480 atcacctgcg tgtcccatct acagacctgc agcttcataa aacttctgat ttctcttcag    6540 cttgaaaag ggttaccctg ggcactggcc tagagcctca cctcctaata gacttagccc    6600
catgagtttg ccatgttgag caggactatt tctggcactt gcaagtccca tgatttcttc    6660
ggtaattctg agggtggggg gagggacatg aaatcatctt agcttagctt tctgtctgtg    6720
aatgtctata tagtgtattg tgtgttttaa caaatgattt acactgactg ttgctgtaaa    6780
agtgaatttg gaaataaagt tattactctg attaaa                              6816
```

<210> SEQ ID NO 133
<211> LENGTH: 2372
<212> TYPE: DNA
<213> ORGANISM: Homo sapiens

<400> SEQUENCE: 133

-continued

```
gcaccgcgcg agcttggctg cttctggggc ctgtgtggcc ctgtgtgtcg gaaagatgga      60
gcaagaagcc gagcccgagg ggcggccgcg acccctctga ccgagatcct gctgctttcg     120
cagccaggag caccgtccct ccccggatta gtgcgtacga gcgcccagtg ccctggcccg     180
gagagtggaa tgatcccga ggcccagggc gtcgtgcttc cgcagtagtc agtccccgtg      240
aaggaaactg gggagtcttg agggaccccc gactccaagc gcgaaaaccc cggatggtga     300
ggagcaggca aatgtgcaat accaacatgt ctgtacctac tgatggtgct gtaaccacct     360
cacagattcc agcttcggaa caagagaccc tggttagacc aaagccattg cttttgaagt     420
tattaaagtc tgttggtgca caaaaagaca cttatactat gaaagaggtt cttttttatc     480
ttggccagta tattatgact aaacgattat atgatgagaa gcaacaacat attgtatatt     540
gttcaaatga tcttctagga gatttgtttg gcgtgccaag cttctctgtg aaagagcaca     600
ggaaaatata taccatgatc tacaggaact tggtagtagt caatcagcag gaatcatcgg     660
actcaggtac atctgtgagt gagaacaggt gtcaccttga aggtgggagt gatcaaaagg     720
accttgtaca agagcttcag gaagagaaac cttcatcttc acatttggtt tctagaccat     780
ctacctcatc tagaaggaga gcaattagtg agacagaaga aaattcagat gaattatctg     840
gtgaacgaca agaaaacgc cacaaatctg atagtatttc cctttccttt gatgaaagcc      900
tggctctgtg tgtaataagg gagatatgtt gtgaagaag cagtagcagt gaatctacag       960
ggacgccatc gaatccggat cttgatgctg gtgtaagtga acattcaggt gattggttgg    1020
atcaggattc agtttcagat cagtttagtg tagaatttga agttgaatct ctcgactcag    1080
aagattatag ccttagtgaa gaaggacaag aactctcaga tgaagatgat gaggtatatc    1140
aagttactgt gtatcaggca ggggagagtg atacagattc atttgaagaa gatcctgaaa    1200
tttccttagc tgactattgg aaatgcactt catgcaatga aatgaatccc cccttccat     1260
cacattgcaa cagatgttgg gcccttcgtg agaattggct tcctgaagat aaagggaaag    1320
ataaagggga aatctctgag aaagccaaac tggaaaactc aacacaagct gaagagggct    1380
ttgatgttcc tgattgtaaa aaactatag tgaatgattc cagagagtca tgtgttgagg     1440
aaaatgatga taaaattaca caagcttcac aatcacaaga aagtgaagac tattctcagc    1500
catcaacttc tagtagcatt atttatagca gccaagaaga tgtgaaagag tttgaaaggg    1560
aagaaaccca agacaaagaa gagagtgtgg aatctagttt gccccttaat gccattgaac    1620
cttgtgtgat ttgtcaaggt cgacctaaaa atggttgcat tgtccatggc aaaacaggac    1680
atcttatggc ctgctttaca tgtgcaaaga agctaaagaa aaggaataag ccctgcccag    1740
tatgtagaca accaattcaa atgattgtgc taacttattt cccctagttg acctgtctat    1800
aagagaatta tatatttcta actatataac cctaggaatt tagacaacct gaaatttatt    1860
cacatatatc aaagtgagaa aatgcctcaa ttcacataga tttcttctct ttagtataat    1920
tgacctactt tggtagtgga atagtgaata cttactataa tttgacttga atatgtagct    1980
catccttac accaactcct aatttaaat aatttctact ctgtcttaaa tgagaagtac       2040
ttggtttttt ttttcttaaa tatgtatatg acatttaaat gtaacttatt atttttttg      2100
agaccgagtc ttgctctgtt acccaggctg gagtgcagtg ggtgatcttg gctcactgca    2160
agctctgccc tccccgggtt cgcaccattc tcctgcctca gcctcccaat agcttggcc     2220
tacagtcatc tgccaccaca cctggctaat ttttttgtact tttagtagag acagggtttc    2280
accgtgttag ccaggatggt ctcgatctcc tgacctcgtg atccgccac ctcggcctcc      2340
caaagtgctg ggattacagg catgagccac cg                                   2372
```

<210> SEQ ID NO 134
<211> LENGTH: 2486
<212> TYPE: DNA
<213> ORGANISM: Homo sapiens

<400> SEQUENCE: 134

```
gagatttgat tcccttggcg ggcggaagcg gccacaaccc ggcgatcgaa aagattctta      60
ggaacgccgt accagccgcg tctctcagga cagcaggccc ctgtccttct gtcgggcgcc     120
gctcagccgt gccctccgcc cctcaggttc tttttctaat tccaaataaa cttgcaagag     180
gactatgaaa gattatgatg aacttctcaa atattatgaa ttacatgaaa ctattgggac     240
aggtggcttt gcaaaggtca aacttgcctg ccatatcctt actggagaga tggtagctat     300
aaaaatcatg gataaaaaca cactagggag tgatttgccc cggatcaaaa cggagattga     360
ggccttgaag aacctgagac atcagcatat atgtcaactc taccatgtgc tagagacagc     420
caacaaaata ttcatggttc ttgagtactg ccctggagga gagctgtttg actatataat     480
ttcccaggat cgcctgtcag aagaggagac ccggggttgtc ttccgtcaga tagtatctgc     540
tgttgcttat gtgcacagcc agggctatgc tcacagggac ctcaagccag aaaatttgct     600
gtttgatgaa tatcataaat taaagctgat tgactttggt ctctgtgcaa acccaaggg     660
taacaaggat taccatctac agacatgctg tgggagtctg gcttatgcag cacctgagtt     720
aatacaaggc aaatcatatc ttggatcaga ggcagatgtt tggagcatgg catactgtt     780
atatgttctt atgtgtggat ttctaccatt tgatgatgat aatgtaatgg ctttatacaa     840
gaagattatg agaggaaaat atgatgttcc caagtggctc tctcccagta gcattctgct     900
tcttcaacaa atgctgcagg tggacccaaa gaaacggatt tctatgaaaa atctattgaa     960
ccatccctgg atcatgcaag attacaacta tcctgttgag tggcaaagca agaatccttt    1020
tattcacctc gatgatgatt gcgtaacaga actttctgta catcacagaa acaacaggca    1080
aacaatggag gatttaattt cactgtggca gtatgatcac ctcacggcta cctatcttct    1140
gcttctagcc aagaaggctc ggggaaaacc agttcgttta aggctttctt ctttctcctg    1200
tggacaagcc agtgctaccc cattcacaga catcaagtca ataattgga gtctggaaga    1260
tgtgaccgca agtgataaaa attatgtggc gggattaata gactatgatt ggtgtgaaga    1320
tgatttatca acaggtgctg ctactccccg aacatcacag tttaccaagt actggacaga    1380
atcaaatggg gtggaatcta aatcattaac tccagcctta tgcagaacac ctgcaaataa    1440
attaaagaac aaagaaaatg tatatactcc taagtctgct gtaaagaatg aagagtactt    1500
tatgtttcct gagccaaaga ctccagttaa taagaaccag cataagagag aaatactcac    1560
tacgccaaat cgttcactac caccctcaaa agctagaaac cagtgcctga agaaactcc    1620
aattaaaata ccagtaaatt caacaggaac agacaagtta atgacaggtg tcattagccc    1680
tgagaggcgg tgccgctcag tggaattgga tctcaaccaa gcacatatgg aggagactcc    1740
aaaaagaaag ggagccaaag tgtttgggag ccttgaaagg gggttggata aggttatcac    1800
tgtgctcacc aggagcaaaa ggaagggttc tgccagagac gggcccagaa gactaaagct    1860
tcactataac gtgactacaa ctagattagt gaatccagat caactgttga atgaaataat    1920
gtctattctt ccaaagaagc atgttgactt tgtacaaaag ggttatacac tgaagtgtca    1980
aacacagtca gatttgggga agtgacaat gcaatttgaa ttagaagtgt gccagcttca    2040
aaaacccgat gtggtgggta tcaggaggca gcggcttaag ggcgatgcct gggtttacaa    2100
```

```
aagattagtg gaagacatcc tatctagctg caaggtataa ttgatggatt cttccatcct    2160
gccggatgag tgtgggtgtg atacagccta cataaagact gttatgatcg ctttgatttt    2220
aaagttcatt ggaactacca acttgtttct aaagagctat cttaagacca atatctcttt    2280 gttttaaac aaaagatatt attttgtgta tgaatctaaa tcaagcccat ctgtcattat    2340
gttactgtct tttttaatca tgtggttttg tatattaata attgttgact ttcttagatt    2400
cacttccata tgtgaatgta agctcttaac tatgtctctt tgtaatgtgt aatttctttc    2460
tgaaataaaa ccatttgtga atatag                                        2486
```

<210> SEQ ID NO 135
<211> LENGTH: 1140
<212> TYPE: DNA
<213> ORGANISM: Homo sapiens
<220> FEATURE:
<221> NAME/KEY: misc_feature
<222> LOCATION: (1140)..(1140)
<223> OTHER INFORMATION: n is a, c, g, or t

<400> SEQUENCE: 135

```
gcagcggagg agcccagtcc acgatggccc ggtccctggt gtgccttggt gtcatcatct      60
tgctgtctgc cttctccgga cctggtgtca ggggtggtcc tatgcccaag ctggctgacc     120
ggaagctgtg tgcggaccag gagtgcagcc accctatctc catggctgtg gcccttcagg     180
actacatggc ccccgactgc cgattcctga ccattcaccg gggccaagtg gtgtatgtct     240
tctccaagct gaagggccgt gggcggctct tctggggagg cagcgttcag ggagattact     300
atggagatct ggctgctcgc ctgggctatt tccccagtag cattgtccga gaggaccaga     360
ccctgaaacc tggcaaagtc gatgtgaaga cagacaaatg ggatttctac tgccagtgag     420
ctcagcctac cgctggccct gccgtttccc ctccttgggt ttatgcaaat acaatcagcc     480
cagtgcaaaa aaaaaaaaa aaaaaaaaa cttcggagaa gagatagcaa caaaaggccg     540
cttgtgtgaa ggcgccaaaa gttttcgccc aagagacctt cggcctcccc cagggcgcgc     600
gcaaaggcgc cttgttttga caacctcttg gacaaccgga ggggctaccg cccggagacc     660
cctgtggtgg accccccggg caacccggtg tgacagggta ctcacccca cggctttgtc     720 gggggtccca ccaaaggccc caaagaggct cttcaaggc actattcctt gttgtagacc     780 tgtgtgtgc cacaggcgcc aaagaaacct cgggggcta acaaacgcac gtgcttggca     840
gctccgagaa ggctctctcc caccgagggg tggacgcaa caggggaat gggccatcat     900 attgttgccc ccggtgggca ccaactcttt ttcccccata gagaggcctt agcacactat     960
gtggggcacg ttattgccgc ctagagaaac cgagcgccag aaaatttcga aggggggggc    1020
gcttctcatc attttgcgca aaaccccctt gtgggagtat gccccgaact cctctggaac    1080
acacaagcga cacttgcgcg gggtctgcaa aaaacctcct gttgggaagc cggcttcacn    1140
```

<210> SEQ ID NO 136
<211> LENGTH: 12507
<212> TYPE: DNA
<213> ORGANISM: Homo sapiens

<400> SEQUENCE: 136

```
taccgggcgg aggtgagcgc ggcgccggct cctcctgcgg cggactttgg gtgcgacttg      60
acgagcggtg gttcgacaag tggccttgcg ggccggatcg tcccagtgga agagttgtaa    120
atttgcttct ggccttcccc tacgattat acctggcctt ccctacgga ttatactcaa    180 cttactgttt agaaaatgtg gcccacgaga cgcctggtta ctatcaaaag gagcggggtc    240
```

```
gacggtcccc actttcccct gagcctcagc acctgcttgt ttggaagggg tattgaatgt    300
gacatccgta tccagcttcc tgttgtgtca aacaacatt  gcaaaattga atccatgag    360
caggaggcaa tattacataa tttcagttcc acaaatccaa cacaagtaaa tgggtctgtt    420
attgatgagc ctgtacggct aaaacatgga gatgtaataa ctattattga tcgttccttc    480
aggtatgaaa atgaaagtct tcagaatgga aggaagtcaa ctgaatttcc aagaaaaata    540
cgtgaacagg agccagcacg tcgtgtctca agatctagct tctcttctga ccctgatgag    600
aaagctcaag attccaaggc ctattcaaaa atcactgaag gaaaagtttc aggaaatcct    660
caggtacata tcaagaatgt caaagaagac agtaccgcag atgactcaaa agacagtgtt    720
gctcagggaa caactaatgt tcattcctca gaacatgctg gacgtaatgg cagaaatgca    780
gctgatccca tttctgggga tttttaaaga atttccagcg ttaaattagt gagccgttat    840
ggagaattga agtctgttcc cactacacaa tgtcttgaca atagcaaaaa aaatgaatct    900
ccctttggga agctttatga gtcagtgaag aaagagttgg atgtaaaatc acaaaaagaa    960
aatgtcctac agtattgtag aaaatctgga ttacaaactg attacgcaac agagaaagaa   1020
agtgctgatg gttacaggg  ggagacccaa ctgttggtct cgcgtaagtc aagaccaaaa   1080
tctggtggga gcggccacgc tgtggcagag cctgcttcac ctgaacaaga gcttgaccag   1140
aacaagggga agggaagaga cgtggagtct gttcagactc ccagcaaggc tgtgggcgcc   1200
agctttcctc tctatgagcc ggctaaaatg aagacccctg tacaatattc acagcaacaa   1260
aattctccac aaaaacataa gaacaaagac ctgtatacta ctggtagaag agaatctgtg   1320
aatctgggta aagtgaagg  cttcaaggct ggtgataaaa ctcttactcc caggaagctt   1380
tcaactagaa atcgaacacc agctaaagtt gaagatgcag ctgactctgc cactaagcca   1440
gaaaatctct cttccaaaac cagaggaagt attcctacag atgtggaagt tctgcctacg   1500
gaaactgaaa ttcacaatga gccatttta  actctgtggc tcactcaagt tgagaggaag   1560
atccaaaagg attccctcag caagcctgag aaattgggca ctacagctgg acagatgtgc   1620
tctgggttac ctggtcttag ttcagttgat atcaacaact ttggtgattc cattaatgag   1680
agtgagggaa tacctttgaa aagaaggcgt gtgtcctttg gtgggcacct aagacctgaa   1740
ctatttgatg aaaacttgcc tcctaatacg cctctcaaaa ggggagaagc cccaaccaaa   1800
agaaagtctc tggtaatgca cactccacct gtcctgaaga aaatcatcaa ggaacagcct   1860
caaccatcag gaaaacaaga gtcaggttca gaaatccatg tggaagtgaa ggcacaaagc   1920
ttggttataa gccctccagc tcctagtcct aggaaaactc cagttgccag tgatcaacgc   1980
cgtaggtcct gcaaaacagc ccctgcttcc agcagcaaat ctcagacaga ggttcctaag   2040
agaggaggga gaaagagtgg caacctgcct tcaaagagag tgtctatcag ccgaagtcaa   2100
catgatattt tacagatgat atgttccaaa agaagaagtg gtgcttcgga agcaaatctg   2160
attgttgcaa atcatgggc  agatgtagta aaacttggtg caaaacaaac acaaactaaa   2220
gtcataaaac atggtcctca aggtcaatg  aacaaaaggc aaagaagacc tgctactcca   2280
aagaagcctg tgggcgaagt tcacagtcaa tttagtacag gccacgcaaa ctctccttgt   2340
accataataa tagggaaagc tcatactgaa aaagtacatg tgcctgctcg accctacaga   2400
gtgctcaaca acttcatttc caaccaaaaa atggacttta aggaagatct ttcaggaata   2460
gctgaaatgt tcaagacccc agtgaaggag caaccgcagt tgacaagcac atgtcacatc   2520
gctatttcaa attcagagaa tttgcttgga aaacagtttc aaggaactga ttcaggagaa   2580
```

```
gaacctctgc tccccacctc agagagtttt ggaggaaatg tgttcttcag tgcacagaat    2640
gcagcaaaac agccatctga taaatgctct gcaagccctc ccttaagacg gcagtgtatt    2700
agagaaaatg gaaacgtagc aaaaacgccc aggaacacct acaaaatgac ttctctggag    2760
acaaaaactt cagatactga gacagagcct tcaaaaacag tatccactgc aaacaggtca    2820
ggaaggtcta cagagttcag gaatatacag aagctacctg tggaaagtaa gagtgaagaa    2880
acaaatacag aaattgttga gtgcatccta aaaagaggtc agaaggcaac actactacaa    2940
caaaggagag aaggagagat gaaggaaata gaaagacctt ttgagacata taaggaaaat    3000
attgaattaa agaaaacga tgaaaagatg aaagcaatga agagatcaag aacttggggg    3060
cagaaatgtg caccaatgtc tgacctgaca gacctcaaga gcttgcctga tacagaactc    3120
atgaaagaca cggcacgtgg ccagaatctc ctccaaaccc aagatcatgc caaggcacca    3180
aagagtgaga aaggcaaaat cactaaaatg ccctgccagt cattcaaacc agaaccaata    3240
aacaccccaa cacacacaaa acaacagttg aaggcatccc tggggaaagt aggtgtgaaa    3300
gaagagctcc tagcagtcgg caagttcaca cggacgtcag gggagaccac gcacacgcac    3360
agagagccag caggagatgg caagagcatc agaacgttta aggagtctcc aaagcagatc    3420
ctggaccag cagcccgtgt aactggaatg aagaagtggc caagaacgcc taaggaagag    3480
gcccagtcac tagaagacct ggctggcttc aaagagctct tccagacacc aggtccctct    3540
gaggaatcaa tgactgatga gaaaactacc aaaatagcct gcaaatctcc accaccagaa    3600
tcagtggaca ctccaacaag cacaaagcaa tggcctaaga gaagtctcag gaaagcagat    3660
gtagaggaag aattcttagc actcaggaaa ctaacaccat cagcagggaa agccatgctt    3720
acgcccaaac cagcaggagg tgatgagaaa gacattaaag catttatggg aactccagtg    3780
cagaaactgg acctggcagg aactttacct ggcagcaaaa gacagctaca gactcctaag    3840
gaaaaggccc aggctctaga gacctggct ggctttaaag agctcttcca gactcctggt    3900
cacaccgagg aattagtggc tgctggtaaa accactaaaa taccctgcga ctctccacag    3960
tcagacccag tggacacccc aacaagcaca aagcaacgac ccaagagaag tatcaggaaa    4020
gcagatgtag agggagaact cttagcgtgc aggaatctaa tgccatcagc aggcaaagcc    4080
atgcacacgc ctaaccatc agtaggtgaa gagaaagaca tcatcatatt tgtgggaact    4140
ccagtgcaga aactggacct gacagagaac ttaccggca gcaagagacg gccacaaact    4200
cctaaggaag aggcccaggc tctggaagac ctgactggct ttaaagagct cttccagacc    4260
cctggtcata ctgaagaagc agtggctgct ggcaaaacta ctaaaatgcc ctgcgaatct    4320
tctccaccag aatcagcaga cacccccaaca agcacaagaa ggcagcccaa gacacctttg    4380
gagaaaaggg acgtacagaa ggagctctca gccctgaaga agctcacaca gacatcaggg    4440
gaaaccacac acacagataa agtaccagga ggtgaggata aaagcatcaa cgcgtttagg    4500
gaaactgcaa aacagaaact ggacccagca gcaagtgtaa ctggtagcaa gaggcaccca    4560
aaaactaagg aaaaggccca cccctagaa gacctggctg gcttgaaaga gctcttccag    4620
acaccagtat gcactgacaa gcccacgact cacgagaaaa ctaccaaaat agcctgcaga    4680
tcacaaccag cccagtgga cacaccaaca agctccaagc acagtccaa gagaagtctc    4740
aggaaagtgg acgtagaaga agaattcttc gcactcagga acgaacacc atcagcaggc    4800
aaagccatgc acacacccaa accagcagta agtggtgaga aaacatcta cgcatttatg    4860
ggaactccag tgcagaaact ggacctgaca gagaacttaa ctggcagcaa gagacggcta    4920
caaactccta aggaaaaggc ccaggctcta gaagacctgg ctggctttaa agagctcttc    4980
```

```
cagacacgag gtcacactga ggaatcaatg actaacgata aaactgccaa agtagcctgc   5040
aaatcttcac aaccagaccc agacaaaaac ccagcaagct ccaagcgacg gctcaagaca   5100
tccctgggga aagtgggcgt gaaagaagag ctcctagcag ttggcaagct cacacagaca   5160
tcaggagaga ctacacacac acacacagag ccaacaggag atggtaagag catgaaagca   5220
tttatggagt ctccaaagca gatcttagac tcagcagcaa gtctaactgg cagcaagagg   5280
cagctgagaa ctcctaaggg aaagtctgaa gtccctgaag acctggccgg cttcatcgag   5340
ctcttccaga caccaagtca cactaaggaa tcaatgacta acgaaaaaac taccaaagta   5400
tcctacagag cttcacagcc agacctagtg acaccccaa caagctccaa gccacagccc   5460
aagagaagtc tcaggaaagc agacactgaa gaagaatttt tagcatttag gaaacaaacg   5520
ccatcagcag gcaaagccat gcacacaccc aaaccagcag taggtgaaga gaaagacatc   5580
aacacgtttt tgggaactcc agtgcagaaa ctggaccagc caggaaattt acctggcagc   5640
aatagacggc tacaaactcg taaggaaaag gcccaggctc tagaagaact gactggcttc   5700
agagagcttt tccagacacc atgcactgat aaccccacga ctgatgagaa aactaccaaa   5760
aaaatactct gcaaatctcc gcaatcgac ccagcggaca ccccaacaaa cacaaagcaa   5820
cggcccaaga gaagcctcaa gaaagcagac gtagaggaag aattttttagc attcaggaaa   5880 ctaacaccat cagcaggcaa agccatgcac acgcctaaag cagcagtagg tgaagagaaa   5940
gacatcaaca catttgtggg gactccagtg gagaaactgg acctgctagg aaatttacct   6000
ggcagcaaga gacggccaca aactcctaaa gaaaaggcca aggctctaga agatctggct   6060
ggcttcaaag agctcttcca gacaccaggt cacactgagg aatcaatgac cgatgacaaa   6120
atcacagaag tatcctgcaa atctccacaa ccagacccag tcaaaacccc aacaagctcc   6180
aagcaacgac tcaagatatc cttggggaaa gtaggtgtga agaagaggt cctaccagtc   6240 ggcaagctca cacagacgtc agggaagacc acacagacac acagagagac agcaggagat   6300
ggaaagagca tcaaagcgtt taaggaatct gcaaagcaga tgctggaccc agcaaactat   6360
ggaactggga tggagaggtg gccaagaaca cctaaggaag aggcccaatc actagaagac   6420
ctggccggct tcaaagagct cttccagaca ccagaccaca ctgaggaatc aacaactgat   6480
gacaaaacta ccaaaatagc ctgcaaatct ccaccaccag aatcaatgga cactccaaca   6540
agcacaagga ggcggcccaa aacacctttg gggaaaaggg atatagtgga agagctctca   6600
gccctgaagc agctcacaca gaccacacac acagacaaag taccaggaga tgaggataaa   6660
ggcatcaacg tgttcaggga aactgcaaaa cagaaactgg acccagcagc aagtgtaact   6720
ggtagcaaga ggcagccaag aactcctaag ggaaaagccc aaccctaga gacttggct    6780 ggcttgaaag agctcttcca gacaccaata tgcactgaca agcccacgac tcatgagaaa   6840
actaccaaaa tagcctgcag atctccacaa ccagacccag tgggtacccc aacaatcttc   6900
aagccacagt ccaagagaag tctcaggaaa gcagacgtag aggaagaatc cttagcactc   6960
aggaaacgaa caccatcagt agggaaagct atggacacac ccaaaccagc aggaggtgat   7020
gagaaagaca tgaaagcatt tatgggaact ccagtgcaga aattggacct gccaggaaat   7080
ttacctggca gcaaaagatg ccacaaaact cctaaggaaa aggcccaggc tctagaagac   7140
ctggctggct tcaaagagct cttccagaca ccaggcactg acaagcccac gactgatgag   7200
aaaactacca aatagcctg caaatctcca caaccagacc cagtgacac cccagcaagc    7260 acaaagcaac ggcccaagag aaacctcagg aaagcagacg tagaggaaga atttttagca   7320
```

```
ctcaggaaac gaacaccatc agcaggcaaa gccatggaca caccaaaacc agcagtaagt    7380
gatgagaaaa atatcaacac atttgtggaa actccagtgc agaaactgga cctgctagga    7440
aatttacctg gcagcaagag acagccacag actcctaagg aaaaggctga ggctctagag    7500
gacctggttg gcttcaaaga actcttccag acaccaggtc acactgagga atcaatgact    7560
gatgacaaaa tcacagaagt atcctgtaaa tctccacagc cagagtcatt caaaacctca    7620
agaagctcca agcaaaggct caagataccc ctggtgaaag tggacatgaa agaagagccc    7680
ctagcagtca gcaagctcac acggacatca ggggagacta cgcaaacaca cacagagcca    7740
acaggagata gtaagagcat caaagcgttt aaggagtctc caaagcagat cctggaccca    7800
gcagcaagtg taactggtag caggaggcag ctgagaactc gtaaggaaaa ggcccgtgct    7860
ctagaagacc tggttgactt caaagagctc ttctcagcac caggtcacac tgaaagtca    7920 atgactattg acaaaaacac aaaaattccc tgcaaatctc ccccaccaga actaacagac    7980
actgccacga gcacaaagag atgccccaag acacgtccca ggaaagaagt aaaagaggag    8040
ctctcagcag ttgagaggct cacgcaaaca tcagggcaaa gcacacacac acacaaagaa    8100
ccagcaagcg gtgatgaggg catcaaagta ttgaagcaac gtgcaaagaa gaaaccaaac    8160
ccagtagaag aggaacccag caggagaagg ccaagagcac taaggaaaaa ggcccaaccc    8220
ctggaagacc tggccggctt cacagagctc tctgaaacat caggtcacac tcaggaatca    8280
ctgactgctg gcaaagccac taaaataccc tgcgaatctc ccccactaga agtggtagac    8340
accacagcaa gcacaaagag gcatctcagg acacgtgtgc agaaggtaca agtaaaagaa    8400
gagccttcag cagtcaagtt cacacaaaca tcaggggaaa ccacggatgc agacaaagaa    8460
ccagcaggtg aagataaagg catcaaagca ttgaaggaat ctgcaaaaca gacaccggct    8520
ccagcagcaa gtgtaactgg cagcaggaga cggccaagag cacccaggga aagtgcccaa    8580
gccatagaag acctagctgg cttcaaagac ccagcagcag gtcacactga gaatcaatg    8640 actgatgaca aaaccactaa aatacccctgc aaatcatcac cagaactaga agacaccgca    8700
acaagctcaa agagacggcc caggacacgt gcccagaaag tagaagtgaa ggaggagctg    8760
ttagcagttg gcaagctcac acaaacctca ggggagacca cgcacaccga caaagagccg    8820
gtaggtgagg gcaaaggcac gaaagcattt aagcaacctg caaagcggaa gctggacgca    8880
gaagatgtaa ttggcagcag gagacagcca agagcaccta aggaaaaggc caacccctg    8940 gaagatctgg ccagcttcca agagctctct caaacaccag gccacactga ggaactggca    9000
aatggtgctg ctgatagctt tacaagcgct ccaaagcaaa cacctgacag tggaaaacct    9060
ctaaaaatat ccagaagagt tcttcgggcc cctaaagtag aacccgtggg agacgtggta    9120
agcaccagag accctgtaaa atcacaaagc aaaagcaaca cttccctgcc cccactgccc    9180
ttcaagaggg gaggtggcaa agatggaagc gtcacgggaa ccaagaggct gcgctgcatg    9240
ccagcaccag aggaaattgt ggaggagctg ccagccagca agaagcagag ggttgctccc    9300
agggcaagag gcaaatcatc cgaacccgtg gtcatcatga agagaagttt gaggacttct    9360
gcaaaaagaa ttgaacctgc ggaagagctg aacagcaacg acatgaaaac caacaaagag    9420
gaacacaaat tacaagactc ggtccctgaa aataagggaa tatccctgcg ctccagacgc    9480
caaaataaga ctgaggcaga acagcaaata actgaggtct tgtattagc agaaagaata    9540 gaaataaaca gaaatgaaaa gaagcccatg aagacctccc cagagatgga cattcagaat    9600
ccagatgatg gagcccggaa acccataact agagacaaag tcactgagaa caaaaggtgc    9660
ttgaggtctg ctagacagaa tgagagctcc cagcctaagg tggcagagga gagcggaggg    9720
```

-continued

```
cagaagagtg cgaaggttct catgcagaat cagaaaggga aaggagaagc aggaaattca    9780
gactccatgt gcctgagatc aagaaagaca aaaagccagc ctgcagcaag cactttggag    9840
agcaaatctg tgcagagagt aacgcggagt gtcaagaggt gtgcagaaaa tccaaagaag    9900
gctgaggaca atgtgtgtgt caagaaaata agaaccagaa gtcataggga cagtgaagat    9960
atttgacaga aaaatcgaac tgggaaaaat ataataaagt tagttttgtg ataagttcta   10020
gtgcagtttt tgtcataaat tacaagtgaa ttctgtaagt aaggctgtca gtctgcttaa   10080
gggaagaaaa ctttggattt gctgggtctg aatcggcttc ataaactcca ctgggagcac   10140
tgctgggctc ctggactgag aatagttgaa caccgggggc tttgtgaagg agtctgggcc   10200
aaggtttgcc ctcagctttg cagaatgaag ccttgaggtc tgtcaccacc cacagccacc   10260
ctacagcagc cttaactgtg acacttgcca cactgtgtcg tcgtttgttt gcctatgtcc   10320
tccagggcac ggtggcagga acaactatcc tcgtctgtcc caacactgag caggcactcg   10380
gtaaacacga atgaatggat gagcgcacgg atgaatggag cttacaagat ctgtctttcc   10440
aatggccggg ggcatttggt ccccaaatta aggctattgg acatctgcac aggacagtcc   10500 tattttttgat gtccttttcct ttctgaaaat aaagttttgt gctttggaga atgactcgtg   10560
agcacatctt tagggaccaa gagtgacttt ctgtaaggag tgactcgtgg cttgccttgg   10620
tctcttggga atactttttct aactagggtt gctctcacct gagacattct ccacccgcgg   10680
aatctcaggg tcccaggctg tgggccatca cgacctcaaa ctggctccta atctccagct   10740
ttcctgtcat tgaaagcttc ggaagtttac tggctctgct cccgcctgtt ttctttctga   10800
ctctatctgg cagcccgatg ccacccagta caggaagtga caccagtact ctgtaaagca   10860
tcatcatcct tggagagact gagcactcag caccttcagc cacgatttca ggatcgcttc   10920
cttgtgagcc gctgcctccg aaatctcctt tgaagcccag acatctttct ccagcttcag   10980
acttgtagat ataactcgtt catcttcatt tactttccac tttgcccct gtcctctctg   11040 tgttccccaa atcagagaat agcccgccat ccccaggtc cctgtctgg attcctcccc   11100 attcacccac cttgccaggt gcaggtgagg atggtgcacc agacagggta gctgtccccc   11160
aaaatgtgcc ctgtgcgggc agtgcccgt ctccacgttt gttcccccag tgtctggcgg   11220
ggagccaggt gacatcataa atacttgctg aatgaatgca gaaatcagcg gtactgactt   11280
gtactatatt ggctgccatg atagggttct cacagcgtca tccatgatcg taagggagaa   11340
tgacattctg cttgagggag ggaatagaaa ggggcaggga ggggacatct gagggcttca   11400
cagggctgca aagggtacag ggattgcacc agggcagaac aggggagggt gttcaaggaa   11460
gagtggctct tagcagaggc actttggaag gtgtgaggca taaatgcttc cttctacgta   11520
ggccaacctc aaaactttca gtaggaatgt tgctatgatc aagttgtctc aacactttag   11580
acttagtagt aattatgaac ctcacataga aaaatttcat ccagccatat gcctgtggag   11640
tggaatattc tgtttagtag aaaaatcctt tagagttcag ctctaaccag aaatcttgct   11700
gaagtatgtc agcaccttt ctcaccctgg taagtacagt atttcaagag cacgctaagg   11760
gtggttttca ttttacaggg ctgttgatga tgggttaaaa atgttcattt aagggctacc   11820
cccgtgttta atagatgaac accacttcta cacaaccctc cttggtactg ggggagggag   11880
agatctgaca aatactgccc attcccctag gctgactgga tttgagaaca aatacccacc   11940
catttccacc atggtatggt aacttctctg agcttcagtt tccaagtgaa tttccatgta   12000
ataggacatt cccattaaat acaagctgtt tttactttt cgcctcccag ggcctgtggg   12060
```

| | |
|---|---|
| atctggtccc ccagcctctc ttgggctttc ttacactaac tctgtaccta ccatctcctg | 12120 |
| cctcccttag gcaggcacct ccaaccacca cacactccct gctgttttcc ctgcctggaa | 12180 |
| ctttccctcc tgccccacca agatcatttc atccagtcct gagctcagct taagggaggc | 12240 |
| ttcttgcctg tgggttccct cacccccatg cctgtcctcc aggctggggc aggttcttag | 12300 |
| tttgcctgga attgttctgt acctctttgt agcacgtagt gttgtggaaa ctaagccact | 12360 |
| aattgagttt ctggctcccc tcctgggggtt gtaagttttg ttcattcatg agggccgact | 12420 |
| gcatttcctg gttactctat cccagtgacc agccacagga gatgtccaat aaagtatgtg | 12480 |
| atgaaatggt cttaaaaaaa aaaaaaa | 12507 |

<210> SEQ ID NO 137
<211> LENGTH: 3771
<212> TYPE: DNA
<213> ORGANISM: Homo sapiens

<400> SEQUENCE: 137

| | |
|---|---|
| gcgccgggac gtggccagtt gcccgcctgc cccggagagc caggcgctaa ccagccgctc | 60 |
| tgcgccccgc gccctgcttg ccccccattat ccagccttgc cccggcgccc tgacctgacg | 120 |
| ccctggcctg acgccctgct tcgtcgcctc ctttctctcc caggtgctgg accagggact | 180 |
| gagcgtcccc cggagagggt ccggtgtgac cccgacaaga agcagaaatg gggaagaaac | 240 |
| tggatctttc caagctcact gatgaagagg cccagcatgt cttggaagtt gttcaacgag | 300 |
| attttgacct ccgaaggaaa gaagaggaac ggctagaggc gttgaagggc aagattaaga | 360 |
| aggaaagctc caagagggag ctgctttccg acactgccca tctgaacgag acccactgcg | 420 |
| cccgctgcct gcagccctac cagctgcttg tgaatagcaa aaggcagtgc ctggaatgtg | 480 |
| gcctcttcac ctgcaaaagc tgtggccgcg tccacccgga ggagcagggc tggatctgtg | 540 |
| accctgcca tctggccaga gtcgtgaaga tcggctcact ggagtggtac tatgagcatg | 600 |
| tgaaagcccg cttcaagagg ttcggaagtg ccaaggtcat ccgtccctc cacgggcggc | 660 |
| tgcagggtgg agctgggcct gaactgatat ctgaagagag aagtggagac agcgaccaga | 720 |
| cagatgagga tggagaacct ggctcagagg cccaggccca ggcccagccc tttggcagca | 780 |
| aaaaaaagcg cctcctctcc gtccacgact tcgacttcga gggagactca gatgactcca | 840 |
| ctcagcctca aggtcactcc ctgcacctgt cctcagtccc tgaggccagg acagcccac | 900 |
| agtccctcac agatgagtcc tgctcagaga aggcagcccc tcacaaggct gagggcctgg | 960 |
| aggaggctga tactgggcc tctgggtgcc actccatcc ggaagagcag ccgaccagca | 1020 |
| tctcaccttc cagacacggc gccctggctg agctctgccc gcctggaggc tccacagga | 1080 |
| tggccctggg gactgctgct gcactcgggt cgaatgtcat caggaatgag cagctgcccc | 1140 |
| tgcagtactt ggccgatgtg gacacctctg atgaggaaag catccgggct cacgtgatgg | 1200 |
| cctcccacca ttccaagcgg agaggccggg cgtcttctga gagtcagatc tttgagctga | 1260 |
| ataagcatat ttcagctgtg gaatgcctgc tgacctacct ggaaacacaa gttgtgcctc | 1320 |
| ccttggccaa gggtctaggt gctggagtgc gcacggaggc cgatgtagag gaggaggccc | 1380 |
| tgaggaggaa gctggaggag ctgaccagca acgtcagtga ccaggagacc tcgtccgagg | 1440 |
| aggaggaagc caaggacgaa aaggcagagc ccaacaggga caaatcagtt gggcctctcc | 1500 |
| cccaggcgga cccggaggtg ggcacggctg cccatcaaac caacagacag gaaaaaagcc | 1560 |
| cccaggaccc tggggacccc gtccagtaca acaggaccac agatgaggag ctgtcagagc | 1620 |
| tggaggacag agtggcagtg acggcctcag aagtccagca ggcagagagc gaggtttcag | 1680 |

```
acattgaatc caggattgca gccctgaggg ccgcagggct cacggtgaag ccctcgggaa    1740
agccccggag gaagtcaaac ctcccgatat ttctccctcg agtggctggg aaacttggca    1800
agagaccaga ggacccaaat gcagaccctt caagtgaggc caaggcaatg gctgtgccct    1860
atcttctgag aagaaagttc agtaattccc tgaaaagtca aggtaaagat gatgattctt    1920
ttgatcggaa atcagtgtac cgaggctcgc tgacacagag aaaccccaac gcgaggaaag    1980
gaatggccag ccacaccttc gcgaaacctg tggtggccca ccagtcctaa cgggacagga    2040
cagagagaca gagcagccct gcactgtttt ccctccacca cagccatcct gtccctcatt    2100
ggctctgtgc tttccactat acacagtcac cgtcccaatg agaaacaaga aggagcaccc    2160
tccacatgga ctcccacctg caagtggaca gcgacattca gtcctgcact gctcacctgg    2220
gtttactgat gactcctggc tgccccacca tcctctctga tctgtgagaa acagctaagc    2280
tgctgtgact tccctttagg acaatgttgt gtaaatcttt gaaggacaca ccgaagacct    2340
ttatactgtg atcttttacc cctttcactc ttggctttct tatgttgctt tcatgaatgg    2400
aatggaaaaa agatgactca gttaaggcac cagccatatg tgtattcttg atggtctata    2460
tcggggtgtg agcagatgtt tgcgtatttc ttgtgggtgt gactggatat tagacatccg    2520
gacaagtgac tgaactaatg atctgctgaa taatgaagga ggaatagaca ccccagtccc    2580
caccctacgt gcacccgctc tgcaagttcc catgtgatct gtagaccagg ggaaattaca    2640
ctgcggtcaa gggcagagcc tgcacatgac agcaagtgag catttgatag atgctcagat    2700
gctagtgcag agagcctgct gggagacgaa gagacagcag gcagagctcc agatgggcaa    2760
ggaagaggct tggttctagc ctggctctgc ccctcactgc agtggatcca gtggggcaga    2820
ggacagaggg tcacaaccaa tgagggatgt ctgccaagga tgggggtgca gaggccacag    2880
gagtcagctt gccactcgcc cattggttac atagatgatc tctcagacag gctgggactc    2940
agagttattt cctagtatcg gtgtgcccca tccagttttta agtggagccc tccaagactc    3000
tccagagctg cctttgaaca tcctaacagt aatcacatct caccctccct gaggttcact    3060
ttagacagga cccaatggct gcactgcctt tgtcagaggg ggtgctgaga ggagtggctt    3120
cttttagaat caaacagtag agacaagagt caagccttgt gtcttcaagc attgaccaag    3180
ttaagtgttt ccttccctct ctcaataaga cacttccagg agctttccaa tctctcactt    3240
aaaactaagg tttgaatctc aaagtgttgc tgggaggctg atactcctgc aacttcagga    3300
gacctgtgag cacacattag cagctgtttc tctgactcct tgtggcatca gataaaaacg    3360
tgggagtttt tccatataat tcccagcctt acttataaat tctattcttt gaaaaaatta    3420
ttcaggctag gtaaggtggc tcatacctat aatcccagcc ctttgagagg ccaaggtggg    3480
agaattgctt gaggccagga gtttgagacc tcctgggcaa catagtgaga tcccatctct    3540
acaaaaaaca aacaaaaaa attacccaag catgatggta tatgcctgta gtcgtaccta    3600
cttacttagg aggctgaggc aggaggatca cttgagcccct ggaggttggg gctgcagtga    3660
gccatgatcg catcactata ctcgagcctg ggcaacagag tgagaccttg tctcttaaaa    3720
aaattaataa taaataaatg aaaataattc ttcagaaaaa aaaaaaaaaa a             3771
```

<210> SEQ ID NO 138
<211> LENGTH: 2240
<212> TYPE: DNA
<213> ORGANISM: Homo sapiens

<400> SEQUENCE: 138

-continued

```
aagcccagca gccccggggc ggatggctcc ggccgcctgg ctccgcagcg cggccgcgcg      60
cgccctcctg cccccgatgc tgctgctgct gctccagccg ccgccgctgc tggcccgggc     120
tctgccgccg gacgcccacc acctccatgc cgagaggagg gggccacagc cctggcatgc     180
agccctgccc agtagcccgg cacctgcccc tgccacgcag gaagcccccc ggcctgccag     240
cagcctcagg cctccccgct gtggcgtgcc cgacccatct gatgggctga gtgcccgcaa     300
ccgacagaag aggttcgtgc tttctggcgg gcgctgggag aagacggacc tcacctacag     360
gatccttcgg ttcccatggc agttggtgca ggagcaggtg cggcagacga tggcagaggc     420
cctaaaggta tggagcgatg tgacgccact cacctttact gaggtgcacg agggccgtgc     480
tgacatcatg atcgacttcg ccaggtactg gcatggggac gacctgccgt ttgatgggcc     540
tgggggcatc ctggcccatg ccttcttccc caagactcac cgagaagggg atgtccactt     600
cgactatgat gagacctgga ctatcgggga tgaccagggc acagacctgc tgcaggtggc     660
agcccatgaa tttggccacg tgctgggggct gcagcacaca acagcagcca aggccctgat     720
gtccgccttc tacaccttc gctacccact gagtctcagc ccagatgact gcaggggcgt     780
tcaacaccta tatggccagc cctggccac tgtcacctcc aggaccccag ccctgggccc     840
ccaggctggg atagacacca atgagattgc accgctggag ccagacgccc cgccagatgc     900
ctgtgaggcc tcctttgacg cggtctccac catccgaggc gagctctttt tcttcaaagc     960
gggctttgtg tggcgcctcc gtgggggcca gctgcagccc ggctaccag cattggcctc    1020
tcgccactgg cagggactgc ccagccctgt ggacgctgcc ttcgaggatg cccagggcca    1080
catttggttc ttccaaggtg ctcagtactg ggtgtacgac ggtgaaaagc cagtcctggg    1140
ccccgcaccc ctcaccgagc tgggcctggt gaggttcccg gtccatgctg ccttggtctg    1200
gggtcccgag aagaacaaga tctacttctt ccgaggcagg gactactggc gtttccaccc    1260
cagcacccgg cgtgtagaca gtcccgtgcc ccgcagggcc actgactgga gagggtgcc    1320
ctctgagatc gacgctgcct tccaggatgc tgatggctat gcctacttcc tgcgcggccg    1380
cctctactgg aagtttgacc ctgtgaaggt gaaggctctg gaaggcttcc cccgtctcgt    1440
gggtcctgac ttctttggct gtgccgagcc tgccaacact ttcctctgac catggcttgg    1500
atgccctcag gggtgctgac ccctgccagg ccacgaatat caggctagag acccatggcc    1560
atctttgtgg ctgtgggcac caggcatggg actgagccca tgtctcctca ggggatgggg    1620
gtggggtaca accaccatga caactgccgg gagggccacg caggtcgtgg tcacctgcca    1680
gcgactgtct cagactgggc agggaggctt tggcatgact taagaggaag ggcagtcttg    1740
ggcccgctat gcaggtcctg gcaaacctgg ctgccctgtc tccatccctg tccctcaggg    1800
tagcaccatg gcaggactgg gggaactgga gtgtccttgc tgtatccctg ttgtgaggtt    1860
ccttccaggg gctggcactg aagcaagggt gctggggccc atggccttc agccctggct    1920
gagcaactgg gctgtagggc agggccactt cctgaggtca ggtcttggta ggtgcctgca    1980
tctgtctgcc ttctggctga caatcctgga aatctgttct ccagaatcca ggccaaaaag    2040
ttcacagtca aatggggagg ggtattcttc atgcaggaga ccccaggccc tggaggctgc    2100
aacatacctc aatcctgtcc caggccggat cctcctgaag ccttttcgc agcactgcta    2160
tcctccaaag ccattgtaaa tgtgtgtaca gtgtgtataa accttcttct tcttttttt    2220
tttttaaact gaggattgtc                                                2240
```

<210> SEQ ID NO 139
<211> LENGTH: 3167

<212> TYPE: DNA
<213> ORGANISM: Homo sapiens

<400> SEQUENCE: 139

```
tagcagcaca caagggttcg tgtttgtgga accaggtagc ttccttcaga gctgacattt      60
gcccacagcc agcctggccc agccccatac caccagccct ggcgctctgg ggcgtgaggt     120
gccttttctg ccccccctgct ctagggcagg tggaaatcac ccatggtggg tctacatctg    180
atagaagcat cttatagttc tgcttctgga ccagaccatc ctgggttttt ctctgttctg    240
ctgaagggtt ccctccacgt gtccatcacc tcggtgaact cttgggagac ctgggaagat    300
gctggcctca cctctcgcct ctcctttccc tcattgtgct gccaccatcc ttctcacaca    360
ggctctccag ggagagctgg gcaggatggg atcttcctgg gttcccacct tgctccgtgc    420
cccctctcac tgttcctgaa gtgtggccac ggactgcctt gttttctgga aagtcccaag    480
tctggaccat gactgagcag cattctcggc tatctgccac ctgtctgggg ctcctggccc    540
ctcttagact cccctctccc ttctgtttcc cccgagcccc tgacttggac ctgcagggtg    600
gggagaggga tgggacgaga acctgtgctg gggccaaagg tcgcactggg ggaaggtgga    660
gccagggcag cagagtgcct ggcgtcggcc cctatcctgt cactagttcc cccgttctgg    720
cccctggcag gtttgtaacc ccagatcaga agtactccat ggacaacact ccccacacgc    780
caacccgtt caagaacgcc ctggagaagt acggaccct gaagccctg gtacgtggtg     840
tggtcactgc cgtggatctc tgcacagtgg gatcccttcg gttcatccaa ccatgttcag    900
tccacaggac ccttccctct gaggtctcat ttgattcttt ctcctgagaa gatgcagaga    960
tcctgataat ataaatgggg aagctgaggc tgctctttgt cacttcctcc gactgctcct   1020
gagcacctga gtttgcaagc acgcgccggc tggtgctaga gacatggtgg tatcccgtga   1080
cactcagcct caggatgggg gagactgatg tgaaatacaa ataacttaaa cactttcagg   1140
caaagataag cactgggcct agttcagaga agtggcaaat tgctactctg gcctgtctct   1200
gaccaactcc cagttctcta cagagcacgg gaaagcccct cggggacgtc tttcctgcag   1260
tgtgcaggct gcccttctcc cctgctcttc ccagttgatg ggatggttgt gtttctcta    1320
tgaaaaaagg agttggcacc ttgggctttc tgaaacacac aggtgtttta gaaatcagtg   1380
gagggtgaga gaaaggcatg gttgtggagg cactggactg tgaacaaggt ctgcagcggg   1440
tccccctgct gtctctctct actgcatgga gcctcctatg aagcccaagg tggctgggg    1500
ctgaggctcc cttgggcctg ccatggaact gattctgagt caagcagact ttccacggac   1560
catgctacat gagccgaggt gaggcactag ttagtgctcc tttcctgttg cagtggagat   1620
ttggctcctc tgtactaaaa tatctgcatg ctctccaaac aggtgtgagg gcaaatcaca   1680
tgaccttggc agctgtaatt aaagtttgtg ggggcttttc ggatgactta tgaggagtgg   1740
ctgtgattcg caccttttcac tcttagtagc actcgccctc ccctgttctc tgttgcctga   1800
agctggagag gtccttggaa ccccgaggcc tgagaaaggg aaatgggttt gagagccccc   1860
attagtgtgg aacaaagggt tgagtgagcc tgggctttga gctgtcgggg tcctaattca   1920
gcagctgtgt gactgtgtgc caggctgttg atctctgagc ttctgtttct acctgcttaa   1980
aatgacggtt actgcacagg gctgtgtgag ggttacagtg cgtctctggg ctgctcccag   2040
ccatggcagg ccctgggaa tcaaggtcat cagctgcttg tccaaggcag cagttagtgg   2100
ttgtgaatgg tgcgtgtgag atctgcatcc tggcgtcagg cctccttcct gcttaccca   2160
ggacagccca gttgcagctg ggttggtccc acagtcccac acacacacag cccgagtgtg   2220
```

| | |
|---|---|
| gtgcctcacg tgggctgccc cgtgcctacc cacagccaca gaccccgcac ctggaggagg | 2280 |
| acttgaagga ggtgctgcgt tctgaggctg gcatcgaact catcatcgag gacgacatca | 2340 |
| ggcccgagaa gcagaagagg aagcctgggc tgcggcggag ccccatcaag aaagtccgga | 2400 |
| agtctctggc tcttgacatt gtggatgagg atgtgaagct gatgatgtcc acactgccca | 2460 |
| agtctctatc cttgccgaca actgccccctt caaactcttc cagcctcacc ctgtcaggta | 2520 |
| tcaaagaaga caacagcttg ctcaaccagg gcttcttgca ggccaagccc gagaaggcag | 2580 |
| cagtggccca gaagcccga agccacttca cgacacctgc ccctatgtcc agtgcctgga | 2640 |
| agacggtggc ctgcgggggg accagggacc agcttttcat gcaggagaaa gcccggcagc | 2700 |
| tcctgggccg cctgaagccc agccacacat ctcggaccct catcttgtcc tgaggtgttg | 2760 |
| agggtgtcac gagcccattc acatgtttac aggggttgtg ggggcagagg gggtctgtga | 2820 |
| atctgagagt cattcaggtg acctcctgca gggagccttc tgccaccagc ccctccccag | 2880 |
| actctcaggt ggaggcaaca gggccatgtg ctgccctgtt gccgagccca gctgtgggcg | 2940 |
| gctcctggtg ctaacaacaa agttccactt ccaggtctgc ctggttcccc ccccaaggcc | 3000 |
| acagggagct ccgtcagctt ctcccaagcc cacgtcaggc ctggcctcat ctcagaccct | 3060 |
| gcttaggatg gggatgtgg ccaggggtgc tcctgtgctc accctctctt ggtgcatttt | 3120 |
| tttggaagaa taaaattgcc tctctctttg aaaaaaaaaa aaaaaaa | 3167 |

<210> SEQ ID NO 140
<211> LENGTH: 2379
<212> TYPE: DNA
<213> ORGANISM: Homo sapiens

<400> SEQUENCE: 140

| | |
|---|---|
| gaccccccgag ctgtgctgct cgcggccgcc accgccgggc cccggccgtc cctggctccc | 60 |
| ctcctgcctc gagaagggca gggcttctca gaggcttggc gggaaaaaga acggagggag | 120 |
| ggatcgcgct gagtataaaa gccggttttc ggggctttat ctaactcgct gtagtaattc | 180 |
| cagcgagagg cagagggagc gagcgggcgg ccggctaggg tggaagagcc gggcgagcag | 240 |
| agctgcgctg cgggcgtcct gggaagggag atccggagcg aataggggc ttcgcctctg | 300 |
| gcccagccct cccgctgatc ccccagccag cggtccgcaa cccttgccgc atccacgaaa | 360 |
| ctttgcccat agcagcgggc gggcactttg cactggaact acaacaccccc gagcaaggac | 420 |
| gcgactctcc cgacgcgggg aggctattct gcccatttgg ggacacttcc ccgccgctgc | 480 |
| caggacccgc ttctctgaaa ggctctcctt gcagctgctt agacgctgga ttttttttcgg | 540 |
| gtagtggaaa accagcagcc tcccgcgacg atgcccctca acgttagctt caccaacagg | 600 |
| aactatgacc tcgactacga ctcggtgcag ccgtatttct actgcgacga ggaggagaac | 660 |
| ttctaccagc agcagcagca gagcgagctg cagccccccgg cgcccagcga ggatatctgg | 720 |
| aagaaattcg agctgctgcc caccccgccc gtgtccccta gccgccgctc cgggctctgc | 780 |
| tcgcctcct acgttgcggt cacacccttc tcccttcggg gagacaacga cggcggtggc | 840 |
| gggagcttct ccacggccga ccagctggag atggtgaccg agctgctggg aggagacatg | 900 |
| gtgaaccaga gtttcatctg cgacccggac gacgagacct tcatcaaaaa catcatcatc | 960 |
| caggactgta tgtggagcgg cttctcggcc gccgccaagc tcgtctcaga gaagctggcc | 1020 |
| tcctaccagg ctgcgcgcaa agacagcggc agcccgaacc cgccccgcgg ccacagcgtc | 1080 |
| tgctccacct ccagcttgta cctgcaggat ctgagcgccg ccgcctcaga gtgcatcgac | 1140 |
| ccctcggtgg tcttccccta ccctctcaac gacagcagct cgccccaagtc ctgcgcctcg | 1200 |

| | |
|---|---|
| caagactcca gcgccttctc tccgtcctcg gattctctgc tctcctcgac ggagtcctcc | 1260 |
| ccgcagggca gcccccgagcc cctggtgctc catgaggaga caccgcccac caccagcagc | 1320 |
| gactctgagg aggaacaaga agatgaggaa gaaatcgatg ttgtttctgt ggaaaagagg | 1380 |
| caggctcctg gcaaaaggtc agagtctgga tcaccttctg ctggaggcca cagcaaacct | 1440 |
| cctcacagcc cactggtcct caagaggtgc cacgtctcca cacatcagca caactacgca | 1500 |
| gcgcctccct ccactcggaa ggactatcct gctgccaaga gggtcaagtt ggacagtgtc | 1560 |
| agagtcctga cacagatcag caacaaccga aaatgcacca gccccaggtc ctcggacacc | 1620 |
| gaggagaatg tcaagaggcg aacacacaac gtcttggagc gccagaggag gaacgagcta | 1680 |
| aaacggagct ttttttgccct gcgtgaccag atcccggagt tggaaaacaa tgaaaaggcc | 1740 |
| cccaaggtag ttatccttaa aaaagccaca gcatacatcc tgtccgtcca agcagaggag | 1800 |
| caaaagctca tttctgaaga ggacttgttg cggaaacgac gagaacagtt gaaacacaaa | 1860 |
| cttgaacagc tacggaactc ttgtgcgtaa ggaaaagtaa ggaaaacgat tccttctaac | 1920 |
| agaaatgtcc tgagcaatca cctatgaact tgtttcaaat gcatgatcaa atgcaacctc | 1980 |
| acaaccttgg ctgagtcttg agactgaaag atttagccat aatgtaaact gcctcaaatt | 2040 |
| ggactttggg cataaaagaa cttttttatg cttaccatct ttttttttc tttaacagat | 2100 |
| ttgtatttaa gaattgtttt taaaaaattt taagatttac acaatgtttc tctgtaaata | 2160 |
| ttgccattaa atgtaaataa cttaataaa acgtttatag cagttacaca gaatttcaat | 2220 |
| cctagtatat agtacctagt attataggta ctataaaccc taatttttt tatttaagta | 2280 |
| cattttgctt tttaaagttg attttttct attgttttta gaaaaaataa aataactggc | 2340 |
| aaatatatca ttgagccaaa tcttaaaaaa aaaaaaaaa | 2379 |

<210> SEQ ID NO 141
<211> LENGTH: 1799
<212> TYPE: DNA
<213> ORGANISM: Homo sapiens

<400> SEQUENCE: 141

| | |
|---|---|
| gtgggaggat tgcattcagt ctagttcctg gttgccggct gaaataacct gctctccaaa | 60 |
| atgtccacaa aagtgactta agtcaggttc ccccaaacca gacaccaaga caagaatcca | 120 |
| tgtgtgtgtg actgaaggaa gtgctgggag agccccagct gcagcctgga tgtgaactgc | 180 |
| aactccaaag tgtgtccaga ctcaaggcaa gggcactagg ctttccagac ctcctactaa | 240 |
| gtcattgatc cagcactgcc ctgccaggac ataaatccct ggcacctctt gctctctgca | 300 |
| aaggagggca aagcagcttc aggagccctt gggagtcctc caaagagagt ctagggtaca | 360 |
| ggtccgaaag tagaagaaca cagaaggcag gccaggggca ctgtgagatg gtaaaagaga | 420 |
| tctgaaggga tccagaattc aagccaggaa gaagcagcaa tctgtcttct ggattaaaac | 480 |
| tgaagatcaa cctactttca acttactaag aaagggatc atggacattg aagcatatct | 540 |
| tgaaagaatt ggctataaga agtctaggaa caaattggac ttggaaacat taactgatat | 600 |
| tcttcaacac cagatccgag ctgttcccct tgagaacctt aacatccatt gtggggatgc | 660 |
| catggactta ggcttagagg ccattttga tcaagttgtg agaagaaatc ggggtggatg | 720 |
| gtgtctccag gtcaatcatc ttctgtactg ggctctgacc actattggtt ttgagaccac | 780 |
| gatgttggga gggtatgttt acagcactcc agccaaaaaa tacagcactg gcatgattca | 840 |
| ccttctcctg caggtgacca ttgatggcag gaactacatt gtcgatgctg ggtttggacg | 900 |

| | |
|---|---|
| ctcataccag atgtggcagc ctctggagtt aatttctggg aaggatcagc ctcaggtgcc | 960 |
| ttgtgtcttc cgtttgacgg aagagaatgg attctggtat ctagaccaaa tcagaaggga | 1020 |
| acagtacatt ccaaatgaag aatttcttca ttctgatctc ctagaagaca gcaaataccg | 1080 |
| aaaaatctac tcctttactc ttaagcctcg aacaattgaa gattttgagt ctatgaatac | 1140 |
| atacctgcag acatctccat catctgtgtt tactagtaaa tcattttgtt ccttgcagac | 1200 |
| cccagatggg gttcactgtt tggtgggctt caccctcacc cataggagat tcaattataa | 1260 |
| ggacaataca gatctaatag agttcaagac tctgagtgag gaagaaatag aaaaagtgct | 1320 |
| gaaaaatata tttaatattt ccttgcagag aaagcttgtg cccaaacatg gtgatagatt | 1380 |
| ttttactatt tagaataagg agtaaaacaa tcttgtctat ttgtcatcca gctcaccagt | 1440 |
| tatcaactga cgacctatca tgtatcttct gtacccttac cttattttga agaaaatcct | 1500 |
| agacatcaaa tcatttcacc tataaaaatg tcatcatata taattaaaca gcttttaaaa | 1560 |
| gaaacataac cacaaacctt ttcaaataat aataataata ataataataa atgtcttta | 1620 |
| aagatggcct gtggttatct tggaaattgg tgatttatgc tagaaagctt ttaatgttgg | 1680 |
| tttattgttg aattcctaga aaagttttat gggtagatga gtaaataaaa tattgtaaaa | 1740 |
| aaacttattg tctataaagt atattaaaac attgttggct aatataaaaa aaaaaaaaa | 1799 |

<210> SEQ ID NO 142
<211> LENGTH: 1644
<212> TYPE: DNA
<213> ORGANISM: Homo sapiens

<400> SEQUENCE: 142

| | |
|---|---|
| gcgcgcgggt ttcgttgacc cgcggcgttc acgggaattg ttcgctttag tgccggcgcc | 60 |
| atggggtcgg agctgatcgg gcgcctagcc ccgcgcctgg gcctcgccga gcccgacatg | 120 |
| ctgaggaaag cagaggagta cttgcgcctg tcccgggtga agtgtgtcgg cctctccgca | 180 |
| cgcaccacgg agaccagcag tgcagtcatg tgcctggacc ttgcagcttc ctggatgaag | 240 |
| tgccccttgg acagggctta tttaattaaa cttttctggtt tgaacaagga gacatatcag | 300 |
| agctgtctta aatcttttga gtgtttactg ggcctgaatt caaatattgg aataagagac | 360 |
| ctagctgtac agtttagctg tatagaagca gtgaacatgg cttcaaagat actaaaaagc | 420 |
| tatgagtcca gtcttcccca gacacagcaa gtggatcttg acttatccag gccacttttc | 480 |
| acttctgctg cactgctttc agcatgcaag attctaaagc tgaaagtgga taaaaacaaa | 540 |
| atggtagcca catccggtgt aaaaaaagct atatttgatc gactgtgtaa acaactagag | 600 |
| aagattggac agcaggtcga cagagaacct ggagatgtag ctactccacc acggaagaga | 660 |
| aagaagatag tggttgaagc cccagcaaag gaaatggaga aggtagagga gatgccacat | 720 |
| aaaccacaga agatgaaga tctgacacag gattatgaag aatggaaaag aaaaattttg | 780 |
| gaaaatgctg ccagtgctca aaaggctaca gcagagtgat ttcagcttcc aaactggtat | 840 |
| acattccaaa ctgatagtac attgccatct ccaggaagac ttgacggctt tgggattttg | 900 |
| tttaaacttt tataataagg atcctaagac tgttgccttt aaatagcaaa gcagcctacc | 960 |
| tggaggctaa gtctgggcag tgggctggcc cctggtgtga gcattagacc agccacagtg | 1020 |
| cctgattggt atagccttat gtgctttcct acaaaatgga attggaggcc gggcgcagtg | 1080 |
| gctcacgcct gtaatcccag cactttggga ggccaaggtg ggtggatcac ctgaggtcag | 1140 |
| gagctcgaga ccagcctggc caacatggtg aaaccccatc tctactaaaa atacaaaaat | 1200 |
| tagccaggtg tgatggtgca tgcctgtaat cccagctcct cagtaggctg agacaggagc | 1260 |

```
atcacttgaa cgtgggaggc agaggttgca gtgagccgag attgcaccac cgcactccag    1320
cctgggtgac agagcgagac ttatctcata aataaataga tagatactcc agcctgggtg    1380
acagagcgag acttatagat agatagatag atagatggat agatagatag atagatagat    1440
agatagataa acggaattgg agccattttg ctttaagtga atggcagtcc cttgtcttat    1500
tcagaatata aaattcagtc tgaatggcat cttacagatt ttacttcaat ttttgtgtac    1560 ggtattttt atttgactaa atcaatatat tgtacagcct aagttaataa atgttattta    1620
tatatgcaaa aaaaaaaaaa aaaa                                           1644
```

<210> SEQ ID NO 143  
<211> LENGTH: 13037  
<212> TYPE: DNA  
<213> ORGANISM: Homo sapiens

<400> SEQUENCE: 143

```
agtccacagc tgtcactaat cggggtaagc cttgttgtat tgtgcgtgt gggtggcatt      60 ctcaatgaga actagcttca cttgtcattt gagtgaaatc tacaacccga ggcggctagt    120
gctcccgcac tactgggatc tgagatcttc ggagatgact gtcgcccgca gtacggagcc    180
agcagaagtc cgacccttcc tgggaatggg ctgtaccgag aggtccgact agccccaggg    240
ttttagtgag ggggcagtgg aactcagcga gggactgaga gcttcacagc atgcacgagt    300 tgatgccag agaaaaagtc gggagataaa ggagccgcgt gtcactaaat tgccgtcgca    360
gccgcagcca ctcaagtgcc ggacttgtga gtactctgcg tctccagtcc tcggacagaa    420
gttggagaac tctcttggag aactccccga gttaggagac gagatctcct aacaattact    480 acttttttctt gcgctcccca cttgccgctc gctgggacaa acgacagcca cagttcccct    540
gacgacagga tggaggccaa gggcaggagc tgaccagcgc cgccctcccc cgcccccgac    600
ccaggaggtg gagatccctc cggtccagcc acattcaaca cccactttct cctccctctg    660
cccctatatt cccgaaaccc cctcctcctt ccctttttccc tcctcctgga gacgggggag    720
gagaaaaggg gagtccagtc gtcatgactg agctgaaggc aaagggtccc cgggctcccc    780
acgtggcggg cggcccgccc tccccgagg tcggatcccc actgctgtgt cgcccagccg    840
caggtccgtt cccggggagc cagacctcgg acaccttgcc tgaagtttcg gccataccta    900
tctccctgga cgggctactc ttccctcggc cctgccaggg acaggacccc tccgacgaaa    960
agacgcagga ccagcagtcg ctgtcggacg tggagggcgc atattccaga gctgaagcta   1020
caaggggtgc tggaggcagc agttctagtc ccccagaaaa ggacagcgga ctgctggaca   1080
gtgtcttgga cactctgttg gcgccctcag gtcccgggca gagccaaccc agccctcccg   1140
cctgcgaggt caccagctct tggtgcctgt ttggccccga acttcccgaa gatccaccgg   1200
ctgcccccgc cacccagcgg gtgttgtccc cgctcatgag ccggtccggg tgcaaggttg   1260
gagacagctc cgggacggca gctgccata aagtgctgcc ccggggcctg tcaccagccc   1320
ggcagctgct gctcccggcc tctgagagcc ctcactggtc cggggcccca gtgaagccgt   1380
ctccgcaggc cgctgcggtg gaggttgagg aggaggatgg ctctgagtcc gaggagtctg   1440
cgggtccgct tctgaagggc aaacctcggg ctctgggtgg cgcggcggct ggaggaggag   1500
ccgcggctgt cccgccgggg gcggcagcag gaggcgtcgc cctggtcccc aaggaagatt   1560
cccgcttctc agcgcccagg gtcgccctgg tggagcagga cgcgccgatg gcgcccgggc   1620
gctccccgct ggccaccacg gtgatggatt tcatccacgt gccctatcctg cctctcaatc   1680
```

```
acgccttatt ggcagcccgc actcggcagc tgctggaaga cgaaagttac gacggcgggg    1740
ccggggctgc cagcgccttt gcccgccgc ggagttcacc ctgtgcctcg tccacccgg     1800 tcgctgtagg cgacttcccc gactgcgcgt acccgcccga cgccgagccc aaggacgacg    1860
cgtaccctct ctatagcgac ttccagccgc ccgctctaaa gataaaggag gaggaggaag    1920
gcgcggaggc ctccgcgcgc tccccgcgtt cctaccttgt ggccggtgcc aaccccgcag    1980
ccttcccgga tttcccgttg gggccaccgc cccgctgcc gccgcgagcg acccatcca     2040 gacccgggga agcggcggtg acggccgcac ccgccagtgc ctcagtctcg tctgcgtcct    2100
cctcggggtc gaccctggag tgcatcctgt acaaagcgga gggcgcgccg cccagcagg     2160 gcccgttcgc gccgccgccc tgcaaggcgc cgggcgcgag cggctgcctg ctcccgcggg    2220
acggcctgcc ctccacctcc gcctctgccg ccgccgccgg gcggccccc gcgctctacc     2280 ctgcactcgg cctcaacggg ctcccgcagc tcggctacca ggccgccgtg ctcaaggagg    2340
gcctgccgca ggtctacccg ccctatctca actacctgag gccggattca gaagccagcc    2400
agagcccaca atacagcttc gagtcattac ctcagaagat ttgtttaatc tgtggggatg    2460
aagcatcagg ctgtcattat ggtgtcctta cctgtgggag ctgtaaggtc ttctttaaga    2520
gggcaatgga agggcagcac aactacttat gtgctggaag aaatgactgc atcgttgata    2580
aaatccgcag aaaaaactgc ccagcatgtc gccttagaaa gtgctgtcag gctggcatgg    2640
tccttggagg tcgaaaattt aaaaagttca ataaagtcag agttgtgaga gcactggatg    2700
ctgttgctct cccacagcca gtgggcgttc caaatgaaag ccaagcccta agccagagat    2760
tcactttttc accaggtcaa gacatacagt tgattccacc actgatcaac ctgttaatga    2820
gcattgaacc agatgtgatc tatgcaggac atgacaacac aaaacctgac acctccagtt    2880
ctttgctgac aagtcttaat caactaggcg agaggcaact tctttcagta gtcaagtggt    2940
ctaaatcatt gccaggtttt cgaaacttac atattgatga ccagataact ctcattcagt    3000
attcttggat gagcttaatg gtgtttggtc taggatggag atcctacaaa cacgtcagtg    3060
ggcagatgct gtattttgca cctgatctaa tactaaatga acagcggatg aaagaatcat    3120
cattctattc attatgcctt accatgtggc agatcccaca ggagtttgtc aagcttcaag    3180
ttagccaaga agagttcctc tgtatgaaag tattgttact tcttaataca attcctttgg    3240
aagggctacg aagtcaaacc cagtttgagg agatgaggtc aagctacatt agagagctca    3300
tcaaggcaat tggtttgagg caaaaggag ttgtgtcgag ctcacagcgt ttctatcaac     3360
ttacaaaact tcttgataac ttgcatgatc ttgtcaaaca acttcatctg tactgcttga    3420
atacatttat ccagtcccgg gcactgagtg ttgaatttcc agaaatgatg tctgaagtta    3480
ttgctgcaca attacccaag atattggcag ggatggtgaa accccttctc tttcataaaa    3540
agtgaatgtc atcttttttct tttaaagaat taaatttgt ggtatgtctt tttgttttgg    3600
tcaggattat gaggtcttga gttttttataa tgttcttctg aaagccttac atttataaca    3660
tcatagtgtg taaatttaaa agaaaaattg tgaggttcta attattttct tttataaagt    3720
ataattagaa tgtttaactg ttttgtttac ccatattttc ttgaagaatt tacaagattg    3780
aaaaagtact aaaattgtta agtaaacta tcttatccat attatttcat accatgtagg    3840
tgaggatttt taacttttgc atctaacaaa tcatcgactt aagagaaaaa atcttacatg    3900
taataacaca aagctattat atgttatttc taggtaactc cctttgtgtc aattatattt    3960
ccaaaaatga acctttaaaa tggtatgcaa aatttgtct atatatattt gtgtgaggag    4020
gaaattcata actttcctca gattttcaaa agtatttta atgcaaaaaa tgtagaaaga    4080
```

```
gtttaaaacc actaaaatag attgatgttc ttcaaactag gcaaaacaac tcatatgtta      4140
agaccatttt ccagattgga aacacaaatc tcttaggaag ttaataagta gattcatatc      4200
attatgcaaa tagtattgtg ggttttgtag gttttttaaaa taaccttttt tggggagaga     4260
attgtcctct aatgaggtat tgcgagtgga cataagaaat cagaagatta tggcctaact     4320
gtactcctta ccaactgtgg catgctgaaa gttagtcact cttactgatt ctcaattctc      4380
tcacctttga aagtagtaaa atatctttcc tgccaattgc tcctttgggt cagagcttat      4440
taacatcttt tcaaatcaaa ggaaagaaga aagggagagg aggaggaggg aggtatcaat     4500
tcacatacct ttctcctctt tatcctccac tatcatgaat tcatattatg tttcagccat      4560
gcaaatcttt ttaccatgaa atttcttcca gaattttccc cctttgacac aaattccatg      4620
catgtttcaa cctttcgagac tcagccaaat gtcattctg taaaatcttc cctgagtctt      4680
ccaagcagta atttgccttc tcctagagtt tacctgccat tttgtgcaca tttgagttac      4740
agtagcatgt tattttacaa ttgtgactct cctgggagtc tgggagccat ataaagtggt      4800
caatagtgtt tgctgactga gagttgaatg acattttctc tctgtcttgg tattactgta      4860
gatttcgatc attctttggt tacatttctg catatttctg tacccatgac tttatcactt      4920
tcttctccca tgctttatct ccatcaatta tcttcattac ttttaaattt tccacctttg      4980
cttcctactt tgtgagatct ctcccttac tgactataac atagaagaat agaagtgtat      5040
tttatgtgtc ttaaggacaa tactttagat tccttgttct aagttttttaa actgaatgaa      5100 tggaatatta tttctctccc taagcaaaat tccacaaaac aattatttct tatgtttatg      5160
tagccttaaa ttgttttgta ctgtaaacct cagcataaaa actttcttca tttctaattt      5220
cattcaacaa atattgattg aatacctggt attagcacaa gaaaaatgtg ctaataagcc      5280
ttatgagaat ttggagctga agaaagacat ataactcagg aaagttacag tccagtagta      5340
ggtataaatt acagtgcctg ataaataggc attttaatat ttgtacactc aacgtatact      5400
aggtaggtgc aaaacattta catataattt tactgatacc catgcagcac aaaggtacta      5460
actttaaata ttaaataaca cctttatgtg tcagtaattc atttgcatta aatcttattg      5520
aaaaggcttt caatatattt tccccacaaa tgtcatccca agaaaaagt attttttaaca     5580 tctcccaaat ataatagtta caggaaatct acctctgtga gagtgacacc tctcagaatg     5640
aactgtgtga cacaagaaaa tgaatgtagg tctatccaaa aaaacccca agaaacaaaa      5700 acaatattat tagcccttta tgcttaagtg atggactcag ggaacagttg atgttgtgat      5760 catttttatta tctgattctt gttactttga attaaaccaa tattttgatg atataaatca     5820
tttccaccag catatattta atttccataa taactttaaa attttctaat ttcactcaac      5880
tatgagggaa tagaatgtgg tggccacagg tttggctttt gttaaaatgt ttgatatctt      5940
cgatgttgat ctctgtctgc aatgtagatg tctaaacact aggatttaat atttaaggct      6000
aagctttaaa aataaagtac cttttttaaaa agaatatggc ttcaccaaat ggaaaatacc     6060
taatttctaa atcttttttct ctacaaagtc ctatctacta atgtctccat tactatttag     6120
tcatcataac cattatcttc atttttacatg tcgtgttctt tctggtagct ctaaaatgac    6180
actaaatcat aagaagacag gttacatatc aggaaaatact tgaaggttac tgaaatagat      6240
tcttgagtta atgaaaatat tttctgtaaa aaggtttgaa aagccatttg agtctaaagc      6300 attataccte cattatcagt agttatgtga caattgtgtg tgtgtttaat gtttaaagat      6360
gtggcacttt ttaataaggc aatgctatgc tattttttcc catttaacat taagataatt      6420
```

```
tattgctata cagatgatat ggaaatatga tgaacaatat ttttttttgcc aaaactatgc    6480 cttgtaagta gccatggaat gtcaacctgt aacttaaatt atccacagat agtcatgtgt    6540
ttgatgatgg gcactgtgga gataactgac ataggactgt gccccccttc tctgccactt    6600
actagctgga tgagattaag caagtcattt aactgctctg attaaacctg cctttcccaa    6660
gtgctttgta atgaatagaa atggaaacca aaaaaaacgt atacaggcct tcagaaatag    6720
taattgctac tattttgttt tcattaagcc atagttctgg ctataatttt atcaaactca    6780
ccagctatat tctacagtga aagcaggatt ctagaaagtc tcactgtttt atttatgtca    6840
ccatgtgcta tgatatattt ggttgaattc atttgaaatt agggctggaa gtattcaagt    6900
aatttcttct gctgaaaaaa tacagtgttt tgagtttagg gcctgtttta tcaaagttct    6960
aaagagccta tcactcttcc attgtagaca ttttaaaata atgacactga ttttaacatt    7020
tttaagtgtc tttttagaac agagagcctg actgaacac  agcccctcca aaacccatg    7080 ctcaaattat ttttactatg gcagcaattc cacaaaggg  aacaatgggt ttagaaatta    7140
caatgaagtc atcaacccaa aaaacatccc tatccctaag aaggttatga tataaaatgc    7200
ccacaagaaa tctatgtctg ctttaatctg tcttttattg ctttggaagg atggctatta    7260 cattttagt  ttttgctgtg aatacctgag cagtttctct catccatact tatccttcac    7320
acatcagaag tcaggataga atatgaatca ttttaaaaac ttttacaact ccagagccat    7380
gtgcataaga agcattcaaa acttgccaaa acatacattt ttttcaaat  ttaaagatac    7440 tctatttttg tattcaatag ctcaacaact gtggtcccca ctgataaagt gaagtggaca    7500
aggagacaag taatggcata agtttgtttt tcccaaagta tgcctgttca atagccattg    7560
gatgtgggaa atttctacat ctcttaaaat tttacagaaa atacatagcc agatagtcta    7620
gcaaaagttc accaagtcct aaattgctta tccttacttc actaagtcat gaatcatttt    7680
taatgaaaag aacatcacct aggttttgtg gtttcttttt ttcttattca tggctgagtg    7740
aaaacaacaa tctctgtttc tccctagcat ctgtggacta tttaatgtac cattattcca    7800
cactctatgg tccttactaa atacaaaatt gaacaaaaag cagtaaaaca actgactctt    7860
cacccatatt ataaaatata atccaagcca gattagtcaa catccataag atgaatccaa    7920
gctgaactgg gcctagatta ttgagttcag gttggatcac atccctatt  attaataaac    7980 ttaggaaaga aggccttaca gaccatcagt tagctggagc taatagaacc tacacttcta    8040
aagttcggcc tagaatcaat gtggccttaa aagctgaaaa gaagcaggaa agaacagttt    8100
tcttcaataa tttgtccacc ctgtcactgg agaaaattta agaatttggg ggtgttggta    8160
gtaagttaaa cacagcagct gttcatggca gaaattattc aatacatacc ttctctgaat    8220
atcctataac caaagcaaag aaaaacacca aggggtttgt tctcctcctt ggagttgacc    8280
tcattccaag gcagagctca ggtcacaggc acagggctg  cgcccaagct tgtccgcagc    8340
cttatgcagc tgtggagtct ggaagactgt gcaggactg  ctggcctagt cccagaatgt    8400
cagcctcatt ttcgatttac tggctcttgt tgctgtatgt catgctgacc ttattgttaa    8460
acacaggttt gtttgctttt tttccactca tggagacatg ggagaggcat tattttttaag    8520 ctggttgaaa gctttaaccg ataaagcatt tttagagaaa tgtgaatcag gcagctaaga    8580
aagcatactc tgtccattac ggtaaagaaa atgcacagat tattaactct gcagtgtggc    8640
attagtgtcc tggtcaatat tcggatagat atgaataaaa tatttaaatg gtattgtaaa    8700
tagttttcag gacatatgct atagcttatt tttattatct tttgaaattg ctcttaatac    8760
atcaaatcct gatgtattca atttatcaga tataaattat tctaaatgaa gcccagttaa    8820
```

```
atgttttgt cttgtcagtt atatgttaag tttctgatct cttgtctat gacgtttact   8880
aatctgcatt tttactgtta tgaattattt tagacagcag tggtttcaag cttttgcca    8940
ctaaaatac cttttatttt ctcctccccc agaaagtct ataccttgaa gtatctatcc     9000
accaaactgt acttctatta agaaatagtt attgtgtttt cttaatgttt tgttattcaa   9060
agacatatca atgaaagctg ctgagcagca tgaataacaa ttatatccac acagatttga   9120
tatattttgt gcagccttaa cttgatagta taaaatgtca ttgcttttta aataatagtt   9180
agtcaatgga cttctatcat agctttccta aactaggtta agatccagag ctttggggtc   9240
ataatatatt acatacaatt aagttatctt tttctaaggg ctttaaaatt catgagaata   9300
accaaaaaag gtatgtggag agttaataca acataccat attcttgttg aaacagagat    9360
gtggctctgc ttgttctcca taaggtagaa atactttcca gaatttgcct aaactagtaa   9420
gccctgaatt tgctatgatt agggatagga agagattttc acatggcaga ctttagaatt   9480
cttcacttta gccagtaaag tatctccttt tgatcttagt attctgtgta ttttaacttt   9540
tctgagttgt gcatgtttat aagaaaaatc agcacaaagg gtttaagtta aagcctttt   9600
actgaaattt gaaagaaaca gaagaaaata tcaaagttct ttgtattttg agaggattaa   9660
atatgattta caaaagttac atggagggct ctctaaaaca ttaaattaat tatttttgt    9720
tgaaaagtct tactttaggc atcattttat tcctcagcaa ctagctgtga agcctttact   9780
gtgctgtatg ccagtcactc tgctagattg tggagattac cagtgttccc gtcttctccg   9840
agcttagagt tggatgggga ataaagacag gtaaacagat agctacaata ttgtactgtg   9900
aatgcttatg ctggaggaag tacagggaac tattggagca cctaagagga gcacctacct   9960
tgaatttagg ggttagcaga ggcatcctga aaaagtcaa agctaagcca caatctataa    10020
gcagtttagg aattagcaga acgtgcgtgg tgaggagatg ccaaaggcaa gaagagaaga   10080
gtattccaaa caggagggat tccaaagaga gaagtatc ccaaacaaca tttgcacaaa     10140
cctgatgggg agagagaatg tggggtgggg atggatgatg agactgaaga agaaagccag   10200
gtctagataa tcagtggcct tgtacaccat gttaaagagt gtagacttga ttctgttgta   10260
aacaggaaag cagcacaatt catatgaata ttttagaaga ctcccactgg aatatggaga   10320
ataaagttgg agatgactaa tcctggaagc agggagaaca ttttgagga agttgcacta    10380
ttttggtgaa aatgatgatc ataaacatga agaattgtag gtgatcatga cctcctctct   10440
aattttccag aagggttttg gaagatataa cataggaaca ttgacaggac tgacgaaagg   10500
agatgaaata caccatataa attgtcaaac acaaggccag atgtctaatt attttgctta   10560
tgtgttgaaa ttacaaattt ttcatcagga aaccaaaaac tacaaaactt agttttccca   10620
agtcccagaa ttctatctgt ccaaacaatc tgtaccactc cacctatatc cctacctttg   10680
catgtctgtc caacctcaaa gtccaggtct atacacacgg gtaagactag agcagttcaa   10740
gtttcagaaa atgagaaaga ggaactgagt tgtgctgaac ccatacaaaa taaacacatt   10800
ctttgtatag attcttggaa cctcgagagg aattcaccta actcataggt atttgatggt   10860
atgaatccat ggctgggctc ggcttttaaa aagccttatc tgggattcct tctatggaac   10920
caagttccat caaagcccat ttaaaagcct acattaaaaa caaaattctt gctgcattgt   10980
atacaaataa tgatgtcatg atcaaataat cagatgccat tatcaagtgg aattacaaaa   11040
tggtataccc actccaaaaa aaaaaaaaaa gctaaattct cagtagaaca ttgtgacttc   11100
atgagccctc cacagccttg gagctgagga gggagcactg gtgagcagta ggttgaagag   11160
```

```
aaaacttggc gcttaataat ctatccatgt tttttcatct aaaagagcct tcttttttgga    11220
ttaccttatt caatttccat caaggaaatt gttagttcca ctaaccagac agcagctggg    11280
aaggcagaag cttactgtat gtacatggta gctgtgggaa ggaggtttct ttctccaggt    11340
cctcactggc catacaccag tcccttgtta gttatgcctg gtcatagacc ccgttgctca    11400
tcatctcata tttaagtctt tggcttgtga atttatctat tctttcagct tcagcactgc    11460
agagtgctgg gactttgcta acttccattt cttgctggct tagcacattc ctcataggcc    11520
cagctctttt ctcatctggc cctgctgtgg agtcaccttg ccccttcagg agagccatgg    11580
cttaccactg cctgctaagc ctccactcag ctgccaccac actaaatcca agcttctcta    11640
agatgttgca gactttacag gcaagcataa aaggcttgat cttcctggac ttccctttac    11700
ttgtctgaat ctcacctcct tcaactttca gtctcagaat gtaggcattt gtcctctttg    11760
ccctacatct tccttcttct gaatcatgaa agcctctcac ttcctcttgc tatgtgctgg    11820
aggcttctgt caggttttag aatgagttct catctagtcc tagtagcttt tgatgcttaa    11880
gtccaccttt taaggatacc tttgagattt agaccatgtt tttcgcttga gaaagcccta    11940
atctccagac ttgcctttct gtggatttca aagaccaact gaggaagtca aaagctgaat    12000
gttgactttc tttgaacatt tccgctataa caattccaat tctcctcaga gcaatatgcc    12060
tgcctccaac tgaccaggag aaaggtccag tgccaaagag aaaaacacaa agattaatta    12120
tttcagttga gcacatactt tcaaagtggt ttgggtattc atatgaggtt ttctgtcaag    12180
agggtgagac tcttcatcta tccatgtgtg cctgacagtt ctcctggcac tggctggtaa    12240
cagatgcaaa actgtaaaaa ttaagtgatc atgtatttta acgatatcat cacatactta    12300
ttttctatgt aatgttttaa atttccccta acatactttg actgttttgc acatggtaga    12360
tattcacatt tttttgtgtt gaagttgatg caatcttcaa agttatctac cccgttgctt    12420
attagtaaaa ctagtgttaa tacttggcaa gagatgcagg gaatctttct catgactcac    12480
gccctattta gttattaatg ctactaccct attttgagta agtagtaggt ccctaagtac    12540
attgtccaga gttatacttt taaagatatt tagccccata tacttcttga atctaaagtc    12600
atacaccttg ctcctcattt ctgagtggga aagacatttg agagtatgtt gacaattgtt    12660
ctgaaggttt ttgccaagaa ggtgaaactg tcctttcatc tgtgtatgcc tggggctggg    12720
tccctggcag tgatggggtg acaatgcaaa gctgtaaaaa ctaggtgcta gtgggcacct    12780
aatatcatca tcatatactt attttcaagc taatatgcaa aatcccatct ctgtttttaa    12840
actaagtgta gatttcagag aaaatatttt gtggttcaca taagaaaaca gtctactcag    12900
cttgacaagt gttttatgtt aaattggctg gtggtttgaa atgaatcatc ttcacataat    12960
gttttcttta aaaatattgt gaatttaact ctaattcttg ttattctgtg tgataataaa    13020
gaataaacta atttcta                                                   13037

<210> SEQ ID NO 144
<211> LENGTH: 3180
<212> TYPE: DNA
<213> ORGANISM: Homo sapiens

<400> SEQUENCE: 144
attctatgct gcagcctaag catcattcct cttctcttct tagtggagat aaaattaccc      60
actgctctcc ttacatttac tttgtccata tttgctccta tgctctaggc tcgtgcacaa     120
caaacacagt gtgggccctt accctagaag ccaacttctc atgacctttc tctatctcca     180
gaatccatgc agtgggaatg aaggtaaaag aaggttttca tgggatccag ctgagagctc     240
```

| | |
|---|---|
| tacggggaaa atggatctga ggagccatgt gctccatctc ttttatttta caggtagaga | 300 |
| ctagggtat agagtgaggt gaattaccgc agtgacccac acattgttgg cagacctagg | 360 |
| attagaactc tgtcttcctg gttcccagct tggtgctttt gaaagcatac ttgctgcttt | 420 |
| cttaccggcc tggtgtctgc cactttggga cagagtgtgg acttgctcac ctgcccatt | 480 |
| tcttagggat tctcattctg tgtttgagca agaatattct tattctggaa agaaccacat | 540 |
| accacaggat tctgggtgag cataaggaag attgtcttgg ggatctgact agctcacgt | 600 |
| atagtggcta tgatgaattc agtgtcttat ttttgcata tgtatatttt tagtctaata | 660 |
| ttgcctgggt gtctgagcaa gtctagatga atttaattgc tctcattttt ccctgcccc | 720 |
| tcttcctttg gtctctcttt taggaaatgt ttttctttca acattcgttt cattcattat | 780 |
| ttactcattc ggccaaccaa catttattga gtgccttccc tgtatcaggg acaggggctt | 840 |
| acaaagtaga atttgatccc acctctgccc tcagtagctc agtgtctaat ggaggtagtg | 900 |
| atgttcatta agcgtcgcca gatactgtgc taggtgctgt gcctgttctc tctcgcttgt | 960 |
| tcctcacaca cttgagaagg ccgaagctga ttcatagctt ggaaggcagg ggccttggat | 1020 |
| ttgaacccag gcctgaccaa tggcagaacc tatcagatgt gtggacagat gacattgcct | 1080 |
| ttctttcttt ggatatatca aaatcagcca gcaggcagga actcccattt tgagcaagca | 1140 |
| atgtgcagga atgatagggt atacagagag gaacaggaga tggcccctga cttccagcat | 1200 |
| gtgtctgatg gacatccagg ctgcaggcat catggtgctg tctagagaga tgagccaggt | 1260 |
| gcccagagcc catgggccaa tgctgcccct tcttgagcat gccaaacaaa gcggttggtg | 1320 |
| tgttagaggc acagtctcct ccactctaag taaaaatcag catgagtcct agcccacatt | 1380 |
| tccctagtga gtacaccaaa gatatctatg aactggcagt catcagtgac ttcctaaggt | 1440 |
| tccggaaatg catctcttac tcaggagtaa gcaatgatgt gcctgcggct ttacgagttc | 1500 |
| tcacagaatg actttctgga cccaaatgtt ttttctgctt caggactgtg aaggccttat | 1560 |
| tgttcgctct gccaccaagg tgaccgctga tgtcatcaac gcagctgaga aactccaggt | 1620 |
| ggtgggcagg gctggcacag gtgtggacaa tgtggatctg gaggccgcaa caaggaaggg | 1680 |
| catcttggtt atgaacaccc ccaatgggaa cagcctcagt gccgcagaac tcacttgtgg | 1740 |
| aatgatcatg tgcctggcca ggcagattcc ccaggcgacg gcttcgatga aggacggcaa | 1800 |
| atgggagcgg aagaagttca tgggaacaga gctgaatgaa aagaccctgg gaattcttgg | 1860 |
| cctgggcagg attgggagag aggtagctac ccggatgcag tcctttggga tgaagactat | 1920 |
| agggtatgac cccatcattt ccccagaggt ctcggcctcc tttggtgttc agcagctgcc | 1980 |
| cctggaggag atctggcctc tctgtgattt catcactgtg cacactcctc tcctgccctc | 2040 |
| cacgacaggc ttgctgaatg acaacacctt gcccagtgc aagaagggg tgcgtgtggt | 2100 |
| gaactgtgcc cgtggaggga tcgtggacga aggcgccctg ctccgggccc tgcagtctgg | 2160 |
| ccagtgtgcc gggctgcac tggacgtgtt tacggaagag ccgccacggg accgggcctt | 2220 |
| ggtggaccat gagaatgtca tcagctgtcc ccacctgggt gccagcacca aggaggctca | 2280 |
| gagccgctgt ggggaggaaa ttgctgttca gttcgtggac atggtgaagg ggaaatctct | 2340 |
| cacgggggtt gtgaatgccc aggcccttac cagtgccttc tctccacaca ccaagccttg | 2400 |
| gattggtctg gcagaagctc tggggacact gatgcgagcc tgggctgggt ccccaaagg | 2460 |
| gaccatccag gtgataacac agggaacatc cctgaagaat gctgggaact gcctaagccc | 2520 |
| cgcagtcatt gtcggcctcc tgaaagaggc ttccaagcag gcggatgtga acttggtgaa | 2580 |

```
cgctaagctg ctggtgaaag aggctggcct caatgtcacc acctcccaca gccctgctgc    2640 accaggggggg caaggcttcg gggaatgcct cctggccgtg gccctggcag gcgcccctta    2700
ccaggctgtg ggcttggtcc aaggcactac acctgtactg caggggctca atggagctgt    2760
cttcaggcca gaagtgcctc tccgcaggga cctgcccctg ctcctattcc ggactcagac    2820 ctctgacccct gcaatgctgc ctaccatgat tggcctcctg gcagaggcag gcgtgcggct    2880
gctgtcctac cagacttcac tggtgtcaga tggggagacc tggcacgtca tgggcatctc    2940
ctccttgctg cccagcctgg aagcgtggaa gcagcatgtg actgaagcct tccagttcca    3000 cttctaaccct tggagctcac tggtccctgc ctctggggct tttctgaaga aacccaccca    3060
ctgtgatcaa tagggagaga aaatccacat tcttgggctg aacgcgagcc tctgacactg    3120
cttacactgc actctgaccc tgtagtacag caataaccgt ctaataaaga gcctaccccc    3180
```

<210> SEQ ID NO 145
<211> LENGTH: 1301
<212> TYPE: DNA
<213> ORGANISM: Homo sapiens
<220> FEATURE:
<221> NAME/KEY: misc_feature
<222> LOCATION: (1301)..(1301)
<223> OTHER INFORMATION: n is a, c, g, or t

<400> SEQUENCE: 145

```
caaacaaaaa cagccaagct tttctgccaa aaagatgact gagaagactg ttaaagcaaa      60
aagctctgtt cctgcctcag atgatgccta tccagaaata gaaaaattct ttcccttcaa     120
tcctctagac tttgagagtt ttgacctgcc tgaagagcac cagattgcgc acctcccctt     180
gagtggagtg cctctcatga tccttgacga ggagagagag cttgaaaagc tgtttcagct     240 gggccccccct tcacctgtga agatgccctc tccaccatgg gaatccaatc tgttgcagtc     300
tccttcaagc attctgtcga ccctggatgt tgaattgcca cctgtttgct gtgacataga     360
tatttaaatt tcttagtgct tcagagtctg tgtgtatttg tattaataaa gcattctttta    420 acagaaaaaa aaaaaaaaaa aaaaaaaaa aaaaaaaaaa aaaaaaaaa aggggggggga     480 gacacaaaaa gaattcccca agaggggggcc acaagataat cagaggatat cacacaagat    540
ctctcggcgc accaacgacg ggggcccccaa ataagggaga gacccagaat cacaacagcc    600 aagcacggt ggacacgacg gaaacaaaca cacagcccag acgggggggc aaacacgcgc       660
gcacaccgcg gacaccatgg gacaaagcag acaccaccca caaaacaaca ccgcggaggg     720
ggaagaacaa caaaacaagt gcgcaaacag aacacaacca cagaaagaga aaaattaaaa    780
cggcccccaa gacggcgaca acacaacaaa acaaccacta cagagcgctc aacagccgag    840
taaaaacaca acaacggaca actaacacac aaaggaatga acaaagcggg ggccacacac    900
cgacaccgga atccggcga acaactcaca ccgagcgagg gtcccagaca acaaatacac    960
agacaacgaa accgagaaac aagaccagca agacgagcag gcaaaagaca aacaagacag   1020
aggagacgac gacgaacgca aaggacaaga ggacacaacg acgcgaggag cgagagcgag   1080
aggaagagac aacaaaaaga cacaaaagaa caacaagcaa gcagcgaaga acgacacaca    1140
accacacgag acagcaggag cagaggcgga gaaaacacaa cgagcaagcc aagaccaaga    1200
gaggagaaca aaataaaaaa atacgagagc aggcggacga gagcacgaga cgaacagaca    1260
aacgggaatc agaagcataa cgatccgcga cgcgaacaac n                        1301
```

<210> SEQ ID NO 146
<211> LENGTH: 3203

<212> TYPE: DNA
<213> ORGANISM: Homo sapiens

<400> SEQUENCE: 146

```
gtgcaccctg tcccagccgt cctgtcctgg ctgctcgctc tgcttcgctg cgcctccact      60
atgctctccc tccgtgtccc gctcgcgccc atcacggacc cgcagcagct gcagctctcg     120
ccgctgaagg ggctcagctt ggtcgacaag gagaacacgc cgccggccct gagcgggacc     180
cgcgtcctgg ccagcaagac cgcgaggagg atcttccagg agaaaacccc cgccgctttg     240
tcatcttccc catcgagtac catgatatct ggcagatgta agaaggca gaggcttcct       300
tttggaccgc cgaggaggtg gacctctcca aggacattca gcactgggaa tccctgaaac     360
ccgaggagag atattttata tcccatgttc tggctttctt tgcagcaagc gatggcatag     420
taaatgaaaa cttggtggag cgatttagcc aagaagttca gattacagaa gcccgctgtt     480
tctatggctt ccaaattgcc atggaaaaca tacattctga aatgtatagt cttcttattg     540
acacttacat aaaagatccc aaagaaaggg aatttctctt caatgccatt gaaacgatgc     600
cttgtgtcaa gaagaaggca gactgggcct tgcgctggat tggggacaaa gaggctacct     660
atggtgaacg tgttgtagcc tttgctgcag tggaaggcat tttctttcc ggttcttttg      720
cgtcgatatt ctggctcaag aaacgaggac tgatgcctgg cctcacattt tctaatgaac     780
ttattagcag agatgagggt ttacactgtg attttgcttg cctgatgttc aaacacctgg     840
tacacaaacc atcggaggag agagtaagag aaataattat caatgctgtt cggatagaac     900
aggagttcct cactgaggcc ttgcctgtga agctcattgg gatgaattgc actctaatga     960
agcaatacat tgagtttgtg gcagacagac ttatgctgga actgggtttt agcaaggttt    1020
tcagagtaga gaacccattt gactttatgg agaatatttc actggaagga aagactaact    1080
tctttgagaa gagagtaggc gagtatcaga ggatgggagt gatgtcaagt ccaacagaga    1140
attcttttac cttggatgct gacttctaaa tgaactgaag atgtgccctt acttggctga    1200
tttttttttt tccatctcat aagaaaaatc agctgaagtg ttaccaacta gccacaccat    1260
gaattgtccg taatgttcat taacagcatc tttaaaactg tgtagctacc tcacaaccag    1320
tcctgtctgt ttatagtgct ggtagtatca ccttttgcca gaaggcctgg ctggctgtga    1380
cttaccatag cagtgacaat ggcagtcttg gctttaaagt gaggggtgac cctttagtga    1440
gcttagcaca gcgggattaa acagtccttt aaccagcaca gccagttaaa agatgcagcc    1500
tcactgcttc aacgcagatt ttaatgttta cttaaatata aacctggcac tttacaaaca    1560
aataaacatt gtttgtactc acaaggcgat aatagcttga tttatttggt ttctacacca    1620
aatacattct cctgaccact aatgggagcc aattcacaat tcactaagtg actaaagtaa    1680
gttaaacttg tgtagactaa gcatgtaatt tttaagtttt attttaatga attaaaatat    1740
ttgttaacca actttaaagt cagtcctgtg tatacctaga tattagtcag ttggtgccag    1800
atagaagaca ggttgtgttt ttatcctgtg gcttgtgtag tgtcctggga ttctctgccc    1860
cctctgagta gagtgttgtg ggataaagga atctctcagg gcaaggagct tcttaagtta    1920
aatcactaga aatttagggg tgatctgggc cttcatatgt gtgagaagcc gtttcatttt    1980
atttctcact gtatttccct caacgtctgg ttgatgagaa aaaattcttg aagagttttc    2040
atatgtggga gctaaggtag tattgtaaaa tttcaagtca tccttaaaca aaatgatcca    2100
cctaagatct tgcccctgtt aagtggtgaa atcaactaga ggtggttcct acaagttgtt    2160
cattctagtt ttgtttggtg taagtaggtt gtgtgagtta attcatttat atttactatg    2220
```

| | |
|---|---:|
| tctgttaaat cagaaatttt ttattatcta tgttcttcta gattttacct gtagttcata | 2280 |
| cttcagtcac ccagtgtctt attctggcat tgtctaaatc tgagcattgt ctaggggat | 2340 |
| cttaaacttt agtaggaaac catgagctgt aatacagtt tccattcaaa tattaatttc | 2400 |
| agaatgaaac ataatttttt ttttttttt ttgagatgga gtctcgctct gttgcccagg | 2460 |
| ctggagtgca gtggcgcgat tttggctcac tgtaacctcc atctcctggg ttcaagcaat | 2520 |
| tctcctgtct cagcctccct agtagctggg actgcaggta tgtgctacca cacctggcta | 2580 |
| attttgtat tttagtaga gatggagttt caccatattg gtcaggctgg tcttgaactc | 2640 |
| ctgacctcag gtgatccacc cacctcggcc tcccaaagtg ctgggattgc aggcgtgata | 2700 |
| aacaaatatt cttaataggg ctactttgaa ttaatctgcc tttatgtttg ggagaagaaa | 2760 |
| gctgagacat tgcatgaaag atgatgagag ataaatgttg atcttttggc cccatttgtt | 2820 |
| aattgtattc agtatttgaa cgtcgtcctg tttattgtta gttttcttca tcatttattg | 2880 |
| tatagacaat ttttaaatct ctgtaatatg atacattttc ctatctttta agttattgtt | 2940 |
| acctaaagtt aatccagatt atatggtcct tatatgtgta caacattaaa atgaaaggct | 3000 |
| ttgtcttgca ttgtgaggta caggcggaag ttggaatcag gttttaggat tctgtctctc | 3060 |
| attagctgaa taatgtgagg attaacttct gccagctcag accatttcct aatcagttga | 3120 |
| aagggaaaca agtatttcag tctcaaaatt gaataatgca caagtcttaa gtgattaaaa | 3180 |
| taaaactgtt cttatgtcag ttt | 3203 |

<210> SEQ ID NO 147
<211> LENGTH: 4482
<212> TYPE: DNA
<213> ORGANISM: Homo sapiens

<400> SEQUENCE: 147

| | |
|---|---:|
| agcgggggca ctccagccct gcagcctccg gagtcagtgc cgcgcgcccg ccgccccgcg | 60 |
| ccttcctgct cgccgcacct ccgggagccg gggcgcaccc agcccgcagc gccgcctccc | 120 |
| cgcccgcgcc gcctccgacc gcaggccgag ggccgccact ggccgggggg accgggcagc | 180 |
| agcttgcggc cgcggagccg ggcaacgctg gggactgcgc ctttgtccc cggaggtccc | 240 |
| tggaagtttg cggcaggacg cgcgcgggga ggcggcggag gcagccccga cgtcgcggag | 300 |
| aacagggcgc agagccggca tgggcatcgg gcgcagcgag ggggggccgcc gcggggcagc | 360 |
| cctgggcgtg ctgctggcgc tgggcgcggc gcttctggcc gtgggctcgg ccagcgagta | 420 |
| cgactacgtg agcttccagt cggacatcgg cccgtaccag agcgggcgct tctacaccaa | 480 |
| gccacctcag tgcgtggaca tccccgcgga cctgcggctg tgccacaacg tgggctacaa | 540 |
| gaagatggtg ctgcccaacc tgctggagca cgagaccatg gcggaggtga agcagcaggc | 600 |
| cagcagctgg gtgccctgc tcaacaagaa ctgccacgcc ggcacccagg tcttcctctg | 660 |
| ctcgctcttc gcgcccgtct gcctggaccg gcccatctac ccgtgtcgct ggctctgcga | 720 |
| ggccgtgcgc gactcgtgcg agccggtcat gcagttcttc ggcttctact ggcccgagat | 780 |
| gcttaagtgt gacaagttcc ccgaggggga cgtctgcatc gccatgacgc gcccaatgc | 840 |
| caccgaagcc tccaagcccc aaggcacaac ggtgtgtcct ccctgtgaca cagagttgaa | 900 |
| atctgaggcc atcattgaac atctctgtgc cagcgagttt gcactgagga tgaaaataaa | 960 |
| agaagtgaaa aagaaaatg gcgacaagaa gattgtcccc aagaagaaga gcccctgaa | 1020 |
| gttggggccc atcaagaaga aggacctgaa gaagcttgtg ctgtacctga gaatggggc | 1080 |
| tgactgtccc tgccaccagc tggacaacct cagccaccac ttcctcatca tgggccgcaa | 1140 |

```
ggtgaagagc cagtacttgc tgacggccat ccacaagtgg gacaagaaaa acaaggagtt    1200
caaaaacttc atgaagaaaa tgaaaaacca tgagtgcccc acctttcagt ccgtgtttaa    1260
gtgattctcc cggggggcagg gtggggaggg agcctcgggt ggggtgggag cgggggggac    1320
agtgccccgg gaacccggtg ggtcacacac acgcactgcg cctgtcagta gtggacattt    1380
aatccagtcg gcttgttctt gcagcattcc cgctcccttc cctccatagc cacgctccaa    1440
accccagggt agccatggcc gggtaaagca agggccattt agattaggaa ggttttttaag   1500 atccgcaatg tggagcagca gccactgcac aggaggaggt gacaaaccat ttccaacagc    1560
aacacagcca ctaaaacaca aaaggggga ttgggcggaa agtgagagcc agcagcaaaa     1620
actacatttt gcaacttgtt ggtgtggatc tattggctga tctatgcctt tcaactagaa    1680
aattctaatg attggcaagt cacgttgttt tcaggtccag agtagtttct ttctgtctgc    1740
tttaaatgga aacagactca taccacactt acaattaagg tcaagcccag aaagtgataa    1800
gtgcagggag gaaagtgca gtccattat gtaatagtga cagcaaaggg accaggggag     1860
aggcattgcc ttctctgccc acagtctttc cgtgtgattg tctttgaatc tgaatcagcc    1920
agtctcagat gccccaaagt ttcggttcct atgagcccgg gcatgatct gatccccaag     1980 acatgtggag gggcagcctg tgcctgcctt tgtgtcagaa aaaggaaacc acagtgagcc    2040
tgagagagac ggcgattttc gggctgagaa ggcagtagtt ttcaaaacac atagttaaaa    2100
aagaaacaaa tgaaaaaaat tttagaacag tccagcaaat tgctagtcag ggtgaattgt    2160
gaaattgggt gaagagctta cgattctaat ctcatgtttt ttcctttttca catttttaaa    2220 agaacaatga caaacaccca cttattttttc aaggttttaa aacagtctac attgagcatt    2280 tgaaggtgt gctagaacaa ggtctcctga tccgtccgag gctgcttccc agaggagcag     2340
ctctccccag gcatttgcca agggaggcgg atttccctgg tagtgtagct gtgtggcttt    2400
ccttcctgaa gagtccgtgg ttgccctaga acctaacacc ccctagcaaa actcacagag    2460 cttttccgttt tttttctttcc tgtaaagaaa catttccttt gaacttgatt gcctatggat    2520
caaagaaatt cagaacagcc tgcctgtccc ccgcacttt ttacatatat ttgtttcatt     2580
tctgcagatg gaaagttgac atgggtgggg tgtccccatc cagcgagaga gtttaaaaag    2640
caaaacatct ctgcagtttt tcccaagtgc cctgagatac ttcccaaagc ccttatgttt    2700
aatcagcgat gtatataagc cagttcactt agacaacttt accctctcctg tccaatgtac    2760 aggaagtagt tctaaaaaaa atgcatatta atttcttccc ccaaagccgg attcttaatt    2820
ctctgcaaca ctttgaggac atttatgatt gtccctctgg gccaatgctt atacccagtg    2880
aggatgctgc agtgaggctg taaagtggcc ccctgcggcc ctagcctgac ccggaggaaa    2940
ggatggtaga ttctgttaac tcttgaagac tccagtatga aaatcagcat gcccgcctag    3000
ttacctaccg gagagttatc ctgataaatt aacctctcac agttagtgat cctgtccttt    3060 taacacctttt tttgtggggt tctctctgac ctttcatcgt aaagtgctgg ggaccttaag   3120
tgatttgcct gtaattttgg atgattaaaa aatgtgtata tatattagct aattagaaat    3180
attctacttc tctgttgtca aactgaaatt cagagcaagt tcctgagtgc gtggatctgg    3240
gtcttagttc tggttgattc actcaagagt tcagtgctca tacgtatctg ctcattttga    3300
caaagtgcct catgcaaccg ggccctctct ctgcggcaga gtccttagtg gagggtttta   3360
cctggaacat tagtagttac cacagaatac ggaagagcag gtgactgtgc tgtgcagctc    3420
tctaaatggg aattctcagg taggaagcaa cagcttcaga aagagctcaa aataaattgg    3480
```

```
aaatgtgaat cgcagctgtg ggttttacca ccgtctgtct cagagtccca ggaccttgag    3540
tgtcattagt tactttattg aaggttttag acccatagca gctttgtctc tgtcacatca    3600
gcaatttcag aaccaaaagg gaggctctct gtaggcacag agctgcacta tcacgagcct    3660
ttgttttttct ccacaaagta tctaacaaaa ccaatgtgca gactgattgg cctggtcatt   3720
ggtctccgag agaggaggtt tgcctgtgat ttcctaatta tcgctagggc caaggtggga    3780
tttgtaaagc tttacaataa tcattctgga tagagtcctg ggaggtcctt ggcagaactc    3840
agttaaatct ttgaagaata tttgtagtta tcttagaaga tagcatggga ggtgaggatt    3900
ccaaaaacat tttattttta aaatatcctg tgtaacactt ggctcttggt acctgtgggt    3960
tagcatcaag ttctccccag ggtagaattc aatcagagct ccagtttgca tttggatgtg    4020
taaattacag taatcccatt tcccaaacct aaaatctgtt tttctcatca gactctgagt    4080
aactggttgc tgtgtcataa cttcatagat gcaggaggct caggtgatct gtttgagcag    4140
agcaccctag gcagcctgca gggaataaca tactggccgt tctgacctgt tgccagcaga    4200
tacacaggac atggatgaaa ttcccgtttc ctctagtttc ttcctgtagt actcctcttt    4260
tagatcctaa gtctcttaca aaagctttga atactgtgaa aatgttttac attccatttc    4320
atttgtgttg ttttttttaac tgcatttttac cagatgtttt gatgttatcg cttatgttaa   4380
tagtaattcc cgtacgtgtt cattttattt tcatgctttt tcagccatgt atcaatattc    4440
acttgactaa aatcactcaa ttaatcaaaa aaaaaaaaaa aa                        4482

<210> SEQ ID NO 148
<211> LENGTH: 3637
<212> TYPE: DNA
<213> ORGANISM: Homo sapiens

<400> SEQUENCE: 148
agtcctgggc gaaggggcg gtggttcccc gcggcgctgc gcgcggcggt aattagtgat      60
tgtcttccag cttcgcgaag gctagggggcg cggctgccgg gtggctgcgc ggcgctgccc    120
ccggaccgag gggcagccaa cccaatgaaa ccaccgcgtg ttcgcgcctg gtagagattt    180
ctcgaagaca ccagtgggcc cgttccgagc cctctggacc gcccgtgtgg aaccaaacct    240
gcgcgcgtgg ccgggccgtg ggacaacgag gccgcggaga cgaaggcgca atggcgagga    300
agttatctgt aatcttgatc ctgacctttg ccctctctgt cacaaatccc cttcatgaac    360
taaaagcagc tgctttcccc cagaccactg agaaaattag tccgaattgg gaatctggca    420
ttaatgttga cttggcaatt tccacacggc aatatcatct acaacagctt ttctaccgct    480
atggagaaaa taattctttg tcagttgaag ggttcagaaa attacttcaa aatataggca    540
tagataagat taaagaatc catatacacc atgaccacga ccatcactca gaccacgagc    600
atcactcaga ccatgagcgt cactcagacc atgagcatca ctcagaccac gagcatcact    660
ctgaccatga tcatcactct caccataatc atgctgcttc tggtaaaaat aagcgaaaag    720
ctctttgccc agaccatgac tcagatagtt caggtaaaga tcctagaaac agccagggga    780
aaggagctca ccgaccagaa catgccagtg gtagaaggaa tgtcaaggac agtgttagtg    840
ctagtgaagt gacctcaact gtgtacaaca ctgtctctga aggaactcac tttctagaga    900
caatagagac tccaagacct ggaaaactct tccccaaaga tgtaagcagc tccactccac    960
ccagtgtcac atcaaagagc cgggtgagcc ggctggctgg taggaaaaca aatgaatctg   1020
tgagtgagcc ccgaaaaggc tttatgtatt ccagaaacac aaatgaaaat cctcaggagt   1080
gtttcaatgc atcaaagcta ctgacatctc atggcatggg catccaggtt ccgctgaatg   1140
```

```
caacagagtt caactatctc tgtccagcca tcatcaacca aattgatgct agatcttgtc    1200
tgattcatac aagtgaaaag aaggctgaaa tccctccaaa gacctattca ttacaaatag    1260
cctgggttgg tggttttata gccatttcca tcatcagttt cctgtctctg ctggggggtta    1320 tcttagtgcc tctcatgaat cgggtgtttt tcaaatttct cctgagtttc cttgtggcac    1380
tggccgttgg gactttgagt ggtgatgctt ttttacacct tcttccacat tctcatgcaa    1440
gtcaccacca tagtcatagc catgaagaac cagcaatgga aatgaaaaga ggaccacttt    1500
tcagtcatct gtcttctcaa aacatagaag aaagtgccta ttttgattcc acgtggaagg    1560
gtctaacagc tctaggaggc ctgtatttca tgtttcttgt tgaacatgtc ctcacattga    1620
tcaaacaatt taaagataag aagaaaaaga atcagaagaa acctgaaaat gatgatgatg    1680
tggagattaa gaagcagttg tccaagtatg aatctcaact ttcaacaaat gaggagaaag    1740
tagatacaga tgatcgaact gaaggctatt tacgagcaga ctcacaagag ccctcccact    1800
ttgattctca gcagcctgca gtcttggaag aagaagaggt catgatagct catgctcatc    1860
cacaggaagt ctacaatgaa tatgtaccca gagggtgcaa gaataaatgc cattcacatt    1920
tccacgatac actcggccag tcagacgatc tcattcacca ccatcatgac taccatcata    1980
ttctccatca tcaccaccac caaaaccacc atcctcacag tcacagccag cgctactctc    2040
gggaggagct gaaagatgcc ggcgtcgcca ctctggcctg gatggtgata atgggtgatg    2100
gcctgcacaa tttcagcgat ggcctagcaa ttggtgctgc ttttactgaa ggcttatcaa    2160
gtggtttaag tacttctgtt gctgtgttct gtcatgagtt gcctcatgaa ttaggtgact    2220
ttgctgttct actaaaggct ggcatgaccg ttaagcaggc tgtcctttat aatgcattgt    2280
cagccatgct ggcgtatctt ggaatggcaa caggaatttt cattggtcat tatgctgaaa    2340
atgtttctat gtggatattt gcacttactg ctggcttatt catgtatgtt gctctggttg    2400
atatggtacc tgaaatgctg cacaatgatg ctagtgacca tggatgtagc cgctgggggt    2460
atttcttttt acagaatgct gggatgcttt tgggttttgg aattatgtta cttatttcca    2520
tatttgaaca taaaatcgtg tttcgtataa atttctagtt aaggtttaaa tgctagagta    2580
gcttaaaaag ttgtcatagt ttcagtaggt cataggggaga tgagtttgta tgctgtacta    2640
tgcagcgttt aaagttagtg ggttttgtga ttttttgtatt gaatattgct gtctgttaca    2700
aagtcagtta aaggtacgtt ttaatattta agttattcta tcttggagat aaaatctgta    2760
tgtgcaattc accggtatta ccagtttatt atgtaaacaa gagatttggc atgacatgtt    2820
ctgtatgttt cagggaaaaa tgtctttaat gcttttcaa gaactaacac agttattcct    2880
atactggatt ttaggtctct gaagaactgc tggtgtttag gaataagaat gtgcatgaag    2940
cctaaaatac caagaaagct tatactgaat ttaagcaaag aaataaagga gaaagagaa    3000 gaatctgaga attggggagg catagattct tataaaaatc acaaatttg ttgtaaatta    3060 gaggggagaa atttagaatt aagtataaaa aggcagaatt agtatagagt acattcatta    3120 aacattttg tcaggattat ttcccgtaaa aacgtagtga gcacttttca tatactaatt    3180
tagttgtaca tttaactttg tataatacag aaatctaaat atatttaatg aattcaagca    3240
atatatcact tgaccaagaa attggaattt caaaatgttc gtgcgggtat ataccagatg    3300
agtacagtga gtagttttat gtatcaccag actgggttat tgccaagtta tatcacca    3360 aaagctgtat gactgatgt tctggttacc tggtttacaa aattatcaga gtagtaaaac    3420
tttgatatat atgaggatat taaaactaca ctaagtatca tttgattcga ttcagaaagt    3480
```

| | |
|---|---|
| actttgatat ctctcagtgc ttcagtgcta tcattgtgag caattgtctt ttatatacgg | 3540 |
| tactgtagcc atactaggcc tgtctgtggc attctctaga tgtttctttt ttacacaata | 3600 |
| aattccttat atcagcttga aaaaaaaaaa aaaaaaa | 3637 |

<210> SEQ ID NO 149
<211> LENGTH: 2208
<212> TYPE: DNA
<213> ORGANISM: Homo sapiens

<400> SEQUENCE: 149

| | |
|---|---|
| aacgcacttg gcgcgcggcg cgggctgcag acggctgcga ggcgctgggc acaggtgtcc | 60 |
| tgatggcaaa tttcaagggc cacgcgcttc cagggagttt cttcctgatc attgggctgt | 120 |
| gttggtcagt gaagtacccg ctgaagtact ttagccacac gcggaagaac agcccactac | 180 |
| attactatca gcgtctcgag atcgtcgaag ccgcaattag gactttgttt tccgtcactg | 240 |
| ggatcctggc agagcagttt gttccggatg ggccccacct gcacctctac catgagaacc | 300 |
| actggataaa gttaatgaat tggcagcaca gcaccatgta cctattcttt gcagtctcag | 360 |
| gaattgttga catgctcacc tatctggtca gccacgttcc cttgggggtg gacagactgg | 420 |
| ttatggctgt ggcagtattc atggaaggtt cctcttccta ctaccacgtc cacaaccggc | 480 |
| ctccgctgga ccagcacatc cactcactcc tgctgtatgc tctgttcgga gggtgtgtta | 540 |
| gtatctccct agaggtgatc ttccgggacc acattgtgct ggaacttttc gaaccagtc | 600 |
| tcatcattct tcagggaacc tggttctggc agattgggtt tgtgctgttc ccacctttg | 660 |
| gaacacccga tgggaccag aaggatgatg ccaacctcat gttcatcacc atgtgcttct | 720 |
| gctggcacta cctggctgcc ctcagcattg tggccgtcaa ctattctctt gtttactgcc | 780 |
| ttttgactcg gatgaagaga cacggaaggg gagaaatcat tggaattcag aagctgaatt | 840 |
| cagatgacac ttaccagacc gccctcttga gtggctcaga tgaggaatga gccgagatgc | 900 |
| ggagggcgca gatgtcccac tgcacagctg gaatgaatgg agttcatccc ctccacctga | 960 |
| atgcctgctg tggtctgatc ttaagggtct atatatttgc acctcctcat tcaacacagg | 1020 |
| gctggaggtt ctacaacagg aaatcaggcc tacagcatcc tgtgtatctt gcagttggga | 1080 |
| tttttaaaca tactataaag tctgtgttgg tatagtaccc ttcataagga aaaatgaagt | 1140 |
| aatgcctata agtagcaggc ctttgtgcct cagtgtcaag agaaatcaag agatgctaaa | 1200 |
| agctttacaa tggaagtggc ctcatggatg aatccggggt atgagcccag gagaacgtgc | 1260 |
| tgcttttggt aacttatccc ttttttctctt aagaaagcag gtactttctt attagaaata | 1320 |
| tgttagaatg tgtaagcaaa cgacagtgcc tttagaatta caattctaac ttacatattt | 1380 |
| tttgaaagta aaataattca caagctttgg tattttaaaa ttattgttaa acatatcata | 1440 |
| actaatcata ccagggtact gcaataccac tgtttataag tgacaaaatt aggccaaagg | 1500 |
| tgatttttttt ttaaatcagg aagctggtta ctggctctac tgagagttgg agccctgatg | 1560 |
| ttctgattct tcaaagtcac cctaaaagaa gatctgacag gaaagctgta taatgagata | 1620 |
| gaaaaacgtc aggtatggaa ggctttcagt tttaatatgg ctgaaagcaa aggataacga | 1680 |
| attcagaatt agtaatgtaa atcttgata ccctaatctt gcttctggat ctgttctttt | 1740 |
| tttaaaaaaa cttccttcac cgcgcctata atcctagcac tttgggaggc cgaggcaggc | 1800 |
| agatcacggg gtcaggagat caagaccatc ctggctaaca tggtgaaacc ccgtctctac | 1860 |
| tgaaaataca aaaaattagc cgggtgtggt ggcgggcgcc tgtagttcca gctactcggg | 1920 |
| aggctgaggc aagagaatgg catgaacccg gtaggggagc ttgcagtgag cccagatcat | 1980 |

```
gccactgtac tccagcctag gtgacagagc aagactctgt ctcaaaaaca agcaaacaga   2040
cttccttcaa caaatattta ttaaatatcc actttgcaac agcactgaaa tggctgtaag   2100
gactcctgag atatgtgtcc agcaaggagt ttacagtcaa acaggagaga catgcctgta   2160
gttacatcca gtgtgatggg tgctgagagg caagtacaaa ccacgatg               2208
```

<210> SEQ ID NO 150
<211> LENGTH: 1678
<212> TYPE: DNA
<213> ORGANISM: Homo sapiens
<220> FEATURE:
<221> NAME/KEY: misc_feature
<222> LOCATION: (523)..(523)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (961)..(961)
<223> OTHER INFORMATION: n is a, c, g, or t
<220> FEATURE:
<221> NAME/KEY: misc_feature
<222> LOCATION: (1021)..(1021)
<223> OTHER INFORMATION: n is a, c, g, or t
<220> FEATURE:
<221> NAME/KEY: misc_feature
<222> LOCATION: (1066)..(1066)
<223> OTHER INFORMATION: n is a, c, g, or t
<220> FEATURE:
<221> NAME/KEY: misc_feature
<222> LOCATION: (1069)..(1069)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1202)..(1202)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1472)..(1472)
<223> OTHER INFORMATION: n is a, c, g, or t

<400> SEQUENCE: 150

```
tcccgccgcg ccacttcgcc tgcctccgtc ccccgcccgc cgcgccatgc ctgtggccgg    60
ctcggagctg ccgcgccggc ccttgccccc cgccgcacag gagcgggacg ccgagccgcg   120
tccgccgcac ggggagctgc agtacctggg gcagatccaa cacatcctcc gctgcggcgt   180
caggaaggac gcccgcccgg gcaccggtac cctgccggta ttcggcatgc aggcgcgcta   240
cagcctgaga gatgaattcc ctctgctgac aaccaaacgt gtgttctgga acggtgcttc   300
ggaggagctg ctgtggctta tcaagggatc cacaaacgct atagacctgt cttccccggc   360
agcgaaaatc tcgggatgcc actggatccc gacactctct ggacaccctg ggattctcca   420
ccagagaaga acgcgacttg ggcccagttt gtggctctca gcggaggcct cctgtggcag   480
aatacataca tttccaatca gatcacttcc cggacacgga ccntgaccag cctgccaaaa   540
agtggatttc cccccacccc agaacccanc ccctgacgca cagaaaccaa cccattcgtt   600
gttgccgcct tgcgaaccc aaccagaatc tctcccccct ggccggcgcg cctgccgctg   660
```

-continued

```
ccaatgcccc tatggcggcc tcttggcccg caccttccaa ttggtcgccc tgcgcaacca      720
gcgagaaaac actggcccgc ccgtctcccc ccgctccgc ctaccccact taatgcgcct      780
ccgtggcatg acgcacgcgt ttggtgtccg ccgccgtctc atgtccgcgc ggtgtggacc      840
cccttttctc tcgcggcaca tccccctat tcccttgccc tttggggggc accccctcta      900
gacccgcgct tctcttctcg tccggtgggg gacattggtt tgcctgccgc ggcggggggcg      960
ntaaaaataa aaacagcctg ttagcccggc ccagtacccc ccccggccg gggccgcctt     1020
ncgtttgcat ttatacccca acccataaag ccgcgcccct ttagcnccnt aacttttgtg     1080
gtgtggcctc ccccctttt cccggggagc agcaacggac atctgtacac taatgctggc     1140
cccgaccttt cccaaaaacc ccccgcccgt gtcccgtata aatttggtgc caancctgac     1200
gngttctccc ccgccctcgc cccgttggcc gccgtttaa agccccccg gtggttgcgc     1260
cgcccaacga gtccacctat agttaantcc accaacaccc ccaccttttc ctccccgccg     1320
catcttcccc acgtaccccc ttttgtcgcg agatggccac tccccccccc ctgtttgttt     1380
aaaacaacga gaatggtgct gccaacgctg gtcttttccc cccccggacc gcgaccgcca     1440
gggggaatac gtaccataag ccccccgcgc cnccttttt cccccctccc cgccaatcaa     1500
gatccgccgt ccattagacg tattattttt cccgcgatac acgaaaaaac agggccgccc     1560
atttataact aaattcccgt cgccgccgcg cggatatgtt tcccaaaata ccacccccc     1620
cccccattt tctttgcccc caactcctgc gcaccggtgt tcaccagcct cgcgccgc     1678
```

<210> SEQ ID NO 151
<211> LENGTH: 1611
<212> TYPE: DNA
<213> ORGANISM: Homo sapiens

<400> SEQUENCE: 151

```
ggacgcgtgg gtcgacccac cgtccggac ccacgcgtcc ggtcgtgttc tccgagttcc       60
tgtctctctg ccaacgccgc ccggatggct tcccaaaacc gcgacccagc cgccactagc      120
gtcgccgccg cccgtaaagg agctgagccg agcggggggcg ccgcccgggg tccggtgggc      180
aaaaggctac agcaggagct gatgacccctc atggtgagtg attaagtgcc cagaacccca      240
gccttccatc caattttcag tagcctcctt ttttccgtca gcttttttgc tagacatagg      300
ggtaatgtaa tttgctccct cctgggaaag aagttcatac accccaccta caccatttct      360
tccagcagtc cctcctccca attccatccc cccacacgaa gttatctcga cacttccct      420
gaagtcatac aagaccctcc ctatccagtg tgtccctact tcctagcccc aaccaagctt      480
tacccacacc caactccccg cccttcttgg tatttctagc ctatgaattt ggttgcttta      540
ttttggatca gagtgatgag attaaggga ggctgggcgc ggtagctcac accttataat      600
cccaaagtgc tgggattaca ggcgtgagcc accgcgcccg gccagcaact aatattctaa      660
ttgaactaaa gcacaggatg ccaatttaca atccttagac caaagagtca ctgatgtctc      720
caccagataa gaggaaagca tcaggctagg catagtggct cacacctgta atctcagcac      780
tttgggaggc tgaggcaggc agatcacatg agcccaggag tttgagactg gcctgggcaa      840
catggtgaaa ccctgtctct aaaataaaaa ctaaactaaa aaacttttt aaaaaggcag      900
tggggagcat cagaaccagc tcaacagttt gtctactgtc cggtcccaga gaaactcaag      960
attctagcaa gccccttgtg tggggcttgg gttgggacat gaggctgctg ctggagctta     1020
ctctgcaact gtttctccaa atgccaggta tatgaagacc tgaggtataa gctctcgcta     1080
gagttcccca gtggctaccc ttacaatgcg cccacagtga agttcctcac gccctgctat     1140
```

```
cacccaacg tggacaccca gggtaacata tgcctggaca tcctgaagga aaagtggtct    1200
gccctgtatg atgtcaggac cattctgctc tccatccaga gccttctagg agaacccaac    1260
attgatagtc ccttgaacac acatgctgcc gagctctgga aaaacccac agcttttaag    1320 aagtacctgc aagaaaccta ctcaaagcag gtcaccagcc aggagccctg acccaggctg    1380
cccagcctgt ccttgtgtcg tcttttaat ttttccttag atggtctgtc cttttgtga     1440 tttctgtata ggactcttta tcttgagctg tggtatttt gttttgtttt tgtcttttaa    1500
attaagcctc ggttgagccc ttgtatatta aataaatgca tttttgtcct tttttaaaaa   1560
aaaaataaaa aaaaaaaaaa aaaaaaaaaa aaaaaaaaaa aaaaaaaaaa a            1611
```